United States Patent
McMinn et al.

(10) Patent No.: US 11,339,193 B2
(45) Date of Patent: May 24, 2022

(54) CDP PROTEIN SECRETION INHIBITORS

(71) Applicants: KEZAR LIFE SCIENCES, South San Francisco, CA (US); THE REGENTS OF THE UNIVERSITY OF CALIFORNIA, Oakland, CA (US)

(72) Inventors: Dustin McMinn, Pacifica, CA (US); John William Taunton, San Francisco, CA (US); Phillip Patrick Sharp, San Francisco, CA (US)

(73) Assignees: KEZAR LIFE SCIENCES, South San Francisco, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/042,009

(22) PCT Filed: Mar. 29, 2019

(86) PCT No.: PCT/US2019/024731
§ 371 (c)(1),
(2) Date: Sep. 25, 2020

(87) PCT Pub. No.: WO2019/191527
PCT Pub. Date: Oct. 3, 2019

(65) Prior Publication Data
US 2021/0017233 A1    Jan. 21, 2021

Related U.S. Application Data

(60) Provisional application No. 62/649,718, filed on Mar. 29, 2018.

(51) Int. Cl.
C07K 11/00 (2006.01)
C07K 11/02 (2006.01)
A61K 38/00 (2006.01)
A61K 45/06 (2006.01)

(52) U.S. Cl.
CPC .............. *C07K 11/02* (2013.01); *A61K 38/00* (2013.01); *A61K 45/06* (2013.01)

(58) Field of Classification Search
None
See application file for complete search history.

(56) References Cited

FOREIGN PATENT DOCUMENTS

| WO | 96/25167 A1 | 8/1996 |
|---|---|---|
| WO | 97/19104 A1 | 5/1997 |
| WO | 02/80856 A2 | 10/2002 |

OTHER PUBLICATIONS

Beaudoin et al., Preparation of unsymmetrical sulfonylureas from N,N'-sulfuryldiimidazoles, J. Org. Chem., 68:115-119(2002).

Bell et al., Synthesis and structure-activity relationship studies of CD4 down-modulating cyclotriazadisulfonamide (CADA) analogues, J. Med. Chem., 49:1291-1312 (2006).
Berge et al., Pharmaceutical salts, J. Pharm. Sci., 66:1-19 (1977).
Chawla et al., Tuning side Arm electronics in unsymmetrical cyclotriazadisulfonamide (CADA) endoplasmic reticulum (ER) translocation inhibitors to improve their human cluster of differentiation 4 (CD4) receptor down-modulating potencies, J. Med. Chem., 59:2633-2647 (2016).
Chen et al., Solution-phase parallel synthesis of a pharmacophore library of HUN-7293 analogues:? A general chemical mutagenesis approach to defining structure-function properties of naturally occurring cyclic (Depsi)peptides, J. Am. Chem. Soc., 124(19):5431-5440 (2002).
Chernichenk et al., Synthesis of Dansyl-Substituted Cryptands Containing Triaza-cycloalkane Moieties and their Evaluation as Fluorescent Chemosensors, Synlett, 28(20):2800-2806 (2017).
Demillo et al., Unsymmetrical Cyclotriazadisulfonamide (CADA) Compounds as Human CD4 Receptor Down-Modulating Agents—Journal of Medicinal Chemistry (ACS Publications), 54(16):5712-5721 (2011).
Garrison et al., A substrate-specific inhibitor of protein translocation into the endoplasmic reticulum, Nat., 436:285-289 (2005).
Greiner et al., Sec62 protein level is crucial for the ER stress tolerance of prostate cancer, Prostate, 71(10):1074-82 (2011).
International Application No. PCT/US2019/022533, International Preliminary Reporton Patentability, dated Oct. 1, 2020.
International Application No. PCT/US2019/022533, International Search Report and Written Opinion, dated May 20, 2019.
International Application No. PCT/US2019/024731, International Preliminary Reporton Patentability, dated Oct. 8, 2020.
International Application No. PCT/US2019/024731, International Search Report and Written Opinion, dated Jul. 4, 2019.
Kalies et al., Inhibitors of protein translocation across the ER membrane, Traffic, 16:1027-1038 (2015).
Lowe et al., Blocking protein secretion and degradation is a novel treatment strategy for malignant cells with high protein load, Blood, 122(21):4439 (2013).
Maifeld et al., Secretory protein profiling reveals TNF-(Alpha) inactivation by selective and promiscuous Sec61 modulators, Chem. Biol., 18:1082-1088, (2011).
Paatero et al., Aprataxin kills cells by direct blockade of the Sec61 protein translocation channel, Cell Chem. Biol., 23(5):561-566 (2016).
Puyenbroeck et al., A Proteomic Survey Indicates Sortilin as a Secondary Substrate of the ER Translocation Inhibitor Cyclotriazadisulfonamide (CADA), Mol. Cell. Prot., 16(2):157-167 (2016).
Puyenbroeck et al., Inhibitors of protein translocation across membranes of the secretory pathway: novel antimicrobial and anticancer agents, Cell Mol. Life Sci., 75(9):1541-1558 (2018).
Riiz-Saenz et al., Targeting HER3 by interfering with its Sec61-mediated cotranslational insertion into the endoplasmic reticulum, Oncogene., 1-7 (2015).

*Primary Examiner* — Jeanette M Lieb
(74) *Attorney, Agent, or Firm* — Marshall, Gerstein & Borun LLP

(57) ABSTRACT

Provided herein are compounds that inhibit protein secretion, e.g., via inhibition of Sec61. Also provided are compositions of the inhibitor compounds, and methods of using these inhibitors. The compounds disclosed herein can be used, e.g., for the treatment of cancer, arthritis, and/or inflammation.

20 Claims, No Drawings

Specification includes a Sequence Listing.

CDP PROTEIN SECRETION INHIBITORS

BACKGROUND

Protein translocation into the endoplasmic reticulum ("ER") constitutes the first step of protein secretion. ER protein import is essential in all eukaryotic cells and is particularly important in fast-growing tumor cells. Thus, the process of protein secretion can serve as a target both for potential cancer drugs and for bacterial virulence factors. See Kalies and Rbmisch, Traffic, 16(10):1027-1038 (2015).

Protein transport to the ER is initiated in the cytosol when N-terminal hydrophobic signal peptides protrude from the ribosome. Binding of signal recognition particle ("SRP") to the signal sequence allows targeting of the ribosome-nascent chain-SRP complex to the ER membrane where contact of SRP with its receptor triggers handing over of the signal peptide to Sec61. Sec61 is an ER membrane protein translocator (aka translocon) that is doughnut-shaped with 3 major subunits (heterotrimeric). It includes a "plug," which blocks transport into or out of the ER. The plug is displaced when the hydrophobic region of a nascent polypeptide interacts with the "seam" region of Sec61, allowing translocation of the polypeptide into the ER lumen. In mammals, only short proteins (<160 amino acids) can enter the ER posttranslationally, and proteins smaller than 120 amino acids are obliged to use this pathway. Some of the translocation competence is maintained by the binding of calmodulin to the signal sequence. Upon arrival at the Sec61 channel, the signal peptide or signal anchor intercalates between transmembrane domains ("TMDs") 2 and 7 of Sec61α, which form the lateral portion of the gate, allowing the channel to open for soluble secretory proteins. As the Sec61 channel consists of 10 TMDs (Sec61α) surrounded by a hydrophobic clamp formed by Sec61γ, channel opening is dependent on conformational changes that involve practically all TMDs.

Inhibition of protein transport across the ER membrane has the potential to treat or prevent diseases, such as the growth of cancer cells and inflammation. Known secretion inhibitors, which range from broad-spectrum to highly substrate-specific, can interfere with virtually any stage of this multistep process, and even with transport of endocytosed antigens into the cytosol for cross-presentation. These inhibitors interact with the signal peptide, chaperones, or the Sec61 channel to block substrate binding or to prevent the conformational changes needed for protein import into the ER. Examples of protein secretin inhibitors include, calmodulin inhibitors (e.g., E6 Berbamine and Ophiobolin A), Lanthanum, sterols, cyclodepsipeptides (e.g., HUN-7293, CAM741, NF1028, Cotrainsin, Apratoxin A, Decatransin, Valinomycin), CADA, Mycolactone, Eeyarestatin I ("ESI"), and Exotoxin A. However, the above secretion inhibitors suffer from one or more of the following: lack selectivity for the Sec61 channel, challenging manufacture due to structural complexity, and molecular weight limited administration, bio-availability and distribution.

Thus, a need exits for new small molecule inhibitors of protein secretion.

SUMMARY

Provided herein are compounds that inhibit Sec61. In particular, provided are compounds, or pharmaceutically acceptable salts thereof, having a structure of Formula (I):

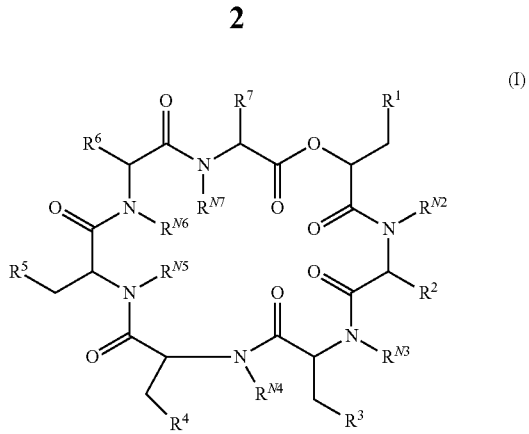

wherein R is H, $C_{0-3}$alkylene-CN, or $C_{2-6}$alkynyl; $R^2$ is isobutyl, $C_{2-8}$alkenyl, $C_{1-8}$haloalkyl, $C_{1-8}$hydroxyalkyl, $C_{0-3}$alkylene-$C_{3-8}$cycloalkyl, $C_{0-3}$alkylene-$C_{3-8}$cycloalkenyl, $C_{0-3}$alkylene-$C_{3-6}$ heterocycloalkyl, or $C_{0-3}$alkylene-$C_{3-6}$heterocycloalkenyl; $R^3$ is $C_{1-6}$alkyl, $C_{2-8}$alkenyl, $C_{1-6}$haloalkyl, $C_{1-8}$hydroxyalkyl, $C_{0-3}$alkylene-$C_{3-8}$cycloalkyl, or $C_{0-3}$alkylene-$C_{3-8}$cycloalkenyl; $R^4$ is $C_{1-8}$alkyl, $C_{2-8}$alkenyl, $C_{1-8}$haloalkyl, $C_{1-8}$hydroxyalkyl, $C_{0-3}$alkylene-$C_{3-8}$cycloalkyl, $C_{0-3}$alkylene-$C_{3-8}$cycloalkenyl, or $C_{0-3}$alkylene-$C_{3-6}$heterocycloalkyl; $R^5$ is $C_{3-8}$cycloalkyl, $C_{3-8}$cycloalkenyl, halo-substituted aryl, benzothiophenyl, tetrahydrobenzothiophenyl, triazolyl, quinolinyl, quinolinonyl, quinolonyl, tetrahydroquinolinyl, tetrahydroquinolinonyl, tetrahydroquinolonyl or indolyl, wherein the indolyl is N-substituted, and the quinolonyl or tetraquinolonyl is optionally N-substituted, and the N-substituent comprises $C_{3-8}$alkynyl, $C_{0-2}$alkylene-$C_{3-8}$cycloalkyl, $C_{0-2}$alkylene-$C_{3-8}$ cycloalkenyl, $C_{0-2}$alkylene-substituted aryl, or $C_{0-2}$alkylene-heteroaryl, and the substituted aryl is substituted with one or more groups selected from halo, alkyl, haloalkyl, OH, and alkoxy; and the benzothiophenyl is substituted with one or more groups selected from halo, haloalkyl, alkyl, OH, and alkoxy; $R$ is $C_{1-8}$alkyl, $C_{2-8}$ alkenyl, $C_{1-8}$haloalkyl, $C_{1-8}$hydroxyalkyl, $C_{0-3}$alkylene-$C_{3-8}$cycloalkyl, $C_{0-3}$alkylene-$C_{3-8}$ cycloalkenyl, $C_{0-3}$alkylene-$C_{3-6}$heterocycloalkyl, or $C_{0-3}$alkylene-$C_{3-6}$heterocycloalkenyl; $R^7$ is $C_{1-8}$alkyl; and each of $R^{N2}$, $R^{N3}$, $R^{N4}$, $R^{N5}$, $R^{N6}$, and $R^{N7}$ is independently H or $C_{1-3}$alkyl. Also provided are compounds as listed in Table A below. Pharmaceutical compositions comprising a compound disclosed herein and a pharmaceutically acceptable excipient are also provided.

Further provided are methods of inhibiting protein secretion in a cell comprising contact the cell with a compound as disclosed herein. Also provided are methods of treating cancer in a subject comprising administering to the subject a compound as disclosed herein in an amount effective to treat the cancer. Further provided are methods of treating arthritis in a subject comprising administering to the subject a compound as disclosed herein in an amount effective to treat arthritis. Also provided are methods of treating inflammation in a subject comprising administering to the subject a compound as disclosed herein in an amount effective to treat the inflammation.

DETAILED DESCRIPTION

Provided herein are compounds that inhibit protein secretion. The compounds described herein can be used to treat or prevent diseases associated with excessive protein secretion, such as inflammation and cancer, improving the quality of life for afflicted individuals.

The compounds provided herein, or a pharmaceutically acceptable salt thereof, have a structure of Formula (I):

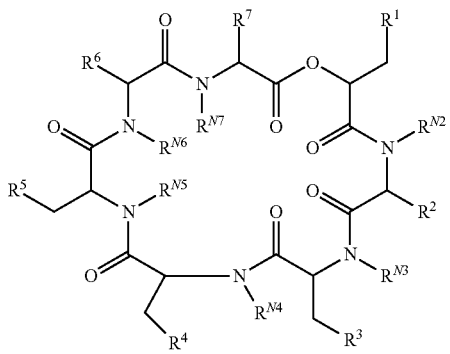

(I)

wherein $R^1$ is H, $C_{0-3}$alkylene-CN, or $C_{2-6}$alkynyl;
$R^2$ is isobutyl, $C_{2-8}$alkenyl, $C_{1-8}$haloalkyl, $C_{1-8}$hydroxyalkyl, $C_{0-3}$alkylene-$C_{3-8}$cycloalkyl, $C_{0-3}$alkylene-$C_{3-8}$cycloalkenyl, $C_{0-3}$alkylene-$C_{3-6}$heterocycloalkyl, or $C_{0-3}$alkylene-$C_{3-6}$ heterocycloalkenyl;
$R^3$ is $C_{1-6}$alkyl, $C_{2-8}$alkenyl, $C_{1-6}$haloalkyl, $C_{1-8}$hydroxyalkyl, $C_{0-3}$alkylene-$C_{3-8}$cycloalkyl, or $C_{0-3}$alkylene-$C_{3-8}$cycloalkenyl;
$R^4$ is $C_{1-8}$alkyl, $C_{2-8}$alkenyl, $C_{1-8}$haloalkyl, $C_{1-8}$hydroxyalkyl, $C_{0-3}$alkylene-$C_{3-8}$cycloalkyl, $C_{0-3}$alkylene-$C_{3-8}$cycloalkenyl, or $C_{0-3}$alkylene-$C_{3-6}$heterocycloalkyl;
$R^5$ is $C_{3-8}$cycloalkyl, $C_{3-8}$cycloalkenyl, halo-substituted aryl, benzothiophenyl, tetrahydrobenzothiophenyl, triazolyl, quinolinyl, quinolinonyl, quinolonyl, tetrahydroquinolinyl, tetrahydroquinolinonyl, tetrahydroquinolonyl or indolyl,
wherein the indolyl is N-substituted, and the quinolonyl or tetraquinolonyl is optionally N-substituted, and the N-substituent comprises $C_{3-8}$alkynyl, $C_{0-2}$alkylene-$C_{3-8}$cycloalkyl, $C_{0-2}$alkylene-$C_{3-8}$cycloalkenyl, $C_{0-2}$alkylene-substituted aryl, or $C_{0-2}$alkylene-heteroaryl, and the substituted aryl is substituted with one or more groups selected from halo, alkyl, haloalkyl, OH, and alkoxy; and
the benzothiophenyl is substituted with one or more groups selected from halo, haloalkyl, alkyl, OH, and alkoxy;
$R^6$ is $C_{1-8}$alkyl, $C_{2-8}$alkenyl, $C_{1-8}$haloalkyl, $C_{1-8}$hydroxyalkyl, $C_{0-3}$alkylene-$C_{3-8}$cycloalkyl, $C_{0-3}$alkylene-$C_{3-8}$cycloalkenyl, $C_{0-3}$alkylene-$C_{3-6}$heterocycloalkyl, or $C_{0-3}$alkylene-$C_{3-6}$heterocycloalkenyl;
$R^7$ is $C_{1-8}$alkyl; and
each of $R^{N2}$, $R^{N3}$, $R^{N4}$, $R^{N5}$, $R^{N6}$, and $R^{N7}$ is independently H or $C_{1-3}$alkyl.

In some cases, the compound or salt of Formula (I) has a structure of Formula (IA):

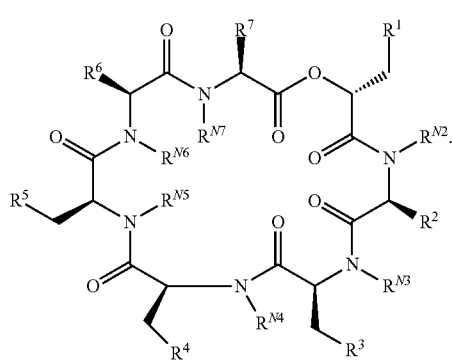

(IA)

In various cases, $R^1$ is H. In some cases, $R^1$ is $CH_2CN$. In some cases, $R^1$ is $(CH_2)_{0-2}C\equiv CH$ (e.g., $CH_2C\equiv CH$ or $CH_2CH_2C\equiv CH$).

In various cases, $R^2$ is $C_{1-8}$haloalkyl or isobutyl. In various cases, $R^2$ is $CH_2CF_3$, $CH_2CH_2CF_3$, $CH_2$-1-cyclohexenyl, $CH_2$-1-cyclopentenyl, $CH_2$-cyclopropyl, $CH_2$-cyclopentyl, $CH_2$-cyclohexyl, or $CH_2$-4-tetrahydropyranyl.

In various cases, $R^3$ is $C_{1-8}$haloalkyl or $CH(CH_3)_2$. In various cases, $R^4$ is $C_{1-8}$haloalkyl or $CH(CH_3)_2$. In various cases, $R^3$ is $C_{0-3}$alkylene-$C_{3-8}$cycloalkyl, or $C_{0-3}$alkylene-$C_{3-8}$cycloalkenyl. In some cases, $R^3$ is 1-cyclopentenyl or 1-cyclohexenyl. In various cases, $R^4$ is $CH(CH_3)_2$, $C(CH_3)_3$, $CH_3$, $CH_2CH_3$, $CF_3$, $CH_2CF_3$, tetrahydropyranyl, or cyclopentyl. In various cases, $R^4$ is $C_{0-3}$alkylene-$C_{3-8}$cycloalkyl or $C_{0-3}$alkylene-$C_{3-8}$cycloalkenyl. In some cases, $R^4$ is 1-cyclopentenyl or 1-cyclohexenyl.

In some cases, $R^3$ and $R^4$ are the same. In some cases, each of $R^3$ and $R^4$ is $CH(CH_3)_2$.

In various cases, $R^5$ comprises cyclohexyl, cyclopentyl, or cyclopentenyl.

In some cases, $R^5$ comprises quinolinyl, quinolinonyl, quinolonyl, tetrahydroquinolinyl, tetrahydroquinolinonyl, tetrahydroquinolonyl. In some cases, $R^5$

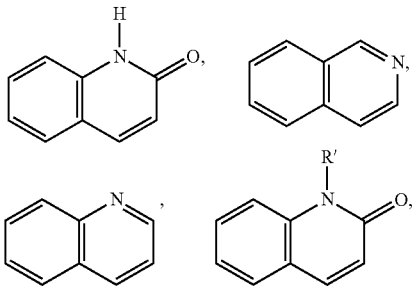

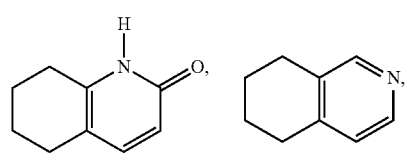

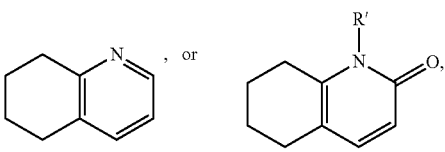

and R is $C_{3-8}$alkynyl, $C_{0-2}$alkyene-$C_{3-8}$cycloalkyl, $C_{0-2}$alkylene-$C_{3-8}$cycloalkenyl, $C_{0-2}$alkylene-aryl, or $C_{0-2}$alkylene-heteroaryl, wherein the aryl or heteroaryl can be unsubstituted or further substituted with one or more (e.g., 1, 2, or 3) groups selected from halo, alkyl, haloalkyl, OH, and alkoxy. The quinolinyl, quinolinonyl, quinolonyl, tetrahydroquinolinyl, tetrahydroquinolinonyl, or tetrahydroquinolonyl can be unsubstituted or further substituted with one or more (e.g., 1, 2, or 3) groups selected from halo, alkyl, haloalkyl, OH, and alkoxy.

In cases where R⁵ comprises indolyl, the structure of R⁵ can be

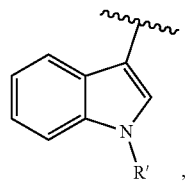

where R' is C₄alkynyl, CH₂-fluoropyridyl, CH₂-methylpyridyl, CH₂-methoxyphenyl, CH₂-methylphenyl (CH₂-tolyl), CH₂-fluorophenyl, CH₂-chlorophenyl, CH₂-bromophenyl, CH₂-difluorophenyl, CH₂-fluoromethoxyphenyl, or CH₂-methylisooxazolyl. In some cases, R is para-fluorobenzyl or para-bromobenzyl.

In cases where R⁵ comprises benzothiophenyl, the benzothiophentyl can be substituted with one or more of chloro, fluoro, bromo, methyl, and methoxy. In some cases, R⁵ comprises chlorobenzothiophenyl (e.g., 5-chlorobenzothiophenyl).

In some cases, R⁶ is CH₃, CH₂CH(CH₃)₂, CH₂CH(CH₃)(CH₂)₃CH₃, CH₂CF₃, or CH₂CH₂CF₃. In various cases, R⁶ is C₁₋₈haloalkyl. In some cases, R⁶ is CH₂CH(CH₃)₂. In various cases, R⁶ is C₀₋₃alkylene-C₃₋₈cycloalkenyl. In some cases, R⁶ is CH₂-1-cyclopentenyl or CH₂-1-cyclohexenyl.

In various cases, R⁷ is methyl. In various cases, at least one of R^{N2}, R^{N3}, R^{N4}, R^{N5}, R^{N6}, and R^{N7} is H. In some cases, at least one of R^{N2}, R^{N3}, R^{N4}, R^{N5}, R^{N6}, and R^{N7} is CH₃. In some cases, R^{N2} is H, R^{N3} is CH₃, R^{N4} is H, R^{N5} is CH₃, R^{N6} is H, and R^{N7} is CH₃.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like.

Without being bound by any particular theory, the compounds described herein inhibit protein secretion by binding to and disabling components of the translocon, including but not limited to Sec61, and in some cases, disrupting in a sequence specific fashion interactions between the nascent signaling sequence of translated proteins with components of the translocon including but not limited to Sec61.

The compounds described herein can inhibit the secretion of a protein of interest (e.g., TNFα, PD1, Her3, VCAM, Prl, IL7, or FLT3) with an IC₅₀ of up to 5 μM, or up to 3 μM, or up to 1 μM. In various cases, the compounds disclosed herein can inhibit the secretion of TNFα with an IC₅₀ of up to 5 μM, or up to 3 μM, or up to 1 μM. In various cases, the compounds disclosed herein can inhibit the secretion of VCAM with an IC₅₀ of up to 5 μM, or up to 3 μM, or up to 1 μM. In some cases, the compounds disclosed herein can inhibit the secretion of Her3 with an IC₅₀ of up to 5 μM, or up to 3 μM, or up to 1 μM. In various cases, the compounds disclosed herein can inhibit the secretion of Prl with an IC₅₀ of up to 5 μM, or up to 3 μM, or up to 1 μM. In various cases, the compounds disclosed herein can inhibit the secretion of IL7 with an IC₅₀ of up to 5 μM, or up to 3 μM, or up to 1 μM. In various cases, the compounds disclosed herein can inhibit the secretion of FLT3 with an IC₅₀ of up to 5 μM, or up to 3 μM, or up to 1 μM.

In some cases, the compound as disclosed herein is a compound, or pharmaceutically acceptable salt thereof, as shown in Table A below. In some cases, the compound or salt is as shown in Table A, or is C-01, which has a structure of:

(C-01)

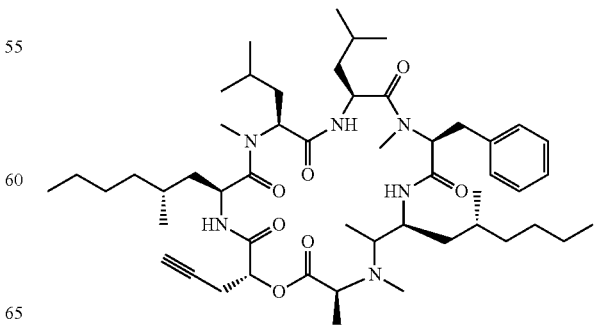

TABLE A

| Ex. # | Structure |
|---|---|
| C-02 | 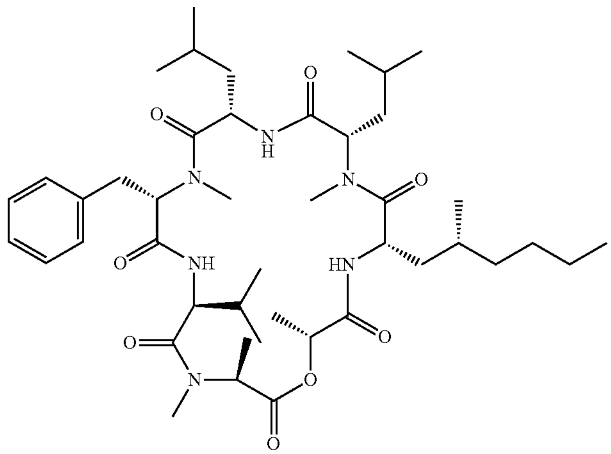 [SMILES: CCCC[C@@H](C)C[C@@H]1NC(=O)[C@@H](C)OC(=O)[C@H](C)N(C)C(=O)[C@H](C(C)C)NC(=O)[C@H](Cc2ccccc2)N(C)C(=O)[C@H](CC(C)C)NC(=O)[C@H](CC(C)C)N(C)C1=O] |
| C-03 | 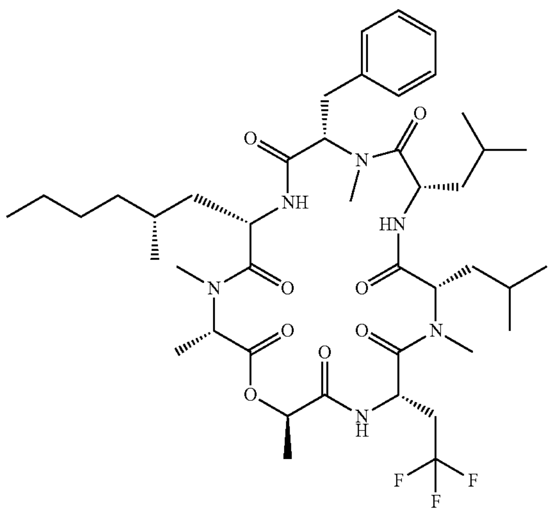 [SMILES: CCCC[C@@H](C)C[C@@H]1NC(=O)[C@H](Cc2ccccc2)N(C)C(=O)[C@H](CC(C)C)NC(=O)[C@H](CC(C)C)N(C)C(=O)[C@H](CC(F)(F)F)NC(=O)[C@@H](C)OC(=O)[C@H](C)N(C)C1=O] |
| C-04 | 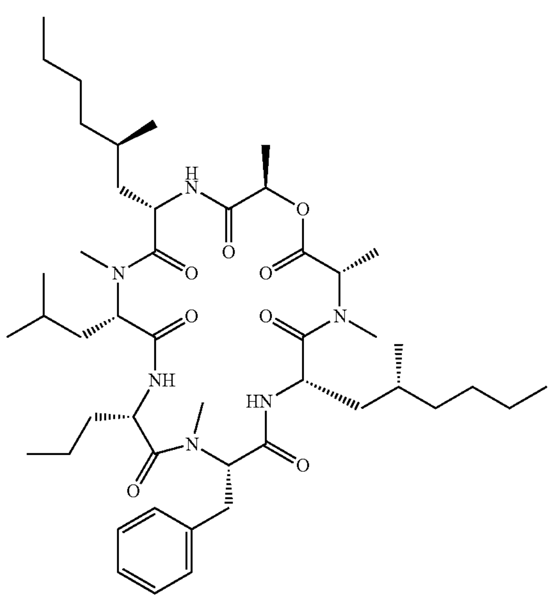 [SMILES: CCCC[C@@H](C)C[C@@H]1NC(=O)[C@H](Cc2ccccc2)N(C)C(=O)[C@H](CCC)NC(=O)[C@H](CC(C)C)N(C)C(=O)[C@H](C[C@H](C)CCCC)NC(=O)[C@@H](C)OC(=O)[C@H](C)N(C)C1=O] |

TABLE A-continued
| Ex. # | Structure |
|---|---|
| C-05 | 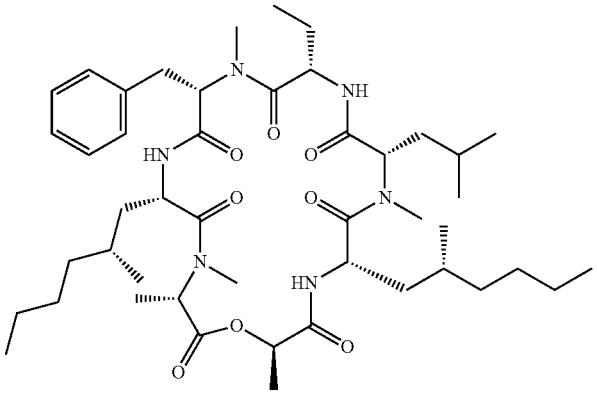 [SMILES: CCCC[C@@H](C)C[C@@H]1NC(=O)[C@H](Cc2ccccc2)N(C)C(=O)[C@H](CC)NC(=O)[C@H](CC(C)C)N(C)C(=O)[C@H](C[C@H](C)CCCC)NC(=O)[C@@H](C)OC(=O)[C@H](C)N(C)C1=O] |
| C-06 | 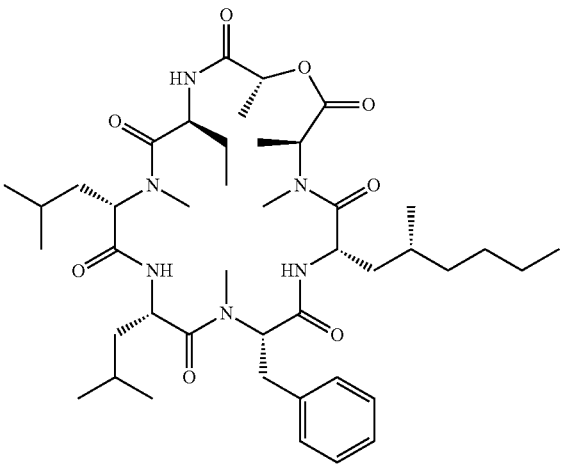 [SMILES: CCCC[C@@H](C)C[C@@H]1NC(=O)[C@H](Cc2ccccc2)N(C)C(=O)[C@H](CC(C)C)NC(=O)[C@H](CC(C)C)N(C)C(=O)[C@H](CC)NC(=O)[C@@H](C)OC(=O)[C@H](C)N(C)C1=O] |
| C-07 | 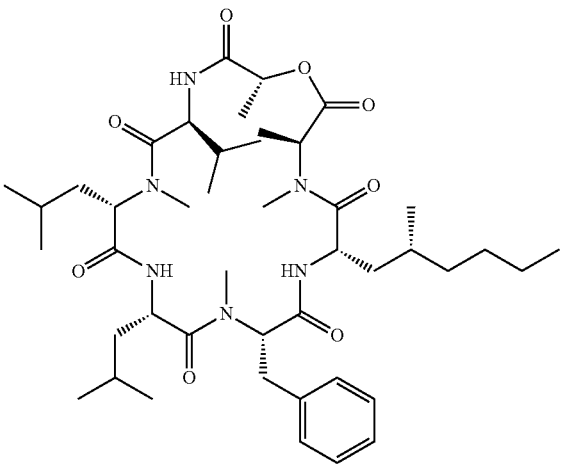 [SMILES: CCCC[C@@H](C)C[C@@H]1NC(=O)[C@H](Cc2ccccc2)N(C)C(=O)[C@H](CC(C)C)NC(=O)[C@H](CC(C)C)N(C)C(=O)[C@H](C(C)C)NC(=O)[C@@H](C)OC(=O)[C@H](C)N(C)C1=O] |

TABLE A-continued

| Ex. # | Structure |
|---|---|
| C-08 | 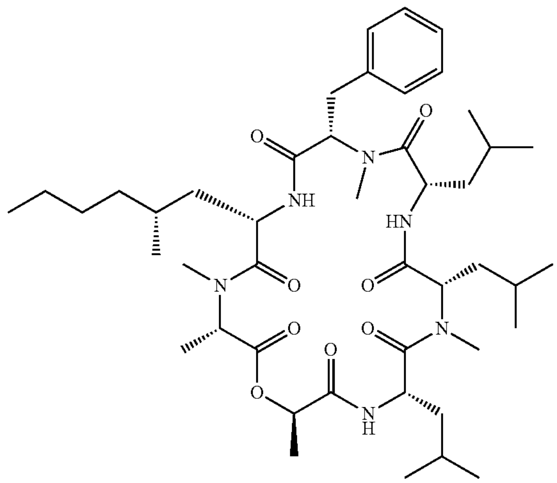 [SMILES: CCCC[C@@H](C)C[C@@H]1NC(=O)[C@H](Cc2ccccc2)N(C)C(=O)[C@H](CC(C)C)NC(=O)[C@H](CC(C)C)N(C)C(=O)[C@H](CC(C)C)NC(=O)[C@@H](C)OC(=O)[C@H](C)N(C)C1=O] |
| C-09 | 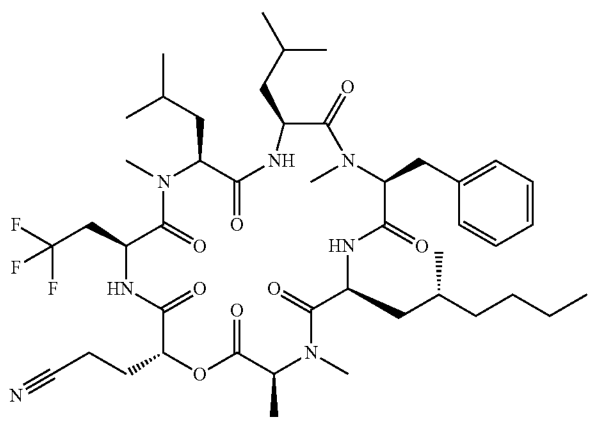 [SMILES: CCCC[C@@H](C)C[C@@H]1NC(=O)[C@H](Cc2ccccc2)N(C)C(=O)[C@H](CC(C)C)NC(=O)[C@H](CC(C)C)N(C)C(=O)[C@H](CC(F)(F)F)NC(=O)[C@@H](CCC#N)OC(=O)[C@H](C)N(C)C1=O] |
| C-10 | 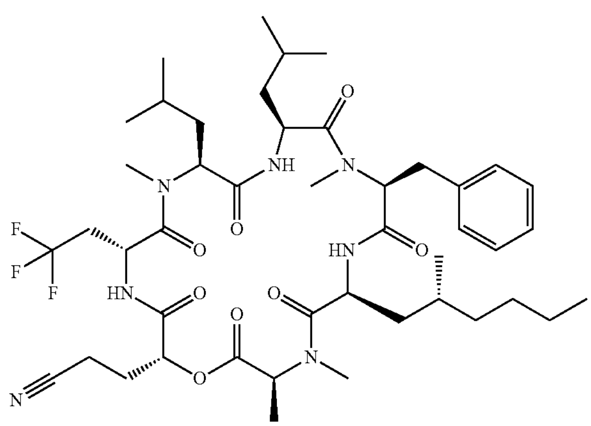 [SMILES: CCCC[C@@H](C)C[C@@H]1NC(=O)[C@H](Cc2ccccc2)N(C)C(=O)[C@H](CC(C)C)NC(=O)[C@H](CC(C)C)N(C)C(=O)[C@@H](CC(F)(F)F)NC(=O)[C@@H](CCC#N)OC(=O)[C@H](C)N(C)C1=O] |

TABLE A-continued
| Ex. # | Structure |
|---|---|
| C-11 | 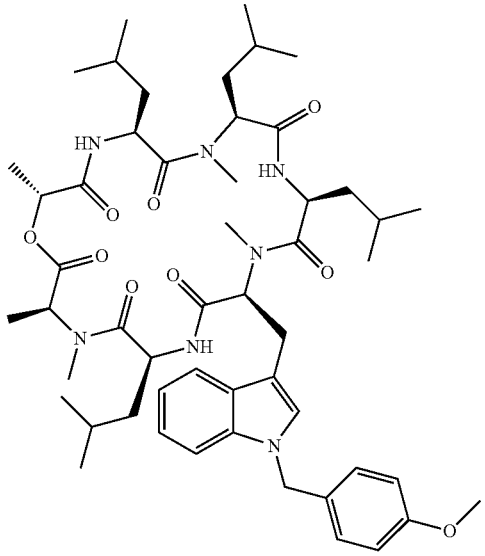 |
| C-12 | 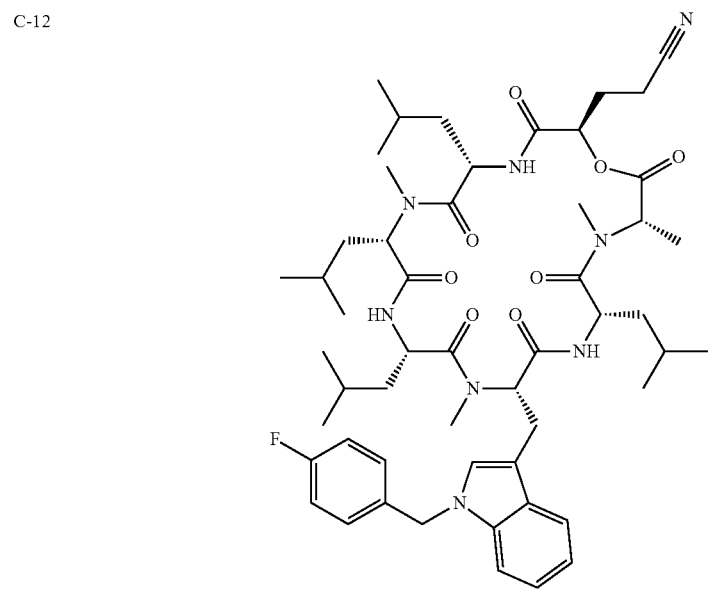 |

TABLE A-continued
| Ex. # | Structure |
|---|---|
| C-13 | 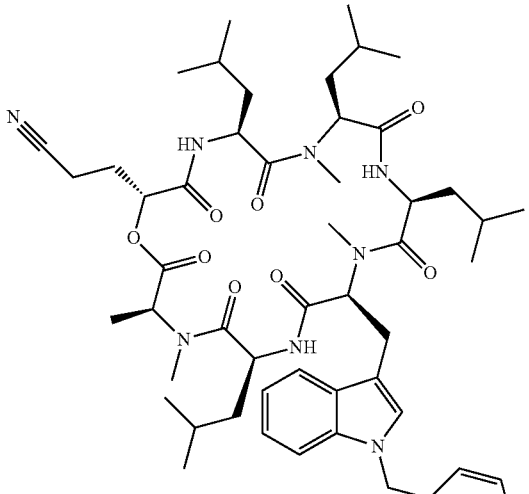 |
| C-14 | 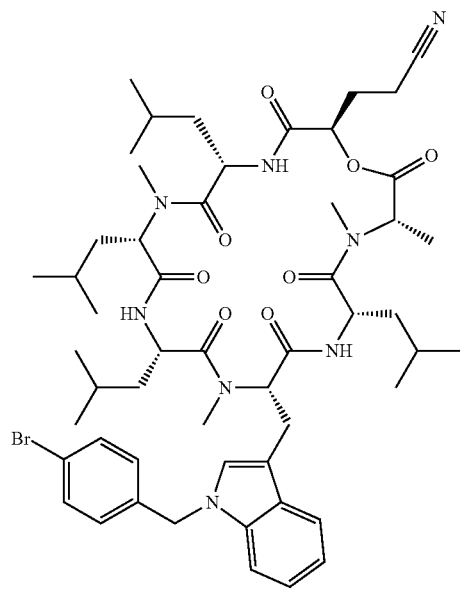 [SMILES: CC(C)C[C@@H]1NC(=O)[C@H](Cc2cn(Cc3ccc(Br)cc3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O] |

TABLE A-continued
| Ex. # | Structure |
|---|---|
| C-15 | 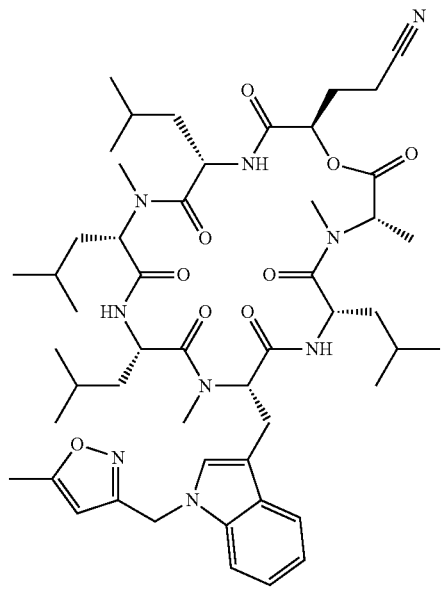 [SMILES: Cc1cc(Cn2cc(C[C@H]3C(=O)N[C@@H](CC(C)C)C(=O)N(C)[C@@H](C)C(=O)O[C@H](CCC#N)C(=O)N[C@@H](CC(C)C)C(=O)N(C)[C@@H](CC(C)C)C(=O)N[C@@H](CC(C)C)C(=O)N3C)c3ccccc32)no1] |
| C-16 | 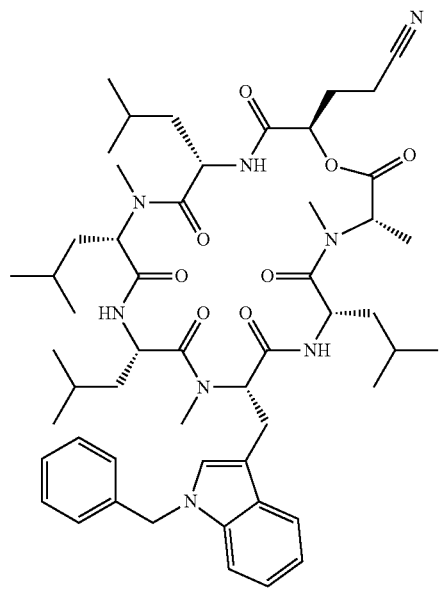 [SMILES: CC(C)C[C@@H]1NC(=O)[C@H](Cc2cn(Cc3ccccc3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O] |

TABLE A-continued
| Ex. # | Structure |
|---|---|
| C-17 | 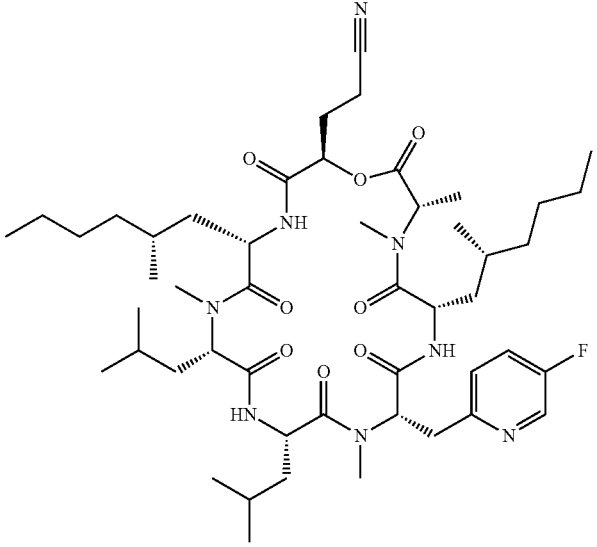 [SMILES: CCCC[C@@H](C)C[C@@H]1NC(=O)[C@H](Cc2ccc(F)cn2)N(C)C(=O)[C@H](CC(C)C)NC(=O)[C@H](CC(C)C)N(C)C(=O)[C@H](C[C@H](C)CCCC)NC(=O)[C@@H](CCC#N)OC(=O)[C@H](C)N(C)C1=O] |
| C-18 | 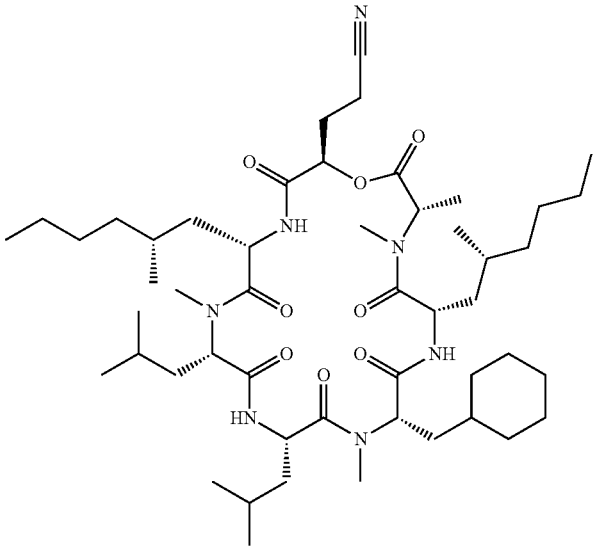 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](C[C@H](C)CCCC)NC(=O)[C@@H](CCC#N)OC(=O)[C@H](C)N(C)C1=O] |
| C-19 | 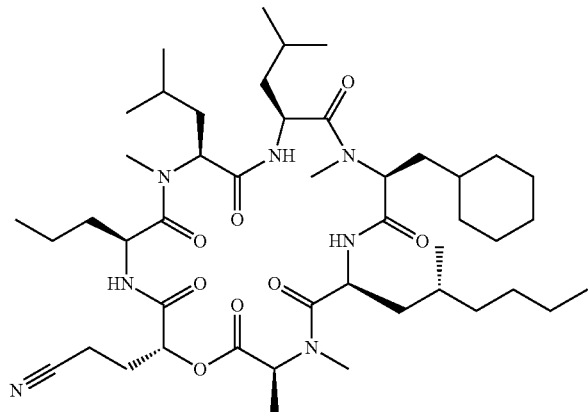 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CCC)NC(=O)[C@@H](CCC#N)OC(=O)[C@H](C)N(C)C1=O] |

TABLE A-continued
| Ex. # | Structure |
|---|---|
| C-20 | 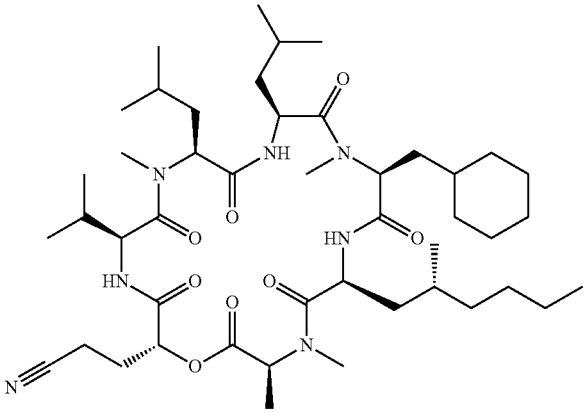 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](C(C)C)NC(=O)[C@@H](CCC#N)OC(=O)[C@H](C)N(C)C1=O] |
| C-21 | 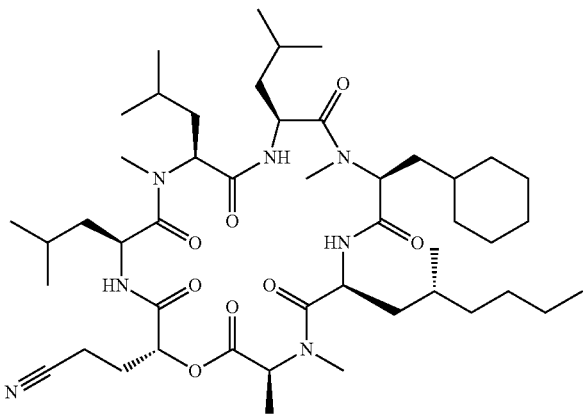 |
| C-22 | 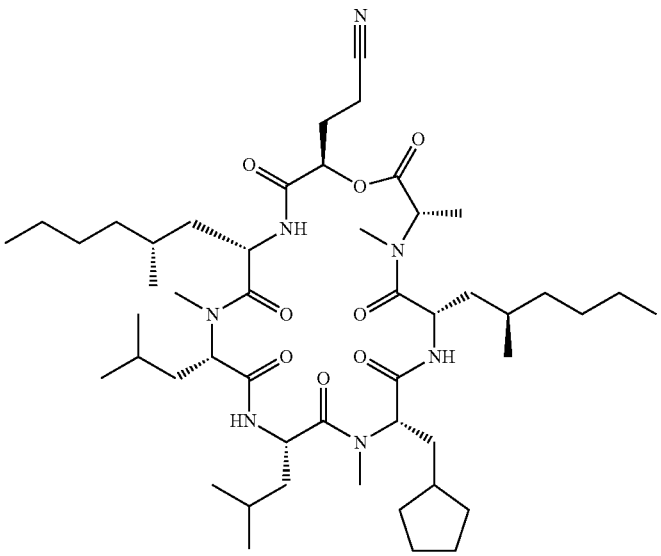 [SMILES: CCCC[C@@H](C)C[C@@H]1NC(=O)[C@H](CC2CCCC2)N(C)C(=O)[C@H](CC(C)C)NC(=O)[C@H](CC(C)C)N(C)C(=O)[C@H](C[C@H](C)CCCC)NC(=O)[C@@H](CCC#N)OC(=O)[C@H](C)N(C)C1=O] |

TABLE A-continued
| Ex. # | Structure |
|---|---|
| C-23 | 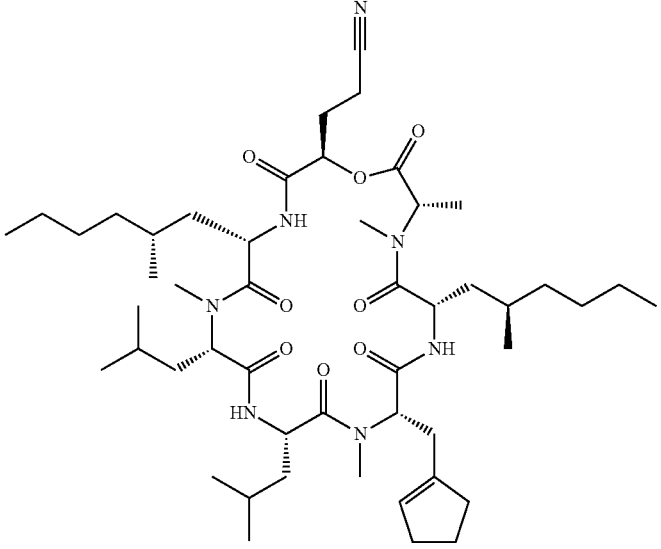 [SMILES: CCCC[C@@H](C)C[C@@H]1NC(=O)[C@H](CC2=CCCC2)N(C)C(=O)[C@H](CC(C)C)NC(=O)[C@H](CC(C)C)N(C)C(=O)[C@H](C[C@H](C)CCCC)NC(=O)[C@@H](CCC#N)OC(=O)[C@H](C)N(C)C1=O] |
| C-24 | 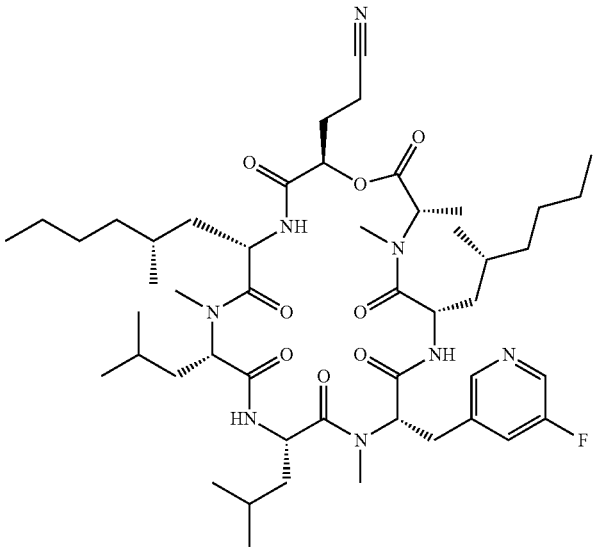 [SMILES: CCCC[C@@H](C)C[C@@H]1NC(=O)[C@H](Cc2cncc(F)c2)N(C)C(=O)[C@H](CC(C)C)NC(=O)[C@H](CC(C)C)N(C)C(=O)[C@H](C[C@H](C)CCCC)NC(=O)[C@@H](CCC#N)OC(=O)[C@H](C)N(C)C1=O] |
| C-25 | 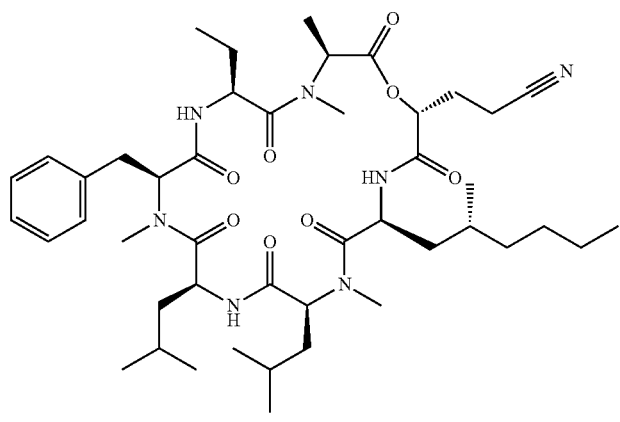 [SMILES: CCCC[C@@H](C)C[C@@H]1NC(=O)[C@@H](CCC#N)OC(=O)[C@H](C)N(C)C(=O)[C@H](CC)NC(=O)[C@H](Cc2ccccc2)N(C)C(=O)[C@H](CC(C)C)NC(=O)[C@H](CC(C)C)N(C)C1=O] |

TABLE A-continued
| Ex. # | Structure |
|---|---|
| C-26 | 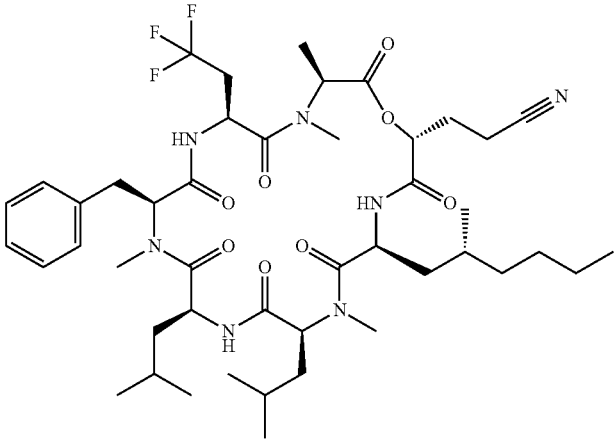 [SMILES: CCCC[C@@H](C)C[C@@H]1NC(=O)[C@@H](CCC#N)OC(=O)[C@H](C)N(C)C(=O)[C@H](CC(F)(F)F)NC(=O)[C@H](Cc2ccccc2)N(C)C(=O)[C@H](CC(C)C)NC(=O)[C@H](CC(C)C)N(C)C1=O] |
| C-27 | 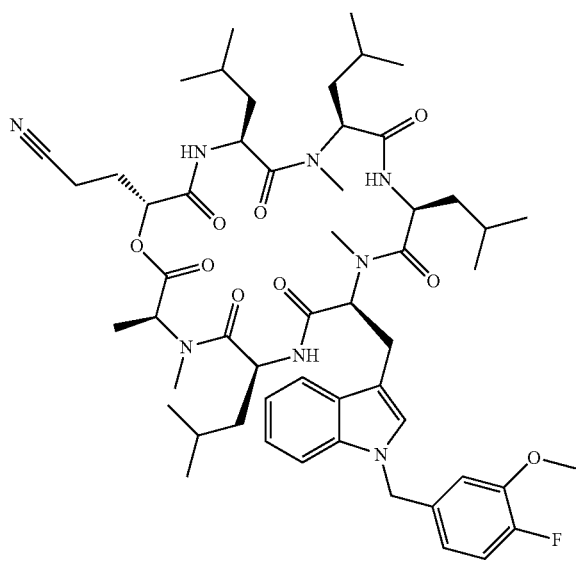 [SMILES: COc1cc(Cn2cc(C[C@H]3C(=O)N[C@@H](CC(C)C)C(=O)N(C)[C@@H](C)C(=O)O[C@H](CCC#N)C(=O)N[C@@H](CC(C)C)C(=O)N(C)[C@@H](CC(C)C)C(=O)N[C@@H](CC(C)C)C(=O)N3C)c3ccccc32)ccc1F] |

TABLE A-continued
| Ex. # | Structure |
|---|---|
| C-28 | 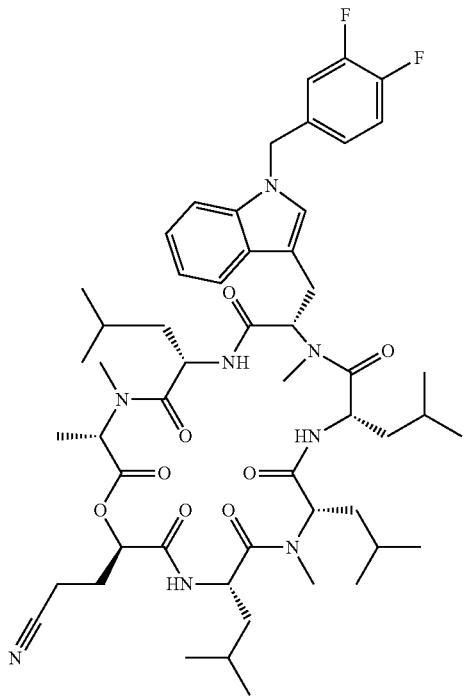 [SMILES: CC(C)C[C@@H]1NC(=O)[C@H](Cc2cn(Cc3ccc(F)c(F)c3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O] |
| C-29 | 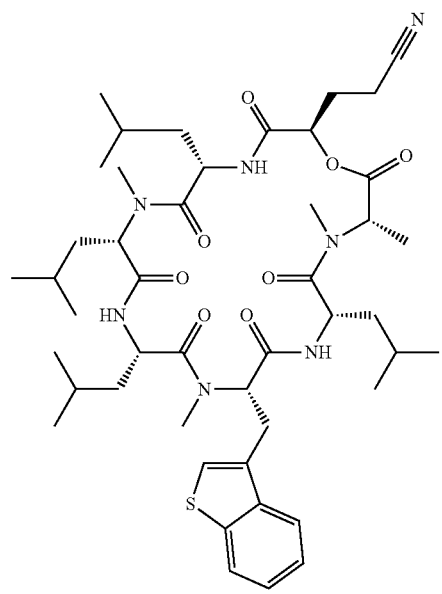 [SMILES: CC(C)C[C@@H]1NC(=O)[C@H](Cc2csc3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O] |

TABLE A-continued
| Ex. # | Structure |
|---|---|
| C-30 | 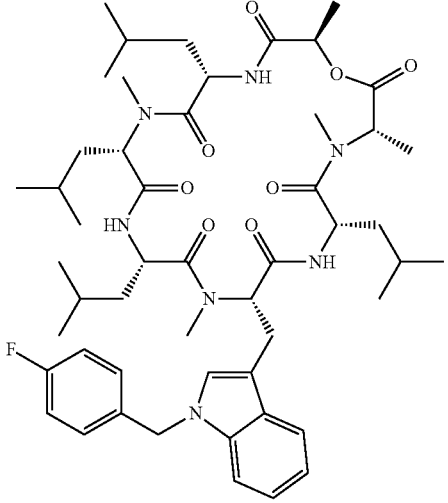 [SMILES: CC(C)C[C@@H]1NC(=O)[C@H](Cc2cn(Cc3ccc(F)cc3)c3ccccc23)N(C)C(=O)[C@H](CC(C)C)NC(=O)[C@H](CC(C)C)N(C)C(=O)[C@H](CC(C)C)NC(=O)[C@@H](C)OC(=O)[C@H](C)N(C)C1=O] |
| C-31 | 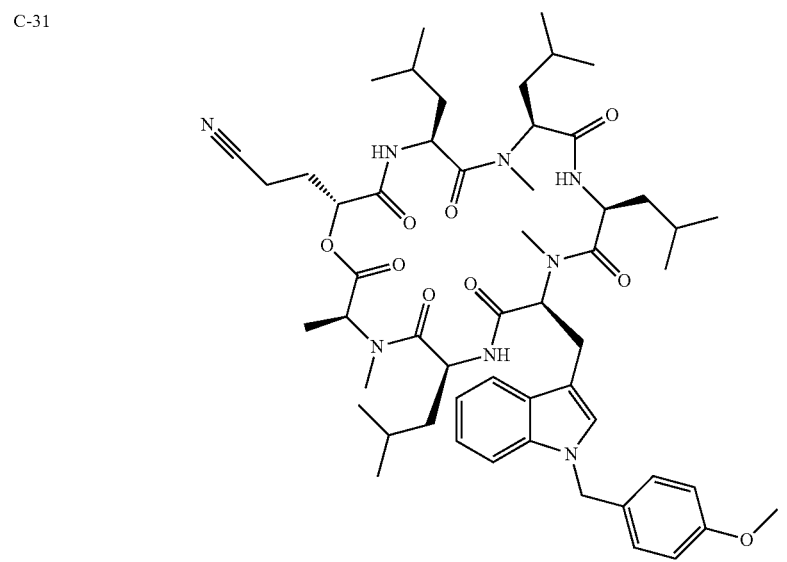 |

TABLE A-continued
| Ex. # | Structure |
|---|---|
| C-32 | 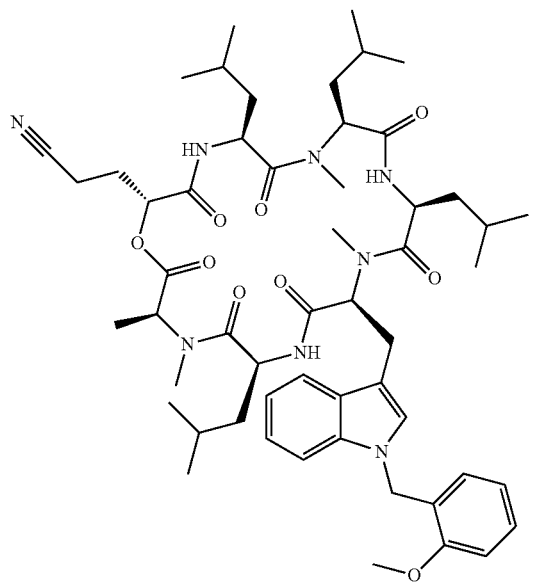 [SMILES: COc1ccccc1Cn1cc(C[C@H]2C(=O)N[C@@H](CC(C)C)C(=O)N(C)[C@@H](C)C(=O)O[C@H](CCC#N)C(=O)N[C@@H](CC(C)C)C(=O)N(C)[C@@H](CC(C)C)C(=O)N[C@@H](CC(C)C)C(=O)N2C)c2ccccc21] |
| C-33 | 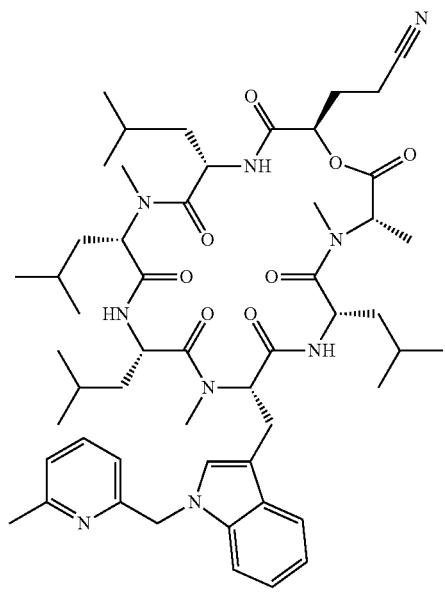 [SMILES: Cc1cccc(Cn2cc(C[C@H]3C(=O)N[C@@H](CC(C)C)C(=O)N(C)[C@@H](C)C(=O)O[C@H](CCC#N)C(=O)N[C@@H](CC(C)C)C(=O)N(C)[C@@H](CC(C)C)C(=O)N[C@@H](CC(C)C)C(=O)N3C)c3ccccc32)n1] |

| Ex. # | Structure |
|---|---|
| C-34 | 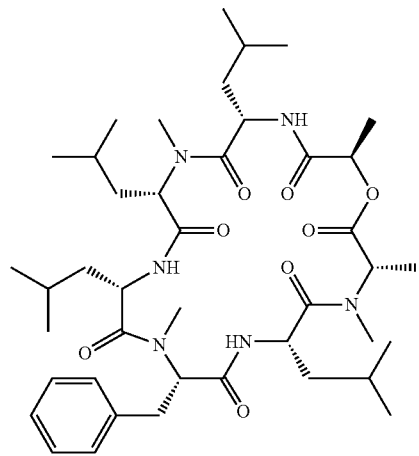 [SMILES: CC(C)C[C@@H]1NC(=O)[C@H](Cc2ccccc2)N(C)C(=O)[C@H](CC(C)C)NC(=O)[C@H](CC(C)C)N(C)C(=O)[C@H](CC(C)C)NC(=O)[C@@H](C)OC(=O)[C@H](C)N(C)C1=O] |
| C-35 | 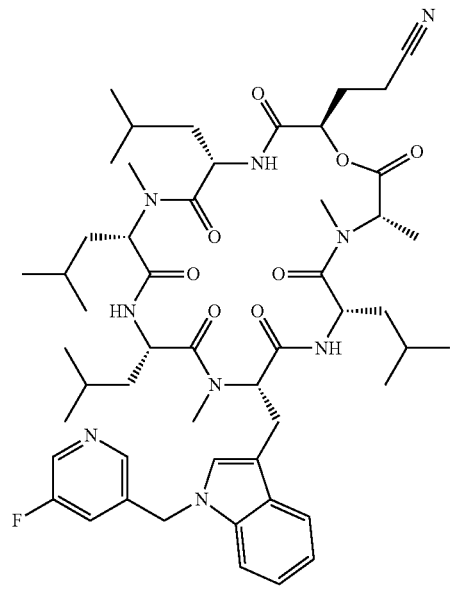 [SMILES: CC(C)C[C@@H]1NC(=O)[C@H](Cc2cn(Cc3cncc(F)c3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O] |

TABLE A-continued
| Ex. # | Structure |
|---|---|
| C-36 | 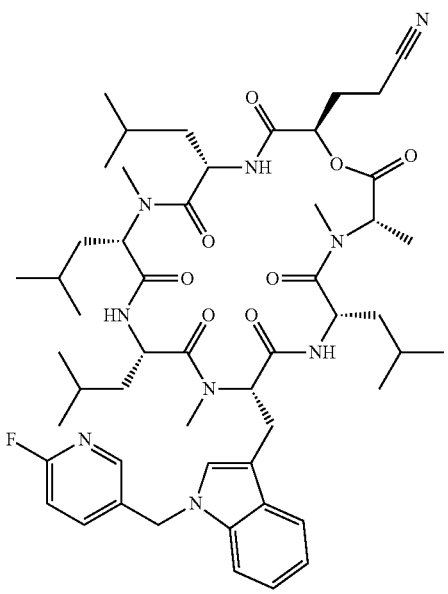 [SMILES: CC(C)C[C@@H]1NC(=O)[C@H](Cc2cn(Cc3ccc(F)nc3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O] |
| C-37 | 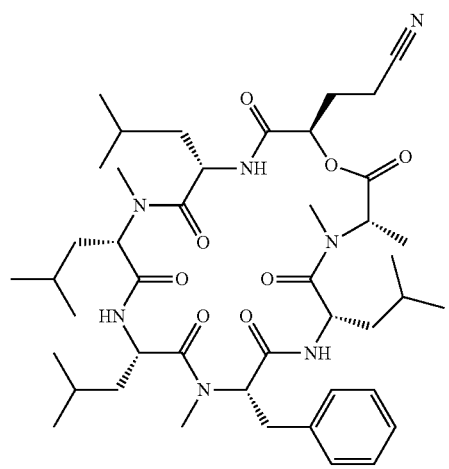 [SMILES: CC(C)C[C@@H]1NC(=O)[C@H](Cc2ccccc2)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O] |

TABLE A-continued
| Ex. # | Structure |
|---|---|
| C-38 | 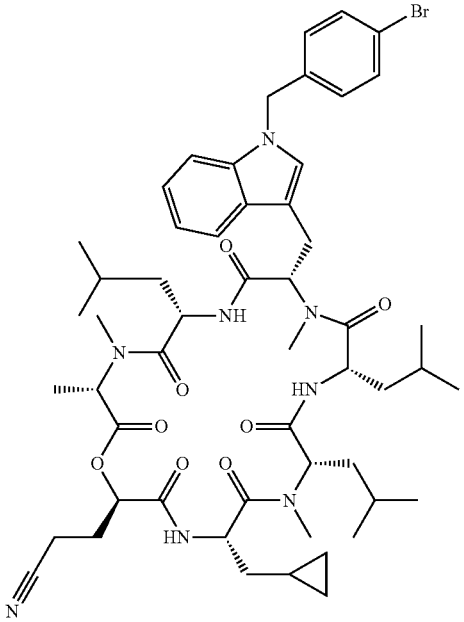 [SMILES: CC(C)C[C@@H]1NC(=O)[C@H](Cc2cn(Cc3ccc(Br)cc3)c3ccccc23)N(C)C(=O)[C@H](CC(C)C)NC(=O)[C@H](CC(C)C)N(C)C(=O)[C@H](CC2CC2)NC(=O)[C@@H](CCC#N)OC(=O)[C@H](C)N(C)C1=O] |
| C-39 | 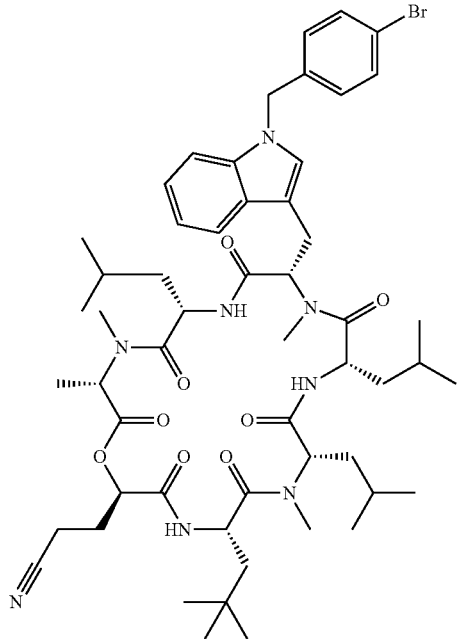 [SMILES: CC(C)C[C@@H]1NC(=O)[C@H](Cc2cn(Cc3ccc(Br)cc3)c3ccccc23)N(C)C(=O)[C@H](CC(C)C)NC(=O)[C@H](CC(C)C)N(C)C(=O)[C@H](CC(C)(C)C)NC(=O)[C@@H](CCC#N)OC(=O)[C@H](C)N(C)C1=O] |

TABLE A-continued
| Ex. # | Structure |
|---|---|
| C-40 | 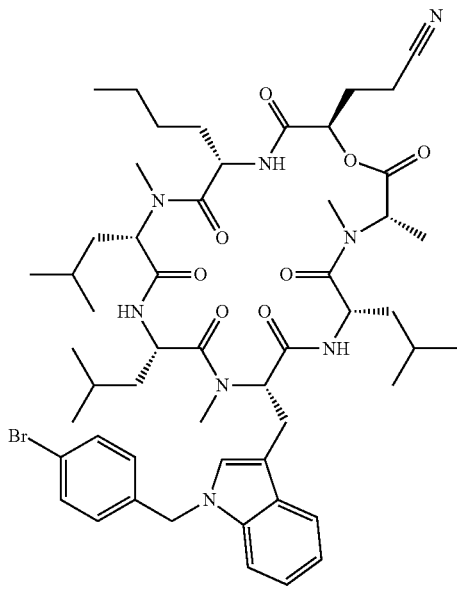 [SMILES: CCCC[C@@H]1NC(=O)[C@@H](CCC#N)OC(=O)[C@H](C)N(C)C(=O)[C@H](CC(C)C)NC(=O)[C@H](Cc2cn(Cc3ccc(Br)cc3)c3ccccc23)N(C)C(=O)[C@H](CC(C)C)NC(=O)[C@H](CC(C)C)N(C)C1=O] |
| C-41 | 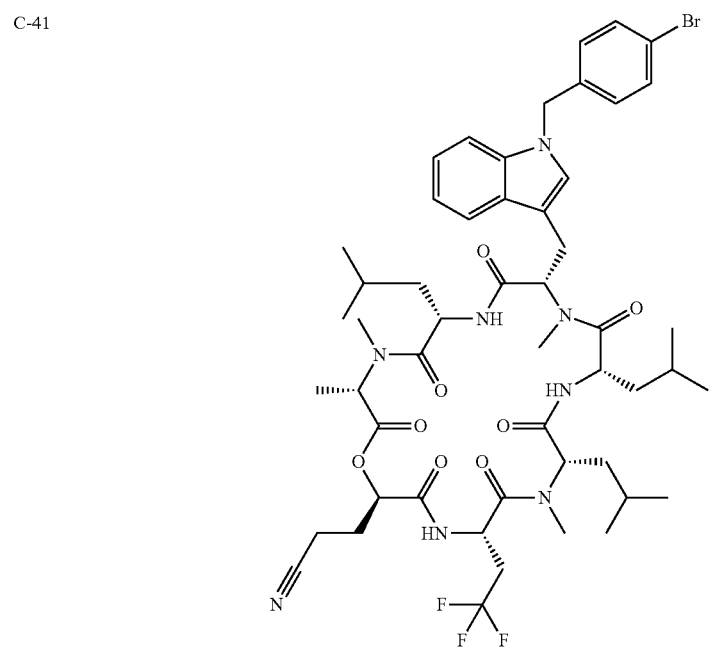 |

TABLE A-continued
| Ex. # | Structure |
|---|---|
| C-42 | 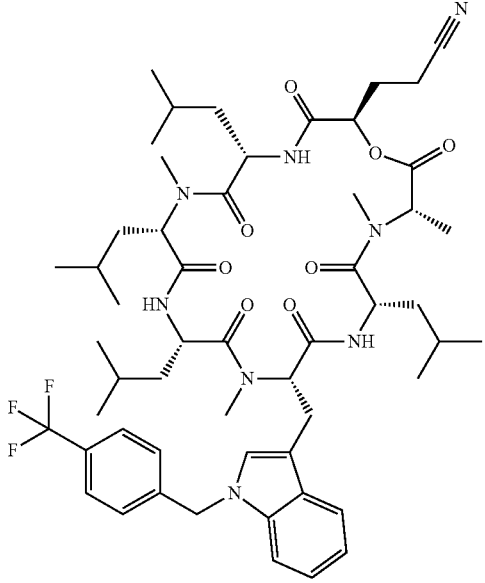 [SMILES: CC(C)C[C@@H]1NC(=O)[C@H](Cc2cn(Cc3ccc(C(F)(F)F)cc3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O] |
| C-43 | 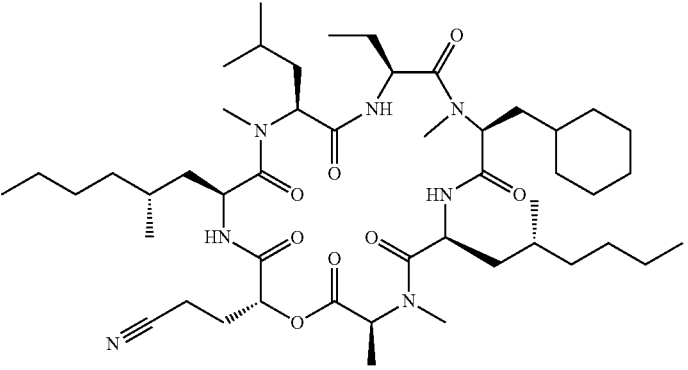 [SMILES: CCCC[C@@H](C)C[C@@H]1NC(=O)[C@H](CC2CCCCC2)N(C)C(=O)[C@H](CC)NC(=O)[C@H](CC(C)C)N(C)C(=O)[C@H](C[C@H](C)CCCC)NC(=O)[C@@H](CCC#N)OC(=O)[C@H](C)N(C)C1=O] |
| C-44 | 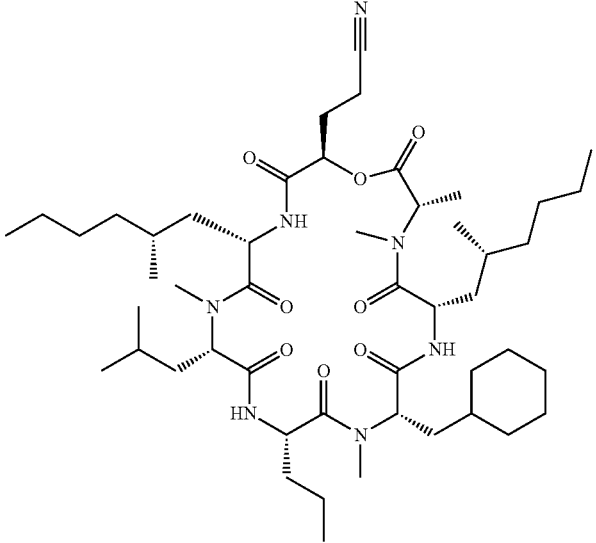 [SMILES: CCCC[C@@H](C)C[C@@H]1NC(=O)[C@H](CC2CCCCC2)N(C)C(=O)[C@H](CCC)NC(=O)[C@H](CC(C)C)N(C)C(=O)[C@H](C[C@H](C)CCCC)NC(=O)[C@@H](CCC#N)OC(=O)[C@H](C)N(C)C1=O] |

TABLE A-continued
| Ex. # | Structure |
|---|---|
| C-45 | 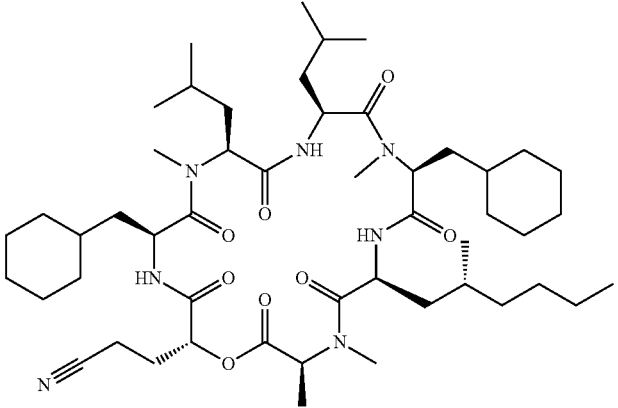 |
| C-46 | 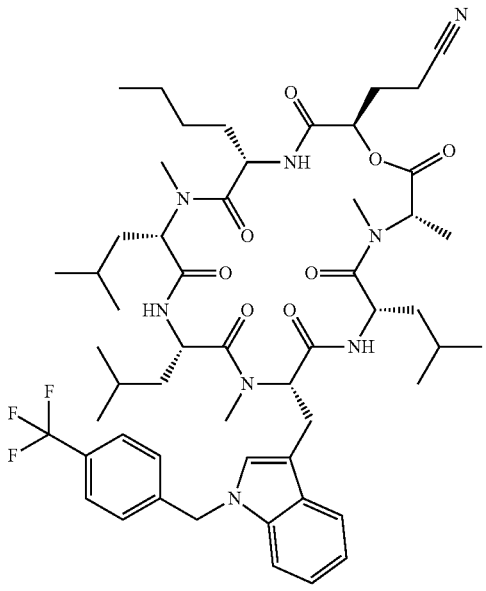 [SMILES: CCCC[C@@H]1NC(=O)[C@@H](CCC#N)OC(=O)[C@H](C)N(C)C(=O)[C@H](CC(C)C)NC(=O)[C@H](Cc2cn(Cc3ccc(C(F)(F)F)cc3)c3ccccc23)N(C)C(=O)[C@H](CC(C)C)NC(=O)[C@H](CC(C)C)N(C)C1=O] |
| C-47 | 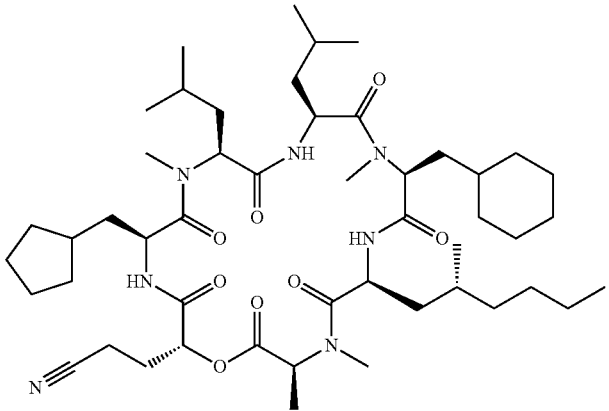 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CC2CCCC2)NC(=O)[C@@H](CCC#N)OC(=O)[C@H](C)N(C)C1=O] |

TABLE A-continued
| Ex. # | Structure |
|---|---|
| C-48 | 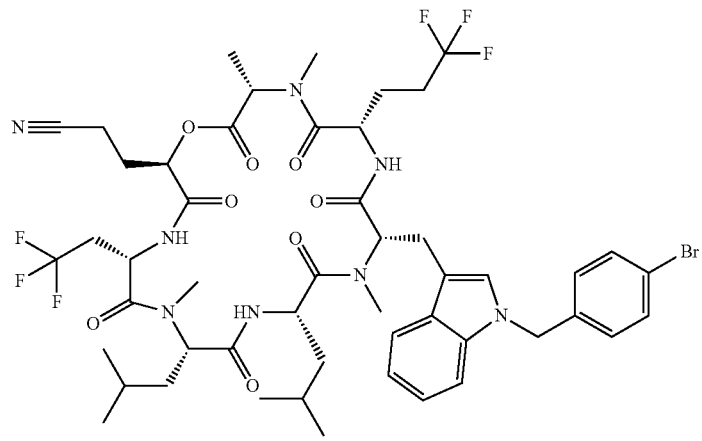 [SMILES: CC(C)C[C@@H]1NC(=O)[C@H](CC(C)C)N(C)C(=O)[C@H](CC(F)(F)F)NC(=O)[C@@H](CCC#N)OC(=O)[C@H](C)N(C)C(=O)[C@H](CCC(F)(F)F)NC(=O)[C@H](Cc2cn(Cc3ccc(Br)cc3)c3ccccc23)N(C)C1=O] |
| C-49 | 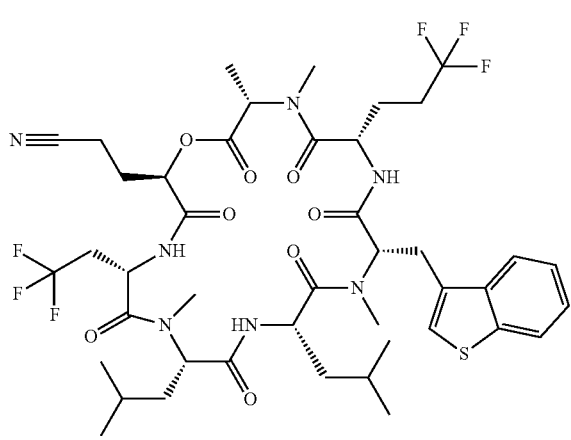 [SMILES: CC(C)C[C@@H]1NC(=O)[C@H](CC(C)C)N(C)C(=O)[C@H](CC(F)(F)F)NC(=O)[C@@H](CCC#N)OC(=O)[C@H](C)N(C)C(=O)[C@H](CCC(F)(F)F)NC(=O)[C@H](Cc2csc3ccccc23)N(C)C1=O] |
| C-50 | 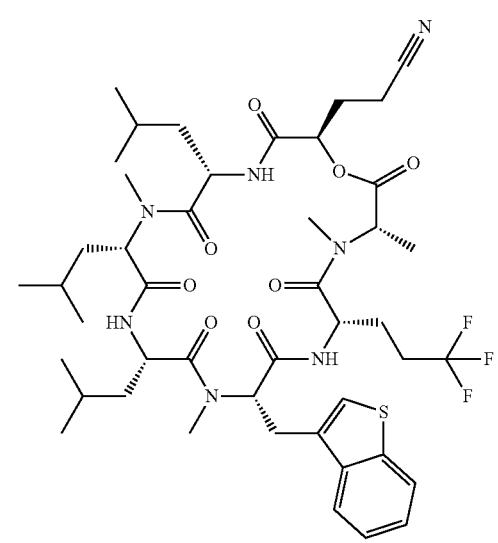 [SMILES: CC(C)C[C@@H]1NC(=O)[C@@H](CCC#N)OC(=O)[C@H](C)N(C)C(=O)[C@H](CCC(F)(F)F)NC(=O)[C@H](Cc2csc3ccccc23)N(C)C(=O)[C@H](CC(C)C)NC(=O)[C@H](CC(C)C)N(C)C1=O] |

TABLE A-continued
| Ex. # | Structure |
|---|---|
| C-51 | 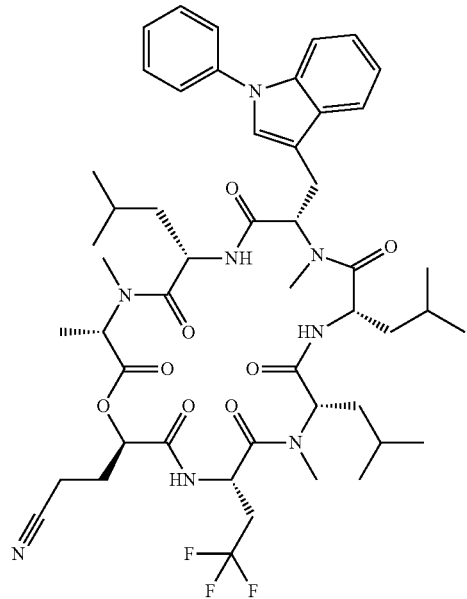 [SMILES: CC(C)C[C@@H]1NC(=O)[C@H](Cc2cn(-c3ccccc3)c3ccccc23)N(C)C(=O)[C@H](CC(C)C)NC(=O)[C@H](CC(C)C)N(C)C(=O)[C@H](CC(F)(F)F)NC(=O)[C@@H](CCC#N)OC(=O)[C@H](C)N(C)C1=O] |
| C-52 | 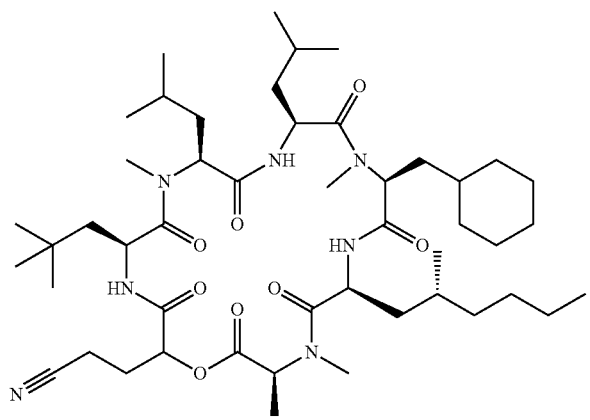 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CC(C)(C)C)NC(=O)C(CCC#N)OC(=O)[C@H](C)N(C)C1=O] |
| C-53 | 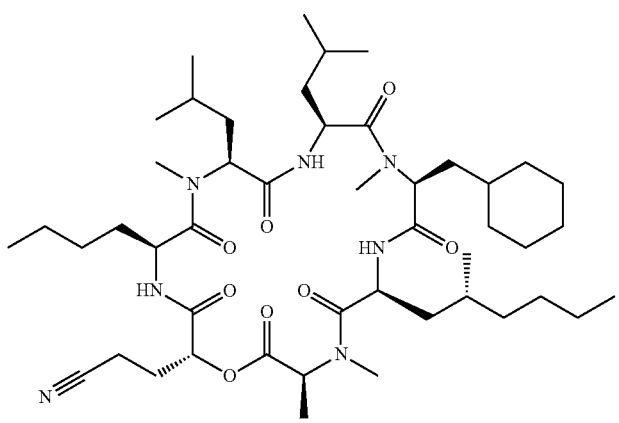 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CCCC)NC(=O)[C@@H](CCC#N)OC(=O)[C@H](C)N(C)C1=O] |

TABLE A-continued

| Ex. # | Structure |
|---|---|
| C-54 | 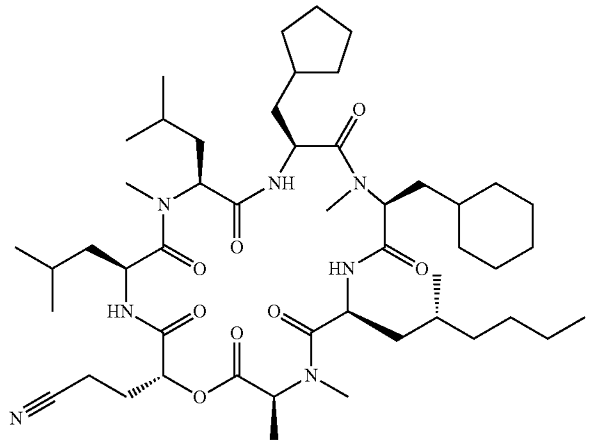 [SMILES: CCCC[C@@H](C)C[C@@H]1NC(=O)[C@H](CC2CCCCC2)N(C)C(=O)[C@H](CC2CCCC2)NC(=O)[C@H](CC(C)C)N(C)C(=O)[C@H](CC(C)C)NC(=O)[C@@H](CCC#N)OC(=O)[C@H](C)N(C)C1=O] |
| C-55 | 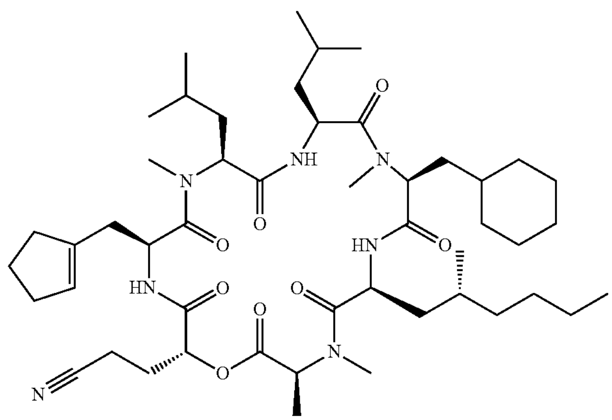 |
| C-56 | 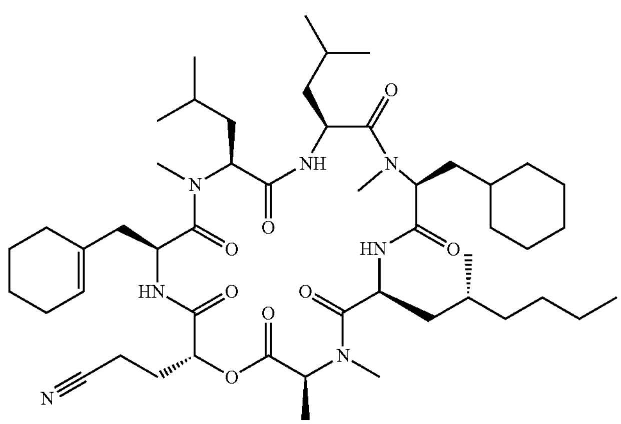 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CC2=CCCCC2)NC(=O)[C@@H](CCC#N)OC(=O)[C@H](C)N(C)C1=O] |

TABLE A-continued
| Ex. # | Structure |
|---|---|
| C-57 | 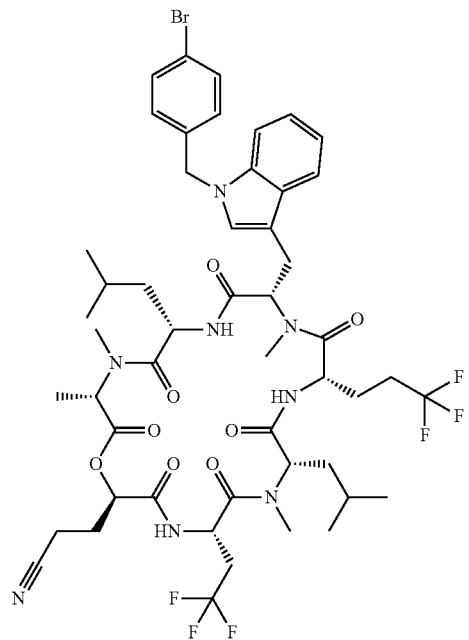 [SMILES: CC(C)C[C@@H]1NC(=O)[C@H](Cc2cn(Cc3ccc(Br)cc3)c3ccccc23)N(C)C(=O)[C@H](CCC(F)(F)F)NC(=O)[C@H](CC(C)C)N(C)C(=O)[C@H](CC(F)(F)F)NC(=O)[C@@H](CCC#N)OC(=O)[C@H](C)N(C)C1=O] |
| C-58 | 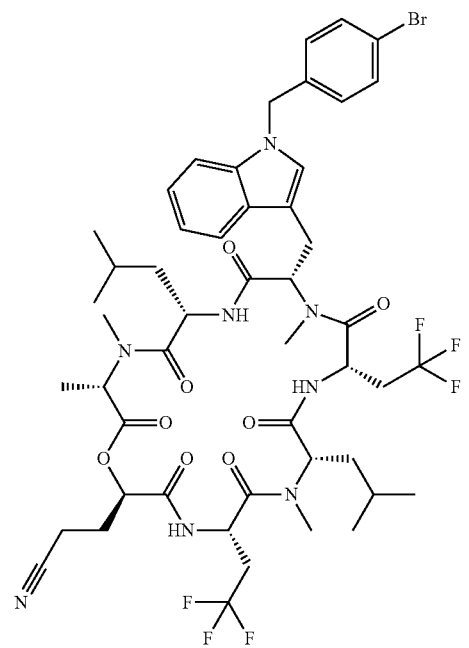 [SMILES: CC(C)C[C@@H]1NC(=O)[C@H](Cc2cn(Cc3ccc(Br)cc3)c3ccccc23)N(C)C(=O)[C@H](CC(F)(F)F)NC(=O)[C@H](CC(C)C)N(C)C(=O)[C@H](CC(F)(F)F)NC(=O)[C@@H](CCC#N)OC(=O)[C@H](C)N(C)C1=O] |

TABLE A-continued
| Ex. # | Structure |
|---|---|
| C-60 | 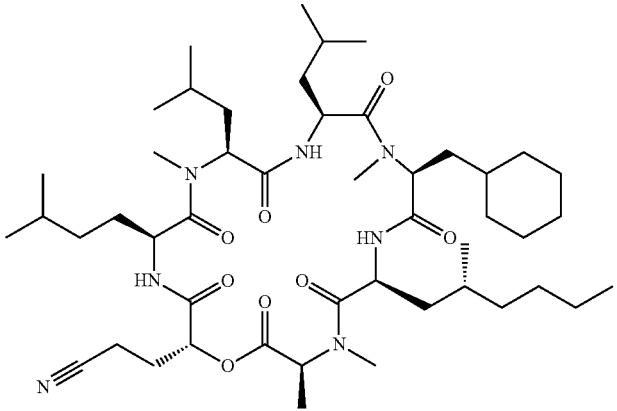 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CCC(C)C)NC(=O)[C@@H](CCC#N)OC(=O)[C@H](C)N(C)C1=O] |
| C-61 | 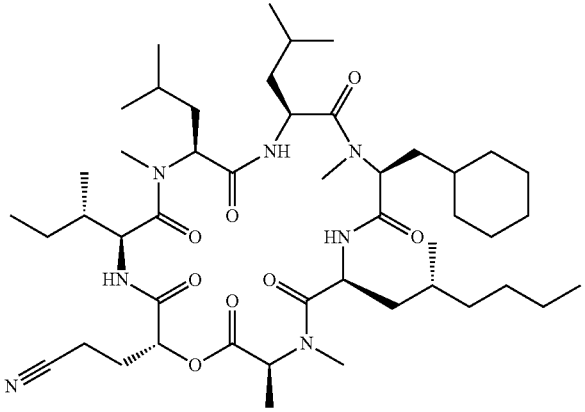 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H]([C@@H](C)CC)NC(=O)[C@@H](CCC#N)OC(=O)[C@H](C)N(C)C1=O] |
| C-62 | 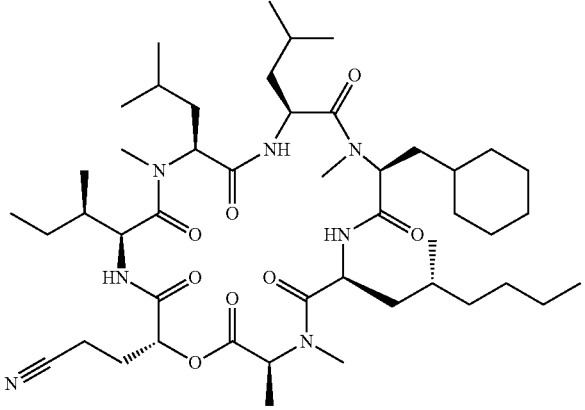 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H]([C@H](C)CC)NC(=O)[C@@H](CCC#N)OC(=O)[C@H](C)N(C)C1=O] |

TABLE A-continued
| Ex. # | Structure |
|---|---|
| C-63 | 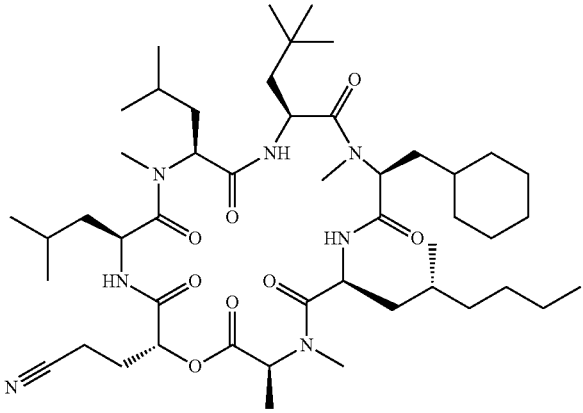 [SMILES: CCCC[C@@H](C)C[C@@H]1NC(=O)[C@H](CC2CCCCC2)N(C)C(=O)[C@H](CC(C)(C)C)NC(=O)[C@H](CC(C)C)N(C)C(=O)[C@H](CC(C)C)NC(=O)[C@@H](CCC#N)OC(=O)[C@H](C)N(C)C1=O] |
| C-64 | 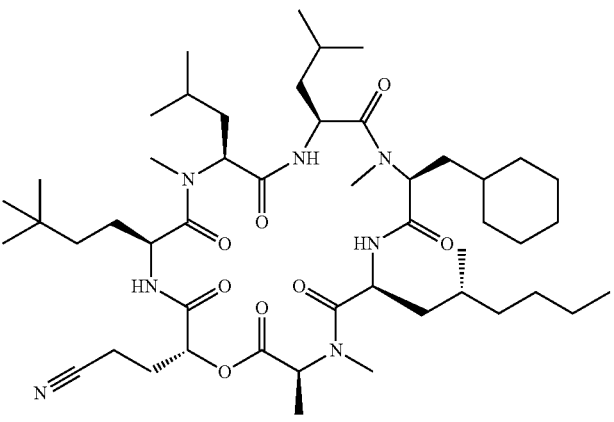 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CCC(C)(C)C)NC(=O)[C@@H](CCC#N)OC(=O)[C@H](C)N(C)C1=O] |
| C-65 | 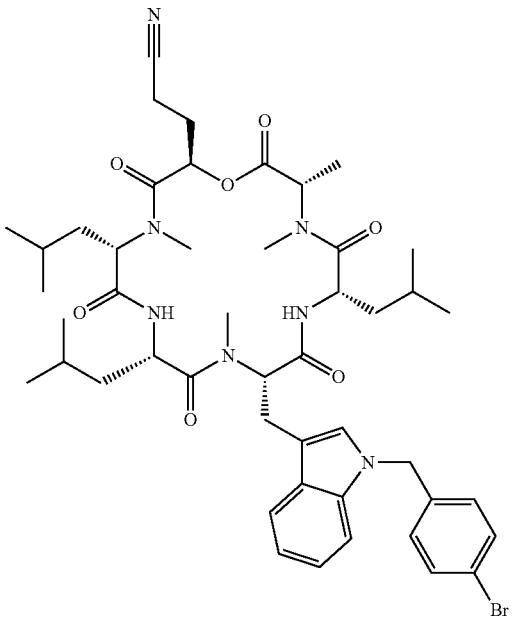 [SMILES: CC(C)C[C@@H]1NC(=O)[C@H](Cc2cn(Cc3ccc(Br)cc3)c3ccccc23)N(C)C(=O)[C@H](CC(C)C)NC(=O)[C@H](CC(C)C)N(C)C(=O)[C@@H](CCC#N)OC(=O)[C@H](C)N(C)C1=O] |

TABLE A-continued
| Ex. # | Structure |
|---|---|
| C-66 | 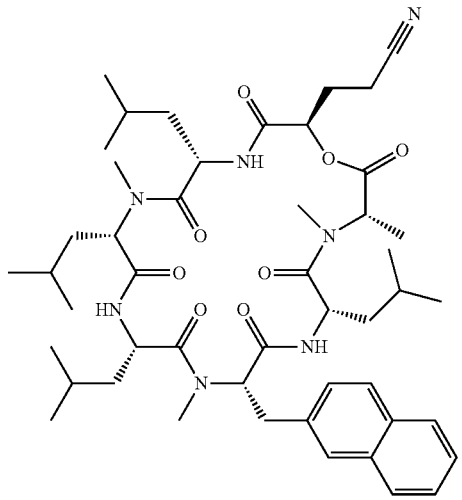 [SMILES: CC(C)C[C@@H]1NC(=O)[C@H](Cc2ccc3ccccc3c2)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O] |
| C-67 | 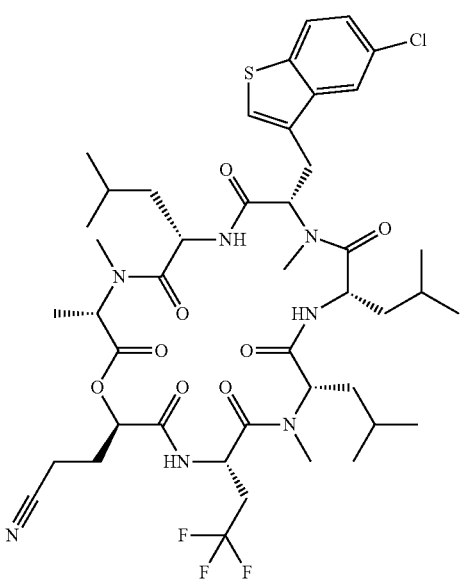 [SMILES: CC(C)C[C@@H]1NC(=O)[C@H](Cc2csc3ccc(Cl)cc23)N(C)C(=O)[C@H](CC(C)C)NC(=O)[C@H](CC(C)C)N(C)C(=O)[C@H](CC(F)(F)F)NC(=O)[C@@H](CCC#N)OC(=O)[C@H](C)N(C)C1=O] |

TABLE A-continued
| Ex. # | Structure |
|---|---|
| C-68 | 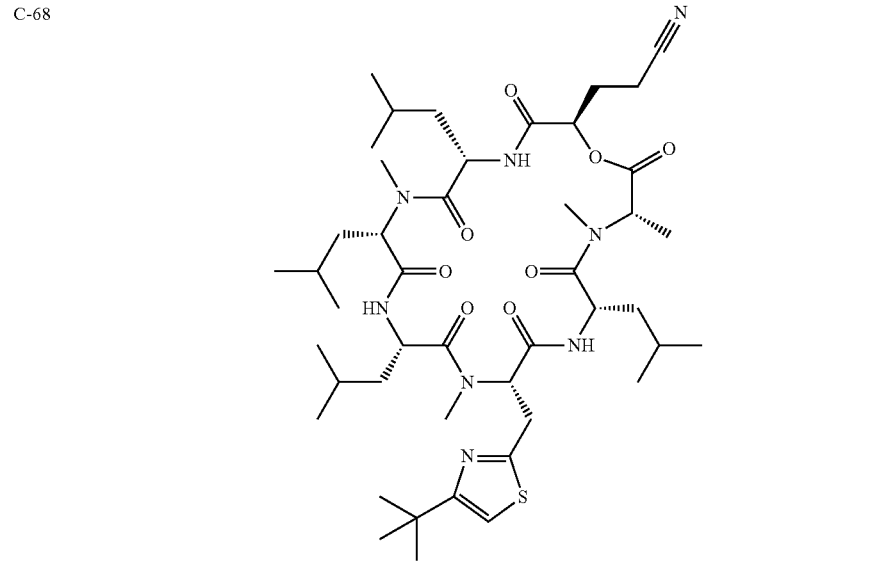 |
| C-69 | 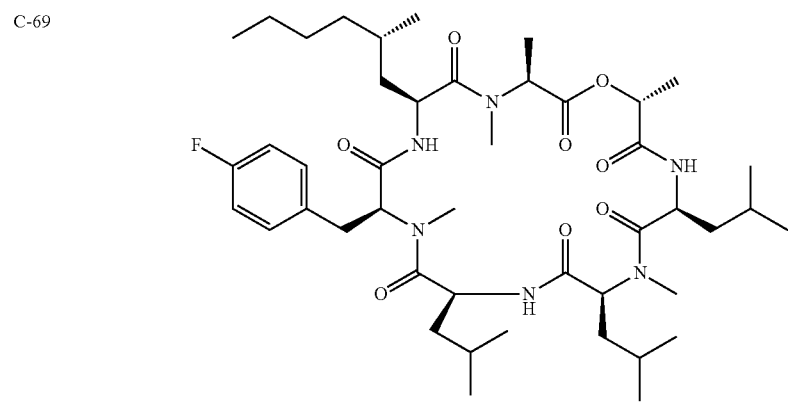 |
| C-71 | 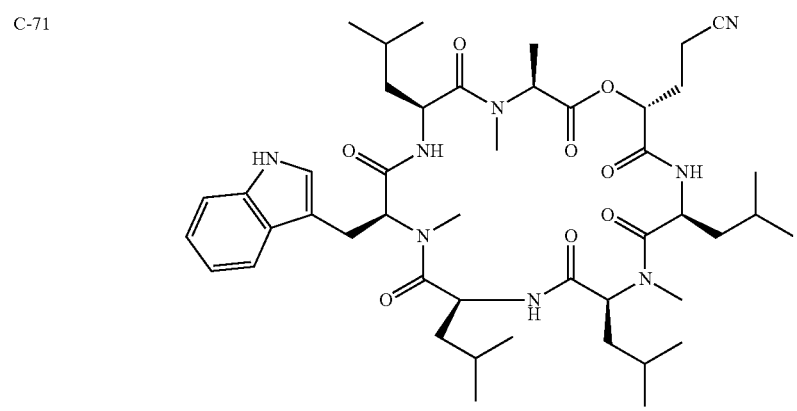 |

TABLE A-continued
| Ex. # | Structure |
|---|---|
| C-72 | 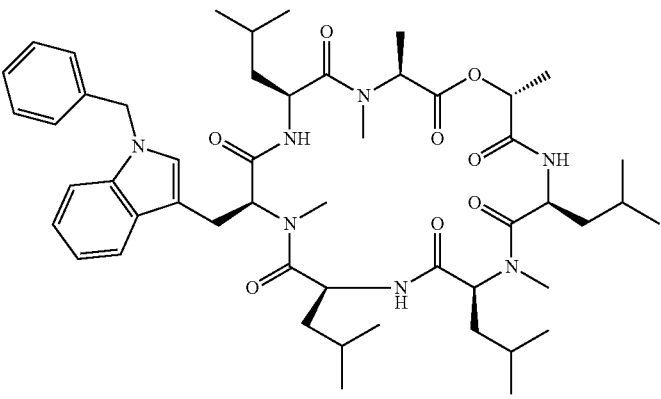 [SMILES: CC(C)C[C@@H]1NC(=O)[C@H](Cc2cn(Cc3ccccc3)c3ccccc23)N(C)C(=O)[C@H](CC(C)C)NC(=O)[C@H](CC(C)C)N(C)C(=O)[C@H](CC(C)C)NC(=O)[C@@H](C)OC(=O)[C@H](C)N(C)C1=O] |
| C-73 | 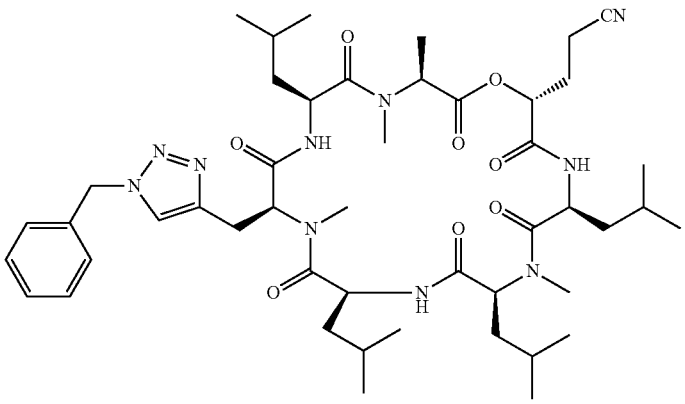 [SMILES: CC(C)C[C@@H]1NC(=O)[C@H](Cc2cn(Cc3ccccc3)nn2)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O] |
| C-74 | 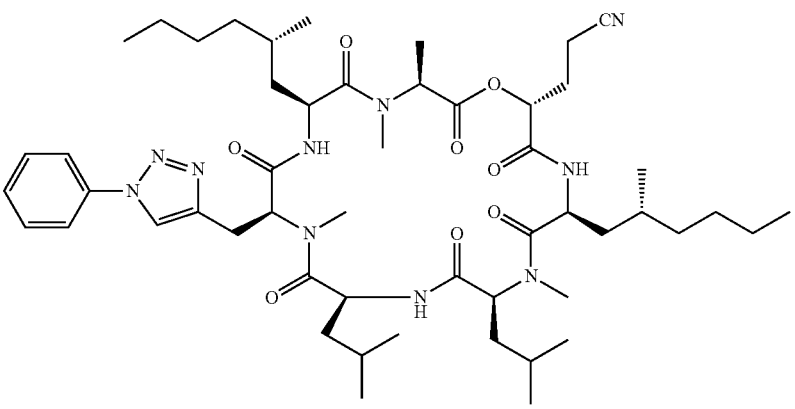 [SMILES: CCCC[C@@H](C)C[C@@H]1NC(=O)[C@@H](CCC#N)OC(=O)[C@H](C)N(C)C(=O)[C@H](C[C@@H](C)CCCC)NC(=O)[C@H](Cc2cn(-c3ccccc3)nn2)N(C)C(=O)[C@H](CC(C)C)NC(=O)[C@H](CC(C)C)N(C)C1=O] |

TABLE A-continued
| Ex. # | Structure |
|---|---|
| C-75 | 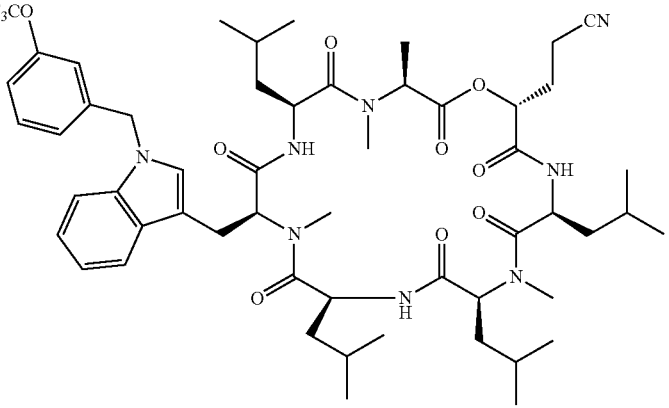 |
| C-76 | 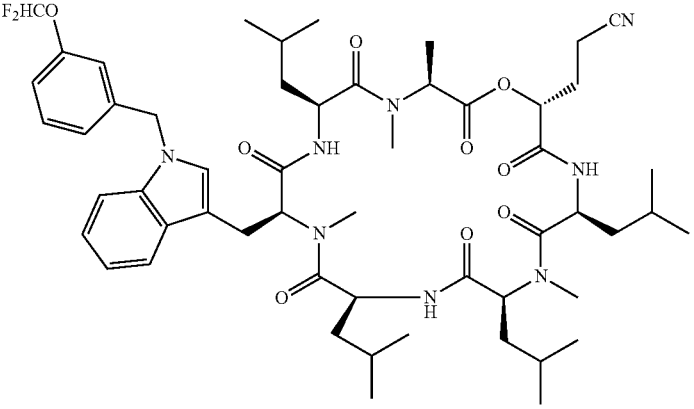 [SMILES: CC(C)C[C@@H]1NC(=O)[C@H](Cc2cn(Cc3cccc(OC(F)F)c3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O] |
| C-77 | 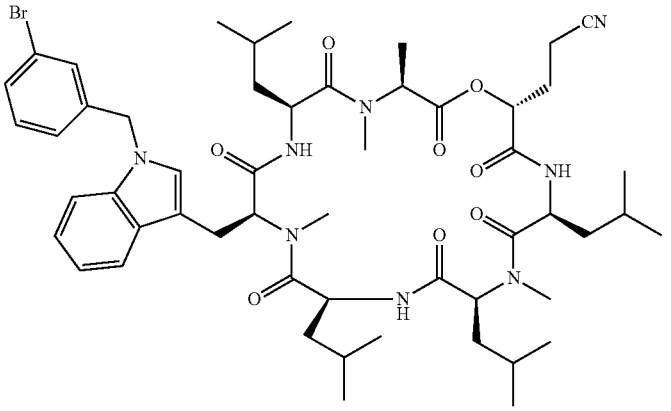 [SMILES: CC(C)C[C@@H]1NC(=O)[C@H](Cc2cn(Cc3cccc(Br)c3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O] |

TABLE A-continued

| Ex. # | Structure |
|---|---|
| C-78 | 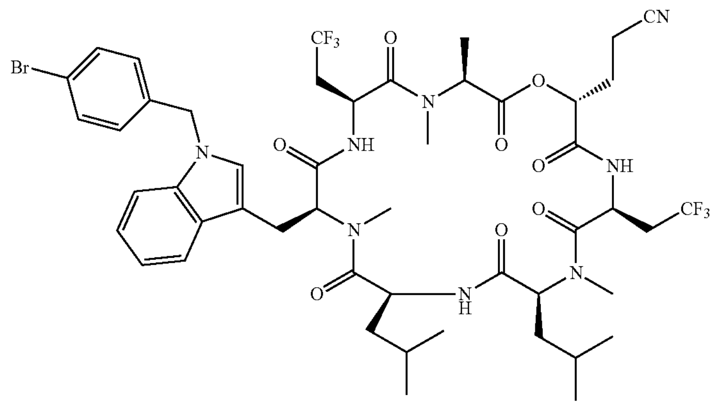 [SMILES: CC(C)C[C@@H]1NC(=O)[C@H](CC(C)C)N(C)C(=O)[C@H](CC(F)(F)F)NC(=O)[C@@H](CCC#N)OC(=O)[C@H](C)N(C)C(=O)[C@H](CC(F)(F)F)NC(=O)[C@H](Cc2cn(Cc3ccc(Br)cc3)c3ccccc23)N(C)C1=O] |
| C-79 | 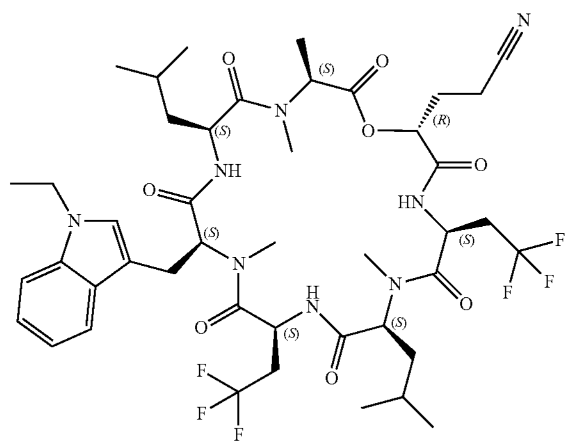 |
| C-80 | 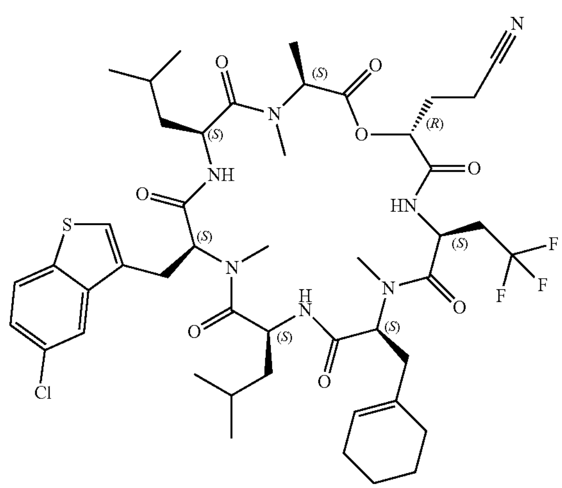 |

TABLE A-continued

| Ex. # | Structure |
|---|---|
| C-81 | 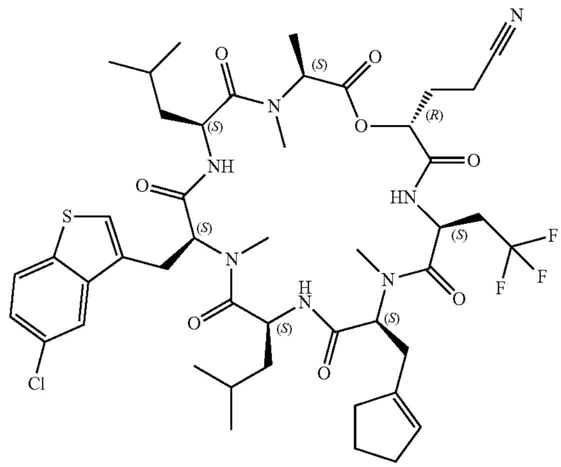 |
| C-82 | 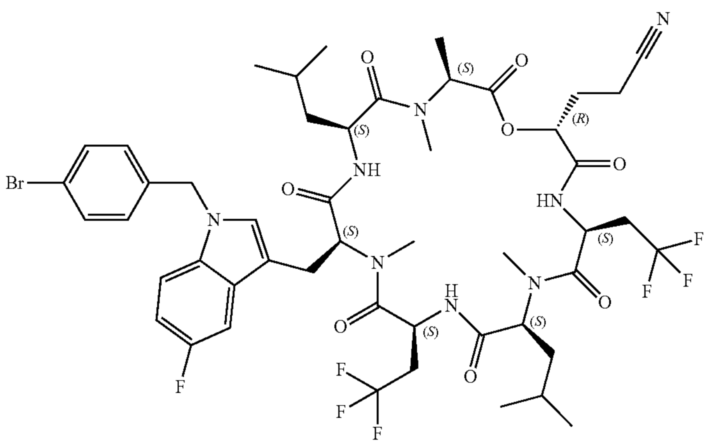 |
| C-83 | 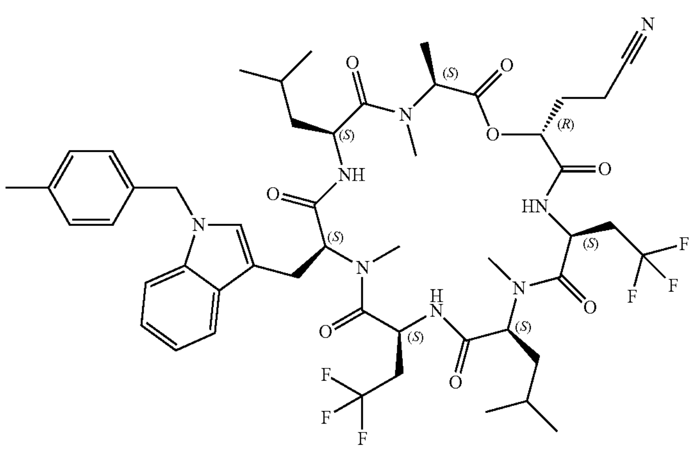 |

TABLE A-continued
| Ex. # | Structure |
|---|---|
| C-84 | 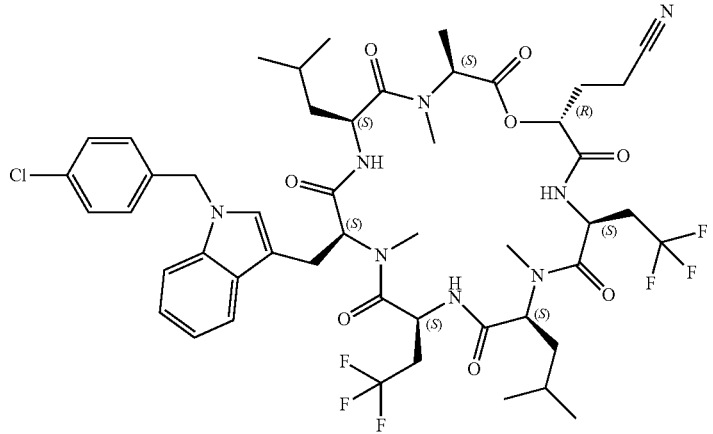 |
| C-85 | 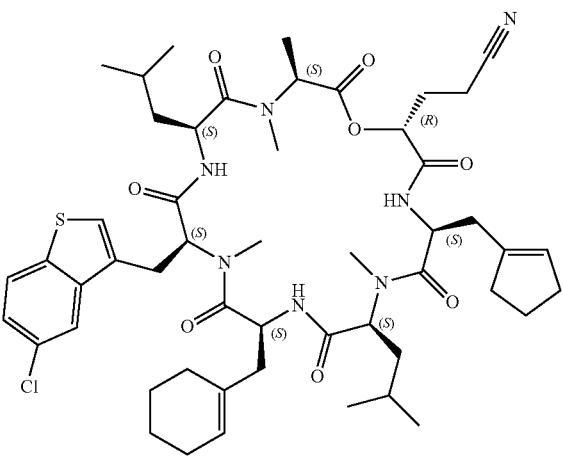 |
| C-86 | 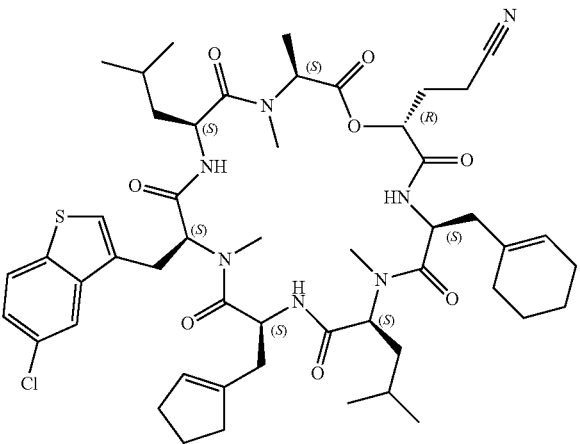 |

TABLE A-continued
| Ex. # | Structure |
|---|---|
| C-87 | 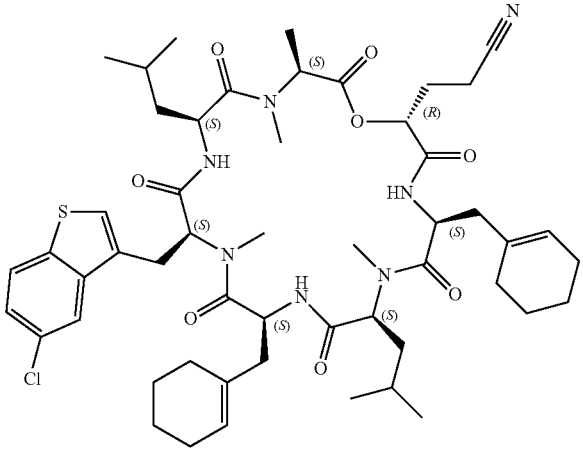 |
| C-88 | 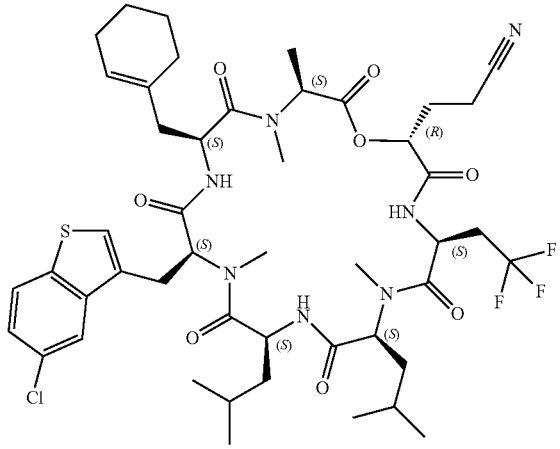 |
| C-89 | 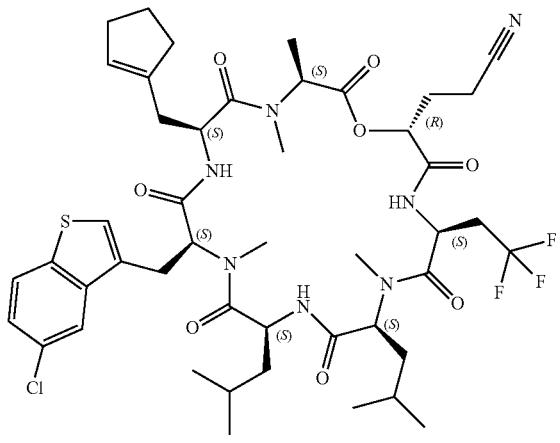 |

TABLE A-continued

| Ex. # | Structure |
|---|---|
| C-90 | 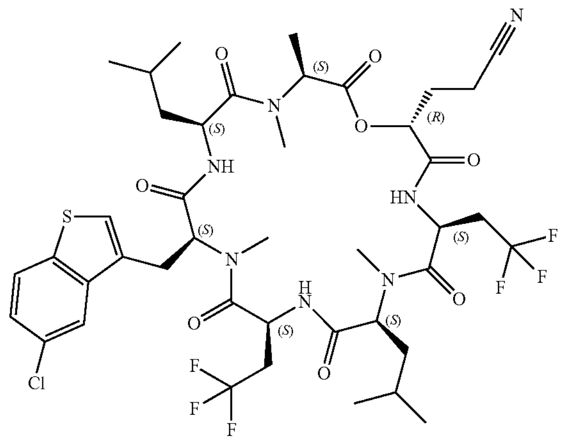 |
| C-91 | 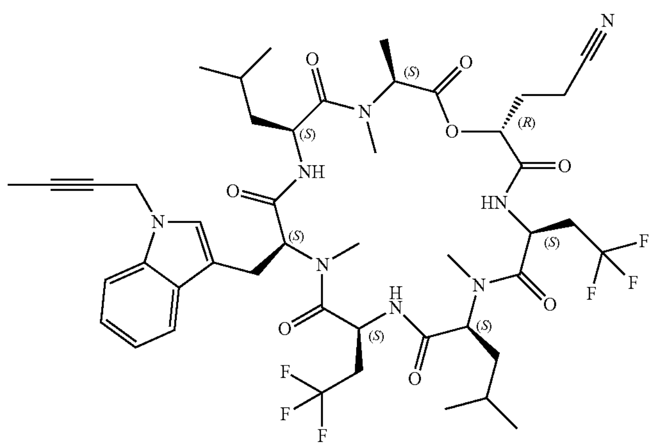 |
| C-92 | 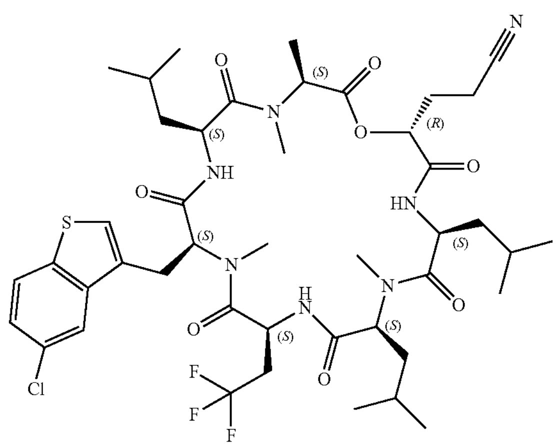 |

TABLE A-continued

| Ex. # | Structure |
|---|---|
| C-93 | 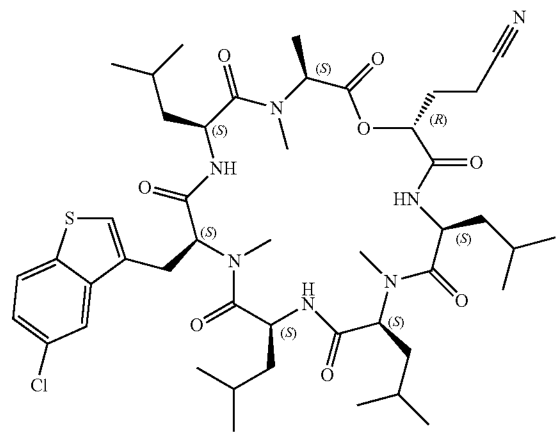 |
| C-94 | 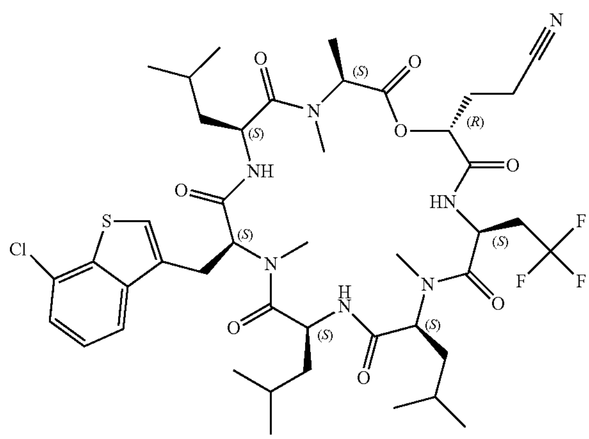 |
| C-95 | 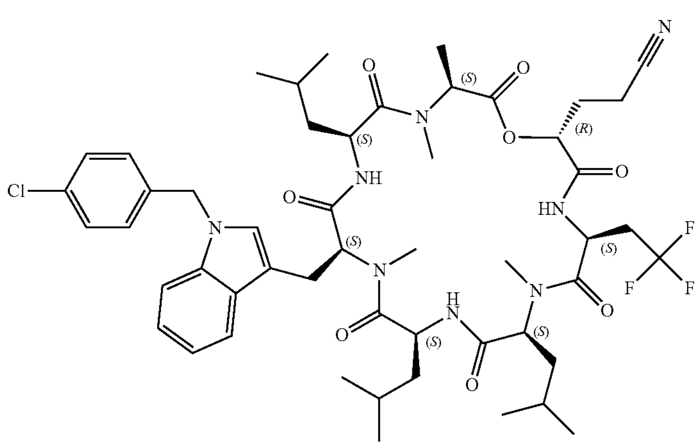 |

TABLE A-continued

| Ex. # | Structure |
|---|---|
| C-96 | 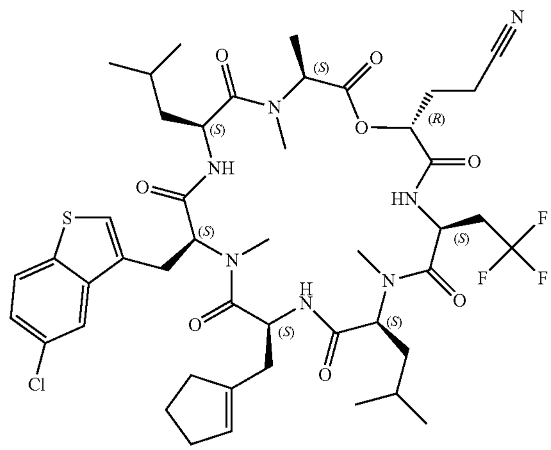 |
| C-97 | 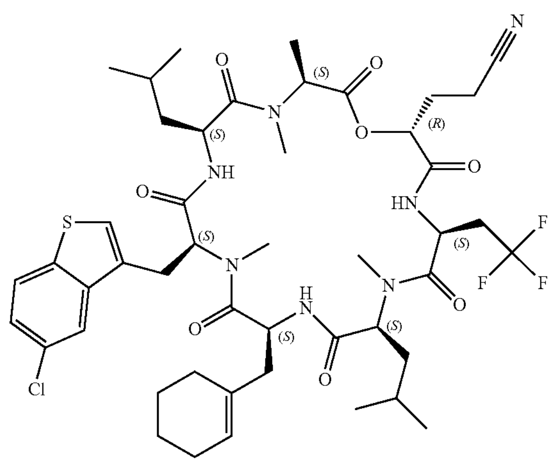 |
| C-98 | 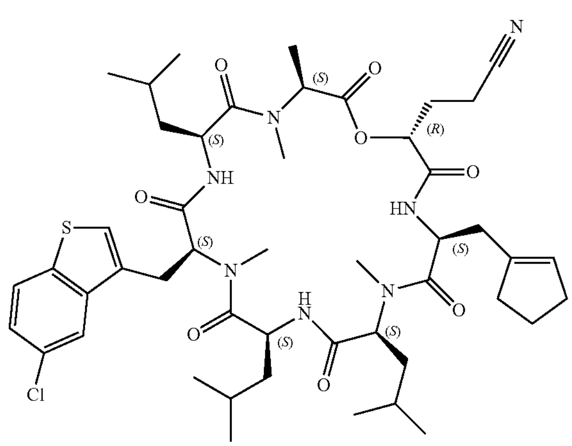 |

TABLE A-continued

| Ex. # | Structure |
|---|---|
| C-99 | (structure) |

Chemical Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-7}$alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1, 1-dimethylethyl), 3,3-dimethylpentyl, and 2-ethylhexyl. Unless otherwise indicated, an alkyl group can be an unsubstituted alkyl group or a substituted alkyl group. "Haloalkyl" indicates an alkyl group wherein one or more hydrogens of the alkyl group are replaced with a halogen atom (e.g., F, Br, Cl, or I). In some cases, all hydrogen atoms of the alkyl group are replaced with a halogen atom. "Hydroxyalkyl" indicates an alkyl group wherein one or more hydrogen atoms of the alkyl group are replaced with an —OH moiety.

As used herein, the term "alkylene" refers to a bivalent saturated aliphatic radical. The term $C_n$ means the alkylene group has "n" carbon atoms. For example, $C_{1-6}$alkylene refers to an alkylene group having a number of carbon atoms encompassing the entire range, as well as all subgroups, as previously described for "alkyl" groups.

As used herein, the term "alkenyl" is defined identically as "alkyl" except for containing at least one carbon-carbon double bond, and having two to thirty carbon atoms, for example, two to twenty carbon atoms, or two to ten carbon atoms. The term $C_n$ means the alkenyl group has "n" carbon atoms. For example, $C_4$ alkenyl refers to an alkenyl group that has 4 carbon atoms. $C_{2-7}$alkenyl refers to an alkenyl group having a number of carbon atoms encompassing the entire range (i.e., 2 to 7 carbon atoms), as well as all subgroups (e.g., 2-6, 2-5, 3-6, 2, 3, 4, 5, 6, and 7 carbon atoms). Specifically contemplated alkenyl groups include ethenyl, 1-propenyl, 2-propenyl, and butenyl. Unless otherwise indicated, an alkenyl group can be an unsubstituted alkenyl group or a substituted alkenyl group.

As used herein, the term "alkynyl" is defined identically as "alkyl" except for containing at least one carbon-carbon triple bond, and having two to thirty carbon atoms, for example, two to twenty carbon atoms, or two to ten carbon atoms. The term $C_n$ means the alkynyl group has "n" carbon atoms. For example, $C_4$ alkynyl refers to an alkynyl group that has 4 carbon atoms. $C_{2-6}$alkynyl refers to an alkynyl group having a number of carbon atoms encompassing the entire range (i.e., 2 to 6 carbon atoms), as well as all subgroups (e.g., 3-5, 2-5, 3-6, 2, 3, 4, 5, and 6 carbon atoms). Specifically contemplated alkynyl groups include ethynyl, 1-propynyl, 2-propynyl, and butynyl. Unless otherwise indicated, an alkynyl group can be an unsubstituted alkynyl group or a substituted alkynyl group.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon ring atoms. For example, $C_5$ cycloalkyl refers to a cycloalkyl group that has 5 carbon atoms in the ring. $C_{5-8}$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group.

As used herein, the term "cycloalkenyl" is defined similarly to "cycloalkyl" except for containing at least one carbon-carbon double bond in the ring, but is not aromatic. The term $C_n$ means the cycloalkenyl group has "n" carbon atoms. For example, $C_5$ cycloalkenyl refers to a cycloalkenyl group that has 5 carbon atoms in the ring. In some cases, the cycloalkenyl is a $C_{5-8}$cycloalkenyl. $C_{5-8}$ cycloalkenyl refers to cycloalkenyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkenyl groups include cyclopropenyl, cyclobutenyl, cyclopentenyl, cyclohexenyl, cycloheptenyl, and cyclooctenyl. Unless otherwise indicated, a cycloalkenyl group can be an unsubstituted cycloalkenyl group or a substituted cycloalkenyl group.

As used herein, the term "heterocycloalkyl" is defined similarly as cycloalkyl and the term "heterocycloalkenyl" is defined similarly as cycloalkenyl, except the ring contains one to three heteroatoms independently selected from oxygen, nitrogen, or sulfur. The term $C_n$ means the heterocycloalkyl or heterocycloalkenyl group has "n" ring carbon atoms—with the remainder (1-3) being heteroatoms. The heterocycloalkyl and heterocyloalkenyl rings can be 3-10 membered with 1-3 ring heteroatoms. Nonlimiting examples of heterocycloalkyl groups include piperdine, tetrahydrofuran, tetrahydropyran, dihydrofuran, morpholine, oxazepaneyl, and the like. Cycloalkyl, cycloalkenyl, heterocycloalkyl, and heterocycloalkenyl groups can be optionally substituted with, for example, one to three groups, independently selected alkyl, alkyleneOH, $C(O)NH_2$, $NH_2$, oxo (=O), aryl, haloalkyl, halo, and OH. Heterocycloalkyl and heterocycloalkenyl groups having a ring nitrogen can be further N-substituted, or the nitrogen ring atom can be present as "NH." In some cases, the ring nitrogen atom is substituted with alkyl. In some cases, the ring nitrogen is substituted with $C_{3-8}$alkynyl, $C_{0-2}$alkylene- $C_{3-8}$cycloalkyl, $C_{0-2}$alkylene- $C_{3-8}$cycloalkenyl, $C_{0-2}$alkylene- aryl, or $C_{0-2}$alkylene-heteroaryl.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, fluorenyl, and tetralinyl. Unless otherwise indicated, an aryl group can be an unsubstituted aryl group or a substituted aryl group. The aryl can be substituted with one or more (e.g., 1, 2, or 3) substituents e.g., selected from halo, haloalkyl, alkyl, OH, and alkoxy. In some cases, the substituted aryl is substituted with one or more groups selected from halo, alkyl, haloalkyl, OH, and alkoxy.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any available ring atoms. The term $C_n$ means the heteroaryl group has "n" ring carbon atoms, with the remainder of the ring atoms (1-4) being heteroatoms. The heteroaryl can be 5-10 membered with 1-4 ring heteroatoms. Nonlimiting examples of heteroaryl groups include, but are not limited to, pyridyl, pyridazinyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, thienyl, quinolinyl, isoquinolinyl, benzoxazolyl, benzimidazolyl, benzofuranyl, benzothiazolyl, triazinyl, triazolyl, purinyl, pyrazinyl, purinyl, indolinyl, phthalzinyl, indazolyl, quinolinyl, isoquinolinyl, cinnolinyl, quinazolinyl, naphthyridinyl, pyridopyridinyl, indolyl, 3H-indolyl, pteridinyl, and quinooxalinyl. Unless otherwise indicated, a heteroaryl group can be an unsubstituted heteroaryl group or a substituted heteroaryl group. The heteroaryl can be substituted with one or more (e.g., 1, 2, or 3) substituents e.g., selected from halo, haloalkyl, alkyl, OH, and alkoxy. In some cases, the substituted heteroaryl is substituted with one or more groups selected from halo, alkyl, haloalkyl, OH, and alkoxy.

As used herein, the term "alkoxy" or "alkoxyl" refers to a "—O-alkyl" group.

As used herein, the term "halo" is defined as fluoro, chloro, bromo, and iodo.

A "substituted" functional group (e.g., a substituted alkyl, alkyleneyl, cycloalkyl, aryl, or heteroaryl) is a functional group having at least one hydrogen radical that is substituted with a non-hydrogen radical (i.e., a substituent). Examples of non-hydrogen radicals (or substituents) include, but are not limited to, alkyl, cycloalkyl, alkenyl, cycloalkenyl, alkynyl, ether, aryl, heteroaryl, heterocycloalkyl, hydroxyl, oxy (or oxo), alkoxyl, ester, thioester, acyl, carboxyl, cyano, nitro, amino, sulfhydryl, and halo. When a substituted alkyl group includes more than one non-hydrogen radical, the substituents can be bound to the same carbon or two or more different carbon atoms.

Pharmaceutical Formulations and Administration

Further disclosed are the manufacture and use of pharmaceutical compositions (alternatively referred to as formulations throughout), which include one or more of the compounds provided herein. Also included are the pharmaceutical compositions themselves. Pharmaceutical compositions typically include a pharmaceutically acceptable carrier. Thus, provided herein are pharmaceutical formulations that include a compound described herein (e.g., a compound of Formula (I), a compound listed in Table A or B, or a pharmaceutically acceptable salt of the foregoing), as previously described herein, and one or more pharmaceutically acceptable carriers.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other nontoxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

Actual dosage levels of the active ingredients in the pharmaceutical compositions provided herein may be varied so as to obtain "therapeutically effective amount," which is an amount of the active ingredient effective to achieve the desired therapeutic response for a particular patient, composition, and mode of administration, without being toxic to the patient.

The concentration of a compound provided herein in a pharmaceutically acceptable mixture will vary depending on several factors, including the dosage of the compound to be administered, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Methods of Use

The compounds disclosed herein can inhibit protein secretion of a protein of interest. The compounds disclosed herein can interfere with the Sec61 protein secretion machinery of a cell. In some cases, a compound as disclosed herein inhibits secretion of one or more of TNFα, PD1, Her3, VCAM, Prl, IL7, and FLT3, or each of TNFα, PD1, Her3, VCAM, Prl, IL7, and FLT3. Protein secretion activity can be assessed in a manner as described in the Examples section below.

As used herein, the term "inhibitor" is meant to describe a compound that blocks or reduces an activity of a pharmacological target (for example, a compound that inhibits Sec61 function in the protein secretion pathway). An inhibitor can act with competitive, uncompetitive, or noncompetitive inhibition. An inhibitor can bind reversibly or irreversibly, and therefore, the term includes compounds that are suicide substrates of a protein or enzyme. An inhibitor can modify one or more sites on or near the active site of the protein, or it can cause a conformational change elsewhere on the enzyme. The term inhibitor is used more broadly herein than scientific literature so as to also encompass other classes of pharmacologically or therapeutically useful agents, such as agonists, antagonists, stimulants, co-factors, and the like.

Thus, provided herein are methods of inhibiting protein secretion in a cell. In these methods, a cell is contacted with a compound described herein, or pharmaceutical formulation thereof, in an amount effective to inhibit secretion of the protein of interest. In some embodiments, the cell is contacted in vitro. In various embodiments, the cell is contacted in vivo. In various embodiments, the contacting includes administering the compound or pharmaceutical formulation to a subject.

The biological consequences of Sec61 inhibition are numerous. For example, Sec61 inhibition has been suggested for the treatment or prevention of inflammation and/or cancer in a subject. Therefore, pharmaceutical formulations for Sec61 specific compounds, provide a means of administering a drug to a subject and treating these conditions. As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment. Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be along-term treatment, for example within the context of a maintenance therapy. As used herein, the terms "patient" and "subject" may be used interchangeably and mean animals, such as dogs, cats, cows, horses, and sheep (i.e., non-human animals) and humans. Particular patients are mammals (e.g., humans). The term patient includes males and females.

Inhibition of Sec61-mediated secretion of inflammatory proteins (e.g., TNFα) can disrupt inflammation signaling. Thus, provided herein is a method of treating inflammation in a subject by administering to the subject a therapeutically effective amount of a compound described herein. In some cases, the compounds disclosed herein, or pharmaceutically acceptable salt thereof, can be used to treat arthritis.

Further, the viability of cancer cells relies upon increased protein secretion into the ER for survival. Therefore, non-selective or partially selective inhibition of Sec61 mediated protein secretion may inhibit tumor growth. Alternatively, in the immune-oncology setting, selective secretion inhibitors of known secreted immune checkpoints proteins (e.g., PD-1, TIM-3, LAG3, etc.) can result in activation of the immune system to against various cancers.

Accordingly, also provided herein is a method of treating cancer in a subject by administering to the subject a therapeutically effective amount of a compound described herein, or a pharmaceutically acceptable salt thereof. Specifically contemplated cancers that can be treated using the compounds and compositions described herein include, but are not limited to melanoma, multiple myeloma, prostate, lung, non small cell lung carconimoa (NSCLC), squamous cell carcinoma, leukemia, acute myelogenous leukemia, chronic myelogenous leukemia, lymphoma, NPM/ALK-transformed anaplastic large cell lymphoma, renal cell carcinoma, rhabdomyosarcoma, ovarian cancer, endometrial cancer, small cell carcinoma, adenocarcinoma, gastric carcinoma, hepatocellular carcinoma, pancreatic cancer, thyroid carcinoma, anaplastic large cell lymphoma, hemangioma, head and neck cancer, bladder, and colorectal cancers. In some cases, the cancer is multiple myeloma, prostate, lung, bladder, or colorectal cancer. In some cases, the cancer is breast cancer or melanoma.

The compounds described herein are also contemplated to be used in the prevention and/or treatment of a multitude of diseases including, but not limited to, proliferative diseases, neurotoxic/degenerative diseases, ischemic conditions, autoimmune and autoinflammatory disorders, inflammation, immune-related diseases, HIV, cancers, organ graft rejection, septic shock, viral and parasitic infections, conditions associated with acidosis, macular degeneration, pulmonary conditions, muscle wasting diseases, fibrotic diseases, bone and hair growth diseases.

Examples of proliferative diseases or conditions include diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases and extrinsic lung disorders).

Inflammatory diseases include acute (e.g., bronchitis, conjunctivitis, myocarditis, pancreatitis) and chronic conditions (e.g., chronic cholecstitis, bronchiectasis, aortic valve stenosis, restenosis, psoriasis and arthritis), along with conditions associated with inflammation such as fibrosis, infection and ischemia.

Immunodeficiency disorders occur when a part of the immune system is not working properly or is not present. They can affect B lymphyctes, T lymphocytes, or phagocytes and be either inherited (e.g., IgA deficiency, severe combined immunodeficiency (SCID), thymic dysplasia and chronic granulomatous) or acquired (e.g., acquired immunodeficiency syndrome (AIDS), human immunodeficiency virus (HIV) and drug-induced immunodeficiencies). Immune-related conditions include allergic disorders such as allergies, asthma and atopic dermatitis like eczema. Other examples of such immune-related conditions include lupus, rheumatoid arthritis, scleroderma, ankylosing spondylitis, dermatomyositis, psoriasis, multiple sclerosis and inflammatory bowel disease (such as ulcerative colitis and Crohn's disease).

Tissue/organ graft rejection occurs when the immune system mistakenly attacks the cells being introduced to the host's body. Graft versus host disease (GVHD), resulting from allogenic transplantation, arises when the T cells from the donor tissue go on the offensive and attack the host's tissues. In all three circumstances, autoimmune disease, transplant rejection and GVHD, modulating the immune system by treating the subject with a compound or composition of the disclosure could be beneficial.

Also provided herein is a method of treating an autoimmune disease in a patient comprising administering a therapeutically effective amount of the compound described herein. An "autoimmune disease" as used herein is a disease or disorder arising from and directed against an individual's own tissues. Examples of autoimmune diseases include, but are not limited to, inflammatory responses such as inflammatory skin diseases including psoriasis and dermatitis (e.g., atopic dermatitis); systemic scleroderma and sclerosis; responses associated with inflammatory bowel disease (such as Crohn's disease and ulcerative colitis); respiratory distress syndrome (including adult respiratory distress syndrome (ARDS)); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g., Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; antiglomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiffman syndrome; Behcet disease; giant cell arteritis; immune complex nephritis; IgA nephropathy; IgM polyneuropathies; immune thrombocytopenic purpura (ITP) or autoimmune thrombocytopenia. Compounds provided herein may be useful for the treatment of conditions associated with inflammation, including, but not limited to COPD, psoriasis, asthma, bronchitis, emphysema, and cystic fibrosis.

Also provided herein is the use of a compound as disclosed herein for the treatment of neurodegenerative diseases. Neurodegenerative diseases and conditions includes, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Further guidance for using compounds and compositions described herein, or a pharmaceutically acceptable salt thereof, for inhibiting protein secretion can be found in the Examples section, below.

Synthesis of Compounds Disclosed Herein

Compounds as disclosed herein can be prepared via a variety of synthetic means. Guidance is provided to the synthetic organic chemist in view of the below general discussion as well as the specific procedures provided in the Examples section.

For example, an amino acid having a suitable $R^5$ substituent can be prepared in line with the below scheme:

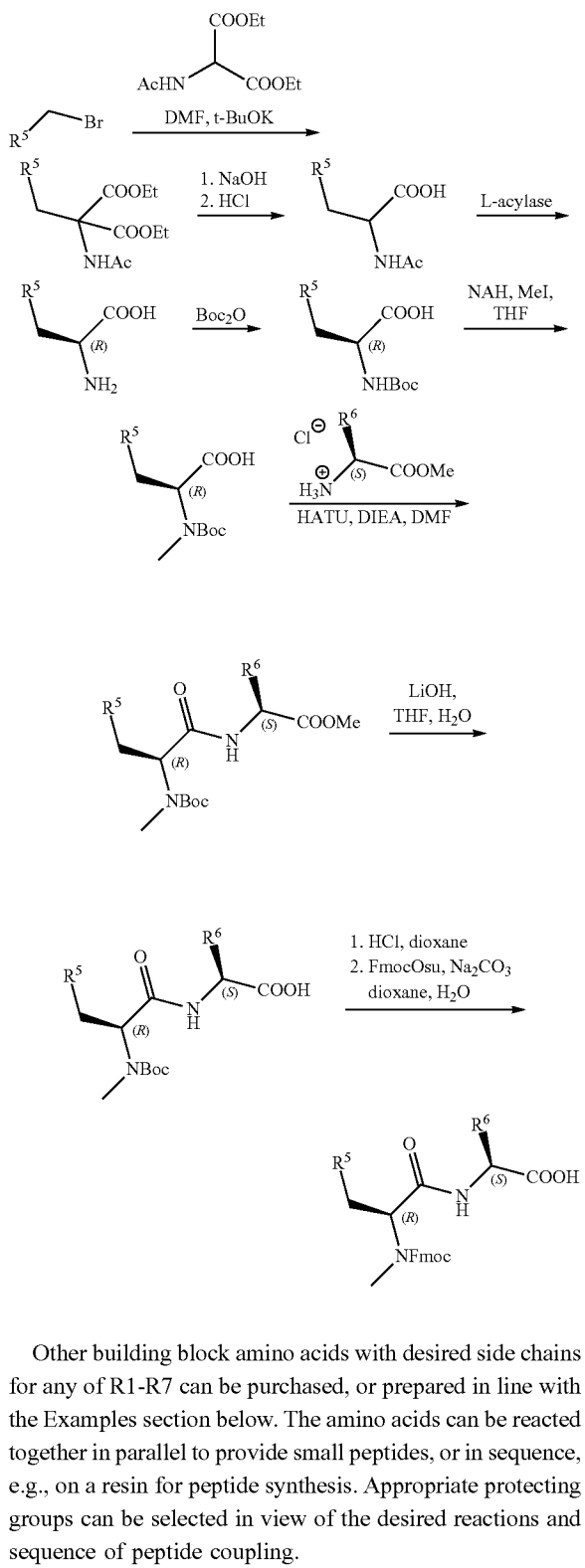

Other building block amino acids with desired side chains for any of R1-R7 can be purchased, or prepared in line with the Examples section below. The amino acids can be reacted together in parallel to provide small peptides, or in sequence, e.g., on a resin for peptide synthesis. Appropriate protecting groups can be selected in view of the desired reactions and sequence of peptide coupling.

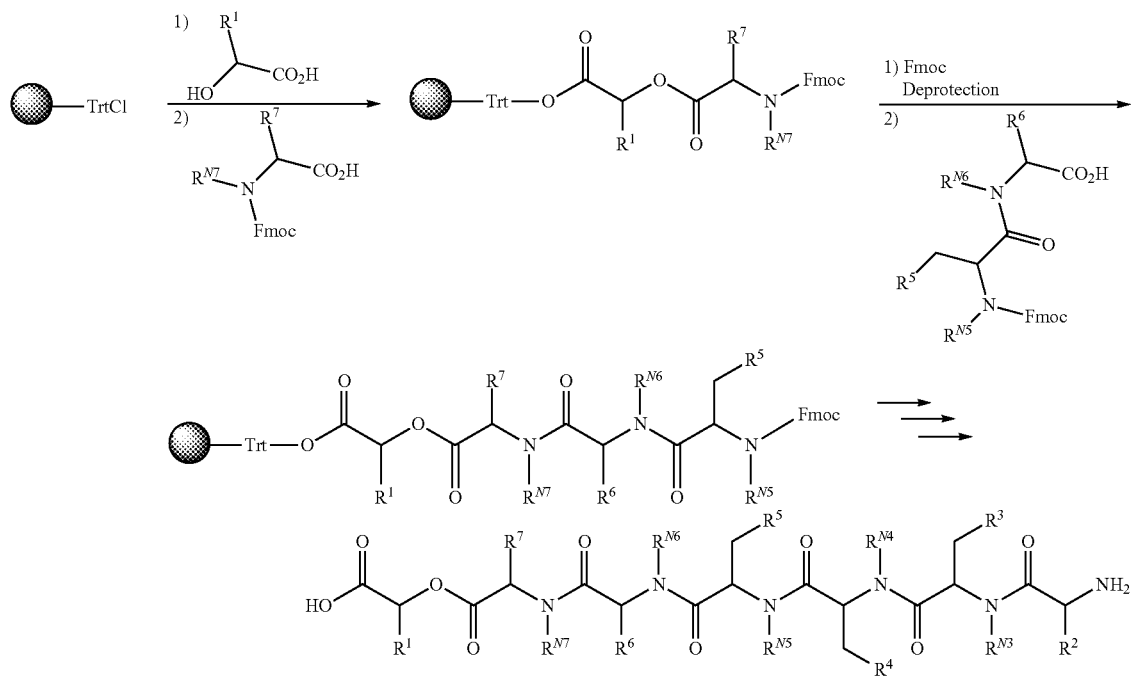
The peptide can then be macrocylized to form a compound of the disclosure.
Macrocyclization can occur via peptide bond formation conditions.
EXAMPLES
Synthesis of Compounds:
Example 1
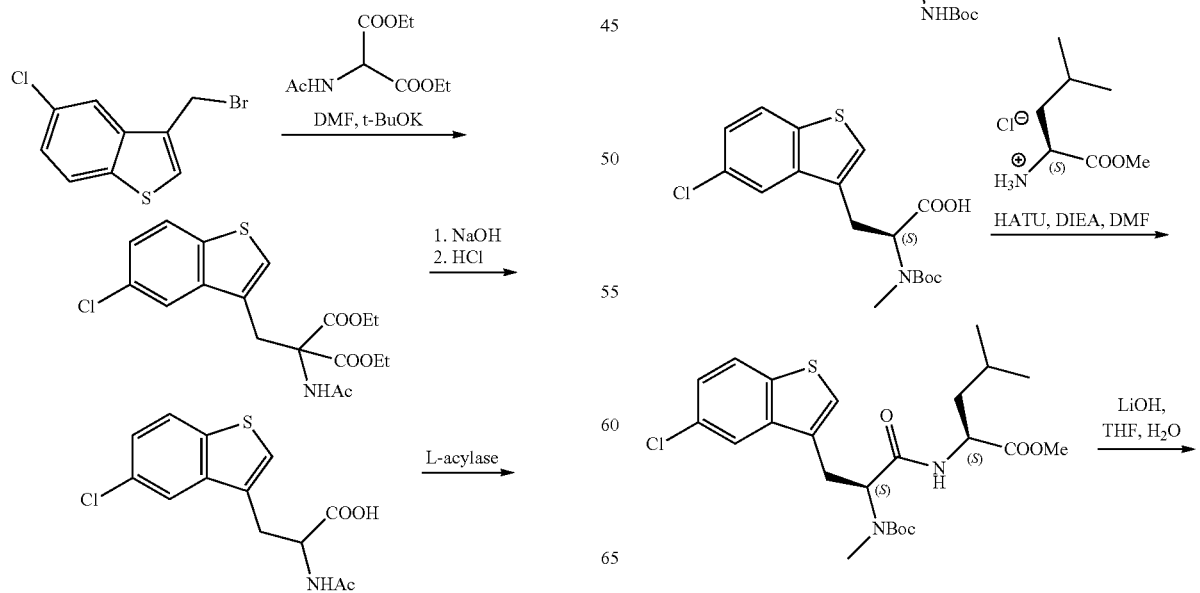

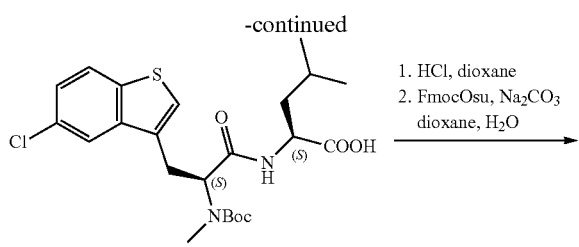

1. HCl, dioxane
2. FmocOsu, Na₂CO₃ dioxane, H₂O

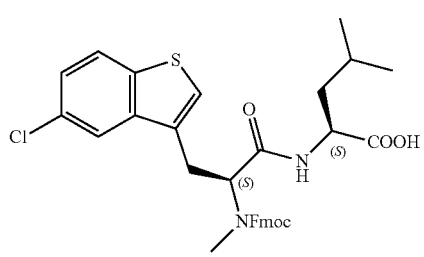

To a solution of diethyl 2-acetamidomalonate (5 g, 0.023 mol) in DMF (25 mL) was added t-BuOK (2.84 g, 0.025 mol) at 0° C. The mixture was stirred for 1 h at room temperature. 3-(Bromomethyl)-5-chlorobenzo[b]thiophene (6.0 g, 0.023 mol) was added and the reaction mixture was stirred overnight. Water (60 mL) was added and the resulting precipitate was collected by filtration and dried to give diethyl 2-acetamido-2-((5-chlorobenzo[b]thiophen-3-yl)methyl)malonate.

To a solution of diethyl 2-acetamido-2-((5-chlorobenzo[b]thiophen-3-yl)methyl)malonate (20 g, 50 mmol) in EtOH (100 mL) was added 4N aqueous NaOH (44 mL). The reaction mixture was heated under reflux for 3 h. The mixture was adjusted to pH=35 with 6N aqueous HCl and then refluxed overnight. The solvent was removed under reduced pressure to a half of the volume. The resulting precipitate was collected by filtration and dried to give compound 2-acetamido-3-(5-chlorobenzo[b]thiophen-3-yl)propanoic acid.

2-Acetamido-3-(5-chlorobenzo[b]thiophen-3-yl)propanoic acid (15 g, 51 mmol) was suspended in distilled water (450 mL) and the mixture was adjusted to pH=89 with 2N aqueous LiOH. L-Acylase (1.5 g) was added and the mixture was heated at 3540° C. for 36 h. Activated carbon (1.5 g) was added and the resulting mixture was heated at 60° C. for 1 h. The activated carbon was filtered off and the filtrate was adjusted to pH=1. The aqueous solution was washed with ethyl acetate (500 mL×2) and then concentrated to give compound (S)-2-amino-3-(5-chlorobenzo[b]thiophen-3-yl)propanoic acid.

To a solution of compound (S)-2-amino-3-(5-chlorobenzo[b]thiophen-3-yl)propanoic acid (13 g, 51 mmol) in water (80 mL) was added a solution of Boc₂O (16.5 g, 76 mmol) in acetone (30 mL). The mixture was adjusted to pH=13 with NaOH and then stirred overnight. The mixture was adjusted to pH=12 with HCl and extracted with ethyl acetate (200 mL). The organic layer was dried over anhydrous sodium sulfate and concentrated. The residue was washed with hexane to give compound (S)-2-((tert-butoxycarbonyl)amino)-3-(5-chlorobenzo[b]thiophen-3-yl)propanoic acid.

To (S)-2-((tert-butoxycarbonyl)amino)-3-(5-chlorobenzo[b]thiophen-3-yl)propanoic acid (2.20 g, 6.18 mmol) in THF (6.5 mL) at 0° C. was added sodium hydride (544 mg, 13.6 mmol, 60% dispersion in mineral oil) portion-wise while maintain temperature <10° C. After 30 min, methyl iodide (1.93 g, 13.6 mmol) was added. The mixture was stirred for 6 h then cooled to 0° C. and added an additional portion of NaH (544 mg, 13.6 mmol) was added followed by MeI (1.93 g, 13.6 mmol). The reaction mixture was warmed to room temperature and stirred for a further 16 h. The reaction was diluted with water (ca. 50 mL), and the basic aqueous was extracted with diethyl ether (2×25 mL). The aqueous was brought to ~pH=3 with citric acid (10%, aqueous) and extracted with EtOAc (3×50 mL). The combined organics were dried over MgSO₄ and concentrated in vacuo to provide (S)-2-((tert-butoxycarbonyl)(methyl)amino)-3-(5-chlorobenzo[b]thiophen-3-yl)propanoic acid.

A flask was charged with (S)-2-((tert-butoxycarbonyl)(methyl)amino)-3-(5-chlorobenzo[b]thiophen-3-yl)propanoic acid (2.00 g, 5.60 mmol), Leu-OMe (1.18 g, 6.50 mmol) and HATU (2.58 g, 6.78 mmol). The mixture was dissolved in DMF (15 mL) under argon and cooled to 0° C., then DIPEA (2.95 mL, 17.0 mmol) was added and the mixture was stirred for 2 h, diluted with EtOAc (20 mL) and washed with water (4×10 mL). The combined aqueous phases were extracted again with EtOAc (10 mL) and the combined organics were washed with brine (10 mL) and dried (Na₂SO₄), filtered and concentrated to afford a yellow solid (3.03 g), that was subjected to the next reaction without further purification.

To a solution of crude dipeptide ester (3.00 g, 6.21 mmol) in THF (10 mL) and water (4 mL) at 0° C. was added LiOH (7.5 mL of a 1 M solution in water, 7.45 mmol) and the reaction mixture was stirred for 1 h, quenched dropwise with 1 M HCl and extracted with EtOAc (3×10 mL). The combined organics were washed with brine (5 mL), dried (MgSO₄), filtered and concentrated to afford ((S)-2-((tert-butoxycarbonyl)(methyl)amino)-3-(5-chlorobenzo[b]thiophen-3-yl)propanoyl)-L-leucine.

To a solution of ((S)-2-((tert-butoxycarbonyl)(methyl)amino)-3-(5-chlorobenzo[b]thiophen-3-yl)propanoyl)-L-leucine (2.83 g, 5.86 mmol) in dioxane (5 mL) was added HCl (5 mL of a 4 M solution in dioxane). After stirring for 1 h LCMS indicated only 50% deprotection had occurred and another aliquot of HCl (5 mL, of a 4 M solution in dioxane) was added. After a further 2 h the deprotection was complete and the reaction mixture was concentrated and co-evaporated with toluene 3 times then once with dioxane. The residue was dissolved in dioxane (37 mL) and water (37 mL) and Na₂CO₃ (1.43 g, 13.48 mmol) was added followed by FmocOSu (2.57 g, 7.62 mmol) and the reaction mixture was stirred overnight. The dioxane was removed by under reduced pressure and the reaction mixture was quenched to pH ~3 with citric acid (10% aqueous) and extracted with EtOAc (3×10 mL). The combined organic fractions were washed with water (5 mL), then brine (5 mL), then dried Na₂SO₄, filtered and concentrated under reduced pressure. The crude material was subjected to flash chromatography (silica, gradient elution, 0 to 5%, v/v, MeOH/DCM) affording ((S)-2-((((9H-fluoren-9-yl)methoxy)carbonyl)(methyl)amino)-3-(5-chlorobenzo[b]thiophen-3-yl)propanoyl)-L-leucine. LCMS (ESI): [M−H]⁻, 603.2.

The following compounds were prepared from respective aryl/heteroaryl bromides or commercially available/known amino acids using the procedures from Example 1:

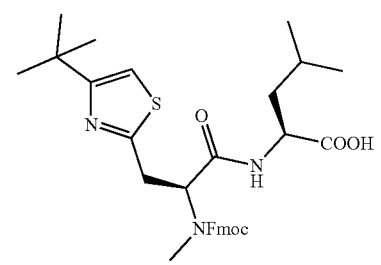
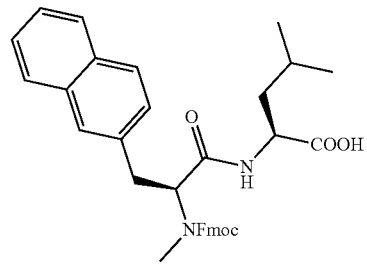
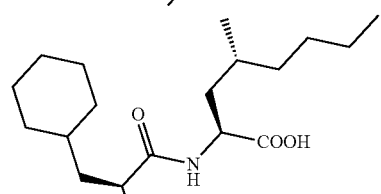
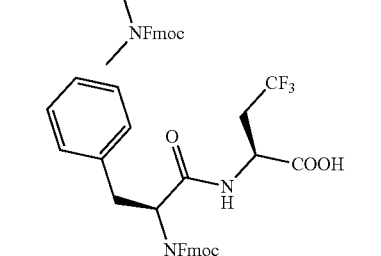
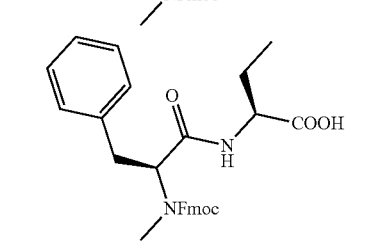
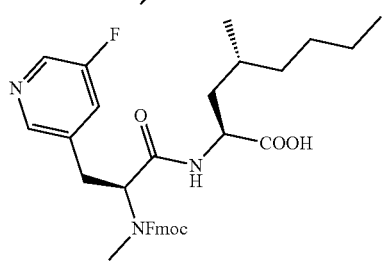
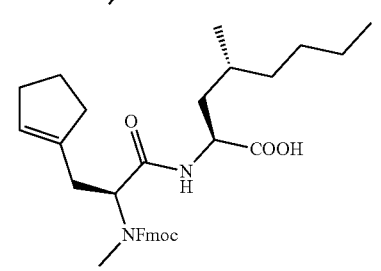
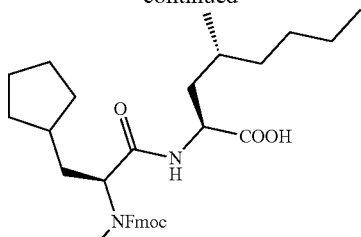
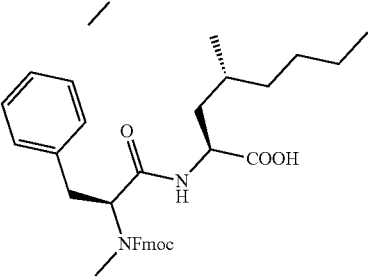
Example 2
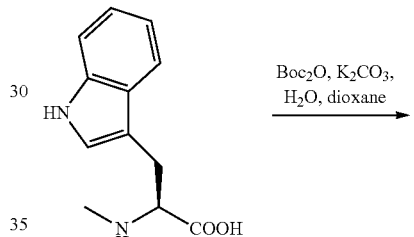
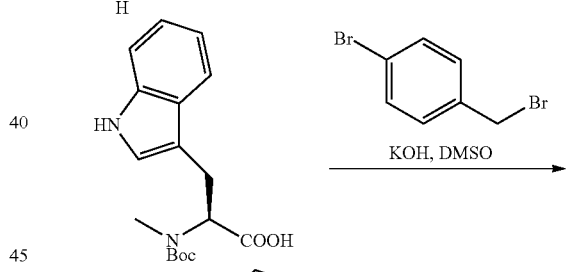
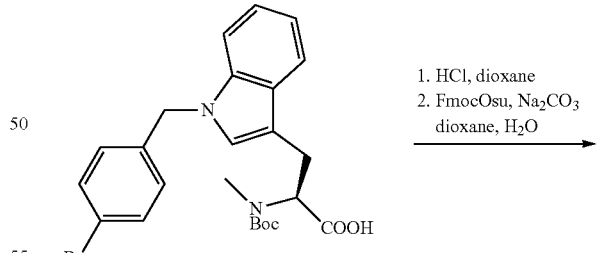
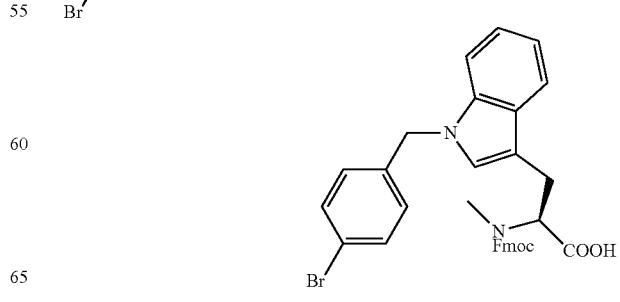

To a suspension of abrine (2.00 g, 9.16 mmol) in water (17 mL) and dioxane (17 mL) was added K$_2$CO$_3$ (3.60 g, 26.12 mmol) and then, dropwise, a solution of Boc$_2$O (2.40 g, 11.00 mmol) in dioxane (10 mL). The mixture was stirred at room temperature for 12 h then concentrated to remove dioxane. The reaction mixture was washed with hexane (2×20 mL) then acidified to pH 3 with citric acid (10% aqueous solution) and extracted with EtOAc (2×20 mL). The combined organic phase was washed with water (10 mL), brine (10 mL), then dried with (Na$_2$SO$_4$), filtered and concentrated under reduced pressure to afford N$^\alpha$-(tert-butoxycarbonyl)-N$^\alpha$-methyl-L-tryptophan.

To a stirred solution of freshly powdered potassium hydroxide (4.32 g, 75.38 mmol) in dimethyl sulfoxide (anhydrous, 37 mL) at room temperature under argon was added N$^\alpha$-(tert-butoxycarbonyl)-N$^\alpha$-methyl-L-tryptophan (6.00 g, 18.85 mmol) and the mixture was stirred for 1 h. 4-Bromobenzyl bromide (5.18 g, 20.73 mmol) was then added and the mixture was stirred under argon for 16 h. The solution was diluted with water (10 mL), washed with diethyl ether (2×5 mL), and then acidified with citric acid (10% aqueous solution) until pH 3. The mixture was extracted with EtOAc (3×20 mL) and the combined fractions were washed with water (10 mL) then brine (10 mL) then dried (Na$_2$SO$_4$) and concentrated under reduced pressure to afford 1-(4-bromobenzyl)-N$^\alpha$-(tert-butoxycarbonyl)-N$^\alpha$-methyl-L-tryptophan.

To a solution of 1-(4-bromobenzyl)-N$^\alpha$-(tert-butoxycarbonyl)-N$^\alpha$-methyl-L-tryptophan (2.50 g, 5.13 mmol) in dioxane (1 mL) was added HCl (5 mL of a 4 M solution in dioxane). The mixture was stirred for 2 h at room temperature then concentrated under reduced pressure, co-evaporated with dioxane several times then redissolved in a mixture of dioxane (12 mL) and water (12 mL). To this mixture was added Na$_2$CO$_3$ (1.25 g, 11.80 mmol) followed by FmocOSu (2.25 g, 6.67 mmol) and the mixture was stirred vigorously overnight. The mixture was concentrated to remove dioxane, acidified with citric acid (10 mL of a 10% aqueous solution) and extracted with EtOAc (3×10 mL) the combined organic fractions were washed with water, then brine, dried (MgSO$_4$), filtered, and concentrated under reduced pressure. The residue was subjected to Flash chromatography (silica, gradient elution, 0-5% MeOH/DCM) to afford N$^\alpha$-(((9H-fluoren-9-yl)methoxy)carbonyl)-1-(4-bromobenzyl)-N$^\alpha$-methyl-L-tryptophan (2.83 g, 91%). $^1$H-NMR (400 MHz; CDCl$_3$, rotamers): δ 7.80-7.73 (m, 3H), 7.67-7.60 (m, 1H), 7.54 (t, J=6.8 Hz, 1H), 7.49-7.39 (m, 5H), 7.36-7.31 (m, 2H), 7.22-7.12 (m, 4H), 6.97 (s, 1H), 6.91-6.86 (m, 2H), 5.18-5.15 (m, 2H), 5.05-5.01 (m, 0.5H), 4.87-4.82 (m, 0.5), 4.51-4.35 (m, 2H), 4.26-4.17 (m, 1.5H), 4.05-4.01 (m, 0.5), 3.56-3.50 (m, 1H), 3.41-3.34 (m, 1H), 2.86 (s, 3H). LCMS (ESI): [2M−H]$^-$, 1218.2.

The following compounds were prepared from respective bromides using the procedures from Example 2:

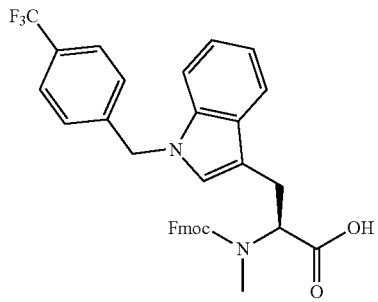

LCMS (ESI): [2M−H]$^-$, 1197.6.

N$^\alpha$-(((9H-fluoren-9-yl)methoxy)carbonyl)-1-(3-methoxybenzyl)-N$^\alpha$-methyl-L-tryptophan

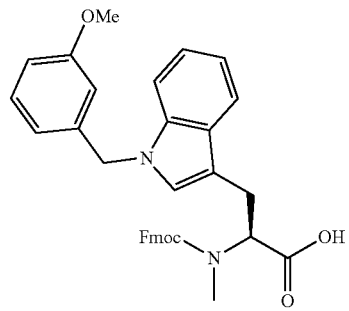

LCMS (ESI): [2M−H]$^-$, 1120.0.

N$^\alpha$-(((9H-fluoren-9-yl)methoxy)carbonyl)-1-((6-fluoropyridin-3-yl)methyl)-N$^\alpha$-methyl-L-tryptophan

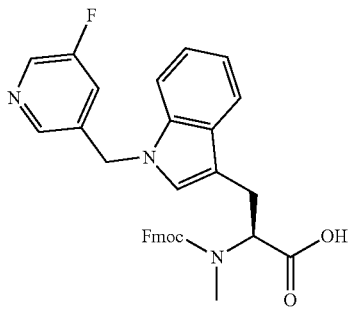

LCMS (ESI): [2M−H]$^-$, 1097.8.

N$^\alpha$-(((9H-fluoren-9-yl)methoxy)carbonyl)-1-((6-fluoropyridin-3-yl)methyl)-N$^\alpha$-methyl-L-tryptophan

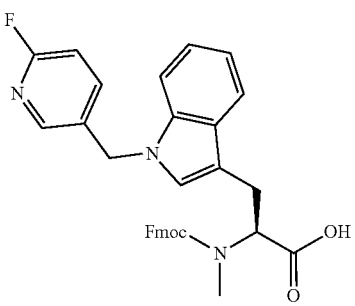

LCMS (ESI): [2M−H]$^-$, 1097.2.

97

N^α-(((9H-fluoren-9-yl)methoxy)carbonyl)-N^α-methyl-1-((6-methylpyridin-2-yl)methyl)-L-tryptophan

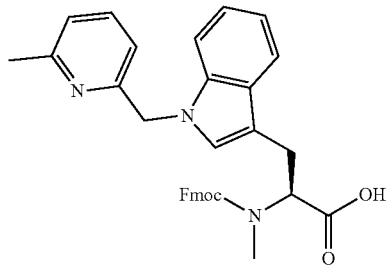

LCMS (ESI): [2M−H]⁻, 1089.3.

N^α-(((9H-fluoren-9-yl)methoxy)carbonyl)-1-(3,4-difluorobenzyl)-N^α-methyl-L-tryptophan

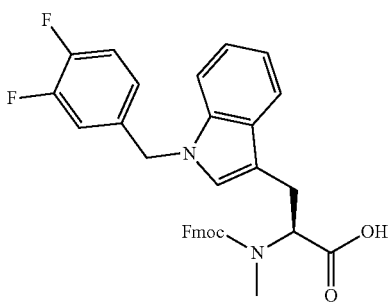

LCMS (ESI): [2M−H]⁻, 1131.3.

S)-2-((((9H-fluoren-9-yl)methoxy)carbonyl)(methyl)amino)-3-(benzo[b]thiophen-3-yl)propanoic Acid

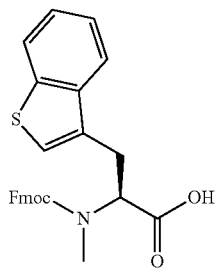

LCMS (ESI): [2M−H]⁻, 913.1.

98

N^α-(((9H-fluoren-9-yl)methoxy)carbonyl)-1-(4-methoxybenzyl)-N^α-methyl-L-tryptophan

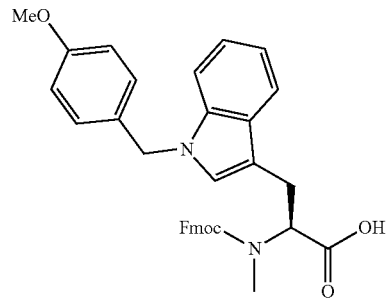

LCMS (ESI): [2M−H]⁻, 1119.7.

N^α-(((9H-fluoren-9-yl)methoxy)carbonyl)-1-(2-methoxybenzyl)-N^α-methyl-L-tryptophan

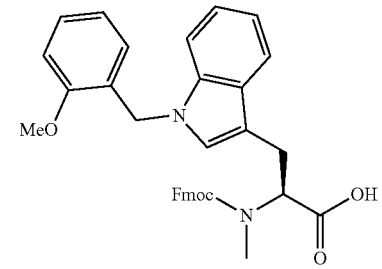

LCMS (ESI): [2M−H]⁻, 1120.0.

N^α-(((9H-fluoren-9-yl)methoxy)carbonyl)-N^α-methyl-1-((3-methylisoxazol-5-yl)methyl)-L-tryptophan

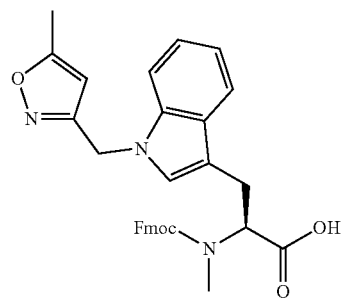

LCMS (ESI): [2M−H]⁻, 1070.0.

N^α-(((9H-fluoren-9-yl)methoxy)carbonyl)-1-(4-fluorobenzyl)-N^α-methyl-L-tryptophan

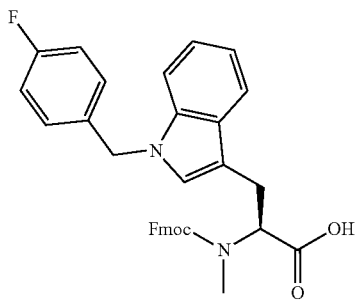

LCMS (ESI): [2M−H]⁻, 1095.9.

Example 3

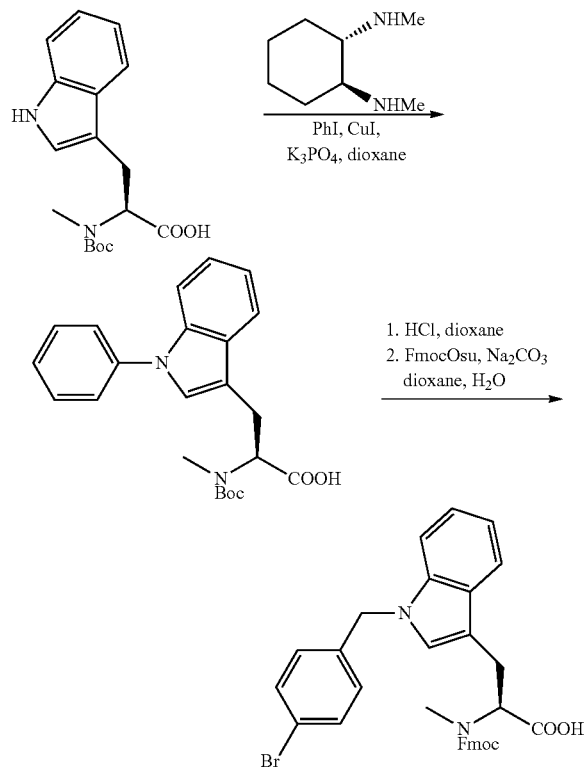

A 20 mL scintillation vial was charged with N^α-(tert-butoxycarbonyl)-N^α-methyl-L-tryptophan (500 mg, 1.57 mmol), iodobenzene (352 mg, 1.72 mmol), copper iodide (30 mg, 0.16 mmol), trans-N,N-Dimethylcyclohexane-1,2-diamine (50 uL, 0.31 mmol), potassium phosphate (733 mg, 3.45 mmol) and dioxane (5 mL). The mixture was degassed by bubbling nitrogen through the mixture for 10 mins then the reaction mixture was heated to 110° C. for 16 h. The reaction mixture was concentrated and treated with citric acid (2 mL of a 10% aqueous solution) and extracted with EtOAc (3×5 mL) and the combined organics were washed with brine (5 mL) filtered, concentrated under reduced pressure and subjected to chromatography (silica, 0 to 10%, v/v MeOH/DCM) to afford N^α-(tert-butoxycarbonyl)-N^α-methyl-1-phenyl-L-tryptophan. ¹H-NMR (400 MHz; CDCl₃, rotamers): δ 7.70-7.68 (m, 1H), 7.58 (d, J=7.8 Hz, 1H), 7.55-7.48 (m, 4H), 7.40-7.34 (m, 1H), 7.26-7.16 (m, 3H), 4.98-4.85 (m, 1H), 3.58-3.39 (m, 1.5H), 3.29-3.22 (m, 0.5H), 2.89 (s, 1.5H), 2.78 (s, 1.5H), 1.45 (s, 4.5H), 1.22 (s, 4.5H). LCMS (ESI): [2M−H]⁻, 789.6.

N^α-(((9H-fluoren-9-yl)methoxy)carbonyl)-N^α-methyl-1-phenyl-L-tryptophan was obtained from N^α-(tert-butoxycarbonyl)-N^α-methyl-1-phenyl-L-tryptophan using the methods of Example 2.

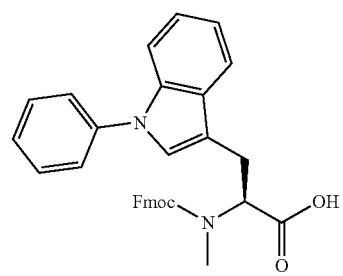

LCMS (ESI): [2M−H]⁻, 1033.5.

Example 4

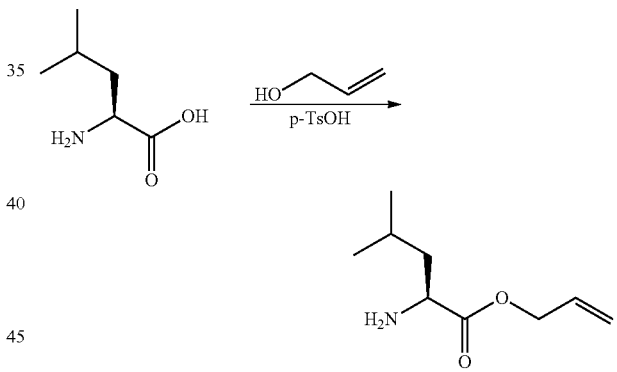

To a solution of L-leucine (2.50 g, 19.06 mmol) in allyl alcohol (25 mL) was added p-TsOH monohydrate and the mixture was stirred at 90° C. (oil bath) for 16 h. The next day the solution was concentrated under reduced pressure to a solid residue, which was dissolved in DCM (25 mL) and washed with NaHCO₃ (10 mL of a saturated aqueous solution). The aqueous fraction was extracted with DCM (2×10 mL) and the combined organics were dried (Na₂SO₄), and filtered directly into HCl (4 equiv, 19 mL of a 4 M solution in dioxane). The solution was concentrated under reduced pressure then precipitated with Et₂O. The mixture was briefly sonicated, left to settle for a few mins then the solution was decanted from the solid using a pipette. The product was dried in vacuo overnight affording the HCl salt of allyl L-leucinate. ¹H-NMR (400 MHz; DMSO-d₆): δ 8.61 (t, J=0.4 Hz, 3H), 5.94 (ddt, J=17.2, 10.6, 5.4 Hz, 1H), 5.39 (dq, J=17.3, 1.6 Hz, 1H), 5.29 (dq, J=10.5, 1.3 Hz, 1H), 4.70 (d, J=5.4 Hz, 2H), 4.01-3.98 (m, 1H), 1.81-1.73 (m, 1H), 1.67 (t, J=7.3 Hz, 2H), 0.91 (dd, J=6.5, 1.2 Hz, 6H).

Allyl(S)-2-amino-4,4,4-trifluorobutanoate Hydrochloride

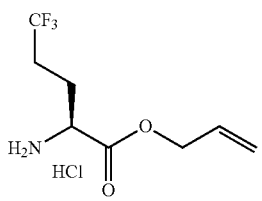

prepared using the procedure described above; ¹H-NMR (400 MHz; CDCl₃): δ 6.00-5.89 (m, 1H), 5.39-5.29 (m, 2H), 4.66 (dd, J=5.9, 1.1 Hz, 1H), 4.20-3.97 (m, 1H), 3.51 (dd, J=8.6, 5.1 Hz, 1H), 2.38-2.21 (m, 1H), 2.05 (ddt, J=13.7, 10.8, 5.4 Hz, 1H), 1.83-1.74 (m, 1H), 1.57-1.53 (m, 1H).

Example 5

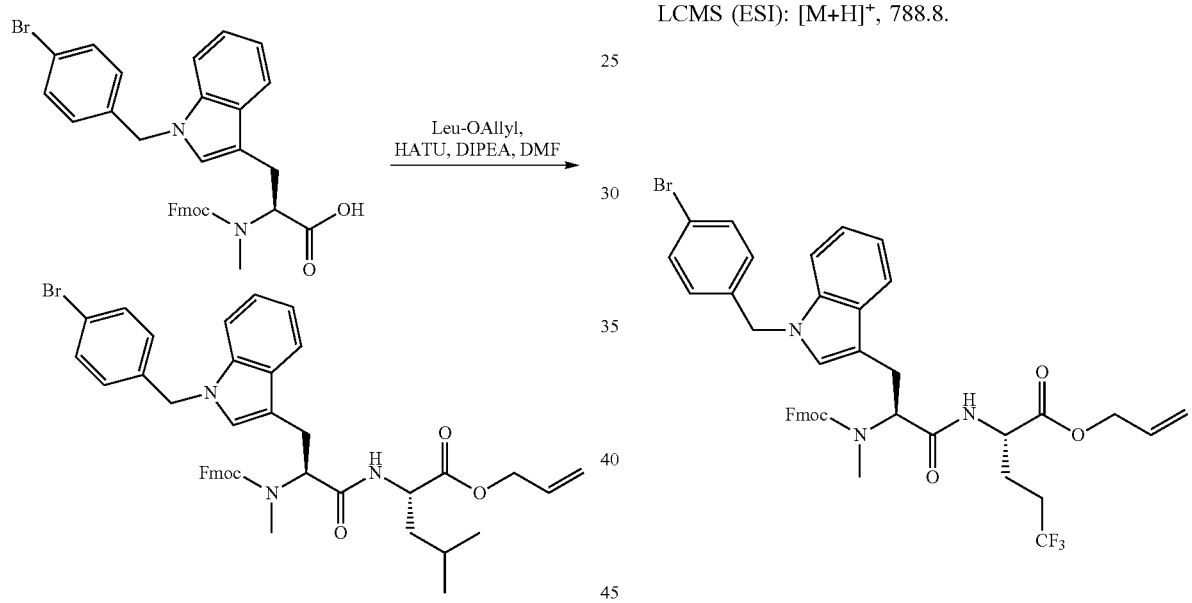

A 100 mL round bottom flask was charged with N^α-(((9H-fluoren-9-yl)methoxy)carbonyl)-1-(4-bromobenzyl)-N^α-methyl-L-tryptophan (6.50 g, 10.66 mmol), Leu-OAllyl (2.54 g, 12.26 mmol) and HATU (4.87 g, 12.87 mmol). The mixture was dissolved in DMF (50 mL) under argon and cooled to 0° C., then DIPEA (5.57 mL, 32.00 mmol) was added and the mixture was stirred for 2 h, diluted with EtOAc (50 mL) and washed with water (4×20 mL). The combined aqueous phases were extracted again with EtOAc (10 mL) and the combined organics were washed with brine (10 mL) and dried (Na₂SO₄), filtered and concentrated to afford allyl N^α-(((9H-fluoren-9-yl)methoxy)carbonyl)-1-(4-bromobenzyl)-N^α-methyl-L-tryptophyl-L-leucinate.
¹H-NMR (400 MHz; CDCl₃, rotamers): δ 7.80-7.79 (m, 2H), 7.73-7.63 (m, 2H), 7.55-7.34 (m, 5H), 7.18 (d, J=0.1 Hz, 3H), 7.00 (s, 1H), 6.90-6.88 (m, 2H), 6.45-6.43 (m, 1H), 6.04-5.86 (m, 1H), 5.38-5.07 (m, 4H), 4.68-4.60 (m, 3H), 4.44-4.35 (m, 1H), 4.23-4.14 (m, 1H), 3.93-3.80 (m, 1H), 3.52-3.43 (m, 1H), 3.28-3.22 (m, 1H), 2.94-2.90 (m, 3H), 1.69-1.51 (m, 4H), 0.99-0.88 (m, 6H). LCMS (ESI): [M+H]⁺, 764.6.

The following compounds were prepared using the procedure as described in Example 5.

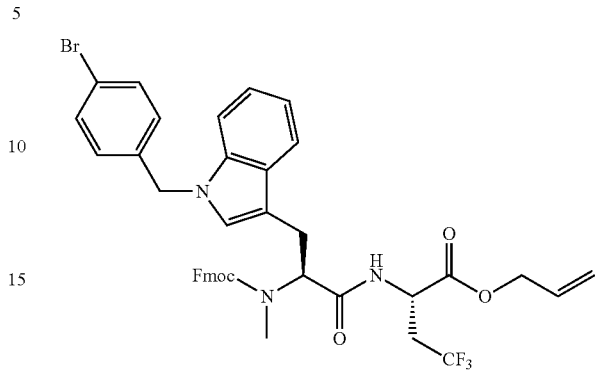

LCMS (ESI): [M+H]⁺, 788.8.

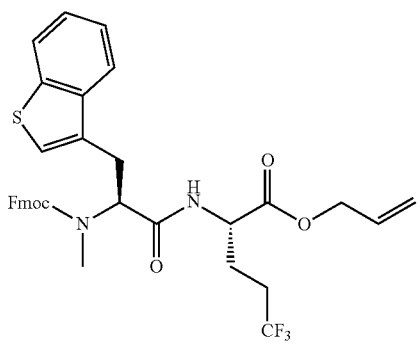

LCMS (ESI): [M+H]⁺, 803.25.

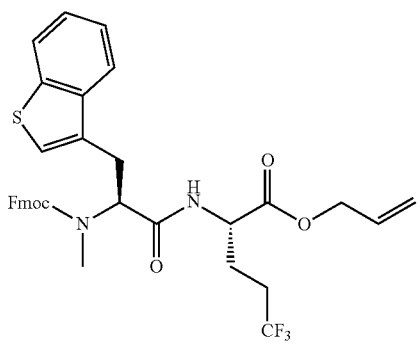

LCMS (ESI): [M+H]⁺, 652.6.

103 tert-Butyl N^α-(((9H-fluoren-9-yl)methoxy)carbonyl)-1-(4-bromobenzyl)-N^α-methyl-L-tryptophyl-L-leucinate

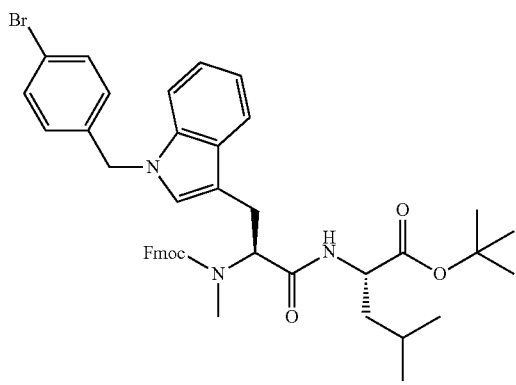

¹H-NMR (400 MHz; CDCl₃, rotamers): δ 7.80-7.77 (m, 1H), 7.73-7.65 (m, 2H), 7.54-7.51 (m, 1H), 7.45-7.38 (m, 3H), 7.35-7.33 (m, 2H), 7.24-7.14 (m, 3H), 7.02-6.99 (m, 1H), 6.95-6.84 (m, 2H), 6.43-6.40 (m, 1H), 5.21-5.08 (m, 2H), 4.51-4.47 (m, 1H), 4.37-4.33 (m, 0.5H), 4.22-4.18 (m, 0.5H), 3.87-3.78 (m, 1H), 3.57-3.42 (m, 1H), 3.28-3.22 (m, 1H), 2.93 (s, 3H), 1.64-1.61 (m, 1H), 1.45 (s, 9H), 1.00-0.86 (m, 6H). LCMS (ESI): [M+H]⁺, 780.2.

tert-Butyl N^α-(((9H-fluoren-9-yl)methoxy)carbonyl)-N^α-methyl-1-(4-(trifluoromethyl)benzyl)-L-tryptophyl-L-leucinate

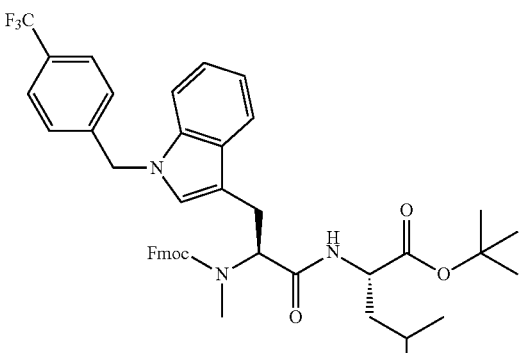

LCMS (ESI): [M+H]⁺, 770.2.

104 tert-Butyl N^α-(((9H-fluoren-9-yl)methoxy)carbonyl)-1-(3-methoxybenzyl)-N^α-methyl-L-tryptophyl-L-leucinate

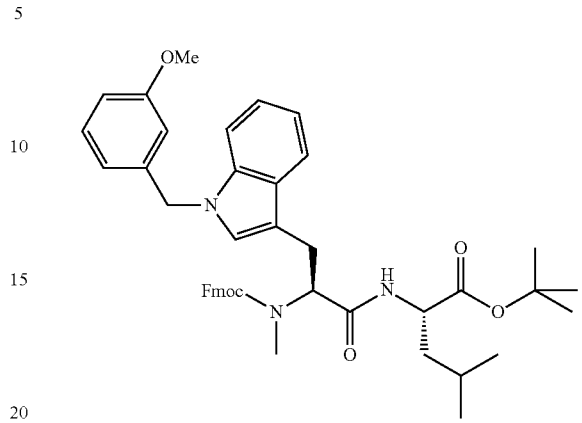

LCMS (ESI): [M+H]⁺, 732.4.

tert-butyl N^α-(((9H-fluoren-9-yl)methoxy)carbonyl)-1-((6-fluoropyridin-3-yl)methyl)-N^α-methyl-L-tryptophyl-L-leucinate

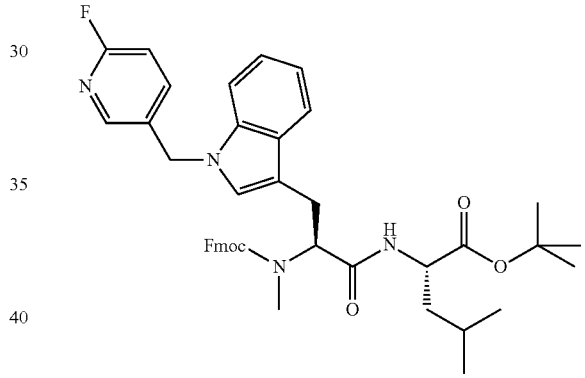

LCMS (ESI): [M+H]⁺, 719.3.

tert-Butyl N^α-(((9H-fluoren-9-yl)methoxy)carbonyl)-1-((5-fluoropyridin-3-yl)methyl)-N^α-methyl-L-tryptophyl-L-leucinate

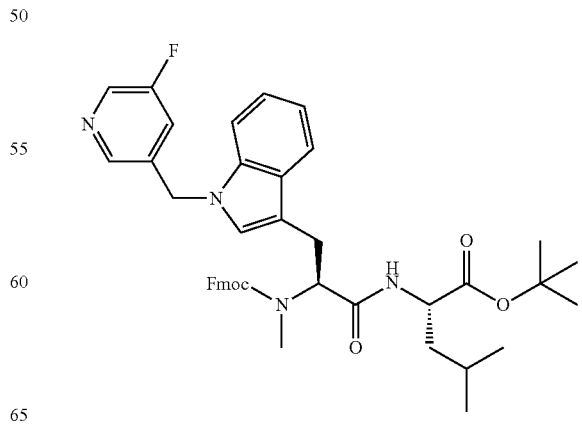

LCMS (ESI): [M+H]⁺, 719.2.

105
tert-Butyl N<sup>α</sup>-(((9H-fluoren-9-yl)methoxy)carbonyl)-N<sup>α</sup>-methyl-1-((6-methylpyridin-2-yl)methyl)-L-tryptophyl-L-leucinate
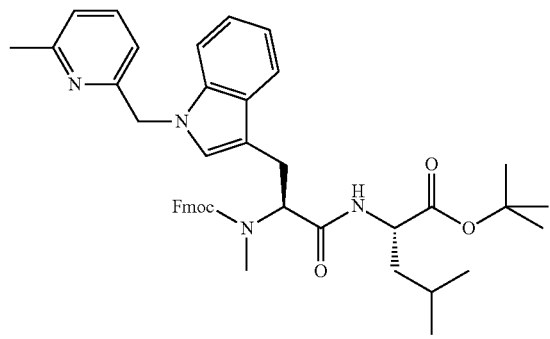
LCMS (ESI): [M+H]<sup>+</sup>, 716.2.
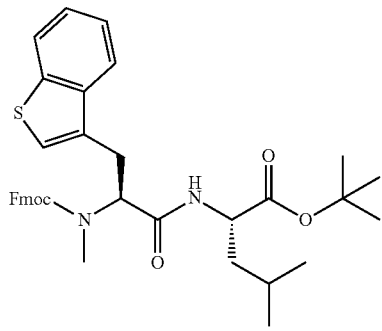
LCMS (ESI): [M+H]<sup>+</sup>, 627.1.
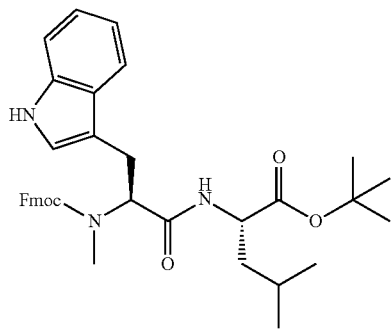
LCMS (ESI): [M−H]<sup>−</sup>, 608.5.
106
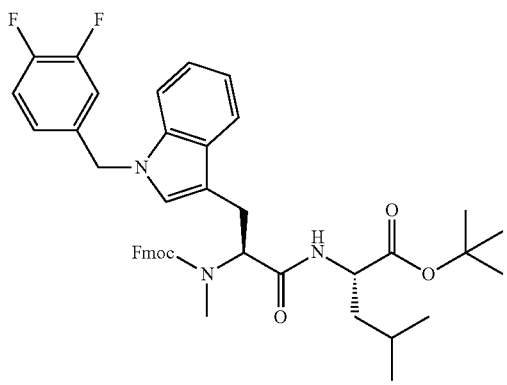
LCMS (ESI): [M+H]<sup>+</sup>, 736.0.
LCMS (ESI): [M+Na]<sup>+</sup>, 593.9.
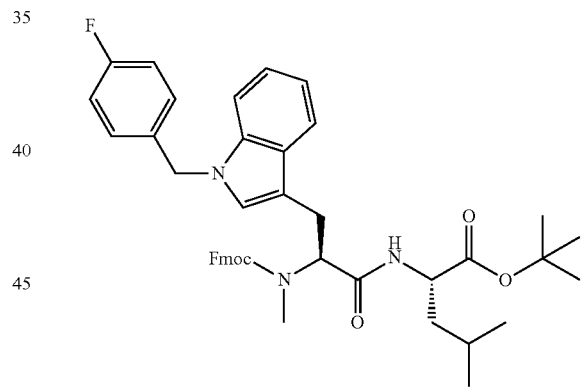
LCMS (ESI): [M+Na]<sup>+</sup>, 739.4.
Example 6
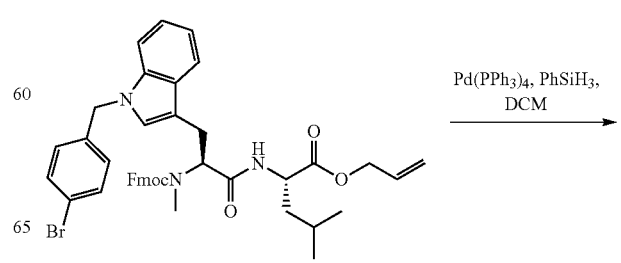

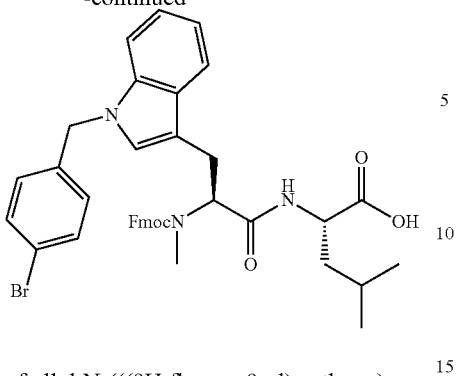

To a solution of allyl N-(((9H-fluoren-9-yl)methoxy)carbonyl)-1-(4-bromobenzyl)-N^α-methyl-L-tryptophyl-L-leucinate (8.29 g, 10.87 mmol) in DCM (75 mL) at room temperature under argon was added PhSiH₃ (2.62 mL, 21.74 mmol) followed by Pd(PPh₃)₄ (628 mg, 0.54 mmol). The mixture was stirred for 2 h then concentrated onto silica and chromatographed (silica, 0-5%, MeOH/DCM) to afford N^α-(((9H-fluoren-9-yl)methoxy)carbonyl)-1-(4-bromobenzyl)-N^α-methyl-L-tryptophyl-L-leucine. ¹H-NMR (400 MHz; CDCl₃, rotamers): δ 7.79 (dd, J=7.2, 0.6 Hz, 2H), 7.66 (d, J=1.4 Hz, 3H), 7.50-7.39 (m, 6H), 7.18-7.15 (m, 3H), 6.97 (d, J=0.3 Hz, 1H), 6.87-6.85 (m, 2H), 5.18-5.06 (m, 3H), 4.60-4.54 (m, 1H), 4.39-4.31 (m, 1H), 4.21-4.14 (m, 1H), 3.54-3.40 (m, 2H), 3.25-3.18 (m, 1H), 2.94-2.84 (m, 3H), 1.72-1.50 (m, 3H), 0.94-0.87 (m, 6H). LCMS (ESI): [M+H]⁺, 722.6.

The following compounds were prepared using the procedure of Example 6:

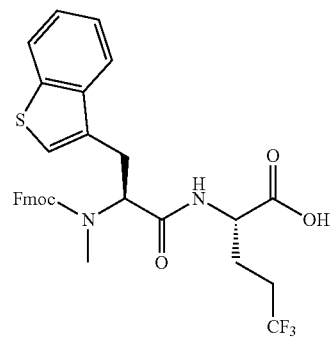

LCMS (ESI): [2M+H]⁺, 1222.5

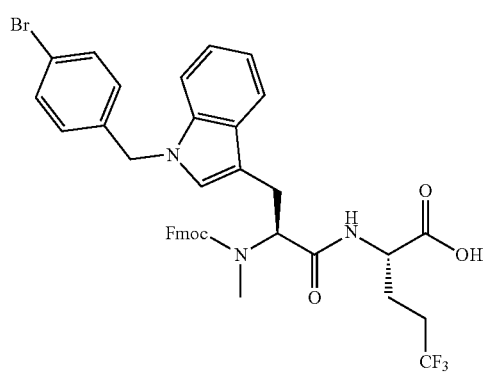

LCMS (ESI): [2M−H]⁻, 1526.3.

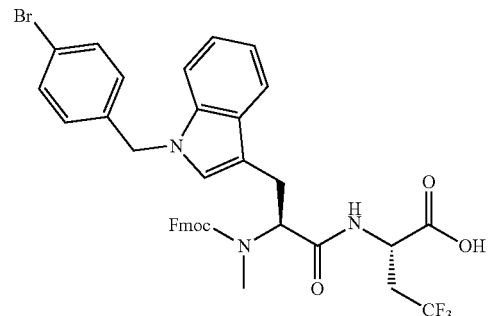

LCMS (ESI): [2M−H]⁻, 1496.6.

Example 7

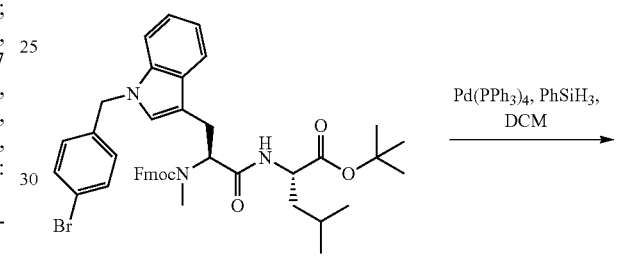

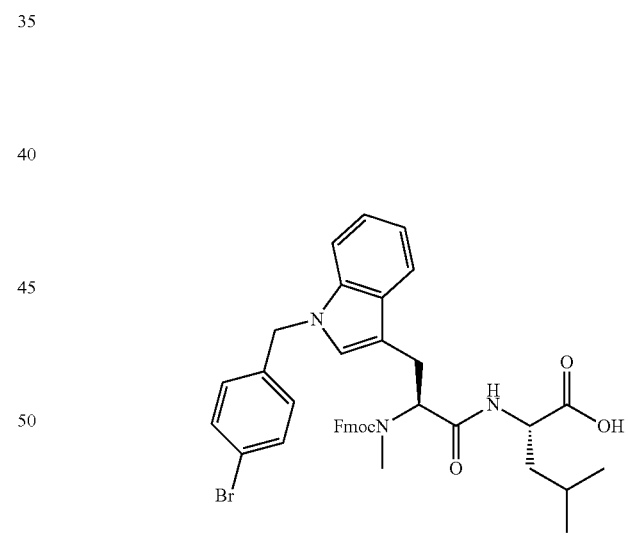

To a solution of tert-butyl N^α-(((9H-fluoren-9-yl)methoxy)carbonyl)-1-(4-bromobenzyl)-N^α-methyl-L-tryptophyl-L-leucinate (98 mg, 0.13 mmol) in DCM (1 mL) was added TFA (1 mL). The mixture was stirred at room temperature for 5 h then concentrated under reduced pressure. The crude residue was chromatographed (silica, 0-5%, MeOH/DCM) to afford N^α-(((9H-fluoren-9-yl)methoxy)carbonyl)-1-(4-bromobenzyl)-N^α-methyl-L-tryptophyl-L-leucine.

The following compounds were prepared using the procedure of Example 7:

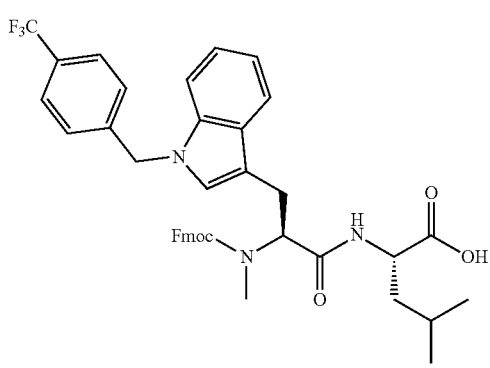
LCMS (ESI): [2M−H]⁻, 1424.8.
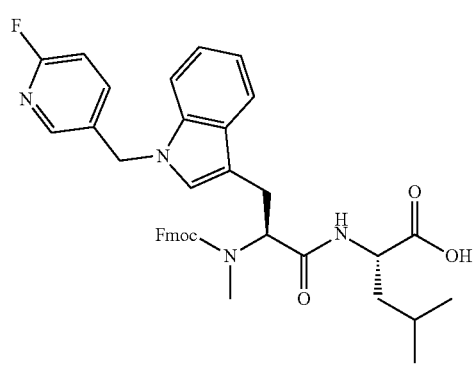
Subjected to the next step without further analysis.
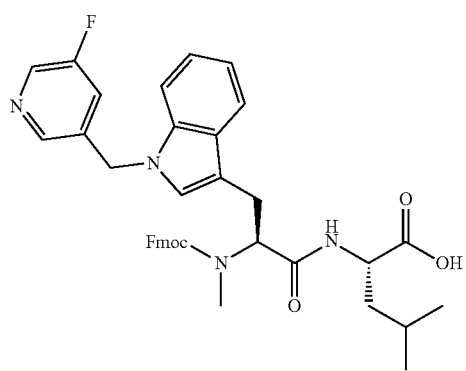
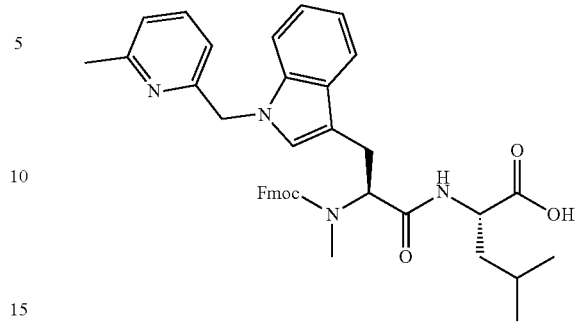
LCMS (ESI): [M−H]⁻, 657.0.
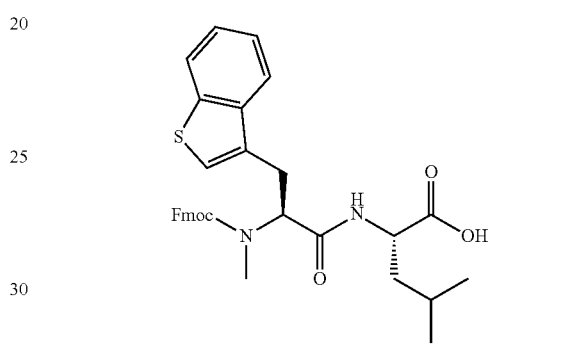
LCMS (ESI): [2M−H]⁻, 1140.3.
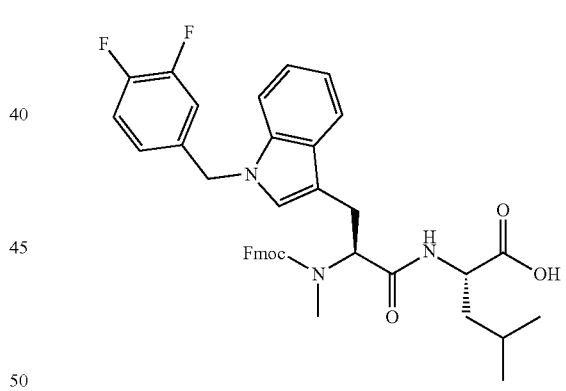
LCMS (ESI): [M+H]⁺, 679.9.
Example 8
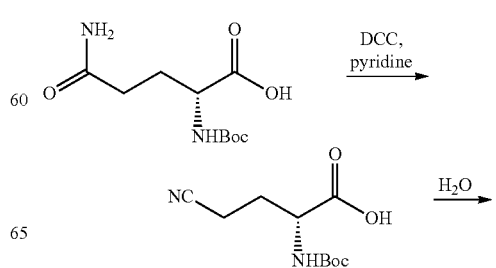

-continued

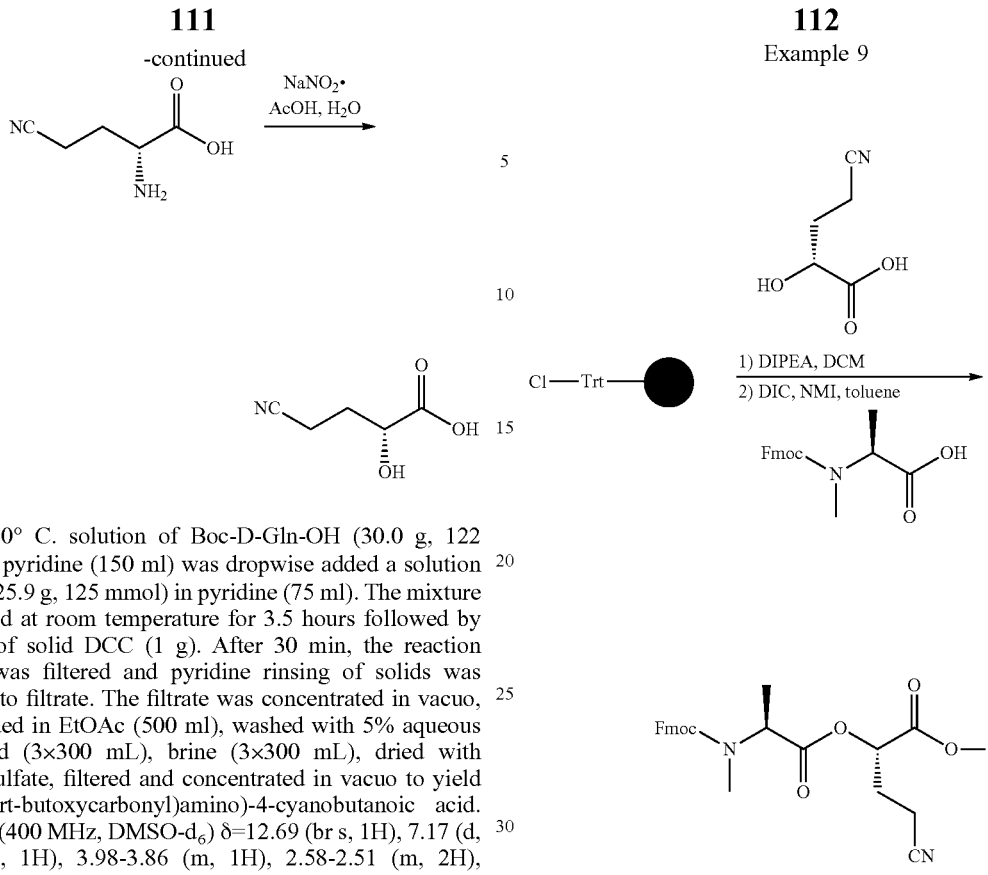

Example 9

To a 10° C. solution of Boc-D-Gln-OH (30.0 g, 122 mmol) in pyridine (150 ml) was dropwise added a solution of DCC (25.9 g, 125 mmol) in pyridine (75 ml). The mixture was stirred at room temperature for 3.5 hours followed by addition of solid DCC (1 g). After 30 min, the reaction mixture was filtered and pyridine rinsing of solids was collected to filtrate. The filtrate was concentrated in vacuo, resuspended in EtOAc (500 ml), washed with 5% aqueous citric acid (3×300 mL), brine (3×300 mL), dried with sodium sulfate, filtered and concentrated in vacuo to yield (R)-2-((tert-butoxycarbonyl)amino)-4-cyanobutanoic acid. $^1$H NMR (400 MHz, DMSO-$d_6$) δ=12.69 (br s, 1H), 7.17 (d, J=8.2 Hz, 1H), 3.98-3.86 (m, 1H), 2.58-2.51 (m, 2H), 2.07-1.96 (m, 1H), 1.83 (m, 1H), 1.39 (s, 9H).

To (R)-2-((tert-butoxycarbonyl)amino)-4-cyanobutanoic acid intermediate (23.2 g, 91.5 mmol) was added water (300 ml), and the mixture was heated to 95° C. for 15 min. The suspension was hot filtered, and the filtrate was concentrated in vacuo to obtain (R)-2-amino-4-cyanobutanoic acid.

To 0° C. solution of (R)-2-amino-4-cyanobutanoic acid 2 (11 g, 86 mmol) in water:AcOH, 4:1 (860 mL) was added with stirring an aqueous NaNO$_2$ solution (2M, 86 mL). The reaction was stirred overnight and the solvent volume was reduced to 150 mL in vacuo. The solution was brought to pH 1-2 with concentrated HCl and the aqueous layer was extracted with EtOAc. The organic layer was concentrated, and triturated with ether to yield (R)-4-cyano-2-hydroxybutanoic acid. The supernatant was concentrated to a residue. The residue was taken up in 500 ml of 4:1 water:AcOH and reacted overnight with 108 mmol of NaNO$_2$ in 50 ml of H$_2$O at 0° C. and allowed to warm to ambient temperature overnight. The reaction was worked up as before to yield more of product. H NMR (400 MHz, D$_2$O) δ=4.36 (dd, J=4.3, 8.3 Hz, 1H), 2.66-2.59 (m, 2H), 2.20 (m, 1H), 2.09-1.96 (m, 1H).

Resin loading: Cl-2-Cl-Trityl resin (2.5 g, 1.6 meq/g, 4.07 mmol) was swollen with DCM (20 mL, anhydrous) for 1 h then filtered. To the resin was added a solution of (2R)-4-cyano-2-hydroxybutanoic acid (789 mg, 6.11 mmol, 1.5 equiv.) and DIPEA (2.11 mL, 12.23 mmol, 3 equiv.) in DCM (20 mL, anhydrous) was added and the mixture was agitated for 16 h. The resin was then filtered and washed with DCM (2×20 mL×1 min) then with toluene (anhydrous, 2×20 mL×1 min gentle shaking). To the filtered resin was added a solution of Fmoc-N-Me-Ala-OH (3.58 g, 11.0 mmol, 2.0 equiv.), DIC (1.72 mL, 11.0 mmol, 2 equiv.) and N-methylimidazole (0.88 mL, 11.0 mmol, 2 equiv.) in toluene (20 mL, anhydrous) and the mixture was agitated for 1 h. The resin was filtered, and the coupling procedure was repeated once more. The resin was then washed using resin 'washing method A' described in Example 10. The resin was then dried under high vacuum overnight affording loaded dry resin.

Example 10

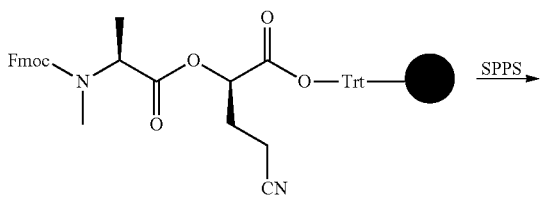

-continued

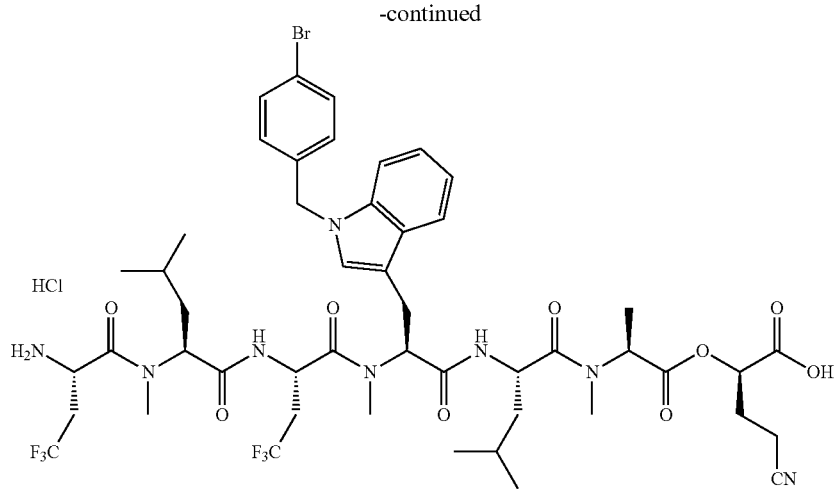

General Procedures for Peptide Elongation on Resin

Resin washing method A: To the resin was added DMF (10 mL/g resin) and the resin agitated by gently shaking for 1 min. The resin was filtered and the procedure is repeated with i-PrOH (1×10 mL/g resin), then DMF (1×10 mL/g resin), then i-PrOH (1×10 mL), then DMF (1×10 mL/g resin), then DCM (3×10 mL/g resin).

Resin washing method B: To the resin was added DMF (10 mL/g resin) and the resin agitated by gently shaking for 1 min. The resin was filtered and the procedure is repeated with i-PrOH (1×10 mL/g resin), then DMF (1×10 mL/g resin), then i-PrOH (1×10 mL/g resin), then DMF (3×10 mL/g resin).

Resin washing method C: To the resin was added DMF (10 mL/g resin) and the resin agitated by gently shaking for about 1 min. The resin was filtered and the procedure is repeated with i-PrOH (1×10 mL/g resin), then DMF (1×10 mL/g resin), then i-PrOH (1×10 mL/g resin), then DMF (1×10 mL/g resin), then toluene (3×10 mL/g resin).

Fmoc removal: A solution of 4-methylpiperidine in DMF (20%, 10 mL/g resin) was added to DMF (or DCM)-swelled resin and the mixture was agitated for 5 min. The resin was filtered under suction and the procedure repeated twice more. The resin was filtered and washed using 'resin washing method B'.

Resin coupling method A: To a solution of Fmoc-AA-OH (2 equiv.) and HATU (2 equiv.) in DMF (0.1 M) was added DIPEA (4 equiv.). The solution was mixed to homogeneity and added to resin. The mixture is agitated for 1 h at room temperature, then filtered and washed using 'resin washing method B'.

Resin coupling method B: To a suspension of Fmoc-AA-OH (2 equiv.) and EEDQ (2 equiv.) in toluene (0.35 M) were added 2 volumes of DMF. The solution is quickly mixed to homogeneity and added to toluene-washed resin. The mixture was agitated for 2 h at room temperature then filtered and washed using 'resin washing method B'.

Synthesis of linear peptide: 2-C-trityl-(R)-2-((N-(((9H-fluoren-9-yl)methoxy)carbonyl)-N-methyl-L-alanyl)oxy)-4-cyanobutanoate resin (3.00 g, 2.46 mmol) was swollen with DCM (25 mL) for 1 h. The resin was then filtered and Fmoc group was removed using 'Fmoc removal' procedure. The resin was then washed using 'resin washing method C' then coupled with Fmoc-N-Me-Trp(4-BrBn)-Leu-OH using 'resin coupling method B', and washed with 'resin washing method B', then Fmoc was removed using 'Fmoc removal' procedure and resin washed with 'resin washing method B'. The peptide was elongated in a similar manner using:

1) Fmoc-Gly($CH_2CF_3$)—OH using 'resin coupling method B'

2) Fmoc-N-Leu-OH using 'resin coupling method A'

3) Fmoc-Gly($CH_2CF_3$)—OH using 'resin coupling method B'

After removal of the last N-terminal Fmoc group, the resin was washed using 'washing method A'.

Resin cleavage: To presumed 2.46 mmol loaded resin was added HFIP (15 mL of a 20% solution in DCM) and the mixture and agitated for 15 min. The solution was filtered and collected into a 250 mL round bottom flask containing HCl (0.25 M solution in EtOAc, 40 mL ~4 equiv.). The cleavage procedure was repeated once more and the solution was collected in the same flask of HCl. The remaining resin was rinsed into the HCl solution with DCM (2×10 mL) and the combined solution was concentrated under reduced pressure. The residue was dissolved in a minimal volume of EtOAc then precipitated with $Et_2O$. Decanting The mixture was sonicated for ~10 seconds and the precipitate left to settle for a few minutes before the liquid was carefully removed using a pipette. The residual solid was triturated with $Et_2O$ and dried under high vacuum to afford (3R,6S,9S,12S,15S,18S,21S)-12-((1-(4-bromobenzyl)-1H-indol-3-yl)methyl)-3-carboxy-1-cyano-23,23,23-trifluoro-9,18-diisobutyl-6,7,13,19-tetramethyl-5,8,11,14,17,20-hexaoxo-15-(2,2,2-trifluoroethyl)-4-oxa-7,10,13,16,19-pentaazatricosan-21-aminium chloride. HRMS (ESI): Calculated for [M−H]⁻ $C_{53}H_{87}N_8O_9$, 1101.3878; Found, 1101.3868.

The following compounds were prepared using the procedure of Example 9 and 10:

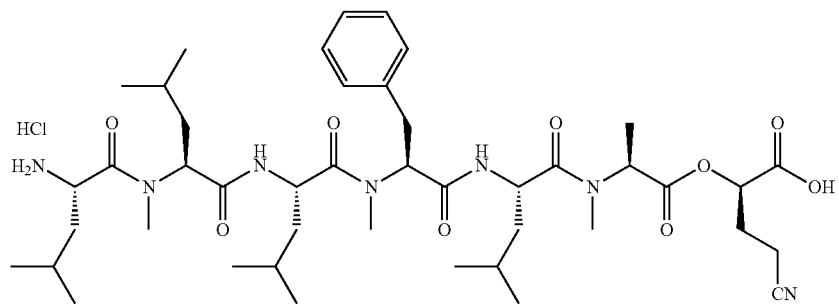 [SMILES: CC(C)C[C@H](NC(=O)[C@H](Cc1ccccc1)N(C)C(=O)[C@H](CC(C)C)NC(=O)[C@H](CC(C)C)N(C)C(=O)[C@@H](N)CC(C)C)C(=O)N(C)[C@@H](C)C(=O)O[C@H](CCC#N)C(=O)O ; Cl]
LCMS (ESI): [M−H]⁻, 841.0.
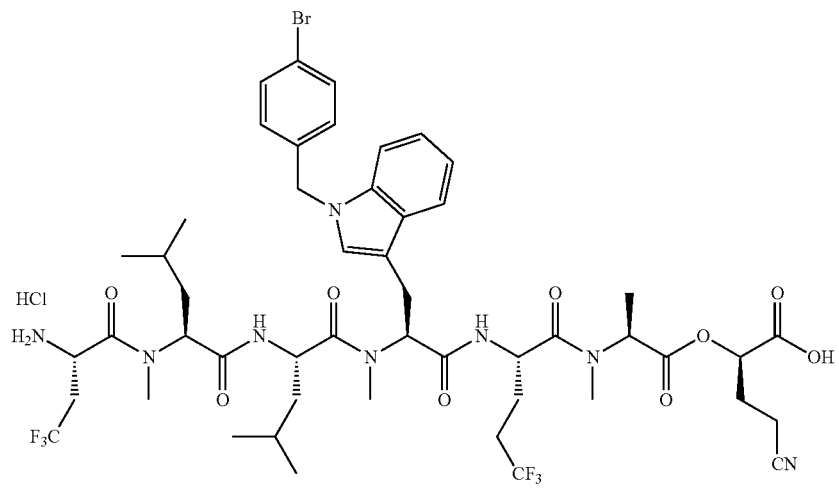 [SMILES: Cl ; CC(C)C[C@H](NC(=O)[C@H](CC(C)C)N(C)C(=O)[C@@H](N)CC(F)(F)F)C(=O)N(C)[C@@H](Cc1cn(Cc2ccc(Br)cc2)c2ccccc12)C(=O)N[C@@H](CCC(F)(F)F)C(=O)N(C)[C@@H](C)C(=O)O[C@H](CCC#N)C(=O)O]
LCMS (ESI): [M+H]⁺, 1116.3.
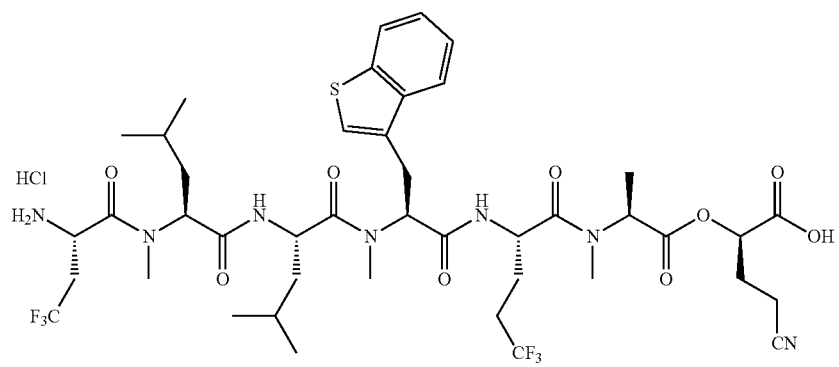
LCMS (ESI): [M−H]⁻, 963.8.

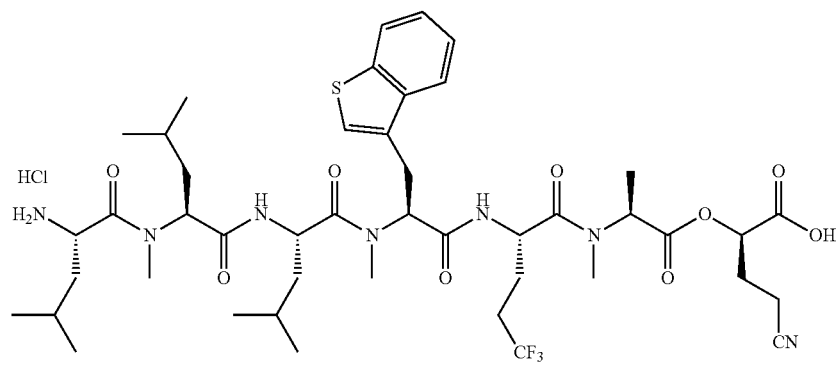 [SMILES: Cl ; CC(C)C[C@H](NC(=O)[C@H](CC(C)C)N(C)C(=O)[C@@H](N)CC(F)(F)F)C(=O)N(C)[C@@H](Cc1csc2ccccc12)C(=O)N[C@@H](CCC(F)(F)F)C(=O)N(C)[C@@H](C)C(=O)O[C@H](CCC#N)C(=O)O]
LCMS (ESI): [M−H]⁻, 937.4.
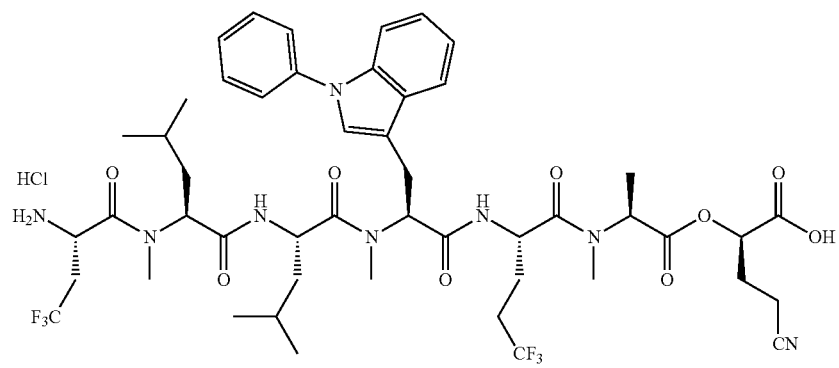 [SMILES: Cl ; CC(C)C[C@H](NC(=O)[C@H](CC(C)C)N(C)C(=O)[C@@H](N)CC(F)(F)F)C(=O)N(C)[C@@H](Cc1cn(-c2ccccc2)c2ccccc12)C(=O)N[C@@H](CCC(F)(F)F)C(=O)N(C)[C@@H](C)C(=O)O[C@H](CCC#N)C(=O)O]
LCMS (ESI): [M+H]⁺, 984.1.
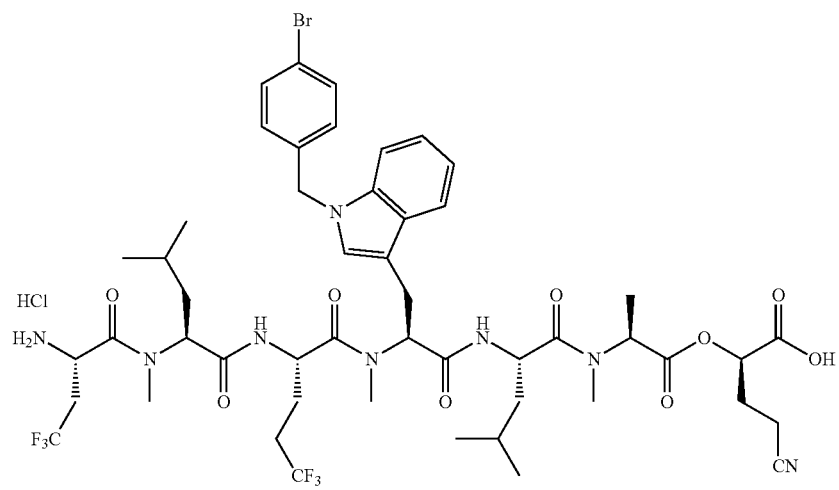 [SMILES: Cl ; CC(C)C[C@H](NC(=O)[C@H](Cc1cn(Cc2ccc(Br)cc2)c2ccccc12)N(C)C(=O)[C@H](CCC(F)(F)F)NC(=O)[C@H](CC(C)C)N(C)C(=O)[C@@H](N)CC(F)(F)F)C(=O)N(C)[C@@H](C)C(=O)O[C@H](CCC#N)C(=O)O]
LCMS (ESI): [M−H]⁻, 1114.1.

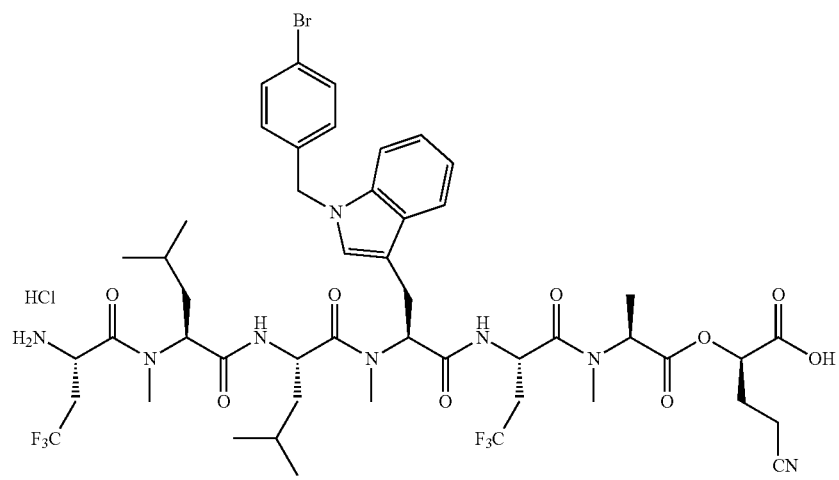 [SMILES: Cl ; CC(C)C[C@H](NC(=O)[C@H](CC(C)C)N(C)C(=O)[C@@H](N)CC(F)(F)F)C(=O)N(C)[C@@H](Cc1cn(Cc2ccc(Br)cc2)c2ccccc12)C(=O)N[C@@H](CC(F)(F)F)C(=O)N(C)[C@@H](C)C(=O)O[C@H](CCC#N)C(=O)O]
LCMS (ESI): [M−H]⁻, 1098.9.
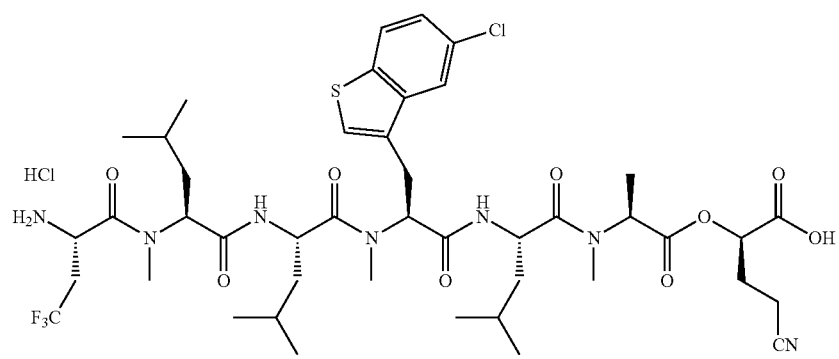 [SMILES: Cl ; CC(C)C[C@H](NC(=O)[C@H](Cc1csc2ccc(Cl)cc12)N(C)C(=O)[C@H](CC(C)C)NC(=O)[C@H](CC(C)C)N(C)C(=O)[C@@H](N)CC(F)(F)F)C(=O)N(C)[C@@H](C)C(=O)O[C@H](CCC#N)C(=O)O]
LCMS (ESI): [M+H]⁺, 958.4.
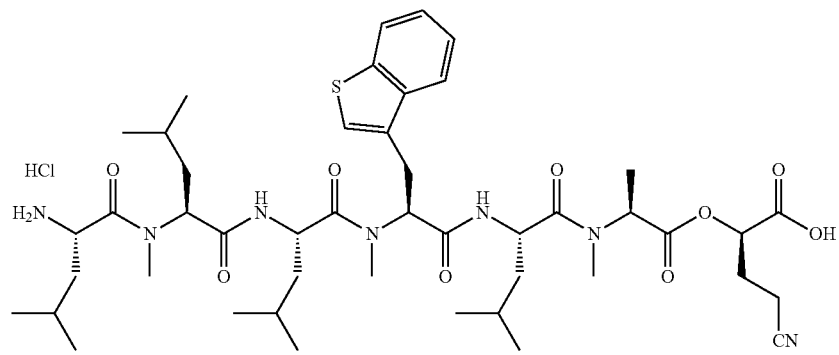 [SMILES: CC(C)C[C@H](NC(=O)[C@H](Cc1csc2ccccc12)N(C)C(=O)[C@H](CC(C)C)NC(=O)[C@H](CC(C)C)N(C)C(=O)[C@@H](N)CC(C)C)C(=O)N(C)[C@@H](C)C(=O)O[C@H](CCC#N)C(=O)O ; Cl]
LCMS (ESI): [M−H]⁻, 986.5.

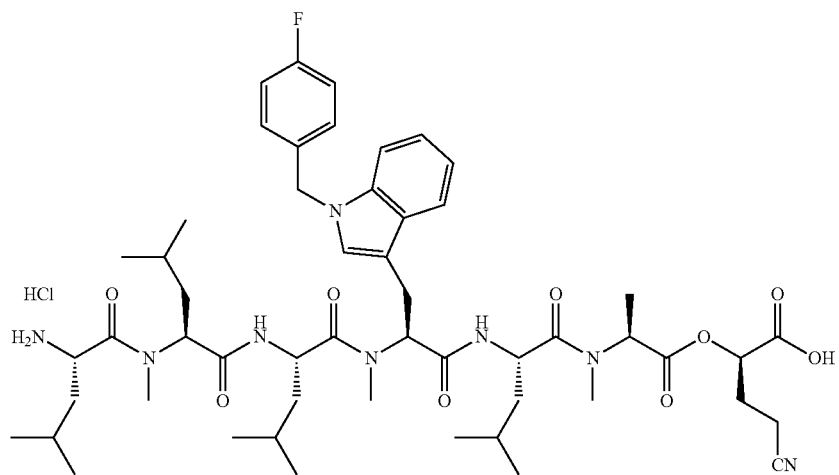 [SMILES: CC(C)C[C@H](NC(=O)[C@H](Cc1cn(Cc2ccc(F)cc2)c2ccccc12)N(C)C(=O)[C@H](CC(C)C)NC(=O)[C@H](CC(C)C)N(C)C(=O)[C@@H](N)CC(C)C)C(=O)N(C)[C@@H](C)C(=O)O[C@H](CCC#N)C(=O)O ; Cl]
LCMS: (ESI): [M−H]⁻, 988.0.
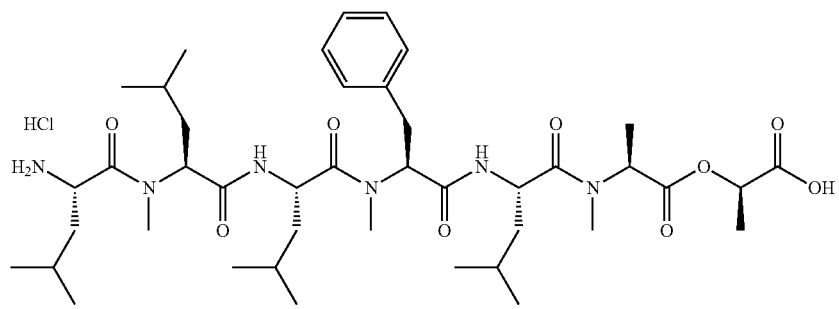 [SMILES: CC(C)C[C@H](NC(=O)[C@H](Cc1ccccc1)N(C)C(=O)[C@H](CC(C)C)NC(=O)[C@H](CC(C)C)N(C)C(=O)[C@@H](N)CC(C)C)C(=O)N(C)[C@@H](C)C(=O)O[C@H](C)C(=O)O ; Cl]
LCMS (ESI): [M−H]⁻, 802.1.
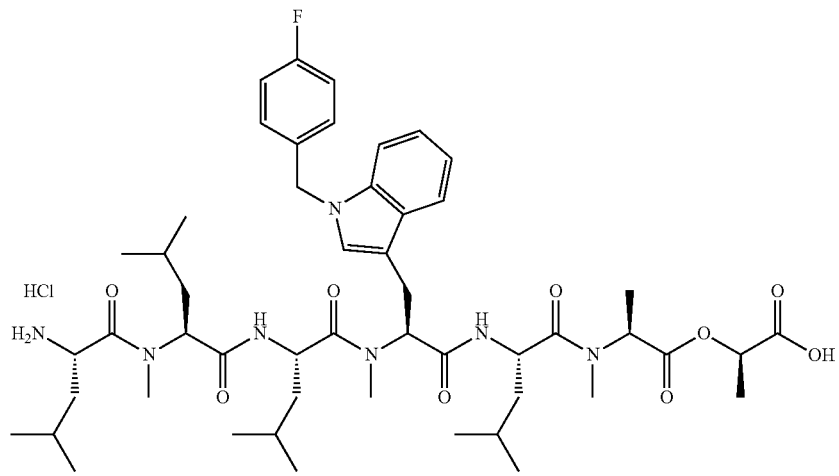 [SMILES: CC(C)C[C@H](NC(=O)[C@H](Cc1cn(Cc2ccc(F)cc2)c2ccccc12)N(C)C(=O)[C@H](CC(C)C)NC(=O)[C@H](CC(C)C)N(C)C(=O)[C@@H](N)CC(C)C)C(=O)N(C)[C@@H](C)C(=O)O[C@H](C)C(=O)O ; Cl]
LCMS (ESI): [M−H]⁻, 949.2.

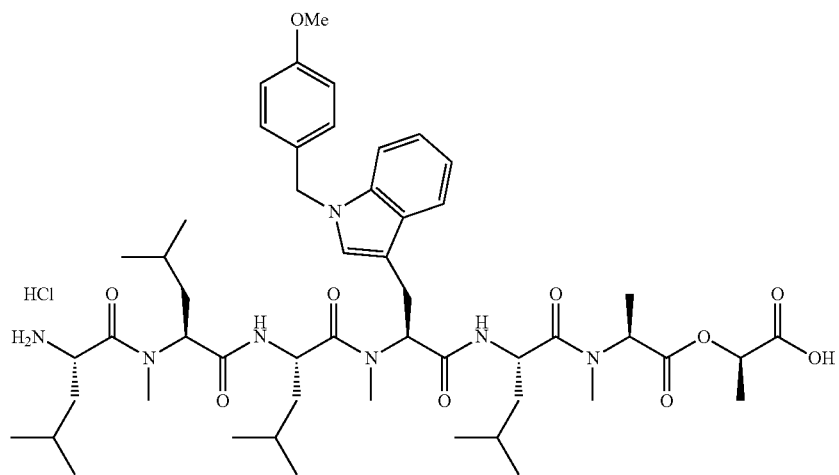 [SMILES: COc1ccc(Cn2cc(C[C@@H](C(=O)N[C@@H](CC(C)C)C(=O)N(C)[C@@H](C)C(=O)O[C@H](C)C(=O)O)N(C)C(=O)[C@H](CC(C)C)NC(=O)[C@H](CC(C)C)N(C)C(=O)[C@@H](N)CC(C)C)c3ccccc32)cc1 ; Cl]
LCMS (ESI): [M−H]⁻, 961.2.
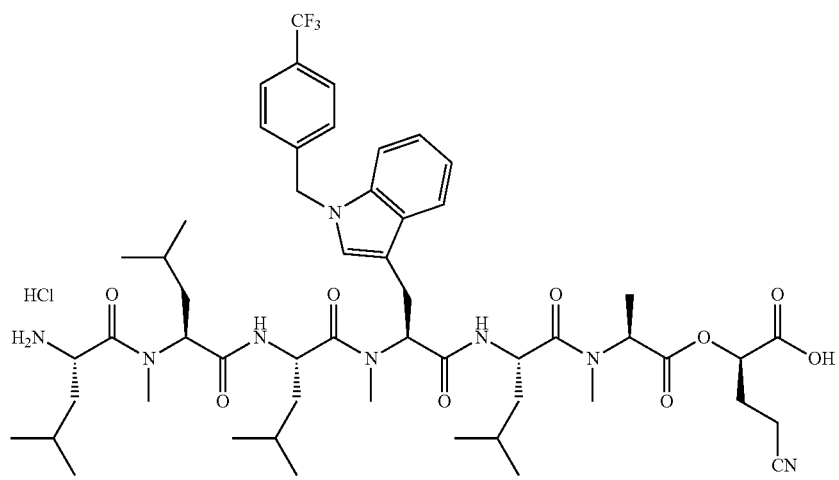 [SMILES: CC(C)C[C@H](NC(=O)[C@H](Cc1cn(Cc2ccc(C(F)(F)F)cc2)c2ccccc12)N(C)C(=O)[C@H](CC(C)C)NC(=O)[C@H](CC(C)C)N(C)C(=O)[C@@H](N)CC(C)C)C(=O)N(C)[C@@H](C)C(=O)O[C@H](CCC#N)C(=O)O ; Cl]
LCMS (ESI): [M−H]⁻, 1037.6.
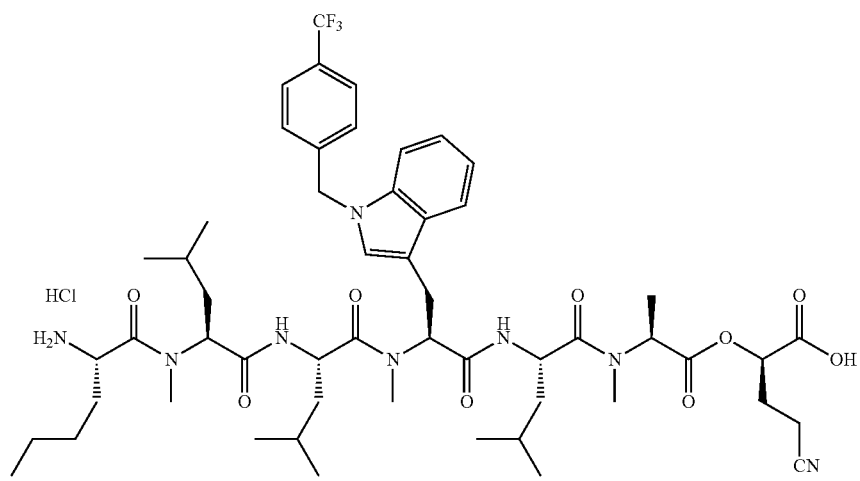 [SMILES: CCCC[C@H](N)C(=O)N(C)[C@@H](CC(C)C)C(=O)N[C@@H](CC(C)C)C(=O)N(C)[C@@H](Cc1cn(Cc2ccc(C(F)(F)F)cc2)c2ccccc12)C(=O)N[C@@H](CC(C)C)C(=O)N(C)[C@@H](C)C(=O)O[C@H](CCC#N)C(=O)O ; Cl]
LCMS: [M+H]⁺, 1040.6.

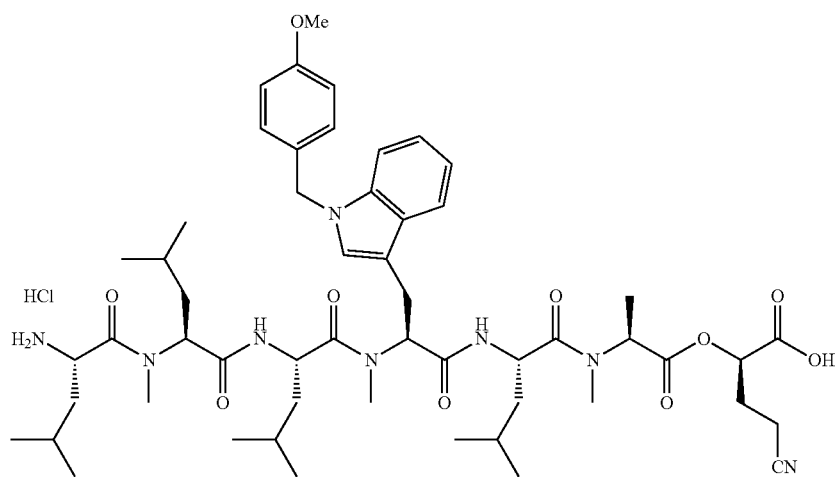 [SMILES: COc1ccc(Cn2cc(C[C@@H](C(=O)N[C@@H](CC(C)C)C(=O)N(C)[C@@H](C)C(=O)O[C@H](CCC#N)C(=O)O)N(C)C(=O)[C@H](CC(C)C)NC(=O)[C@H](CC(C)C)N(C)C(=O)[C@@H](N)CC(C)C)c3ccccc32)cc1 ; Cl]
LCMS: (ESI): [M−H]⁻ ,1000.2.
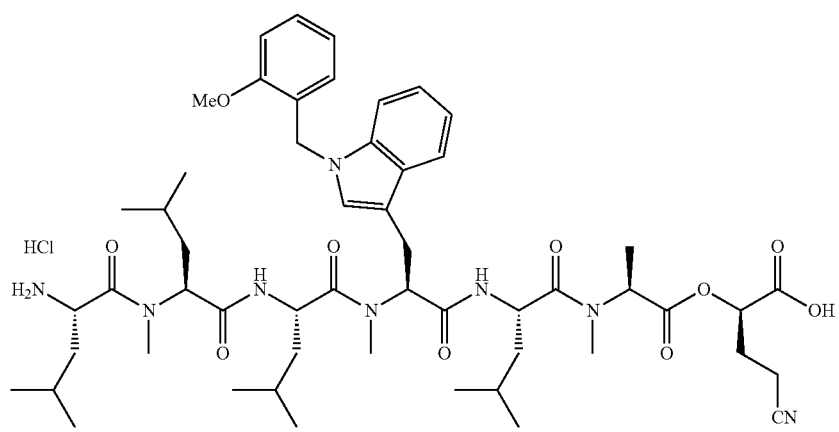 [SMILES: COc1ccccc1Cn1cc(C[C@@H](C(=O)N[C@@H](CC(C)C)C(=O)N(C)[C@@H](C)C(=O)O[C@H](CCC#N)C(=O)O)N(C)C(=O)[C@H](CC(C)C)NC(=O)[C@H](CC(C)C)N(C)C(=O)[C@@H](N)CC(C)C)c2ccccc21 ; Cl]
LCMS (ESI): [M−H]⁻, 1000.2.
LCMS (ESI): [M−H]⁻, 1000.1.
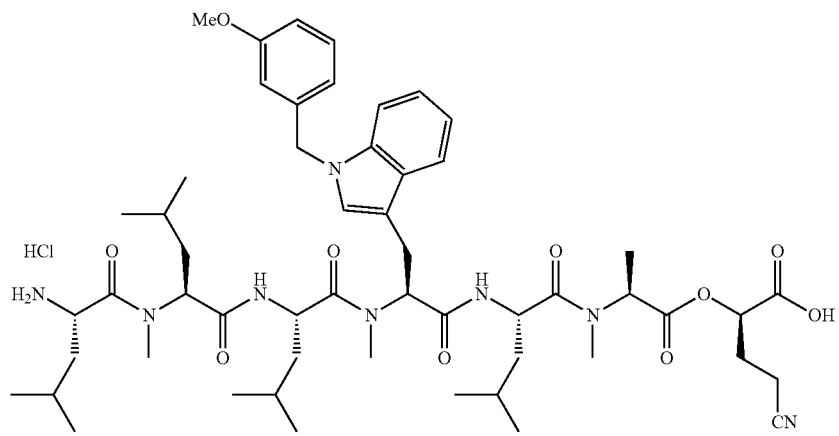 [SMILES: COc1cccc(Cn2cc(C[C@@H](C(=O)N[C@@H](CC(C)C)C(=O)N(C)[C@@H](C)C(=O)O[C@H](CCC#N)C(=O)O)N(C)C(=O)[C@H](CC(C)C)NC(=O)[C@H](CC(C)C)N(C)C(=O)[C@@H](N)CC(C)C)c3ccccc32)c1 ; Cl]

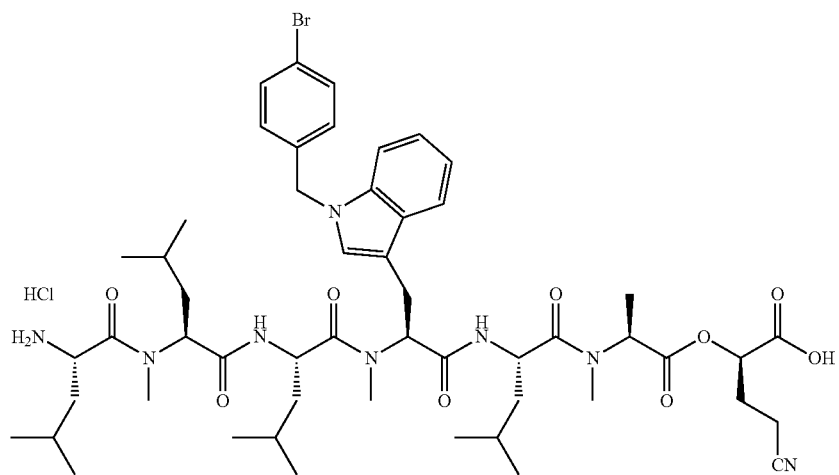 [SMILES: CC(C)C[C@H](NC(=O)[C@H](Cc1cn(Cc2ccc(Br)cc2)c2ccccc12)N(C)C(=O)[C@H](CC(C)C)NC(=O)[C@H](CC(C)C)N(C)C(=O)[C@@H](N)CC(C)C)C(=O)N(C)[C@@H](C)C(=O)O[C@H](CCC#N)C(=O)O ; Cl]
LCMS (ESI): [M−H]⁻, 1049.6.
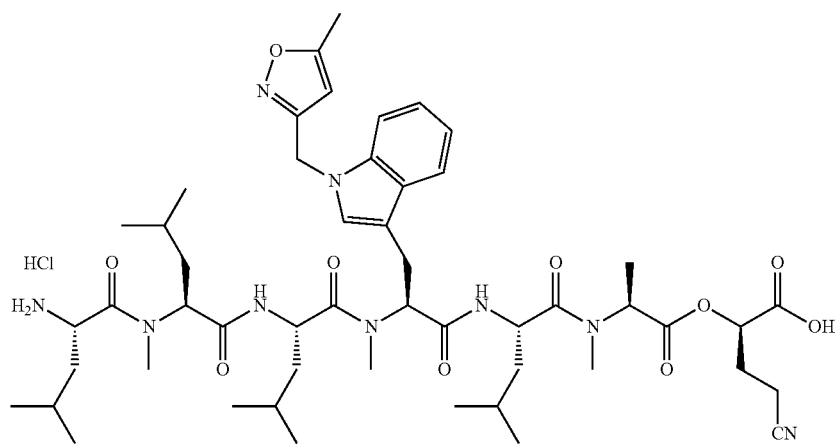 [SMILES: Cc1cc(Cn2cc(C[C@@H](C(=O)N[C@@H](CC(C)C)C(=O)N(C)[C@@H](C)C(=O)O[C@H](CCC#N)C(=O)O)N(C)C(=O)[C@H](CC(C)C)NC(=O)[C@H](CC(C)C)N(C)C(=O)[C@@H](N)CC(C)C)c3ccccc32)no1 ; Cl]
LCMS (ESI): [M−H]⁻, 974.6.
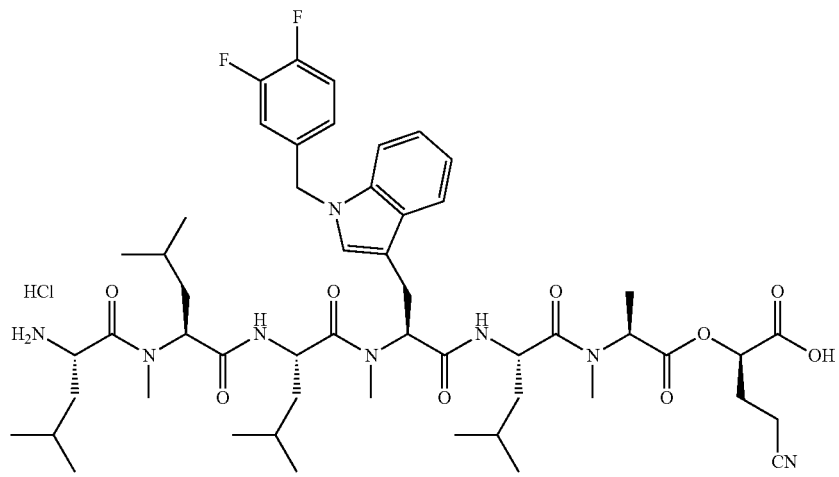 [SMILES: CC(C)C[C@H](NC(=O)[C@H](Cc1cn(Cc2ccc(F)c(F)c2)c2ccccc12)N(C)C(=O)[C@H](CC(C)C)NC(=O)[C@H](CC(C)C)N(C)C(=O)[C@@H](N)CC(C)C)C(=O)N(C)[C@@H](C)C(=O)O[C@H](CCC#N)C(=O)O ; Cl]
LCMS: (ESI): [M−H], 1005.5.

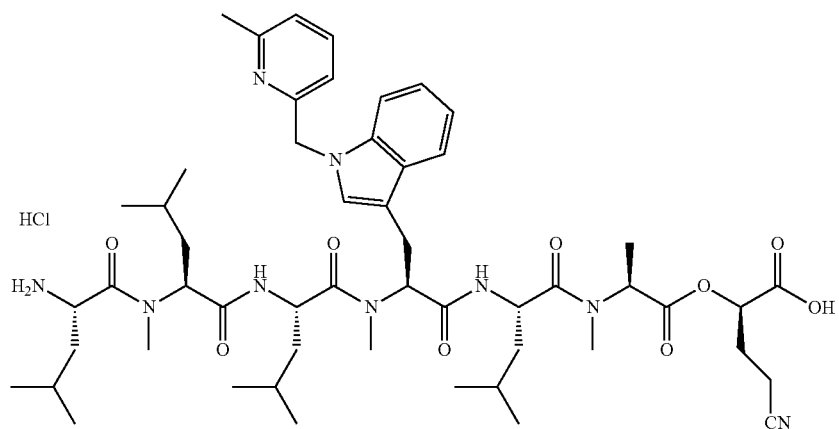 [SMILES: Cc1cccc(Cn2cc(C[C@@H](C(=O)N[C@@H](CC(C)C)C(=O)N(C)[C@@H](C)C(=O)O[C@H](CCC#N)C(=O)O)N(C)C(=O)[C@H](CC(C)C)NC(=O)[C@H](CC(C)C)N(C)C(=O)[C@@H](N)CC(C)C)c3ccccc32)n1 ; Cl]
LCMS (ESI): [M−H]⁻, 884.5.
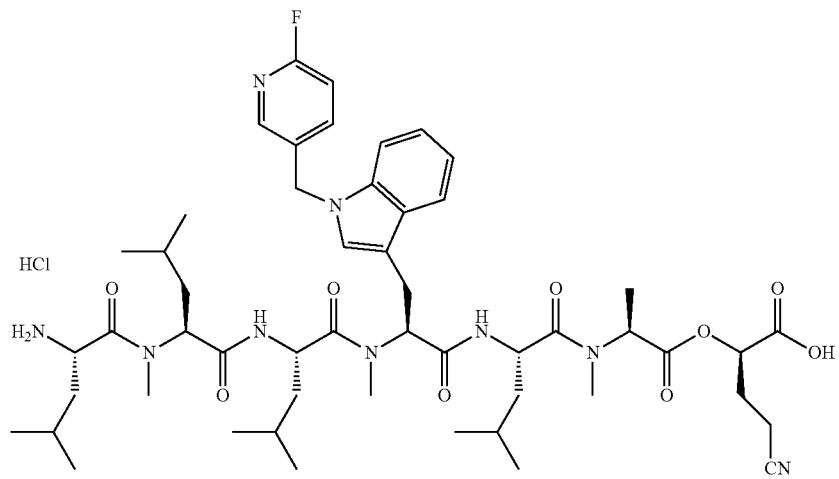 [SMILES: CC(C)C[C@H](NC(=O)[C@H](Cc1cn(Cc2ccc(F)nc2)c2ccccc12)N(C)C(=O)[C@H](CC(C)C)NC(=O)[C@H](CC(C)C)N(C)C(=O)[C@@H](N)CC(C)C)C(=O)N(C)[C@@H](C)C(=O)O[C@H](CCC#N)C(=O)O ; Cl]
Linear peptide was subjected to macrocyclization without spectroscopic analysis.
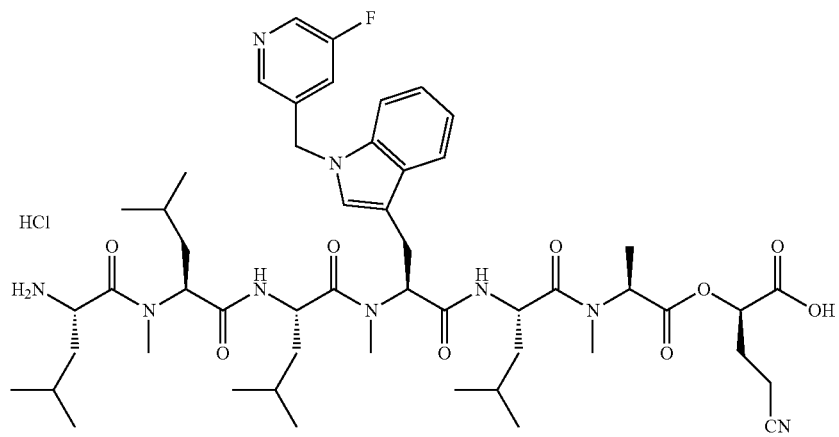 [SMILES: CC(C)C[C@H](NC(=O)[C@H](Cc1cn(Cc2cncc(F)c2)c2ccccc12)N(C)C(=O)[C@H](CC(C)C)NC(=O)[C@H](CC(C)C)N(C)C(=O)[C@@H](N)CC(C)C)C(=O)N(C)[C@@H](C)C(=O)O[C@H](CCC#N)C(=O)O ; Cl]
Linear peptide was subjected to macrocyclization without spectroscopic analysis.

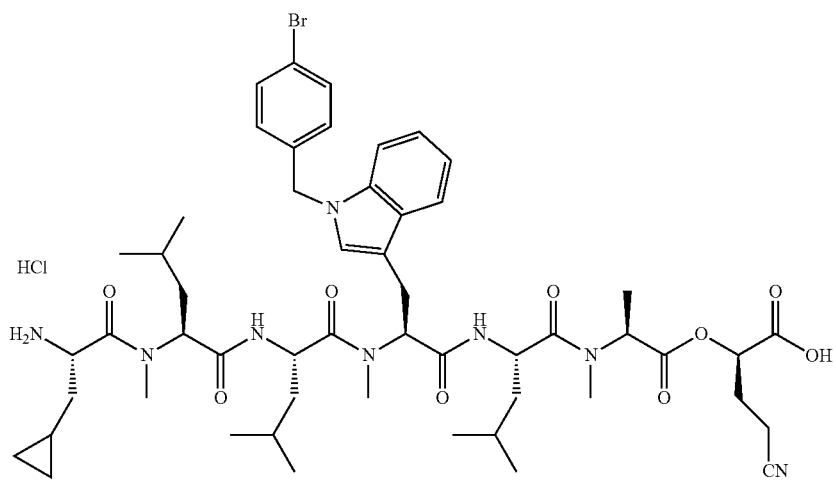 [SMILES: CC(C)C[C@H](NC(=O)[C@H](Cc1cn(Cc2ccc(Br)cc2)c2ccccc12)N(C)C(=O)[C@H](CC(C)C)NC(=O)[C@H](CC(C)C)N(C)C(=O)[C@@H](N)CC1CC1)C(=O)N(C)[C@@H](C)C(=O)O[C@H](CCC#N)C(=O)O ; Cl]
LCMS (ESI): [M−H]⁻, 1047.4.
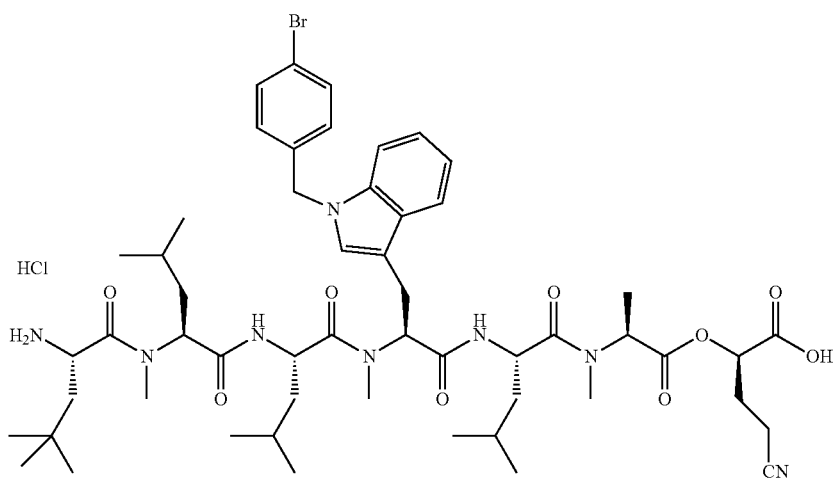 [SMILES: CC(C)C[C@H](NC(=O)[C@H](Cc1cn(Cc2ccc(Br)cc2)c2ccccc12)N(C)C(=O)[C@H](CC(C)C)NC(=O)[C@H](CC(C)C)N(C)C(=O)[C@@H](N)CC(C)(C)C)C(=O)N(C)[C@@H](C)C(=O)O[C@H](CCC#N)C(=O)O ; Cl]
LCMS (ESI): [M+H]⁺, 1064.6.
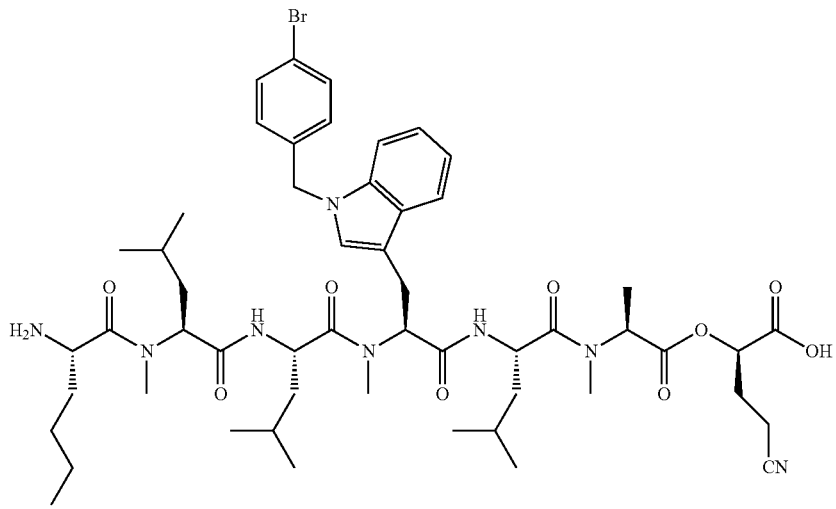 [SMILES: CCCC[C@H](N)C(=O)N(C)[C@@H](CC(C)C)C(=O)N[C@@H](CC(C)C)C(=O)N(C)[C@@H](Cc1cn(Cc2ccc(Br)cc2)c2ccccc12)C(=O)N[C@@H](CC(C)C)C(=O)N(C)[C@@H](C)C(=O)O[C@H](CCC#N)C(=O)O]
LCMS (ESI): [M+H]⁺, 1050.6.

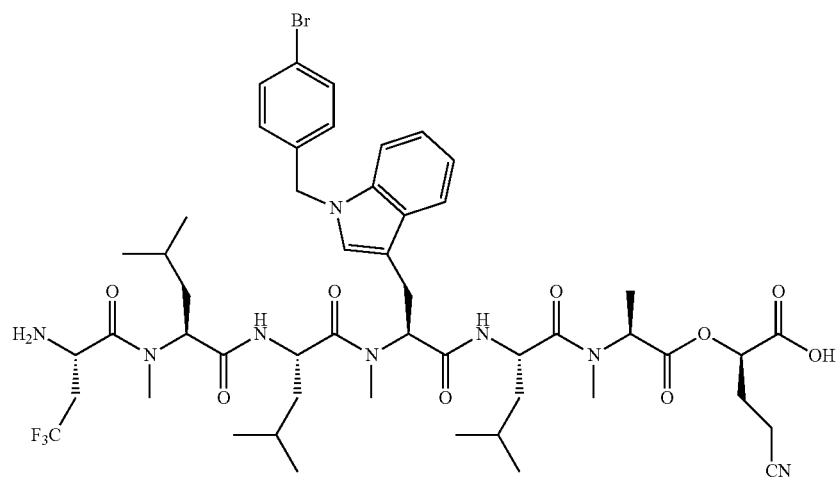 [SMILES: CC(C)C[C@H](NC(=O)[C@H](Cc1cn(Cc2ccc(Br)cc2)c2ccccc12)N(C)C(=O)[C@H](CC(C)C)NC(=O)[C@H](CC(C)C)N(C)C(=O)[C@@H](N)CC(F)(F)F)C(=O)N(C)[C@@H](C)C(=O)O[C@H](CCC#N)C(=O)O]
LCMS (ESI): [M+H]⁺, 1076.7.
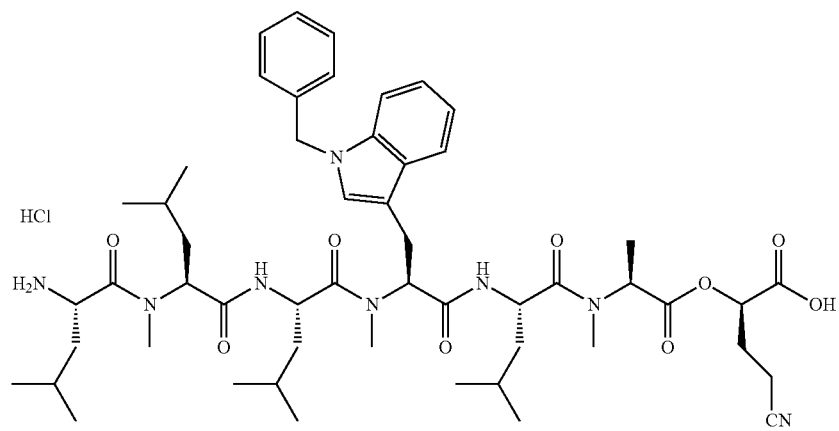 [SMILES: CC(C)C[C@H](NC(=O)[C@H](Cc1cn(Cc2ccccc2)c2ccccc12)N(C)C(=O)[C@H](CC(C)C)NC(=O)[C@H](CC(C)C)N(C)C(=O)[C@@H](N)CC(C)C)C(=O)N(C)[C@@H](C)C(=O)O[C@H](CCC#N)C(=O)O ; Cl]
LCMS (ESI): [M−H]⁻, 969.6.
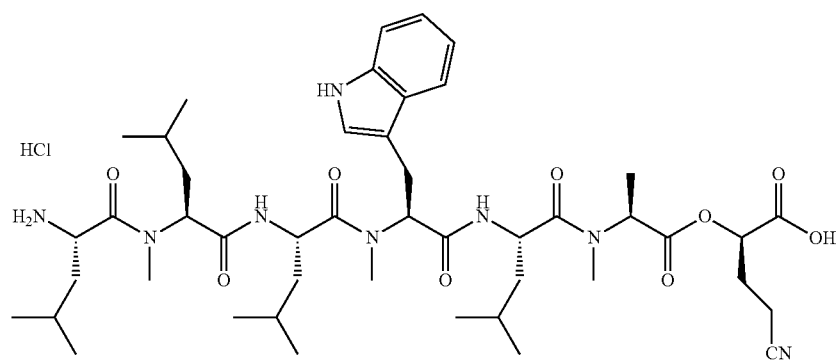 [SMILES: CC(C)C[C@H](NC(=O)[C@H](Cc1c[nH]c2ccccc12)N(C)C(=O)[C@H](CC(C)C)NC(=O)[C@H](CC(C)C)N(C)C(=O)[C@@H](N)CC(C)C)C(=O)N(C)[C@@H](C)C(=O)O[C@H](CCC#N)C(=O)O ; Cl]
LCMS (ESI): [M−H]⁻, 879.3.

Example 11 C-58

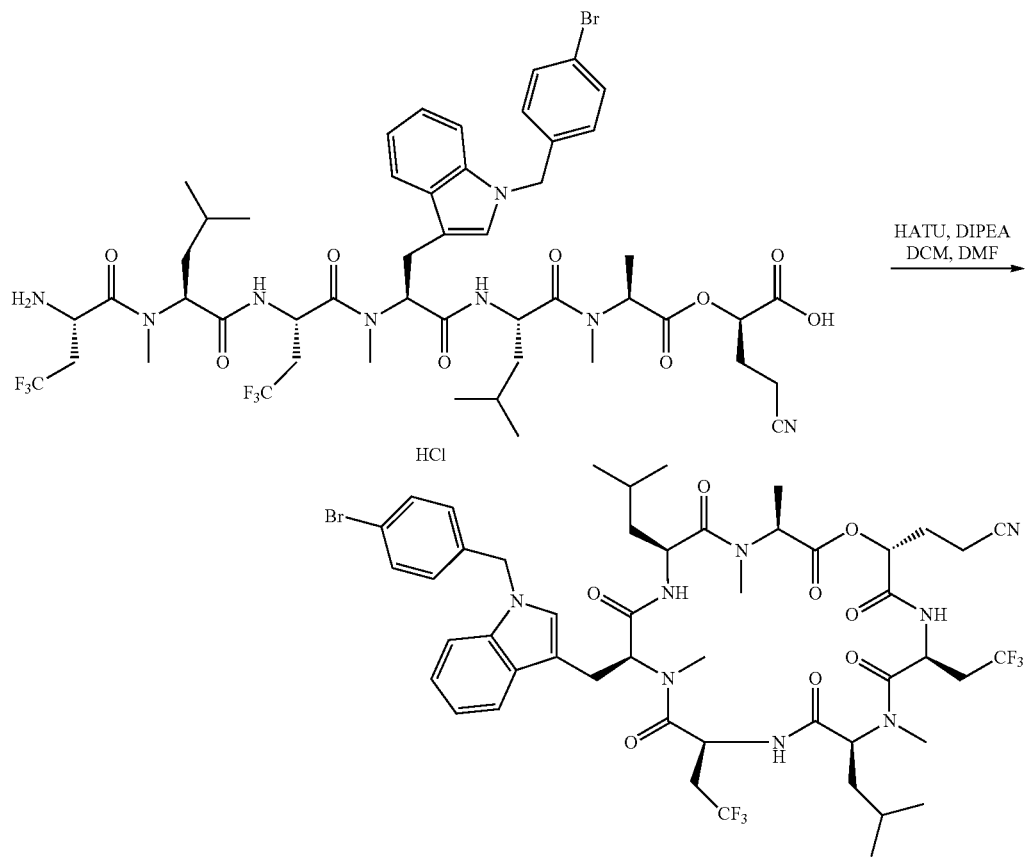

A solution of (3R,6S,9S,12S,15S,18S,21S)-12-((1-(4-bromobenzyl)-1H-indol-3-yl)methyl)-3-carboxy-1-cyano-23,23,23-trifluoro-9,18-diisobutyl-6,7,13,19-tetramethyl-5,8,11,14,17,20-hexaoxo-15-(2,2,2-trifluoroethyl)-4-oxa-7,10,13,16,19-pentaazatricosan-21-aminium chloride (930 mg, 0.816 mmol) and DIPEA (427 μL, 2.45 mmol, 3 equiv.) in DCM (313 mL) was added, via a dropping funnel (at a rate of ~1 drop/sec), to a rapidly stirred solution of HATU (316 mg, 0.858 mmol), DMF (6 mL) and DCM (1.31 L). After complete addition, the funnel was rinsed into the reaction mixture with DCM (10 mL) and the reaction was stirred for 18 h. An additional portion of HATU (158 mg, 429 mmol) was added and the reaction stirred for another 2 h. The reaction mixture was washed with HCl (500 mL of a 0.2 M aqueous solution), then with NaHCO$_3$ (500 mL of a 33% saturated aqueous solution). The DCM layer was then dried (MgSO$_4$), filtered and concentrated under reduced pressure. The residue purified by Flash chromatography (silica, step gradient elution, 5-50% acetone:hexane). Concentration of the appropriate fractions afforded 3-((2R,5S,8S,11S,14S,17S,20S)-14-((1-(4-bromobenzyl)-1H-indol-3-yl)methyl)-8,17-diisobutyl-7,13,19,20-tetramethyl-3,6,9,12,15,18,21-heptaoxo-5,11-bis(2,2,2-trifluoroethyl)-1-oxa-4,7,10,13,16,19-hexaazacyclohenicosan-2-yl)propanenitrile. $^1$H-NMR (400 MHz; acetone-d$_6$): δ 8.45 (d, J=10.1 Hz, 1H), 8.25 (d, J=9.6 Hz, 1H), 8.01 (d, J=7.0 Hz, 1H), 7.71 (dd, J=7.1, 0.9 Hz, 1H), 7.50-7.47 (m, 2H), 7.41 (t, J=5.9 Hz, 1H), 7.36 (s, 1H), 7.18-7.09 (m, 4H), 5.45-5.34 (m, 2H), 5.26-5.06 (m, 3H), 4.76-4.71 (m, 1H), 4.37 (dd, J=10.9, 3.6 Hz, 1H), 3.99-3.94 (m, 1H), 3.38-3.32 (m, 1H), 3.29 (s, 3H), 3.17-3.09 (m, 1H), 2.94 (s, 3H), 2.58 (s, 3H), 2.52-2.48 (m, 2H), 2.37-2.18 (m, 4H), 2.07 (dt, J=4.4, 2.2 Hz, 2H), 1.96-1.82 (m, 2H), 1.57-1.45 (m, 8H), 1.04-0.94 (m, 10H), 0.90-0.85 (m, 2H), 0.49-0.42 (m, 1H). LCMS (ESI): Calculated for C$_{49}$H$_{62}$BrF$_6$N$_8$O$_8$ [M+H]$^+$, 1083.4; Found, 1083.2.

The following compounds were prepared using the procedure of Example 11:

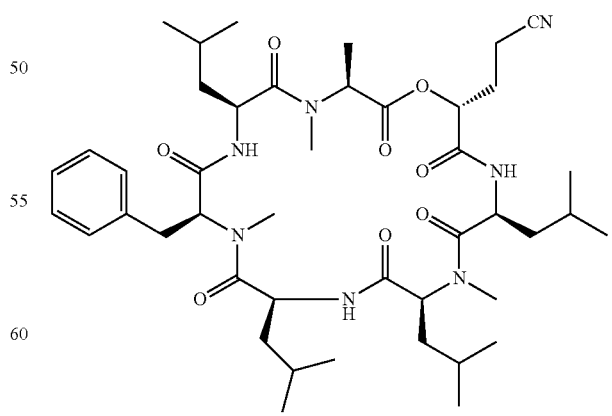

$^1$H-NMR (400 MHz; acetone-d$_6$): δ 8.73 (d, J=10.0 Hz, 1H), 7.99 (d, J=9.6 Hz, 1H), 7.73 (d, J=6.7 Hz, 1H), 7.36-7.33 (m, 2H), 7.31-7.25 (m, 3H), 5.10-4.97 (m, 3H), 4.88 (dt, J=9.5, 7.1 Hz, 1H), 4.52 (ddd, J=11.7, 7.0, 3.6 Hz, 1H), 4.43 (dd, J=10.9, 4.2 Hz, 1H), 3.92 (q, J=6.8 Hz, 1H), 3.20 (s, 3H), 3.12-3.09 (m, 2H), 2.87 (s, 3H), 2.60 (t, J=3.7 Hz, 2H), 2.54 (s, 3H), 2.31-2.25 (m, 1H), 2.08-1.97 (m, 1H), 1.81 (dtd, J=13.9, 12.5, 5.4 Hz, 2H), 1.70-1.38 (m, 13H), 1.08 (d, J=6.4 Hz, 3H), 1.01-0.90 (m, 16H), 0.71-0.66 (m, 6H), −0.18 (ddd, J=14.1, 10.7, 3.4 Hz, 1H). LCMS (ESI): Calculated for $C_{44}H_{70}N_7O_8$ [M+H]$^+$, 824.5; Found, 824.6.

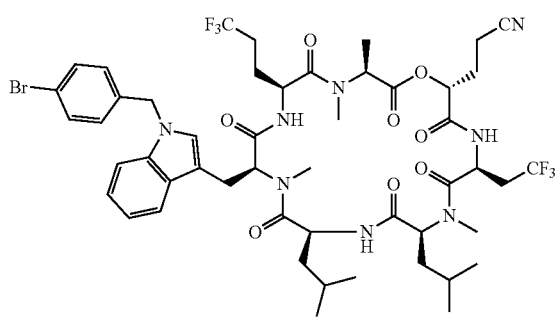 [SMILES: CC(C)C[C@@H]1NC(=O)[C@H](CC(C)C)N(C)C(=O)[C@H](CC(F)(F)F)NC(=O)[C@@H](CCC#N)OC(=O)[C@H](C)N(C)C(=O)[C@H](CCC(F)(F)F)NC(=O)[C@H](Cc2cn(Cc3ccc(Br)cc3)c3ccccc23)N(C)C1=O]

C-48 $^1$H-NMR (400 MHz; acetone-$d_6$): δ 8.88 (d, J=9.9 Hz, 1H), 8.18 (d, J=9.4 Hz, 1H), 7.75 (t, J=8.4 Hz, 2H), 7.49-7.43 (m, 3H), 7.29 (s, 1H), 7.23-7.18 (m, 2H), 7.16-7.09 (m, 2H), 5.39 (s, 2H), 5.23-5.12 (m, 2H), 5.06 (dt, J=10.2, 3.7 Hz, 2H), 4.45-4.39 (m, 1H), 4.30 (dd, J=11.1, 4.1 Hz, 1H), 4.01 (q, J=6.8 Hz, 1H), 3.30 (s, 4H), 3.25-3.10 (m, 2H), 2.94 (s, 3H), 2.57 (s, 3H), 2.56-2.52 (m, 2H), 2.35-2.18 (m, 3H), 2.16-2.15 (m, 1H), 2.01-1.93 (m, 2H), 1.87-1.80 (m, 1H), 1.75-1.61 (m, 2H), 1.58-1.46 (m, 4H), 1.38-1.26 (m, 2H), 1.02 (d, J=6.4 Hz, 3H), 0.99-0.95 (m, 3H), 0.87-0.84 (m, 1H), 0.37-0.27 (m, 3H), 0.01 (t, J=6.0 Hz, 3H), −0.55 (s, 1H). LCMS (ESI): Calculated for $C_{50}H_{64}BrF_6N_8O_8$ [M+H]$^+$, 1097.4; Found, 1097.2.

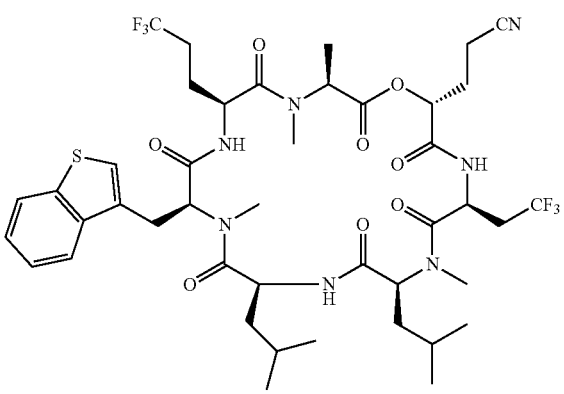 [SMILES: CC(C)C[C@@H]1NC(=O)[C@H](CC(C)C)N(C)C(=O)[C@H](CC(F)(F)F)NC(=O)[C@@H](CCC#N)OC(=O)[C@H](C)N(C)C(=O)[C@H](CCC(F)(F)F)NC(=O)[C@H](Cc2csc3ccccc23)N(C)C1=O]

C-49 $^1$H-NMR (400 MHz; acetone-$d_6$): δ 8.92 (d, J=10.0 Hz, 1H), 8.20 (d, J=9.5 Hz, 1H), 8.02 (dd, J=16.7, 7.9 Hz, 2H), 7.79-7.78 (m, 1H), 7.51-7.40 (m, 3H), 5.18 (ddd, J=16.4, 9.6, 4.6 Hz, 2H), 5.09 (td, J=11.3, 3.7 Hz, 2H), 4.39-4.31 (m, 1H), 4.28 (t, J=5.5 Hz, 1H), 4.04 (qd, J=9.1, 5.3 Hz, 1H), 3.47 (dd, J=15.0, 10.8 Hz, 2H), 3.33 (s, 3H), 3.19-3.11 (m, 1H), 2.96 (s, 3H), 2.57 (s, 4H), 2.34-2.20 (m, 3H), 2.19-2.01 (m, 4H), 1.98-1.88 (m, 1H), 1.87-1.80 (m, 1H), 1.74-1.64 (m, 2H), 1.49 (d, J=6.8 Hz, 4H), 1.37 (d, J=10.1 Hz, 2H), 1.22 (s, 1H), 1.01 (d, J=6.4 Hz, 3H), 0.95 (d, J=6.6 Hz, 3H), 0.49-0.48 (m, 3H), −0.08 (d, J=6.6 Hz, 2H), −0.41--0.48 (m, 1H). LCMS (ESI): Calculated for $C_{43}H_{58}F_6N_7O_8S$ [M+H]$^+$, 947.4; Found, 947.3.

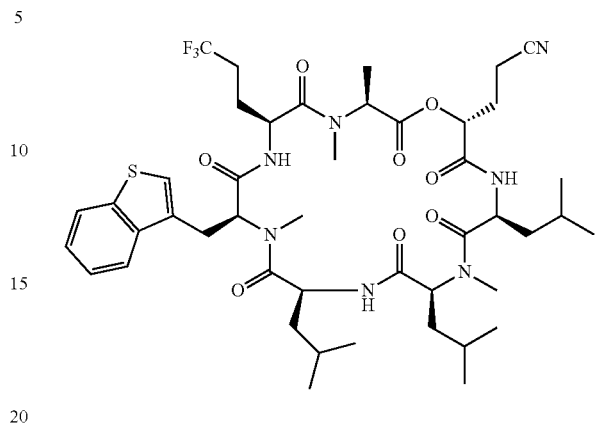

C-50 $^1$H-NMR (400 MHz; acetone-$d_6$): δ 8.96 (d, J=10.0 Hz, 1H), 8.05-7.95 (m, 3H), 7.70 (d, J=6.7 Hz, 1H), 7.52-7.40 (m, 3H), 5.17-5.04 (m, 2H), 4.88-4.82 (m, 1H), 4.36 (ddd, J=17.9, 9.5, 4.1 Hz, 2H), 4.01 (quintet, J=7.0 Hz, 1H), 3.47-3.36 (m, 2H), 3.31 (s, 3H), 2.96 (s, 3H), 2.52 (s, 4H), 2.27-2.21 (m, 3H), 1.94-1.73 (m, 4H), 1.66-1.45 (m, 8H), 1.39-1.33 (m, 2H), 1.05 (d, J=6.4 Hz, 3H), 0.96 (d, J=6.5 Hz, 3H), 0.92-0.88 (m, 5H), 0.83 (dd, J=9.6, 6.4 Hz, 1H), 0.50 (d, J=6.5 Hz, 3H), −0.07 (d, J=6.6 Hz, 3H), −0.42 (ddd, J=14.3, 11.1, 3.4 Hz, 1H). LCMS (ESI): Calculated for $C_{45}H_{65}F_3N_7O_8S$ [M+H]$^+$, 920.5; Found, 920.9.

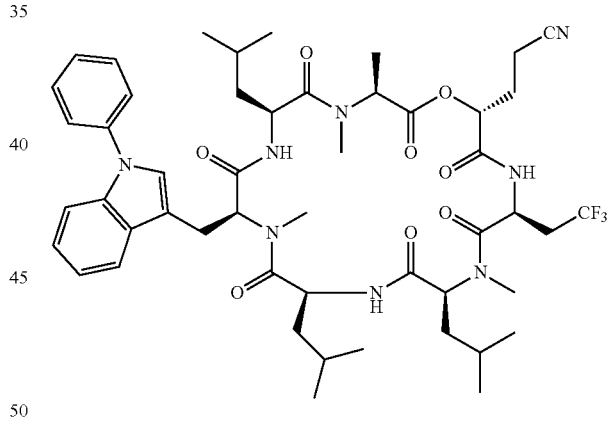

C-51 $^1$H-NMR (400 MHz; acetone-$d_6$): δ 8.70 (d, J=10.1 Hz, 1H), 8.28 (d, J=9.5 Hz, 1H), 7.84 (dd, J=7.0, 1.3 Hz, 1H), 7.71 (d, J=6.9 Hz, 1H), 7.64-7.53 (m, 5H), 7.42-7.38 (m, 1H), 7.36 (d, J=11.9 Hz, 1H), 7.28-7.20 (m, 2H), 5.22 (dt, J=9.4, 6.2 Hz, 1H), 5.13-5.06 (m, 3H), 4.41 (ddd, J=11.5, 7.4, 3.7 Hz, 1H), 4.31 (dd, J=10.9, 4.3 Hz, 1H), 3.97 (q, J=6.8 Hz, 1H), 3.37-3.31 (m, 5H), 3.16 (ddd, J=14.9, 11.2, 6.3 Hz, 1H), 2.95 (s, 3H), 2.59 (s, 3H), 2.52 (t, J=6.2 Hz, 2H), 2.32 (ddd, J=15.1, 11.0, 5.8 Hz, 1H), 2.23-2.16 (m, 1H), 1.97 (dtd, J=9.8, 7.5, 5.4 Hz, 1H), 1.83 (ddd, J=14.1, 10.8, 3.4 Hz, 1H), 1.68-1.34 (m, 12H), 1.03-0.94 (m, 13H), 0.41 (d, J=6.5 Hz, 3H), −0.06 (d, J=6.6 Hz, 3H), −0.38 (td, J=9.6, 4.1 Hz, 1H). LCMS (ESI): Calculated for $C_{50}H_{68}F_3N_8O_8$ [M+H]$^+$, 965.5; Found, 966.0.

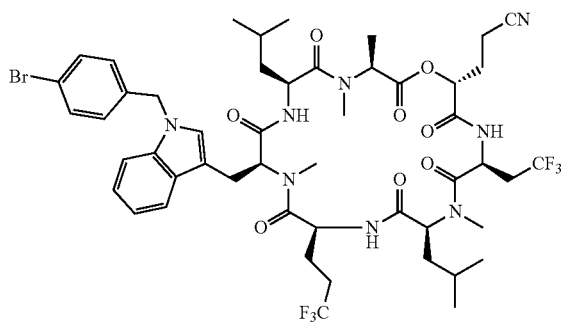 [SMILES: CC(C)C[C@@H]1NC(=O)[C@H](Cc2cn(Cc3ccc(Br)cc3)c3ccccc23)N(C)C(=O)[C@H](CCC(F)(F)F)NC(=O)[C@H](CC(C)C)N(C)C(=O)[C@H](CC(F)(F)F)NC(=O)[C@@H](CCC#N)OC(=O)[C@H](C)N(C)C1=O]

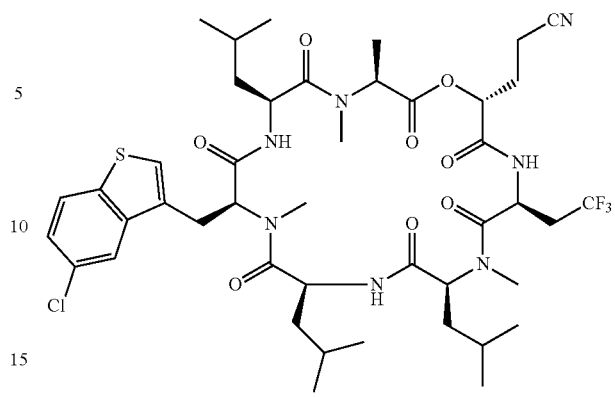

C-57 ¹H-NMR (400 MHz; acetone-d₆): δ 8.31 (dd, J=9.8, 5.1 Hz, 2H), 7.91 (d, J=7.0 Hz, 1H), 7.80-7.77 (m, 1H), 7.49-7.44 (m, 3H), 7.34 (d, J=2.9 Hz, 1H), 7.19-7.16 (m, 4H), 5.35 (d, J=4.0 Hz, 1H), 5.23 (dd, J=10.5, 4.8 Hz, 1H), 5.13 (td, J=9.9, 3.9 Hz, 2H), 4.36 (dd, J=11.0, 4.3 Hz, 1H), 4.13-4.09 (m, 1H), 4.00 (q, J=6.8 Hz, 1H), 3.34 (s, 3H), 3.23-3.15 (m, 2H), 2.89 (s, 3H), 2.66 (ddd, J=11.7, 7.9, 4.9 Hz, 2H), 2.59 (s, 3H), 2.36-2.25 (m, 2H), 2.16-2.13 (m, 1H), 1.82-1.77 (m, 2H), 1.68 (td, J=11.5, 4.3 Hz, 1H), 1.53-1.47 (m, 9H), 1.03 (d, J=6.5 Hz, 3H), 0.99-0.93 (m, 9H), 0.86 (dd, J=9.6, 6.6 Hz, 2H), 0.06-0.05 (m, 1H). LCMS (ESI): Calculated for C₅₀H₆₄BrF₆N₈O₈ [M+H]⁺, 1097.4; Found, 1097.0.

C-67 ¹H-NMR (400 MHz; d6-acetone): δ 8.76 (d, J=10.1 Hz, 1H), 8.30 (d, J=9.4 Hz, 1H), 8.16 (d, J=1.9 Hz, 1H), 8.01 (d, J=8.6 Hz, 1H), 7.77 (d, J=6.7 Hz, 1H), 7.47 (s, 1H), 7.43 (dd, J=8.6, 2.0 Hz, 1H), 5.18 (dt, J=9.4, 6.2 Hz, 1H), 5.12-5.02 (m, 3H), 4.38-4.25 (m, 2H), 3.98 (q, J=6.8 Hz, 1H), 3.45 (dd, J=15.1, 11.1 Hz, 1H), 3.34-3.30 (m, 3H), 3.27 (d, J=3.7 Hz, 1H), 3.20-3.08 (m, 2H), 2.91 (s, 3H), 2.59-2.56 (m, 5H), 1.99-1.93 (m, 1H), 1.82 (ddd, J=14.1, 10.9, 3.4 Hz, 1H), 1.67-1.61 (m, 2H), 1.59-1.29 (m, 12H), 1.01-0.91 (m, 15H), 0.46 (d, J=6.5 Hz, 3H), -0.04 (d, J=6.6 Hz, 3H), -0.55 (ddd, J=13.9, 10.7, 3.2 Hz, 1H). HRMS (ESI): Calculated for C₄₄H₆₀ClF₃N₇O₈S [M-H]⁻, 938.3870; Found, 938.3849.

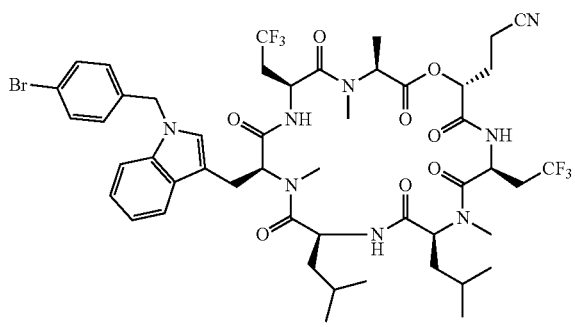 [SMILES: CC(C)C[C@@H]1NC(=O)[C@H](CC(C)C)N(C)C(=O)[C@H](CC(F)(F)F)NC(=O)[C@@H](CCC#N)OC(=O)[C@H](C)N(C)C(=O)[C@H](CC(F)(F)F)NC(=O)[C@H](Cc2cn(Cc3ccc(Br)cc3)c3ccccc23)N(C)C1=O]

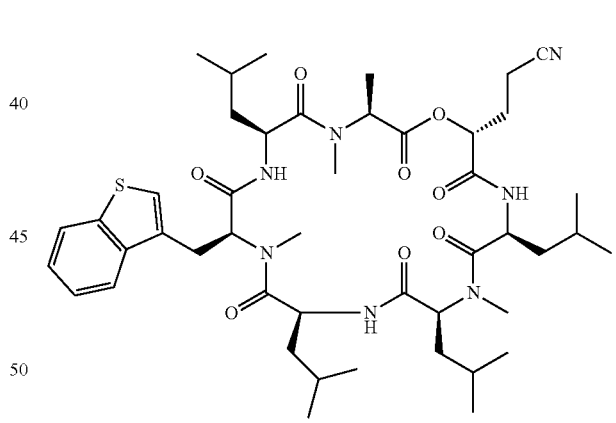

C-78 1:4 mixture of epimers; ¹H-NMR (400 MHz; acetone-d₆, major epimer): δ 8.97 (d, J=10.1 Hz, 1H), 8.15 (d, J=9.6 Hz, 1H), 7.80-7.77 (m, 2H), 7.49-7.43 (m, 3H), 7.30 (d, J=9.7 Hz, 1H), 7.23-7.09 (m, 5H), 5.51 (td, J=9.8, 4.3 Hz, 1H), 5.39-5.35 (m, 2H), 5.25 (dd, J=6.2, 3.3 Hz, 1H), 5.16-5.05 (m, 2H), 4.44-4.35 (m, 2H), 4.05-3.99 (m, 1H), 3.31 (s, 3H), 3.23-3.07 (m, 3H), 2.90 (s, 4H), 2.58 (s, 6H), 2.41-2.33 (m, 1H), 2.27-2.21 (m, 1H), 1.98-1.82 (m, 2H), 1.68-1.51 (m, 3H), 1.52-1.46 (m, 4H), 1.37-1.28 (m, 4H), 1.02 (d, J=6.4 Hz, 3H), 0.98-0.91 (m, 4H), 0.90-0.84 (m, 3H), 0.33 (d, J=6.4 Hz, 3H), -0.03 (d, J=6.6 Hz, 3H), -0.55--0.62 (m, 1H). LCMS (ESI): Calculated for C₄₉H₆₂BrF₆N₈O₈ [M+H]⁺, 1083.4; Found, 1083.2.

C-29 ¹H-NMR (400 MHz; acetone-d₆): δ 8.78 (d, J=10.1 Hz, 1H), 8.06-7.99 (m, 3H), 7.69-7.67 (m, 1H), 7.52-7.41 (m, 2H), 7.38 (s, 1H), 5.04 (t, J=5.0 Hz, 3H), 4.89-4.83 (m, 1H), 4.40-4.37 (m, 1H), 4.33-4.28 (m, 1H), 3.96 (q, J=6.8 Hz, 1H), 3.48-3.39 (m, 3H), 3.33 (s, 3H), 2.93 (s, 3H), 2.54 (d, J=2.3 Hz, 5H), 2.23-2.18 (m, 1H), 1.98-1.89 (m, 1H), 1.83-1.76 (m, 2H), 1.64-1.57 (m, 2H), 1.53-1.43 (m, 9H), 1.41-1.31 (m, 3H), 1.05 (d, J=6.4 Hz, 3H), 0.98-0.89 (m, 17H), 0.84 (dd, J=12.5, 5.6 Hz, 1H), 0.51 (d, J=6.4 Hz, 3H), -0.07 (d, J=6.5 Hz, 3H), -0.37--0.45 (m, 1H). LCMS (ESI): Calculated for C₄₆H₇ON₇O₈S [M+H]⁺, 880.5; Found, 880.4.

The following compounds were prepared using combined procedures within Examples 9-11:
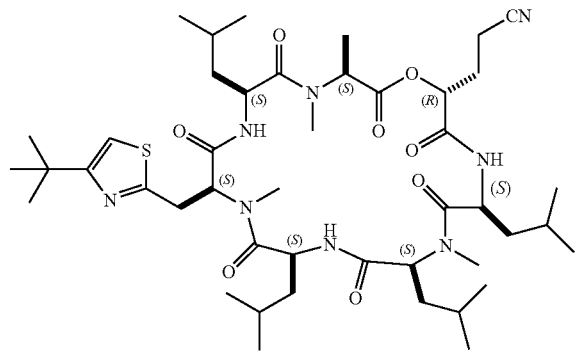
C-68 LC-MS (ESI): m/z 887.5 [M+H]+
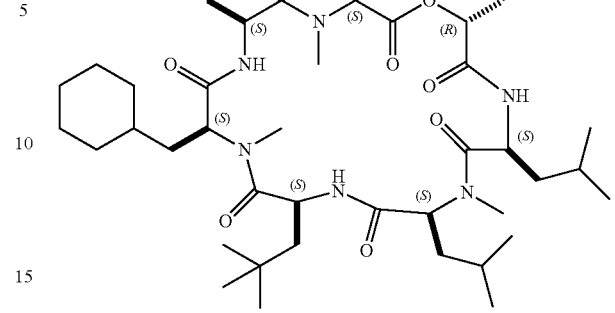
C-63 LC-MS (ESI): m/z 886.6 [M+H]+
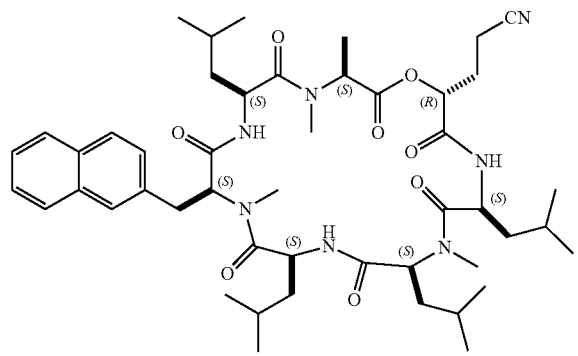
C-66 LC-MS (ESI): m/z 874.5 [M+H]+
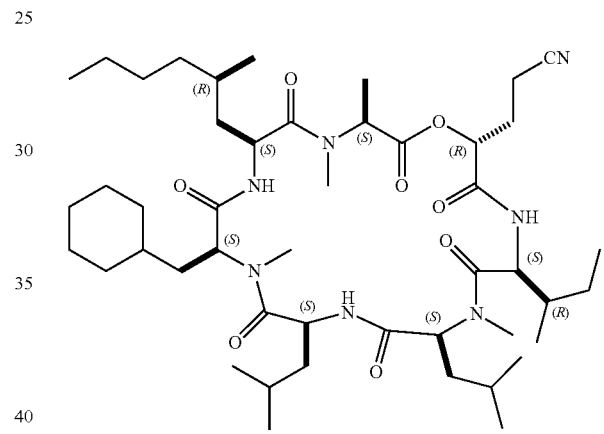
C-62 LC-MS (ESI): m/z 872.6 [M+H]+
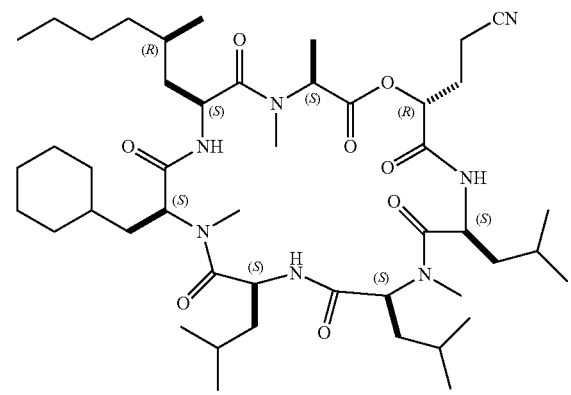
C-64 LC-MS (ESI): m/z 872.6 [M+H]+
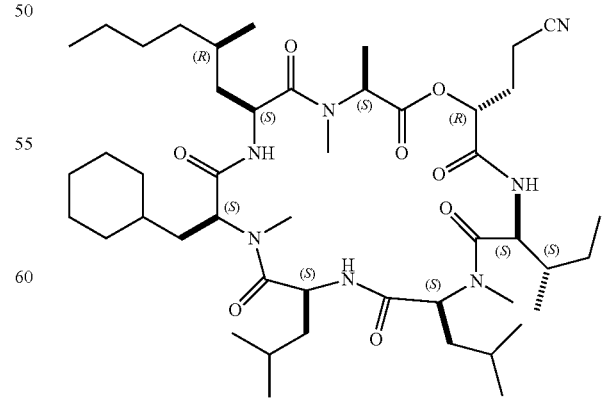
C-61 LC-MS (ESI): m/z 872.6 [M+H]+

143
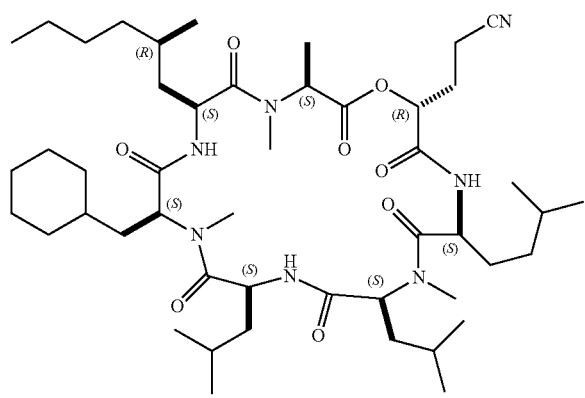
C-60 LC-MS (ESI): m/z 886.6 [M+H]+
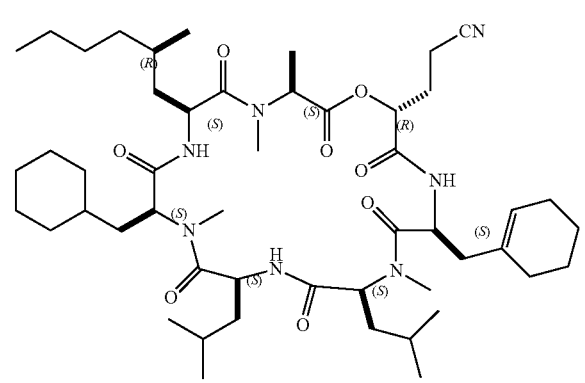
C-56 LC-MS (ESI): m/z 910.6 [M+H]+
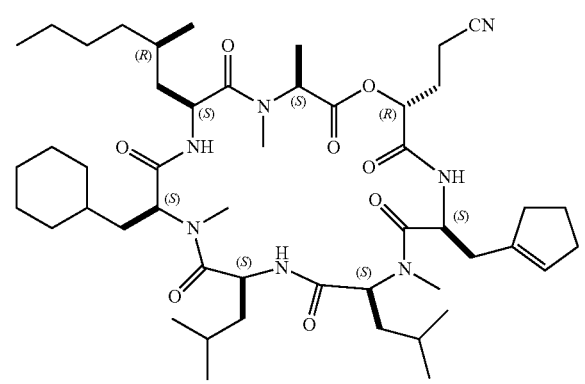
C-55 LC-MS (ESI): m/z 896.6 [M+H]+
144
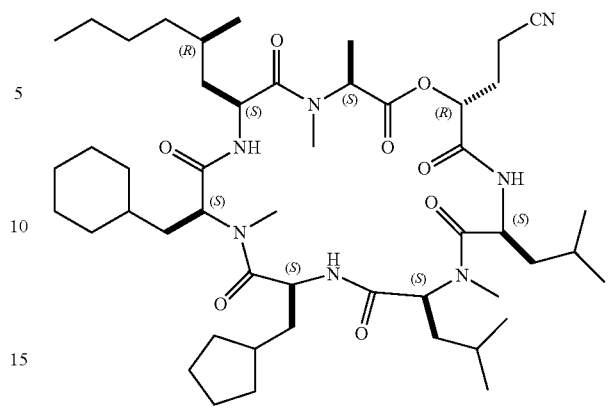
C-54 LC-MS (ESI): m/z 898.6 [M+H]+
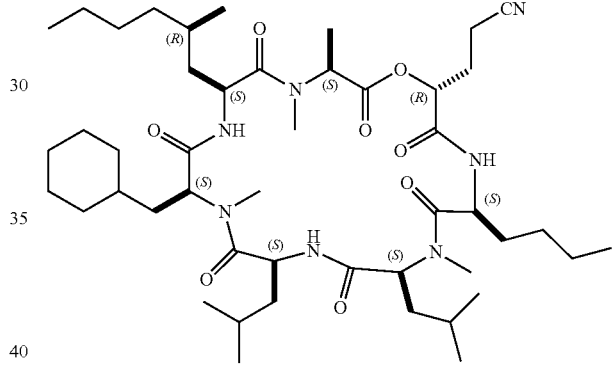
C-53 LC-MS (ESI): m/z 872.6 [M+H]+
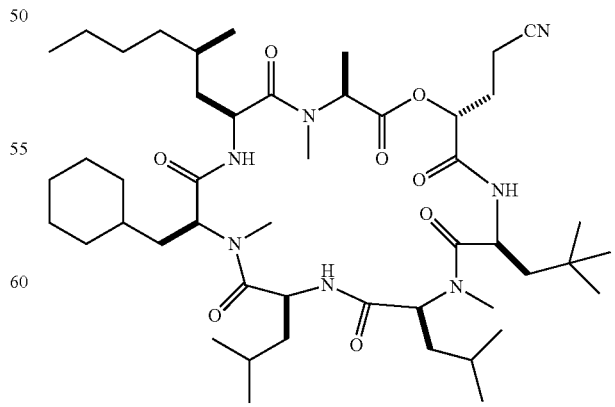
C-52 LC-MS (ESI): m/z 886.6 [M+H]+

145
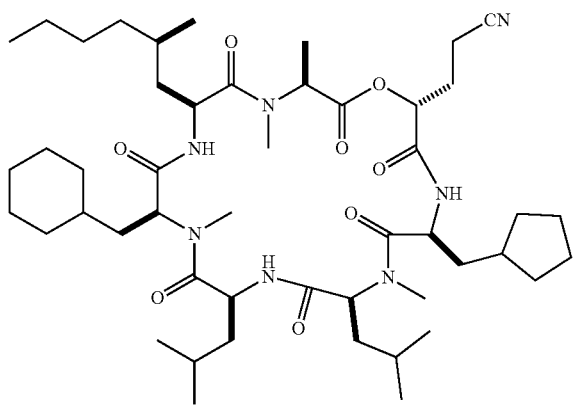
C-47 LC-MS (ESI): m/z 898.6 [M+H]+
146
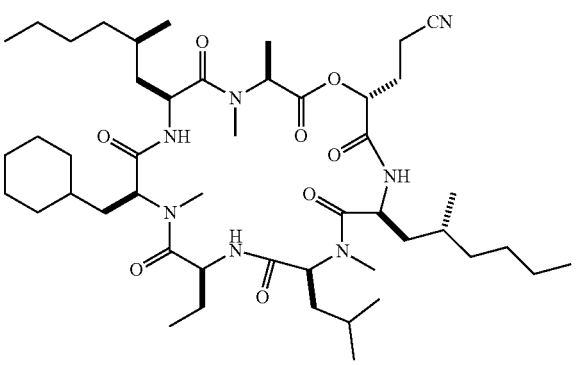
C-4 LCMS (ESI): m/z 88.6 [M+H]+
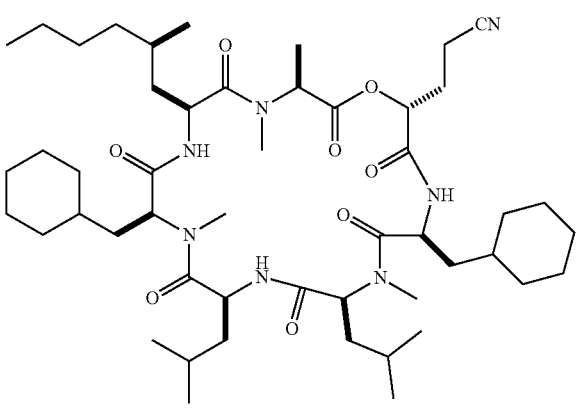
C-45 LC-MS (ESI): m/z 912.6 [M+H]+
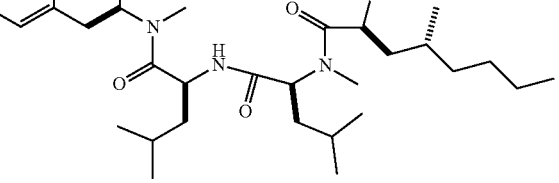
C-26 LCMS (ESI): m/z 892.5 [M+H]+
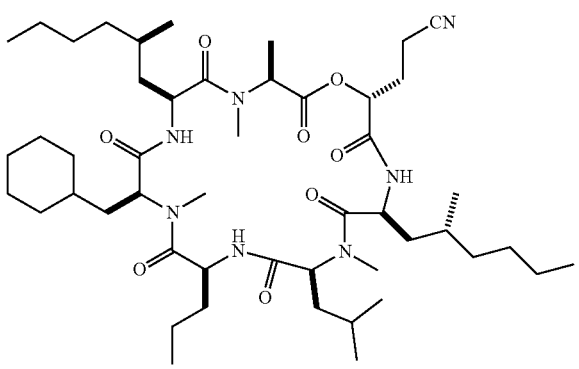
C-4 LC-MS (ESI): m/z 900.6 [M+H]+
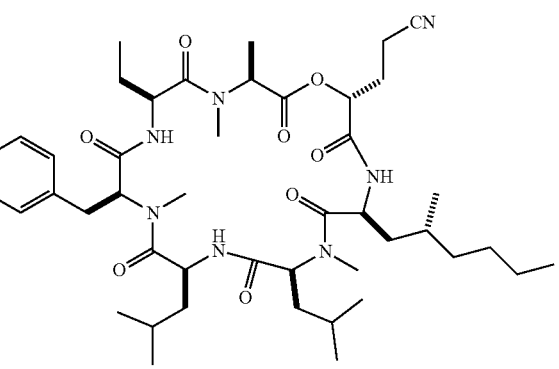
C-25 LC-MS (ESI): m/z 838.5 [M+H]+

147
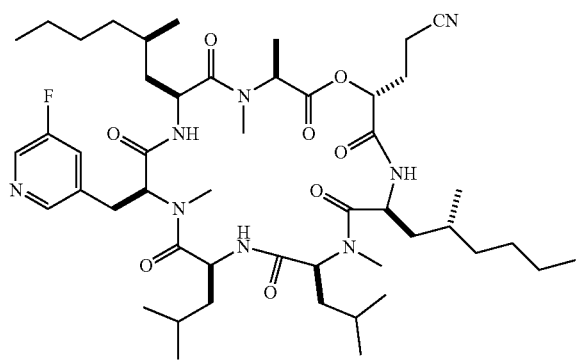
C-24 LC-MS (ESI): m/z 927.6 [M+H]+
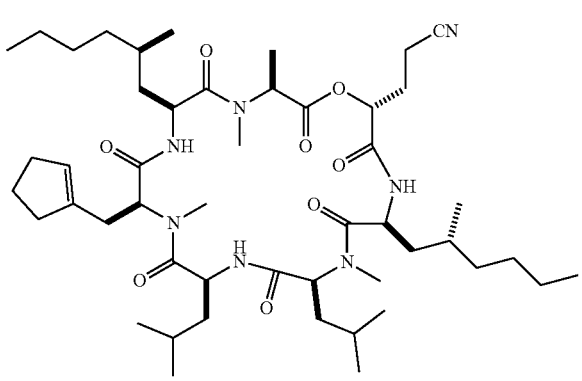
C-23 LC-MS (ESI): m/z 898.6 [M+H]+
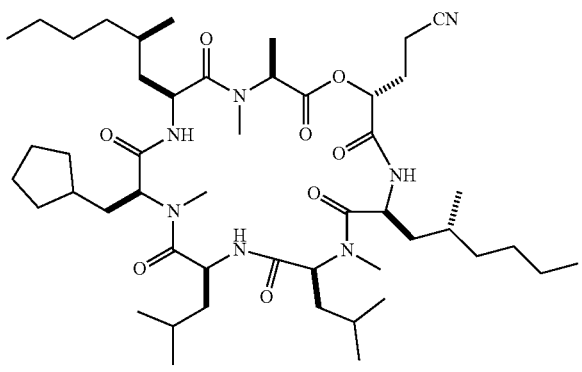
C-22 LC-MS (ESI): m/z 900.6 [M+H]+
148
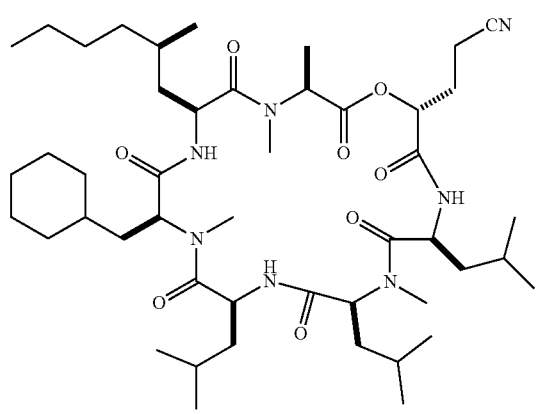
C-21 LC-MS (ESI): m/z 872.6 [M+H]+
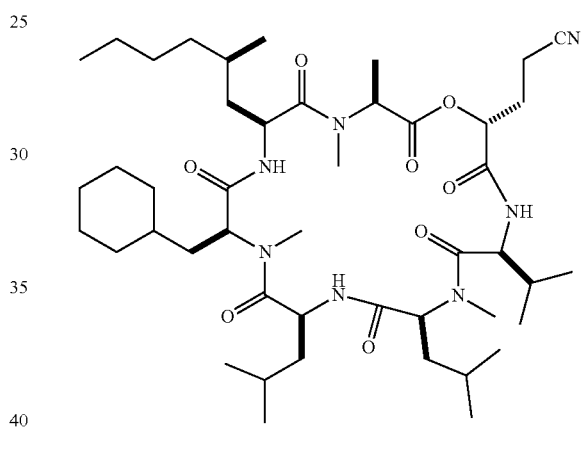
C-20 LC-MS (ESI): m/z 858.6 [M+H]+
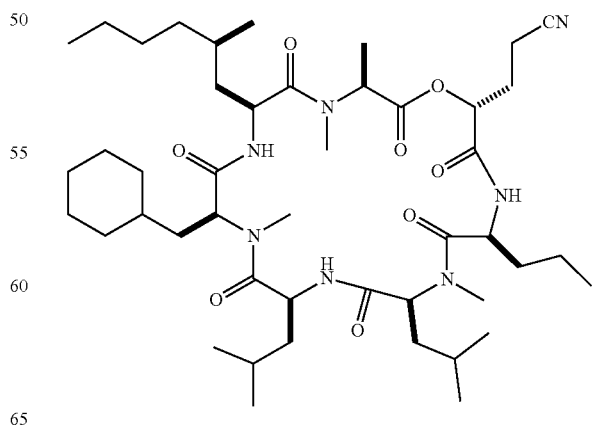
C-1.9 LC-MS (ESI): m/z 858.6 [M+H]+

149
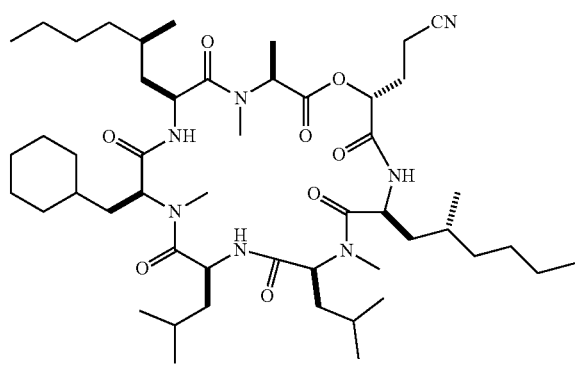
C-18 LC-MS (ESI): m/z 914.7 [M+H]$^+$
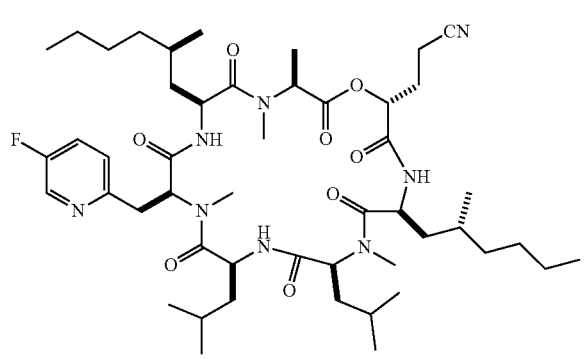
C-17 LC-MS (ESI): m/z 927.6 [M+H]$^+$
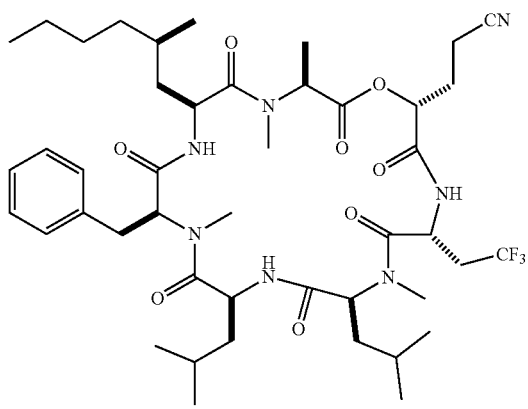
C-10 LC-MS (ESI): m/z 892.5 [M+H]$^+$
150
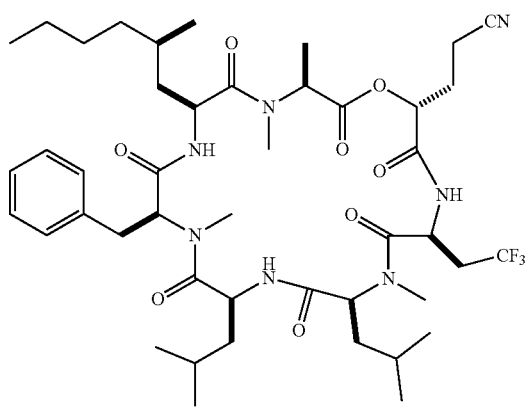
C-09 LC-MS (ESI): m/z 892.5 [M+H]$^+$
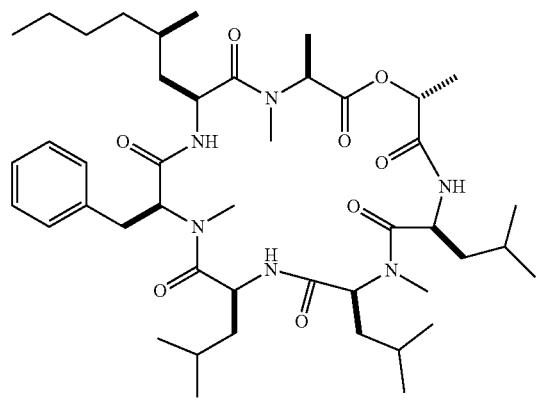
C-08 LC-MS (ESI): m/z 827.6 [M+H]$^+$
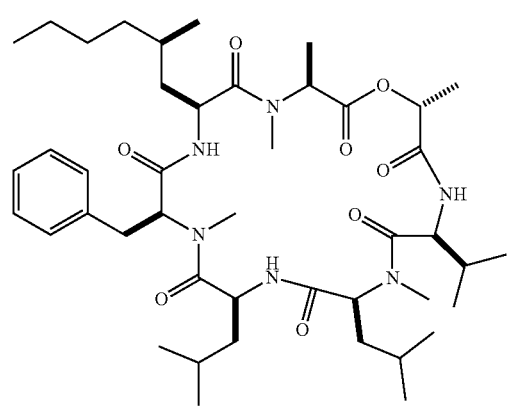
C-07 LC-MS (ESI): m/z 813.5 [M+H]$^+$

151
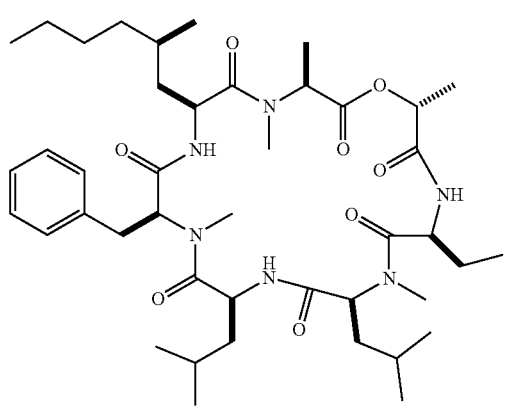
C-06 LC-MS (ESI): m/z 799.5 [M+H]⁺
152
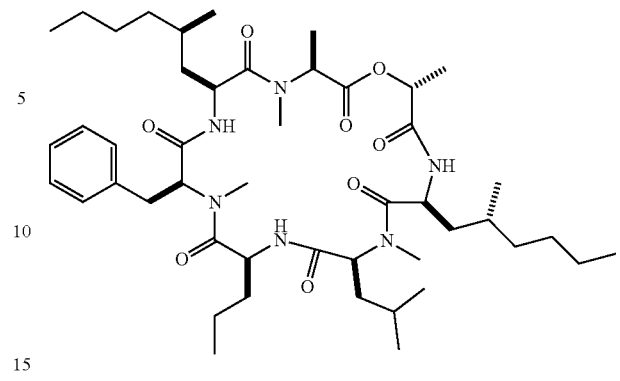
C-04 L-MS (ESI): m/z 855.6 [M+H]⁺
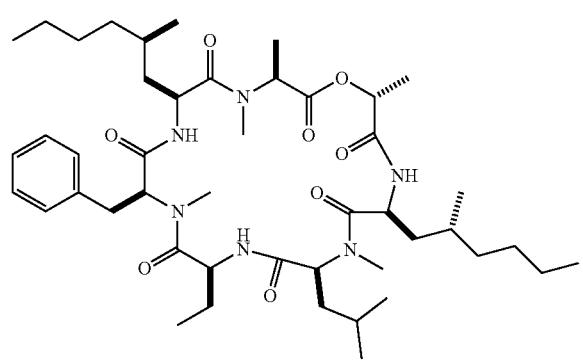
C-05 LC-MS (ESI): m/z 841.6 [M+H]⁺
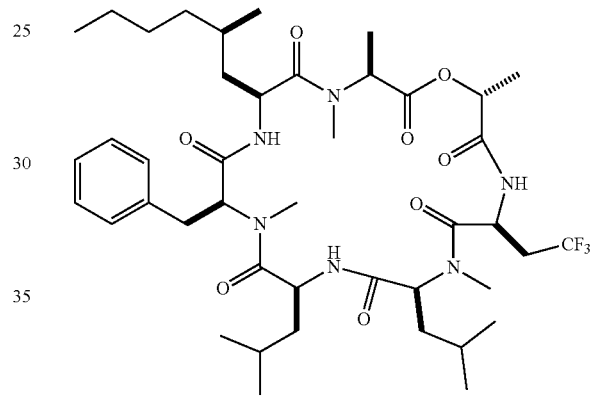
Example 12 C12
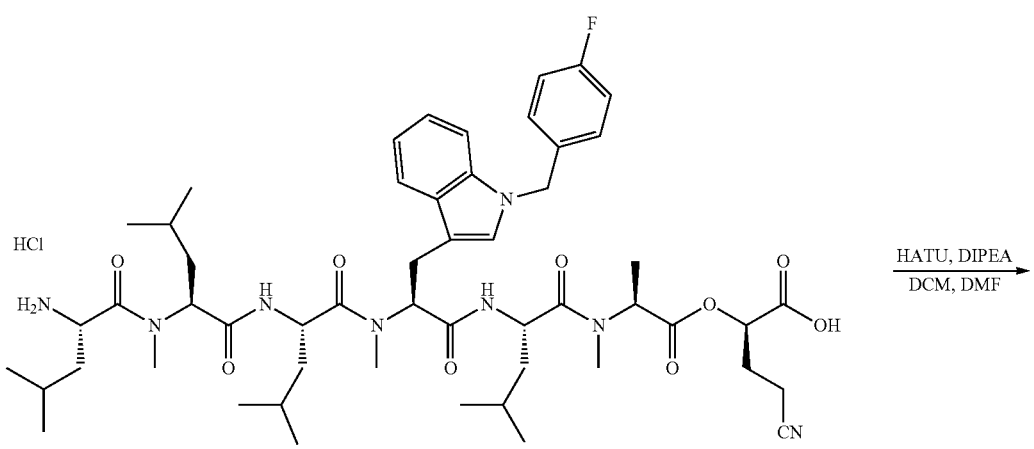

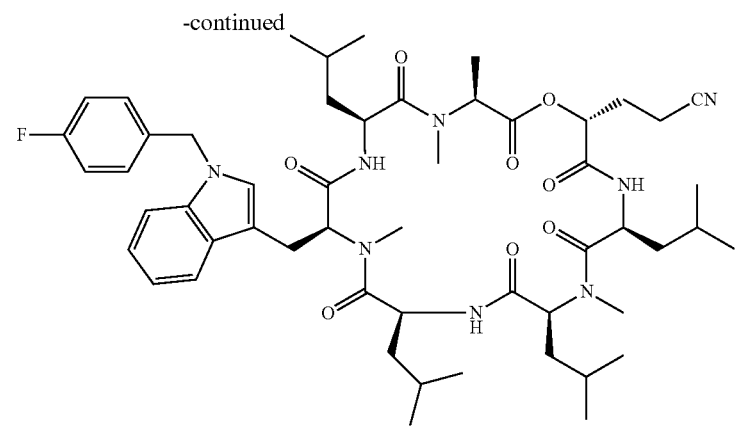

Simultaneously, solutions of both HATU (20 mg, 0.052 mmol) and HOAt (5.4 mg, 0.040 mmol) in DMF (2.5 mL) and linear heptadepsipeptide (44 mg, 0.040 mmol) were added via syringe pump, at a rate of 1 mL/h, to a solution of DIPEA (21 µL, 0.12 mmol) in DCM (35 mL) at room temperature under argon. After complete addition the reaction was stirred for 16 h, then concentrated under reduced pressure. The crude material was purified by reverse phase HPLC. $^1$H-NMR (400 MHz; acetone-$d_6$): δ 8.73 (d, J=9.9 Hz, 1H), 8.03 (d, J=9.6 Hz, 1H), 7.73 (d, J=7.6 Hz, 1H), 7.61 (d, J=6.7 Hz, 1H), 7.46 (d, J=8.1 Hz, 1H), 7.32 (td, J=6.0, 2.7 Hz, 2H), 7.27 (s, 1H), 7.18-7.05 (m, 4H), 5.43-5.37 (m, 3H), 5.09-5.01 (m, 3H), 4.89-4.83 (m, 1H), 4.41-4.32 (m, 2H), 3.94 (d, J=6.8 Hz, 2H), 3.31 (s, 3H), 3.28-3.24 (m, 1H), 2.91 (s, 3H), 2.54 (s, 3H), 2.50 (t, J=6.3 Hz, 2H), 2.22-2.16 (m, 1H), 1.97-1.93 (m, 1H), 1.84-1.75 (m, 2H), 1.64-1.56 (m, 3H), 1.56-1.44 (m, 9H), 1.38-1.26 (m, 3H), 1.05 (d, J=6.3 Hz, 3H), 0.98-0.89 (m, 18H), 0.36 (d, J=6.5 Hz, 3H), −0.01 (d, J=6.6 Hz, 3H), −0.52−−0.58 (m, 1H). LCMS (ESI): Calculated for $C_{53}H_{76}FN_8O_8$ [M+H]$^+$, 971.6; Found, 971.9.

The following compounds were prepared using the procedure of Example 12:

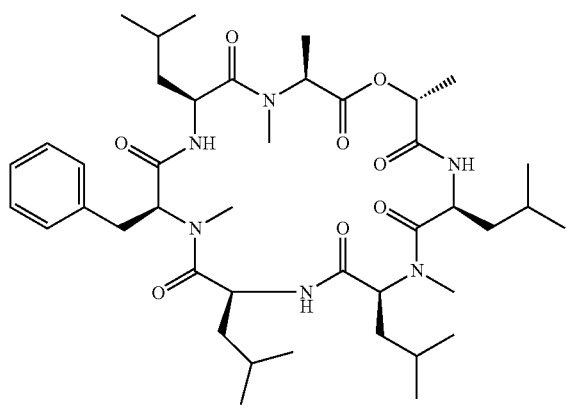 [SMILES: CC(C)C[C@@H]1NC(=O)[C@H](Cc2ccccc2)N(C)C(=O)[C@H](CC(C)C)NC(=O)[C@H](CC(C)C)N(C)C(=O)[C@H](CC(C)C)NC(=O)[C@@H](C)OC(=O)[C@H](C)N(C)C1=O]

C-34 $^1$H-NMR (400 MHz; DMSO-$d_6$): δ 8.77 (d, J=9.9 Hz, 1H), 8.36-8.34 (m, 1H), 7.69-7.67 (m, 1H), 7.30 (t, J=7.1 Hz, 2H), 7.25-7.20 (m, 3H), 4.84-4.77 (m, 3H), 4.68-4.66 (m, 1H), 4.33-4.28 (m, 1H), 4.19-4.14 (m, 1H), 3.92-3.87 (m, 2H), 3.19-3.14 (m, 1H), 2.94 (s, 3H), 2.74 (s, 3H), 2.41 (s, 3H), 1.71-1.63 (m, 3H), 1.51-1.43 (m, 5H), 1.34-1.23 (m, 10H), 1.20 (d, J=7.0 Hz, 4H), 0.98 (dd, J=8.8, 5.2 Hz, 6H), 0.89-0.82 (m, 15H), 0.69-0.67 (m, 3H), 0.58-0.57 (m, 3H). LCMS (ESI): Calculated for $C_{42}H_{69}N_6O_8$ [M+H]$^+$, 785.5; Found, 784.5.

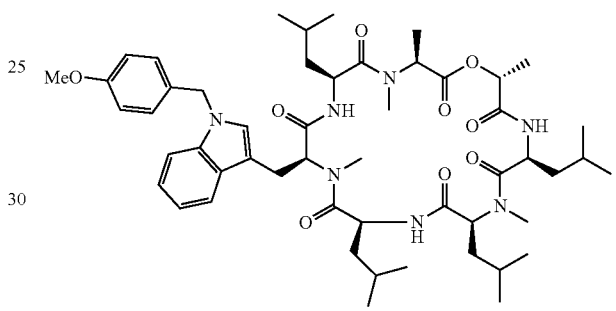

C-11 1H-NMR (400 MHz; acetone-d6): δ 8.85-8.83 (m, 1H), 7.80-7.77 (m, 1H), 7.59-7.54 (m, 2H), 7.46 (d, J=8.3 Hz, 1H), 7.23-7.12 (m, 4H), 7.07-7.03 (m, 1H), 6.89-6.86 (m, 2H), 5.32-5.31 (m, 2H), 5.01-4.84 (m, 3H), 4.46-4.42 (m, 1H), 4.38-4.33 (m, 1H), 3.77 (s, 4H), 3.46-3.39 (m, 1H), 3.21-3.15 (m, 1H), 3.07 (s, 3H), 2.90 (s, 3H), 2.53 (s, 3H), 1.82-1.74 (m, 3H), 1.62 (dd, J=8.9, 0.2 Hz, 3H), 1.54-1.42 (m, 11H), 1.33-1.30 (m, 4H), 1.23 (d, J=7.1 Hz, 3H), 1.06 (d, J=6.4 Hz, 3H), 0.99-0.89 (m, 17H), 0.50 (d, J=6.5 Hz, 3H), 0.11 (d, J=6.5 Hz, 3H), 0.01−−0.07 (m, 1H). LCMS (ESI): Calculated for $C_{52}H_{78}N_7O_9$ [M+H]$^+$, 944.6; Found, 945.2.

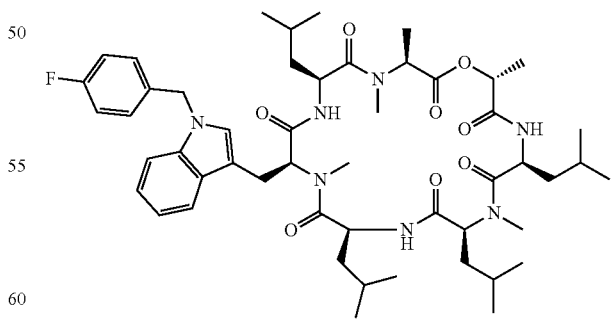

C-30 $^1$H-NMR (400 MHz; acetone-$d_6$): δ 8.90-8.86 (m, 1H), 7.83-7.79 (m, 1H), 7.60-7.55 (m, 2H), 7.47-7.45 (m, 1H), 7.33-7.29 (m, 2H), 7.29-7.24 (m, 1H), 7.17-7.13 (m, 1H), 7.11-7.04 (m, 3H), 5.43-5.39 (m, 2H), 5.04-4.83 (m, 4H), 4.45-4.41 (m, 1H), 4.35-4.32 (m, 1H), 3.84-3.79 (m, 2H), 3.14 (m, 5H), 2.90 (s, 3H), 2.53 (s, 2H), 1.81-1.72 (m, 2H), 1.63-1.56 (m, 3H), 1.54-1.42 (m, 7H), 1.31-1.20 (m, 6H), 1.06 (d, J=6.3 Hz, 3H), 0.99-0.88 (m, 18H), 0.45-0.43 (m, 3H), 0.07-0.06 (m, 3H), −0.15−−0.21 (m, 1H). LCMS (ESI): Calculated for $C_{51}H_{75}FN_7O_8$ [M+H]$^+$, 932.6; Found, 933.1.

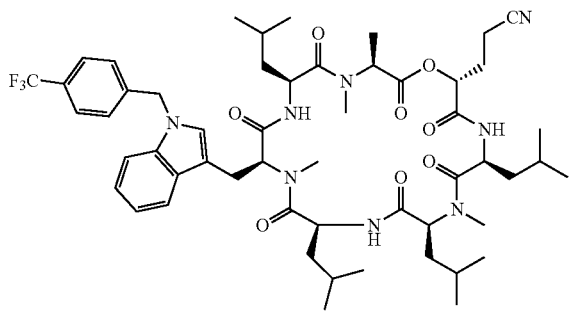 [SMILES: CC(C)C[C@@H]1NC(=O)[C@H](Cc2cn(Cc3ccc(C(F)(F)F)cc3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]

C-42 $^1$H-NMR (400 MHz; aceton-d$_6$): δ 8.75-8.72 (m, 1H), 8.04-8.02 (m, 1H), 7.77-7.75 (m, 1H), 7.71-7.60 (m, 3H), 7.47-7.43 (m, 2H), 7.40-7.32 (m, 2H), 7.19-7.10 (m, 2H), 5.54 (s, 2H), 5.10-5.02 (m, 3H), 4.90-4.83 (m, 1H), 4.42-4.35 (m, 1H), 3.97-3.92 (m, 1H), 3.31 (s, 2H), 3.27-3.01 (m, 4H), 2.92 (s, 2H), 2.54-2.53 (m, 2H), 2.50 (d, J=6.2 Hz, 1H), 2.23-2.16 (m, 1H), 2.00-1.92 (m, 1H), 1.80-1.75 (m, 2H), 1.64-1.57 (m, 3H), 1.56-1.45 (m, 9H), 1.39-1.28 (m, 4H), 1.06-0.85 (m, 12H), 0.55-0.51 (m, 1H), 0.37-0.36 (m, 2H), 0.02-0.00 (m, 2H), −0.45−−0.53 (m, 1H). LCMS (ESI): Calculated for $C_{54}H_6F_3N_8O_8$ [M+H]$^+$, 1021.6; Found, 1021.9.

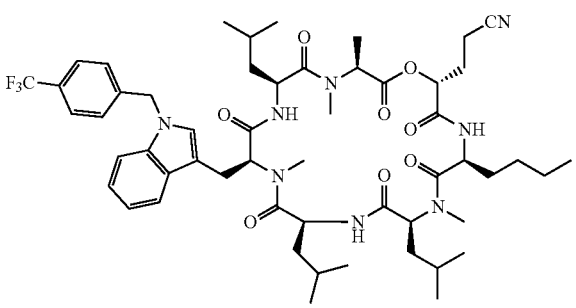 [SMILES: CCCC[C@@H]1NC(=O)[C@@H](CCC#N)OC(=O)[C@H](C)N(C)C(=O)[C@H](CC(C)C)NC(=O)[C@H](Cc2cn(Cc3ccc(C(F)(F)F)cc3)c3ccccc23)N(C)C(=O)[C@H](CC(C)C)NC(=O)[C@H](CC(C)C)N(C)C1=O]

C-46 $^1$H-NMR (400 MHz; acetone-d$_6$): δ 8.75-8.72 (m, 1H), 8.05-8.01 (m, 1H), 7.77-7.75 (m, 1H), 7.67-7.60 (m, 2H), 7.47-7.43 (m, 2H), 7.32 (s, 1H), 7.18-7.10 (m, 2H), 5.54 (s, 2H), 5.11-5.02 (m, 2H), 4.81-4.74 (m, 1H), 4.41-4.33 (m, 2H), 3.97-3.92 (m, 1H), 3.31 (s, 2H), 3.27-3.22 (m, 2H), 2.92 (s, 2H), 2.55-2.53 (m, 2H), 2.51-2.50 (m, 1H), 2.23-2.16 (m, 1H), 2.01-1.90 (m, 1H), 1.82-1.74 (m, 1H), 1.66-1.57 (m, 2H), 1.57-1.47 (m, 5H), 1.40-1.22 (m, 5H), 1.04-0.87 (m, 10H), 0.37-0.35 (m, 3H), 0.01 (dd, J=6.2, 2.6 Hz, 3H), −0.45−−0.53 (m, 1H). LCMS (ESI): Calculated for $C_{54}H_{76}F_3N_8O_8$ [M+H]$^+$, 1021.6; Found, 1022.4.

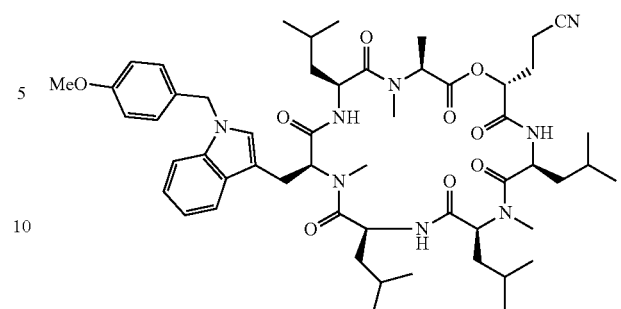

C-31 $^1$H-NMR (400 MHz; acetone-d$_6$): δ 8.65-8.63 (m, 1H), 8.05-8.03 (m, 1H), 7.91-7.89 (m, 1H), 7.62-7.59 (m, 2H), 7.32-7.30 (m, 1H), 7.16-7.12 (m, 2H), 7.07-7.05 (m, 2H), 6.87-6.84 (m, 2H), 5.64 (s, 1H), 5.15-5.04 (m, 4H), 4.90-4.86 (m, 2H), 4.44-4.40 (m, 1H), 4.34-4.28 (m, 2H), 3.77 (s, 5H), 3.32 (s, 3H), 3.30-3.26 (m, 2H), 2.94 (s, 3H), 2.58-2.56 (m, 3H), 2.54 (s, 2H), 2.23-2.17 (m, 2H), 2.00-1.94 (m, 2H), 1.81-1.73 (m, 4H), 1.64-1.54 (m, 6H), 1.54-1.42 (m, 10H), 1.36-1.29 (m, 8H), 1.06 (d, J=6.4 Hz, 2H), 1.01-0.85 (m, 18H), 0.52-0.51 (m, 3H), −0.03−−0.05 (m, 3H), −0.29−−0.36 (m, 1H). LCMS (ESI): Calculated for $C_{54}H_{79}N_8O_9$ [M+H]$^+$, 983.6; Found, 984.2.

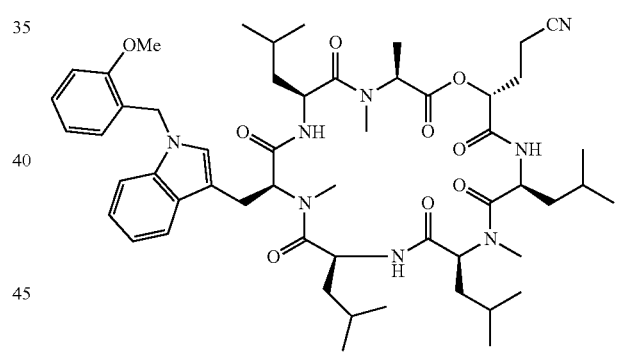

C-32 $^1$H-NMR (400 MHz; acetone-d$_6$) δ 8.74-8.71 (m, 1H), 8.04-8.01 (m, 1H), 7.73-7.71 (m, 1H), 7.59-7.57 (m, 1H), 7.49 (d, J=8.2 Hz, 1H), 7.29-7.21 (m, 2H), 7.17-7.06 (m, 2H), 7.04-7.01 (m, 2H), 6.84 (td, J=7.5, 0.9 Hz, 1H), 5.37-5.26 (m, 2H), 5.10-5.01 (m, 3H), 4.89-4.83 (m, 2H), 4.40-4.33 (m, 2H), 3.93 (s, 5H), 3.30 (d, J=6.7 Hz, 3H), 3.26-3.23 (m, 2H), 2.92 (s, 2H), 2.54 (s, 3H), 2.49 (t, J=6.2 Hz, 2H), 2.22-2.15 (m, 2H), 1.97-1.89 (m, 2H), 1.83-1.75 (m, 3H), 1.63-1.57 (m, 4H), 1.52-1.39 (m, 9H), 1.39-1.19 (m, 7H), 1.05 (d, J=6.3 Hz, 4H), 1.00-0.88 (m, 18H), 0.28 (d, J=6.5 Hz, 3H), −0.08 (d, J=6.6 Hz, 3H), −0.54−−0.61 (m, 1H). LCMS (ESI): Calculated for $C_{54}H_{79}N_8O_9$ [M+H]$^+$, 983.6; Found, 984.1.

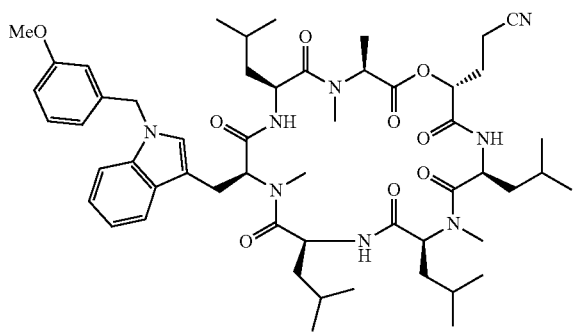 [SMILES: COc1cccc(Cn2cc(C[C@H]3C(=O)N[C@@H](CC(C)C)C(=O)N(C)[C@@H](C)C(=O)O[C@H](CCC#N)C(=O)N[C@@H](CC(C)C)C(=O)N(C)[C@@H](CC(C)C)C(=O)N[C@@H](CC(C)C)C(=O)N3C)c3ccccc32)c1]

C-13 ¹H-NMR (400 MHz; acetone-d₆): δ 8.71-8.68 (m, 1H), 8.03-8.00 (m, 1H), 7.74-7.72 (m, 1H), 7.63-7.61 (m, 1H), 7.48-7.46 (m, 1H), 7.27-7.20 (m, 2H), 7.18-7.08 (m, 2H), 6.88-6.82 (m, 2H), 5.36-5.35 (m, 2H), 5.07-5.00 (m, 3H), 4.90-4.83 (m, 1H), 4.42-4.32 (m, 2H), 3.92 (t, J=6.8 Hz, 2H), 3.77 (s, 4H), 3.28 (m, 5H), 2.91 (s, 3H), 2.54 (s, 3H), 2.48-2.45 (m, 2H), 2.23-2.14 (m, 2H), 1.98-1.90 (m, 2H), 1.84-1.73 (m, 3H), 1.67-1.59 (m, 4H), 1.52-1.47 (m, 8H), 1.38-1.30 (m, 5H), 1.05 (d, J=6.3 Hz, 3H), 1.00-0.89 (m, 19H), 0.41 (d, J=6.4 Hz, 2H), 0.01 (d, J=6.6 Hz, 2H), −0.38−−0.46 (m, 1H). LCMS (ESI): Calculated for C₅₄H₇₉N₈O₉ [M+H]⁺, 983.6; Found, 983.9.

C-15 ¹H-NMR (400 MHz; acetone-d₆): δ 8.71-8.69 (m, 1H), 8.03-8.00 (m, 1H), 7.74-7.72 (m, 1H), 7.62 (ddt, J=6.3, 1.3, 0.4 Hz, 1H), 7.51 (d, J=8.2 Hz, 1H), 7.24 (s, 1H), 7.22-7.18 (m, 1H), 7.14-7.11 (m, 1H), 5.96 (d, J=0.3 Hz, 1H), 5.39 (d, J=1.8 Hz, 2H), 5.07-5.01 (m, 2H), 4.89-4.85 (m, 1H), 4.42-4.32 (m, 2H), 3.97-3.91 (m, 1H), 3.29 (s, 4H), 3.27-3.25 (m, 2H), 2.91 (s, 3H), 2.54 (s, 2H), 2.47 (dd, J=6.4, 6.2 Hz, 2H), 2.34 (d, J=2.9 Hz, 3H), 2.23-2.14 (m, 2H), 1.96-1.90 (m, 2H), 1.81-1.74 (m, 2H), 1.74-1.66 (m, 2H), 1.64-1.56 (m, 3H), 1.52-1.47 (m, 7H), 1.39-1.30 (m, 6H), 1.05 (d, J=6.3 Hz, 3H), 0.98-0.89 (m, 18H), 0.43 (d, J=6.4 Hz, 2H), 0.23-0.18 (m, 1H), 0.01 (d, J=6.6 Hz, 2H), −0.41−−0.49 (m, 1H). LCMS (ESI): Calculated for C₅₁H₇₆N₉O₉ [M+H]⁺, 958.6; Found, 958.9.

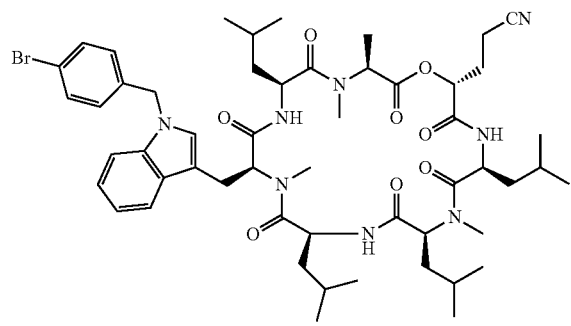 [SMILES: CC(C)C[C@@H]1NC(=O)[C@H](Cc2cn(Cc3ccc(Br)cc3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]

C-14 ¹H-NMR (400 MHz; acetone-d₆): δ 8.73 (d, J=10.0 Hz, 1H), 8.02 (d, J=9.7 Hz, 1H), 7.74 (d, J=7.6 Hz, 1H), 7.61 (d, J=6.9 Hz, 1H), 7.50-7.47 (m, 2H), 7.44 (d, J=8.1 Hz, 1H), 7.27 (s, 1H), 7.20 (t, J=9.7 Hz, 2H), 7.18-7.09 (m, 2H), 5.39 (s, 2H), 5.11-5.01 (m, 3H), 4.89-4.83 (m, 1H), 4.41-4.33 (m, 2H), 3.30-3.21 (m, 5H), 2.91 (s, 3H), 2.54 (s, 3H), 2.50 (t, J=6.3 Hz, 2H), 2.22-2.15 (m, 1H), 1.98-1.90 (m, 1H), 1.83-1.71 (m, 3H), 1.64-1.44 (m, 12H), 1.39-1.29 (m, 3H), 1.05 (d, J=6.3 Hz, 3H), 0.94 (dt, J=21.9, 7.8 Hz, 19H), 0.36 (d, J=6.4 Hz, 3H), 0.00 (d, J=6.6 Hz, 3H), −0.48−−0.55 (m, 1H). LCMS (ESI): Calculated for C₅₃H₇₆BrN₈O₈ [M+H]⁺, 1031.5; Found, 1031.2.

C-28 ¹H-NMR (400 MHz; acetone-d₆): δ 8.75-8.73 (m, 1H), 8.03 (dd, J=9.6, 0.2 Hz, 1H), 7.76-7.74 (m, 1H), 7.65-7.63 (m, 1H), 7.47 (d, J=8.0 Hz, 1H), 7.31-7.22 (m, 3H), 7.19-7.10 (m, 2H), 5.45-5.39 (m, 2H), 5.10-5.01 (m, 3H), 4.89-4.83 (m, 1H), 4.41-4.32 (m, 2H), 3.97-3.92 (m, 1H), 3.32 (s, 3H), 3.25-3.24 (m, 2H), 2.91 (s, 3H), 2.54 (s, 3H), 2.52 (t, J=6.3 Hz, 2H), 2.23-2.16 (m, 2H), 2.00-1.90 (m, 1H), 1.83-1.76 (m, 3H), 1.64-1.40 (m, 12H), 1.40-1.26 (m, 4H), 1.06-1.00 (m, 3H), 1.03-0.87 (m, 17H), 0.83-0.77 (m, 1H), 0.34 (d, J=6.5 Hz, 3H), −0.03 (d, J=6.6 Hz, 3H), −0.54−−0.61 (m, 1H). LCMS (ESI): Calculated for C₅₃H₇₅F₂N₈O₈ [M+H]⁺, 989.6; Found, 989.5.

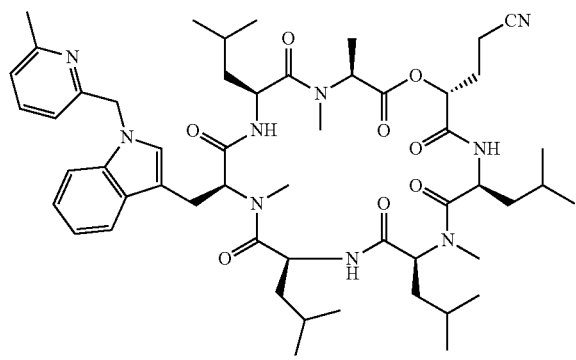 [SMILES: Cc1cccc(Cn2cc(C[C@H]3C(=O)N[C@@H](CC(C)C)C(=O)N(C)[C@@H](C)C(=O)O[C@H](CCC#N)C(=O)N[C@@H](CC(C)C)C(=O)N(C)[C@@H](CC(C)C)C(=O)N[C@@H](CC(C)C)C(=O)N3C)c3ccccc32)n1]

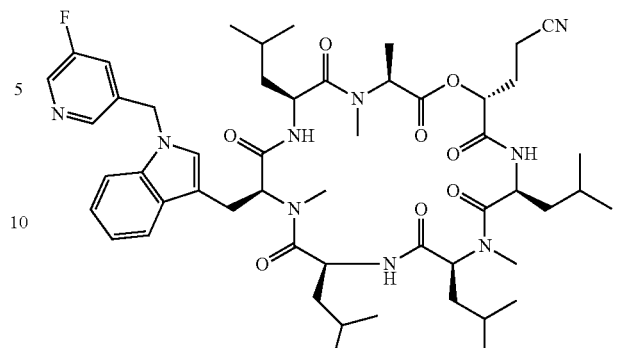

C-33 $^1$H-NMR (400 MHz; acetone-$d_6$): δ 8.74-8.71 (m, 1H), 8.04-8.01 (m, 1H), 7.74 (dt, J=7.7, 0.4 Hz, 1H), 7.62-7.57 (m, 2H), 7.47-7.45 (m, 1H), 7.31 (s, 1H), 7.18-7.11 (m, 3H), 6.81-6.79 (m, 1H), 5.47-5.42 (m, 2H), 5.10-5.01 (m, 3H), 4.90-4.83 (m, 1H), 4.42-4.32 (m, 2H), 3.97-3.92 (m, 1H), 3.31 (s, 3H), 3.26 (t, J=0.3 Hz, 2H), 2.92 (s, 3H), 2.55 (s, 3H), 2.50 (t, J=6.3 Hz, 2H), 2.23-2.14 (m, 2H), 1.97-1.90 (m, 2H), 1.83-1.75 (m, 2H), 1.65-1.45 (m, 11H), 1.39-1.27 (m, 4H), 1.05 (d, J=6.3 Hz, 2H), 0.99-0.84 (m, 16H), 0.84-0.76 (m, 1H), 0.41-0.39 (m, 2H), 0.01--0.01 (m, 2H), −0.45--0.52 (m, 1H). LCMS (ESI): Calculated for $C_{53}H_{78}N_9O_8$ [M+H]$^+$, 968.6; Found, 968.5.

C-35 $^1$H-NMR (400 MHz; acetone-$d_6$): δ 8.74 (d, J=10.0 Hz, 1H), 8.48-8.44 (m, 2H), 8.04 (d, J=9.7 Hz, 1H), 7.77-7.75 (m, 1H), 7.66-7.64 (m, 1H), 7.52 (d, J=8.3 Hz, 2H), 7.36 (s, 2H), 7.21-7.11 (m, 2H), 5.55 (s, 2H), 5.11-5.01 (m, 3H), 4.89-4.83 (m, 1H), 4.41-4.33 (m, 2H), 3.95 (q, J=6.8 Hz, 1H), 3.38-3.33 (s, 3H), 3.32-3.25 (m, 2H), 2.92 (s, 3H), 2.54 (s, 3H), 2.51 (d, J=6.2 Hz, 2H), 2.23-2.15 (m, 1H), 1.99-1.90 (m, 1H), 1.84-1.74 (m, 2H), 1.71-1.56 (m, 3H), 1.56-1.44 (m, 8H), 1.38-1.26 (m, 3H), 1.05 (d, J=6.3 Hz, 3H), 1.01-0.87 (m, 18H), 0.31 (d, J=6.4 Hz, 3H), −0.03 (d, J=6.5 Hz, 2H), −0.55--0.61 (m, 1H). LCMS (ESI): Calculated for $C_{52}H_{75}FN_9O_8$ [M+H]$^+$, 972.6; Found, 973.6.

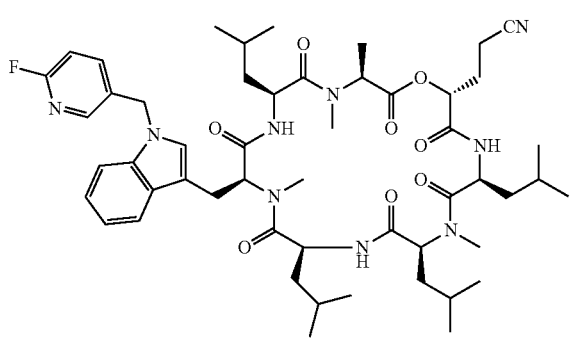 [SMILES: CC(C)C[C@@H]1NC(=O)[C@H](Cc2cn(Cc3ccc(F)nc3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]

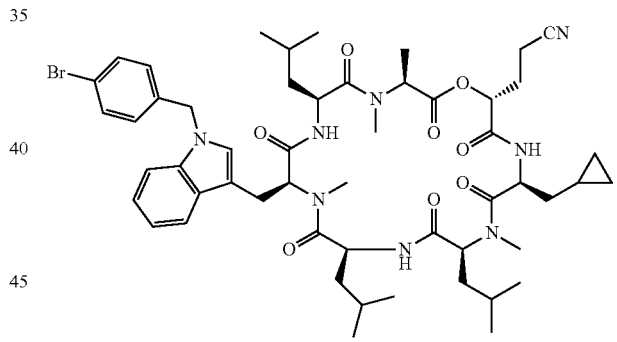

C-36 $^1$H-NMR (400 MHz; acetone-$d_6$): δ 8.75 (d, J=10.0 Hz, 1H), 8.25-8.24 (m, 1H), 8.03 (d, J=9.7 Hz, 1H), 7.87 (td, J=8.1, 2.5 Hz, 1H), 7.75 (d, J=7.6 Hz, 1H), 7.64-7.62 (m, 1H), 7.53 (d, J=8.1 Hz, 1H), 7.34 (d, J=2.9 Hz, 1H), 7.20-7.10 (m, 2H), 7.02 (dd, J=8.4, 2.9 Hz, 1H), 5.48 (s, 2H), 5.07-5.01 (m, 2H), 4.89-4.83 (m, 2H), 4.40-4.31 (m, 2H), 3.95 (q, J=6.8 Hz, 1H), 3.32 (s, 3H), 3.25-3.20 (m, 2H), 2.91 (s, 3H), 2.54-2.51 (m, 3H), 2.50 (s, 1H), 2.23-2.15 (m, 1H), 1.99-1.89 (m, 1H), 1.83-1.75 (m, 2H), 1.64-1.55 (m, 3H), 1.55-1.44 (m, 8H), 1.37-1.21 (m, 3H), 1.05 (d, J=6.3 Hz, 3H), 0.98-0.89 (m, 18H), 0.29 (d, J=6.5 Hz, 3H), −0.04 (d, J=6.6 Hz, 3H), −0.62--0.69 (m, 1H). LCMS (ESI): Calculated for $C_{52}H_{75}FN_9O_8$ [M+H]$^+$, 972.6; Found, 973.6.

C-38 $^1$H-NMR (400 MHz; acetone-$d_6$): δ 8.74-8.71 (m, 1H), 8.06-8.02 (m, 1H), 7.76-7.73 (m, 1H), 7.64-7.61 (m, 1H), 7.50-7.43 (m, 3H), 7.28 (d, J=2.6 Hz, 1H), 7.24-7.21 (m, 1H), 7.21-7.09 (m, 3H), 5.43-5.38 (m, 2H), 5.10-5.02 (m, 2H), 4.95-4.89 (m, 2H), 4.40-4.36 (m, 2H), 3.96-3.91 (m, 2H), 3.30 (s, 3H), 3.24-3.20 (m, 3H), 2.91 (s, 3H), 2.55 (s, 3H), 2.51-2.48 (m, 2H), 2.22-2.15 (m, 2H), 2.02-1.97 (m, 1H), 1.62-1.54 (m, 4H), 1.47 (d, J=6.8 Hz, 3H), 1.39-1.28 (m, 3H), 1.06 (d, J=6.2 Hz, 2H), 0.99-0.94 (m, 8H), 0.74-0.70 (m, 1H), 0.37-0.34 (m, 3H), 0.19-0.14 (m, 1H), 0.14-0.05 (m, 2H), 0.01--0.00 (m, 2H), −0.49--0.56 (m, 1H). LC-MS (ESI): Calculated for $C_{53}H_{74}BrN_8O_8$ [M+H]$^+$, 1029.5; Found, 1029.4.

161

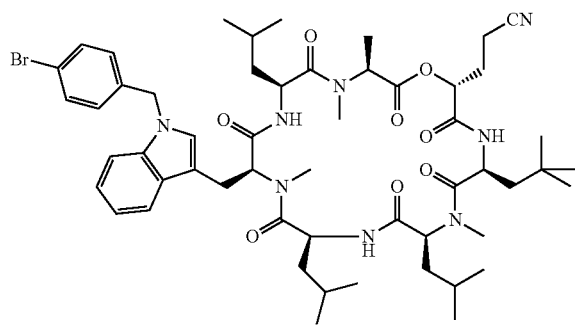 [SMILES: CC(C)C[C@@H]1NC(=O)[C@H](Cc2cn(Cc3ccc(Br)cc3)c3ccccc23)N(C)C(=O)[C@H](CC(C)C)NC(=O)[C@H](CC(C)C)N(C)C(=O)[C@H](CC(C)(C)C)NC(=O)[C@@H](CCC#N)OC(=O)[C@H](C)N(C)C1=O]

C-39 ¹H-NMR (400 MHz; acetone-d₆): δ 8.69-8.66 (m, 1H), 8.08-8.05 (m, 1H), 7.77-7.73 (m, 1H), 7.61-7.59 (m, 1H), 7.50-7.43 (m, 3H), 7.27 (dd, J=1.3, 0.4 Hz, 1H), 7.24-7.20 (m, 1H), 7.17-7.09 (m, 2H), 5.40-5.38 (m, 2H), 5.08-4.99 (m, 2H), 4.89-4.84 (m, 1H), 4.47-4.39 (m, 2H), 4.37-4.34 (m, 1H), 3.97-3.92 (m, 1H), 3.46-3.43 (m, 2H), 3.29 (s, 3H), 2.91 (s, 3H), 2.53 (s, 3H), 2.49 (td, J=6.2, 0.5 Hz, 1H), 2.42-2.37 (m, 3H), 2.23-2.16 (m, 2H), 1.98-1.88 (m, 2H), 1.82-1.76 (m, 2H), 1.67-1.63 (m, 3H), 1.56-1.51 (m, 2H), 1.51-1.45 (m, 3H), 1.41-1.28 (m, 4H), 1.09-1.07 (m, 2H), 1.02-0.85 (m, 12H), 0.37-0.35 (m, 3H), 0.01--0.01 (m, 3H), -0.48--0.52 (m, 1H). LCMS (ESI): Calculated for $C_{54}H_{78}BrN_8O_8$ [M+H]⁺, 1045.5; Found, 1046.3.

162

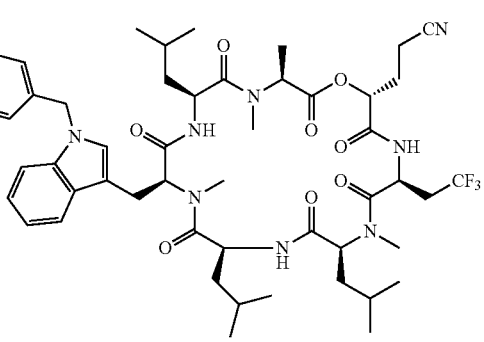

C-41 ¹H-NMR (400 MHz; acetone-d₆): δ 8.70 (d, J=10.0 Hz, 1H), 8.27 (d, J=9.5 Hz, 1H), 7.75 (dt, J=7.9, 0.9 Hz, 1H), 7.71-7.69 (m, 1H), 7.49-7.43 (m, 3H), 7.27 (s, 1H), 7.23-7.18 (m, 2H), 7.16-7.09 (m, 2H), 5.39 (d, J=3.1 Hz, 2H), 5.24-5.19 (m, 1H), 5.11-5.03 (m, 3H), 4.41-4.35 (m, 1H), 4.30 (dd, J=10.9, 4.3 Hz, 1H), 3.99-3.94 (m, 1H), 3.32-3.28 (m, 3H), 3.27-3.22 (m, 1H), 3.21-3.11 (m, 2H), 2.91 (s, 3H), 2.59 (s, 3H), 2.52 (dd, J=7.0, 5.6 Hz, 2H), 2.35-2.28 (m, 1H), 2.27-2.16 (m, 1H), 2.00-1.92 (m, 1H), 1.86-1.79 (m, 1H), 1.67-1.44 (m, 8H), 1.38-1.28 (m, 3H), 1.03-0.93 (m, 13H), 0.89-0.85 (m, 3H), 0.54 (dd, J=9.5, 6.5 Hz, 1H), 0.34 (d, J=6.5 Hz, 3H), -0.01 (d, J=6.6 Hz, 3H), -0.52--0.58 (m, 1H). LCMS (ESI): Calculated for $C_{51}H_{69}BrF_3N_8O_8$ [M+H]⁺, 1057.4; Found, 1057.0.

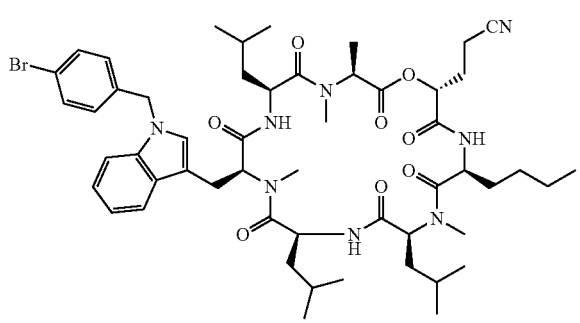 [SMILES: CCCC[C@@H]1NC(=O)[C@@H](CCC#N)OC(=O)[C@H](C)N(C)C(=O)[C@H](CC(C)C)NC(=O)[C@H](Cc2cn(Cc3ccc(Br)cc3)c3ccccc23)N(C)C(=O)[C@H](CC(C)C)NC(=O)[C@H](CC(C)C)N(C)C1=O]

C-40 ¹H-NMR (400 MHz; acetone-d₆): δ 8.73 (dd, J=9.9, 0.2 Hz, 1H), 8.03 (d, J=9.8 Hz, 1H), 7.74 (dd, J=7.6, 0.3 Hz, 1H), 7.62-7.61 (m, 1H), 7.50-7.47 (m, 2H), 7.45-7.43 (m, 1H), 7.27 (s, 1H), 7.22 (d, J=8.4 Hz, 2H), 7.16-7.11 (m, 2H), 5.39 (s, 2H), 5.09-5.02 (m, 3H), 4.80-4.74 (m, 1H), 4.38-4.32 (m, 3H), 3.96-3.91 (m, 2H), 3.30-3.21 (m, 5H), 3.01 (d, J=10.4 Hz, 1H), 2.91 (s, 3H), 2.54 (s, 3H), 2.50 (t, J=6.2 Hz, 2H), 2.21-2.15 (m, 1H), 1.96-1.87 (m, 2H), 1.82-1.75 (m, 1H), 1.61 (t, J=10.9 Hz, 2H), 1.53-1.47 (m, 7H), 1.36-1.26 (m, 7H), 1.03 (d, J=6.4 Hz, 3H), 0.98-0.87 (m, 12H), 0.81-0.79 (m, 1H), 0.36 (d, J=6.4 Hz, 3H), 0.00 (d, J=6.6 Hz, 3H). LCMS (ESI): Calculated for $C_{53}H_{76}BrN_8O_8$ [M+H]⁺, 1031.5; Found, 1031.6.

C-16 ¹H-NMR (400 MHz; acetone-d₆): δ 8.72 (dd, J=10.4, 0.6 Hz, 1H), 8.03-8.01 (m, 1H), 7.73 (dd, J=7.7, 0.2 Hz, 1H), 7.63-7.61 (m, 1H), 7.45 (d, J=8.0 Hz, 1H), 7.31-7.25 (m, 6H), 7.13 (tdd, J=14.8, 6.9, 1.1 Hz, 2H), 5.48-5.41 (m, 2H), 5.40 (d, J=1.7 Hz, 2H), 5.12-5.01 (m, 3H), 4.89-4.83 (m, 1H), 4.41-4.33 (m, 2H), 3.93 (q, J=6.8 Hz, 1H), 3.29 (s, 3H), 3.02 (t, J=7.4 Hz, 1H), 2.91 (s, 3H), 2.54 (s, 3H), 2.23-2.14 (m, 2H), 1.96-1.89 (m, 1H), 1.81-1.75 (m, 2H), 1.65-1.64 (m, 3H), 1.52-1.47 (m, 7H), 1.41-1.30 (m, 3H), 1.05 (d, J=6.4 Hz, 2H), 0.99-0.89 (m, 15H), 0.40 (d, J=6.4 Hz, 3H), 0.02 (d, J=6.6 Hz, 3H), -0.41--0.48 (m, 1H). LCMS (ESI): Calculated for $C_{53}H_{77}N_8O_8$ [M+H]⁺, 953.6; Found, 953.5.

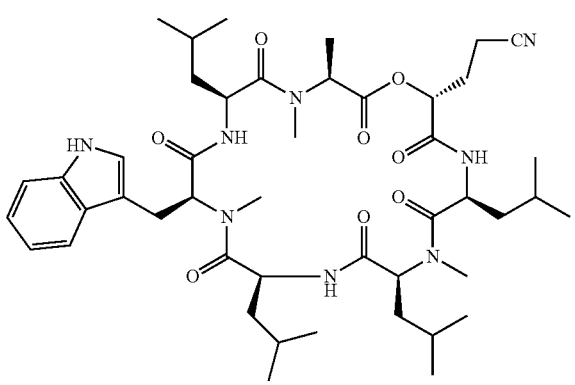 [SMILES: CC(C)C[C@@H]1NC(=O)[C@H](Cc2c[nH]c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]

C-71 ¹H-NMR (400 MHz; acetone-d₆): δ 10.19-10.19 (m, 1H), 8.69-8.67 (m, 1H), 8.03-8.01 (m, 1H), 7.71 (d, J=7.7 Hz, 1H), 7.59-7.58 (m, 1H), 7.43 (d, J=8.1 Hz, 1H), 7.15-7.06 (m, 3H), 5.09-5.02 (m, 3H), 4.90-4.84 (m, 1H), 4.42-4.38 (m, 1H), 4.35-4.30 (m, 1H), 3.94 (q, J=6.8 Hz, 1H), 3.30 (s, 3H), 3.30-3.22 (m, 3H), 2.91 (s, 3H), 2.53-2.51 (m, 4H), 2.22-2.16 (m, 1H), 2.01-1.91 (m, 1H), 1.80-1.74 (m, 3H), 1.65-1.56 (m, 3H), 1.55-1.44 (m, 8H), 1.39-1.30 (m, 3H), 1.05 (d, J=6.3 Hz, 3H), 0.99-0.89 (m, 17H), 0.50 (d, J=6.4 Hz, 3H), 0.02 (d, J=6.6 Hz, 3H), −0.39-−0.47 (m, 1H). LCMS (ESI): Calculated for $C_{46}H_{70}N_8O_8$ [M−H]⁻, 862.5; Found, 861.4.

A 4 mL dram vial was charged with indole (6.6 mg, 0.076 mmol) was added DMF (0.5 mL, anhydrous) was added sodium hydride (600 uL of a 100 mg/mL fine suspension in DMF) under argon. After stirring for 30 mins 4-(bromomethyl)-2-fluoro-1-methoxybenzene (120 μL of a 7 mM solution in DMF, 8.4 μM) was added and the solution was stirred overnight. The reaction mixture was quenched with a solution a solution of acetonitrile:water:TFA (0.5 mL, 94.9:5:0.1) and the solution was passed through a PTFE filter and subjected directly to HPLC purification to afford the benzyl indole C-27. ¹H-NMR (400 MHz; acetone-d₆): δ 8.75-8.71 (m, 1H), 8.04-8.01 (m, 1H), 7.75-7.73 (m, 1H), 7.64-7.62 (m, 1H), 7.52 (dd, J=8.1, 0.4 Hz, 1H), 7.30 (s, 1H), 7.21-7.14 (m, 2H), 7.12-7.01 (m, 2H), 6.88-6.84 (m, 1H), 5.34 (d, J=3.0 Hz, 2H), 5.10-5.01 (m, 3H), 4.89-4.83 (m, 1H), 4.40-4.36 (m, 1H), 4.32-4.27 (m, 1H), 3.97-3.89 (m, 1H), 3.88-3.83 (s, 3H), 3.32 (s, 3H), 2.92 (s, 3H), 2.54 (s, 4H), 2.23-2.15 (m, 2H), 1.99-1.90 (m, 2H), 1.82-1.69 (m, 4H), 1.52 (s, 5H), 1.52-1.47 (m, 6H), 1.26-1.16 (m, 2H), 1.09-1.02 (m, 3H), 0.98-0.85 (m, 18H), 0.27-0.25 (m, 3H), −0.10 (d, J=6.5 Hz, 3H), −0.64-−0.71 (m, 1H). LCMS (ESI): Calculated for $C_{54}H_{78}FN_8O_9$ [M+H]⁺, 1001.6; Found, 1001.5.

Example 13—C-80-C-99

Compounds C-80 through C-99 were prepared in a manner similar to that described above in Examples 1-12. LCMS (ESI) m/z[M+H] were measured and are shown in the below table.

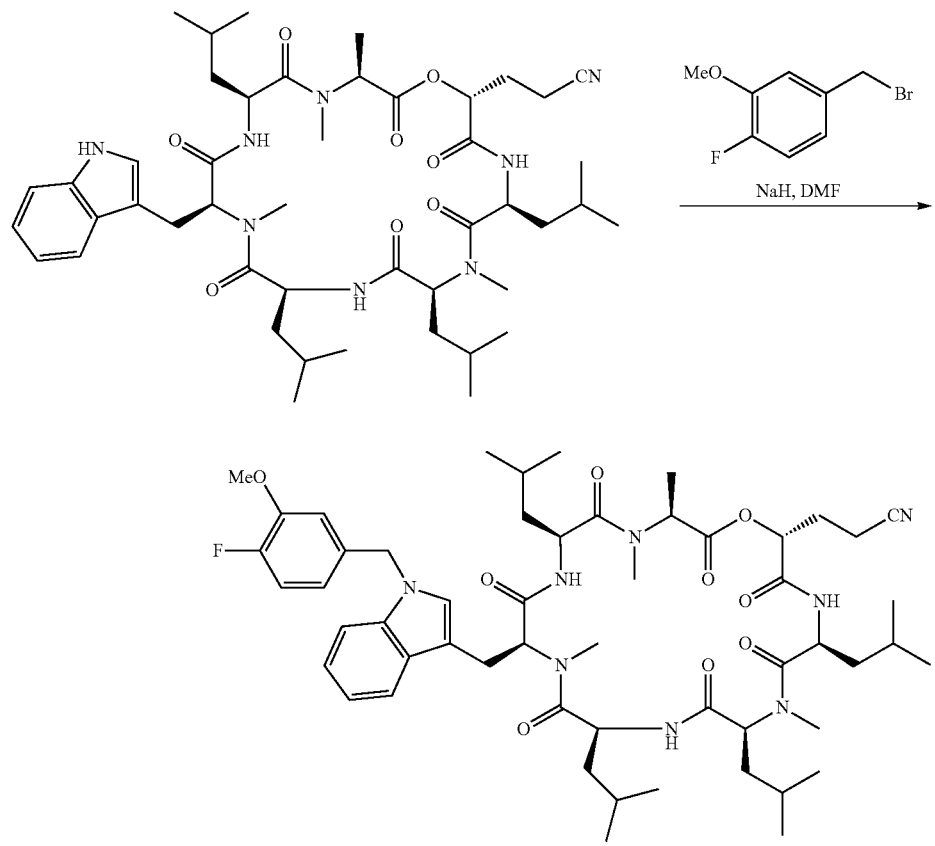

| Compound | LC-MS (ESI):<br>m/z [M + H] |
|---|---|
| C-80 | 978.5 |
| C-81 | 964 |
| C-82 | 1101.1 |
| C-83 | 1019.5 |
| C-84 | 1039.4 |
| C-85 | 976.5 |
| C-86 | 976.4 |
| C-87 | 990.3 |
| C-88 | 978.3 |
| C-89 | 964.3 |
| C-90 | 966.4 |
| C-91 | 967.3 |
| C-92 | 940.4 |
| C-93 | 914.3 |
| C-94 | 940.3 |
| C-95 | 1013.4 |
| C-96 | 964.3 |
| C-97 | 978.3 |
| C-98 | 938.4 |
| C-99 | 952 |

Assays

Constitutively Active VCAM-ss-Gluc Assay

Flp-In 293 T-REx™ cells were transfected with pcDNA™5/FRT plasmid inserted with cDNA encoding Gaussia Luciferase fused to the 3' end of cDNA encoding VCAM signal sequence plus 10 amino acids (N-MPGKMV-VILGASNILWIMFAASQAFKIETTPESR-C) (SEQ ID NO: 1). Transfected cells were selected for resistance to the selectable markers Hygromycin and Blasticidin to create a stable cell line that constitutively expressed the VCAMss+10aa/Gaussia Luciferase fusion protein. The day before assay, cells were trypsinized and plated in 384-well tissue culture plates. The next day, culture media was removed from the wells and replaced with fresh media. Compound dilutions in DMSO/media were added to the wells and incubated at 37° C., 5% $CO_2$. 24 hours later, coelenterazine substrate was added to each well and luciferase signal was quantified using Tecan Infinite M1000 Pro for potency determination.

Results for select compounds provided herein are shown below.

Dox Induced VCAM-ss-Gluc Assay

Flp-In 293 T-REx™ cells were transfected with pcDNA™5/FRT/TO plasmid inserted with cDNA encoding Gaussia Luciferase fused to the 3' end of cDNA encoding VCAM signal sequence plus 10 amino acids (N-MPGKMV-VILGASNILWIMFAASQAFKIETTPESR-C) (SEQ ID NO:2). Transfected cells were selected for resistance to the selectable markers Hygromycin and Blasticidin to create a stable cell line that contained the VCAMss+10aa/Gaussia Luciferase cDNA insert whose expression was regulated under the T-REx™ system. The day before assay, cells were trypsinized and plated in 384-well tissue culture plates. The next day, compound dilutions in DMSO/media containing doxycycline were added to the wells and incubated at 37° C., 5% $CO_2$. 24 hours later, coelenterazine substrate was added to each well and luciferase signal was quantified using Tecan Infinite M1000 Pro for potency determination.

Results for select compounds provided herein are shown below.

Dox Induced TNFα-FL-Gluc Assay

Flp-In 293 T-REx™ cells were transfected with pcDNA™5/FRT/TO plasmid inserted with cDNA encoding Gaussia Luciferase fused to the 3' end of cDNA encoding full length TNFα (amino acids 1-233). Transfected cells were selected for resistance to the selectable markers Hygromycin and Blasticidin to create a stable cell line that contained the TNFα-FL/Gaussia Luciferase cDNA insert whose expression was regulated under the T-REx™ system. The day before assay, cells were trypsinized and plated in 384-well tissue culture plates. The next day, compound dilutions in DMSO/media containing doxycycline were added to the wells and incubated at 37° C., 5% $CO_2$. 24 hours later, coelenterazine substrate was added to each well and luciferase signal was quantified using Tecan Infinite M1000 Pro for potency determination.

Results for select compounds provided herein are shown below.

Dox Induced PD1-ss-Gluc Assay

Flp-In 293 T-REx™ cells were transfected with pcDNA™5/FRT/TO plasmid inserted with cDNA encoding Gaussia Luciferase fused to the 3' end of cDNA encoding PD1 signal sequence plus 10 amino acids (N-MQIPQAPWPVVWAVLQLGWRPGWFLDSPDR-C) (SEQ ID NO:3). Transfected cells were selected for resistance to the selectable markers Hygromycin and Blasticidin to create a stable cell line that contained the PD1-ss+10aa/Gaussia Luciferase cDNA insert whose expression was regulated under the T-REx™ system. The day before assay, cells were trypsinized and plated in 384-well tissue culture plates. The next day, compound dilutions in DMSO/media containing doxycycline were added to the wells and incubated at 37° C., 5% $CO_2$. 24 hours later, coelenterazine substrate was added to each well and luciferase signal was quantified using Tecan Infinite M1000 Pro for potency determination.

Results for select compounds provided herein are shown below.

Constitutively Active Prl-ss-Gluc Assay

Flp-In 293 T-REx™ cells were transfected with pcDNA™5/FRT plasmid inserted with cDNA encoding Gaussia Luciferase fused to the 3' end of cDNA encoding Prl signal sequence plus 10 amino acids (N-MNIKGSPWKGSLLLLLVSNLLLCQSVAPLPICPG-GAAR-C) (SEQ ID NO:4). Transfected cells were selected for resistance to the selectable markers Hygromycin and Blasticidin to create a stable cell line that constitutively expressed the Prlss+10aa/Gaussia Luciferase fusion protein. The day before assay, cells were trypsinized and plated in 384-well tissue culture plates. The next day, culture media was removed from the wells and replaced with fresh media. Compound dilutions in DMSO/media were added to the wells and incubated at 37° C., 5% $CO_2$. 24 hours later, coelenterazine substrate was added to each well and luciferase signal was quantified using Tecan Infinite M1000 Pro for potency determination.

Results for select compounds provided herein are shown below.

24 hr Dox Inducible Prl-ss-Gluc Assay

Flp-In 293 T-REx™ cells were transfected with pcDNA™5/FRT/TO plasmid inserted with cDNA encoding Gaussia Luciferase fused to the 3' end of cDNA encoding Prl signal sequence plus 10 amino acids (N-MNIKGSPWKGSLLLLLVSNLLLCQSVAPLPICPG-GAAR-C) (SEQ ID NO:5). Transfected cells were selected for resistance to the selectable markers Hygromycin and Blasticidin to create a stable cell line that contained the Prl-ss+10aa/Gaussia Luciferase cDNA insert whose expression was regulated under the T-REx™ system. The day before assay, cells were trypsinized and plated in 384-well tissue culture plates. The next day, compound dilutions in DMSO/media containing doxycycline were added to the wells and incubated at 37° C., 5% $CO_2$. 24 hours later, coelenterazine substrate was added to each well and luciferase signal was quantified using Tecan Infinite M1000 Pro for potency determination.

Results for select compounds provided herein are shown in the Table below.

IL7Rss Assay

The mature domain of secreted luciferase from *Gaussia princeps* (GLuc) was cloned into pcDNA5/FRT/TO. The signal sequence plus four amino acids of the mature domain from IL7R (MTILGTTFGMVFSLLQVVSGESGY) (SEQ ID NO:6) were cloned upstream of GLuc mature domain and used in transient transfection experiment. HEK-293T T-rex cells were cultured in Dulbecco's modified Eagle's medium with 10% FBS at 5% CO2. Cells were plated 1×10e6 cells per well in a 6-well plate and incubated for 6 h. Cells were transiently transfected with IL7Rss-Gluc using Lipofectamine 2000 (Invitrogen). After overnight incubation, transfected cells were replated in a clear-bottomed, black 96-well plate at a density of 20,000 cells per well. Six hours after plating, the cells were treated with doxycycline (1 µg/ml) and increasing concentrations of the indicated compounds for 24 h. Secreted luciferase in the conditioned media was quantified by luminescence using the BioLux *Gaussia* Luciferase Assay Kit (New England Biolabs, Ipswich, Mass., USA) and a SpectraMax M5 plate reader (Molecular Devices).

C-01 exhibited an IC50 of 23 nM and C-16 exhibited an IC50 of 10 nM.

FLT3ss Assay

The mature domain of secreted luciferase from *Gaussia princeps* (GLuc) was cloned into pcDNA5/FRT/TO. The signal sequence plus four amino acids of the mature domain from FLT3 (MPALARDGGQLPLLVVFSAMIFGTITNQDL) (SEQ ID NO:7) were cloned upstream of GLuc mature domain and used in transient transfection experiment.

HEK-293T T-rex cells were cultured in Dulbecco's modified Eagle's medium with 10% FBS at 5% $CO_2$. Cells were plated 1×10e6 cells per well in a 6-well plate and incubated for 6 h. Cells were transiently transfected with FLT3ss-Gluc using Lipofectamine 2000 (Invitrogen). After overnight incubation, transfected cells were replated in a clear-bottomed, black 96-well plate at a density of 20,000 cells per well. Six hours after plating, the cells were treated with doxycycline (1 µg/ml) and increasing concentrations of the indicated compounds for 24 h. Secreted luciferase in the conditioned media was quantified by luminescence using the BioLux *Gaussia* Luciferase Assay Kit (New England Biolabs, Ipswich, Mass., USA) and a SpectraMax M5 plate reader (Molecular Devices).

C-01 exhibited an IC50 of 52 nM and C-16 exhibited an IC50 of 32 nM.

HER3ss Assay

The mature domain of secreted luciferase from *Gaussia princeps* (GLuc) was cloned into pcDNA5/FRT/TO. The signal sequence plus four amino acids of the mature domain from HER3 (MRANDALQVLGLLFSLARGSEVG) (SEQ ID NO:8) were cloned upstream of GLuc mature domain and used in transient transfection experiment. HEK-293T T-rex cells were cultured in Dulbecco's modified Eagle's medium with 10% FBS at 5% $CO_2$. Cells were plated 1×10e6 cells per well in a 6-well plate and incubated for 6 h. Cells were transiently transfected with HER3ss-Gluc using Lipofectamine 2000 (Invitrogen). After overnight incubation, transfected cells were replated in a clear-bottomed, black 96-well plate at a density of 20,000 cells per well. Six hours after plating, the cells were treated with doxycycline (1 µg/ml) and increasing concentrations of the indicated compounds for 24 h. Secreted luciferase in the conditioned media was quantified by luminescence using the BioLux *Gaussia* Luciferase Assay Kit (New England Biolabs, Ipswich, Mass., USA) and a SpectraMax M5 plate reader (Molecular Devices).

Results for select compounds provided herein are shown in the Table below.

BT474 or JJN-3 Assay

BT474 is a human breast tumor cell line. JJN3 is a human plasma cell leukemia cell line. Cell lines (BT474 or JJN3 cells) were obtained from the American Type Culture Collection (ATCC) and cultured at 37° C. with 5% $CO_2$ in RPMI-1640 media supplemented with 10% fetal bovine serum, penicillin, streptomycin and L-glutamine. Cells were seeded at 100 000 cells/mL. Aliquots of 5000 cells (50 µL) were added to each well in black, clear bottom 96-well plates. Compounds or control (50 uL of 1% DMSO in cell culture medium) were added to the cells to the indicated final concentrations and cells were incubated for 72 h (unless otherwise specified). After incubation was complete, Alamar blue (10 uL of a 1 mg/mL solution) was added to each well and plates were incubated for 5 h. Fluorescence was then measured (excitation 545 nm, emission 590 nm) and is reported as relative luminescence units (RLU) normalized to DMSO control.

Results for select compounds provided herein are shown in the Table below.

U266 Assay

The human multiple myeloma cell line U266B1 was cultured in RPMI 1640 media supplemented with 10% fetal bovine serum, 2 mM Glutamine, and 1× Penicillin/Streptomycin. Cells were plated in 384-well tissue culture plates and treated with compound dilutions in DMSO/media. Plates were incubated at 37° C., 5% $CO_2$ for 48 hours. After 48 hours, Celltiter-Glo@ (Promega) was added to each well and luciferase signal was quantified using Tecan Infinite M1000 Pro for cell viability determination.

Results for select compounds provided herein are shown in the Table below.

H929 Assay

The human multiple myeloma cell line NCI-H929 was cultured in Advanced RPMI 1640 media (Gibco@) supplemented with 6% fetal bovine serum, 2 mM Glutamine, and 1× Penicillin/Streptomycin. On the day of assay, cells were resuspended in RPMI 1640 media supplemented with 10% fetal bovine serum, 2 mM Glutamine, and 1× Penicillin/Streptmycin and plated in 384-well tissue culture plates and treated with compound dilutions in DMSO/media. Plates were incubated at 37° C., 5% $CO_2$ for 48 hours. After 48 hours, Celltiter-Glo@ (Promega) was added to each well and luciferase signal was quantified using Tecan Infinite M1000 Pro for cell viability determination.

Results for select compounds provided herein are shown in the Table below.

TABLE

| Ex # | PD1ss Gluc IC50 (nM) | TNFa FL Gluc IC50 (nM) | H929 EC50 (nM) | Prl IC50 (nM) | VCAM ss IC50 (nM) | HER3 ss IC50 (nM) | BT 474 EC50 (nM) | JJN-3 EC50 (nM) | U266 EC50 (nM) |
|---|---|---|---|---|---|---|---|---|---|
| C-01 | 56 | 79 | 454 | 11603 | 15 | 40 | 730 | 222 | 23540 |
| C-02 | 460 | 779 | 4061 | | | | | | |
| C-03 | 385 | 525 | 5068 | | | | | | |
| C-04 | 86 | 104 | 1258 | | | | | | |
| C-05 | 75 | 115 | 1186 | | | | | | |
| C-06 | | | 6710 | | | | | | |
| C-07 | 656 | 1258 | 5546 | | | | | | |
| C-08 | 360 | 526 | 4455 | | | | | | |
| C-09 | 114 | 158 | 1819 | | | | | | |
| C-11 | 52 | 295 | 2560 | 4498 | 2090 | | | 792 | 23702 |
| C-12 | 8 | 44 | 740 | 1111 | 230 | 31 | 627 | 71 | 6960 |
| C-13 | 30 | 118 | 830 | 1895 | 1032 | 69 | 1360 | 192 | 17031 |
| C-14 | 18 | 108 | 1277 | 361 | 492 | 51 | 850 | 235 | 8000 |
| C-15 | 475 | 4697 | 5929 | 6446 | 4013 | 284 | 2619 | 4858 | 20208 |
| C-16 | 27 | 92 | 941 | 1816 | 82 | 38 | 745 | 245 | 13428 |
| C-17 | 149 | 274 | 2199 | 6340 | 14 | | | | 9129 |
| C-18 | 37 | 84 | 429 | | | | | | |
| C-19 | 374 | 1390 | 5146 | | | | | | |
| C-20 | 432 | 1679 | 5301 | | | | | | |
| C-21 | 212 | 716 | 3403 | | | | | | |
| C-22 | 115 | 236 | 950 | | | | | | |
| C-23 | 66 | 88 | 953 | | | | | | |
| C-24 | 86 | 131 | 1480 | 1662 | 22 | | | | 5536 |
| C-25 | 297 | 376 | 2365 | | | | | | |
| C-26 | 59 | 92 | 1011 | | | | | | |
| C-27 | 57 | 234 | 1679 | 856 | 140 | 101 | 2136 | 319 | 17289 |
| C-28 | 27 | 125 | 611 | 428 | 61 | 60 | 940 | 140 | |
| C-29 | 100 | 314 | 2643 | 3395 | 26 | 22 | 1335 | 316 | |
| C-30 | | | | | | | | 14236 | |
| C-31 | 380 | 4058 | | | | 264 | 5889 | 2056 | |
| C-32 | 203 | 1047 | 4716 | 14152 | | 161 | 5279 | | |
| C-33 | 385 | 1362 | 4248 | 6030 | 240 | 216 | 4194 | 1479 | 8879 |
| C-34 | 1049 | | 6542 | | 274 | 963 | | | |
| C-35 | 108 | 373 | 2835 | 1254 | 207 | 126 | 1260 | 242 | |
| C-36 | 94 | 358 | 2870 | 1090 | 351 | 345 | 1541 | 289 | |
| C-37 | 582 | 1020 | 6290 | 18541 | | 267 | 6363 | 8806 | 20857 |
| C-38 | 105 | 389 | 3700 | 6106 | 320 | 317 | 3876 | 957 | |
| C-39 | 67 | 265 | 3110 | 3287 | 301 | 330 | 3570 | 621 | |
| C-40 | 48 | 184 | 2285 | 3265 | 122 | 802 | 2153 | 327 | |
| C-41 | 19 | 77 | 1284 | 1013 | 32 | 23 | 832 | 73 | |
| C-42 | 37 | 357 | 3950 | 5471 | 167 | | 3297 | 894 | 19947 |
| C-43 | 67 | 211 | 593 | 1534 | | | | | |
| C-44 | 37 | 109 | 376 | 740 | | | | | |
| C-45 | 248 | 911 | 4913 | 2500 | | | | | |
| C-46 | 35 | 296 | 3066 | 14953 | 141 | | 3117 | 640 | |
| C-47 | 367 | 1126 | 6963 | | | | | | |
| C-48 | 27 | 133 | 1628 | 1344 | 36 | | 1239 | 284 | |
| C-49 | 168 | 550 | 3374 | | 22 | 17 | 1798 | 623 | |
| C-50 | 201 | 644 | 4541 | 9059 | 30 | | 2448 | 1076 | |
| C-51 | 133 | 836 | 6201 | | 72 | | 3443 | 1069 | |
| C-52 | 751 | 5733 | | | | | | | |
| C-53 | 495 | 1556 | 5856 | | | | | | |
| C-54 | 2141 | | | | | | | | |
| C-55 | 119 | 464 | 1874 | | | | | | |
| C-56 | 94 | 238 | 1652 | | | | | | |
| C-57 | 26 | 112 | 834 | 1496 | | | 832 | 154 | |
| C-58 | 25 | 90 | 629 | 619 | | | 444 | 111 | |
| C-60 | 335 | 1118 | 4733 | | | | | | |
| C-61 | 392 | 1888 | 4562 | | | | | | |
| C-62 | 277 | 1661 | 4222 | | | | | | |
| C-63 | 3053 | | | | | | | | |
| C-64 | 334 | 1963 | 5511 | | | | | | |
| C-66 | 1037 | 2798 | 8804 | | | | | | |
| C-67 | 397 | 754 | 4086 | | | 9 | | | |
| C-68 | 1055 | | 11213 | | | | | | |
| C-69 | | | | | 1698 | | | | |
| C-71 | | | | | 354 | 445 | | | |
| C-72 | | | | | 327 | 226 | | | |
| C-73 | | | | | 3152 | | | | |
| C-75 | | | | | | 857 | 8218 | 920 | |
| C-76 | | | | | | 245 | 5837 | 669 | |
| C-77 | | | | | | 787 | 15054 | 2502 | |
| C-79 | 390 | 1493 | 4735 | I.A. | 112 | | | | I.A. |
| C-80 | I.A. | I.A. | 3437 | 23702 | I.A. | | | | 5680 |
| C-81 | 934 | I.A. | I.A. | I.A. | 88 | | | | I.A. |

TABLE-continued

| Ex # | PD1ss Gluc IC50 (nM) | TNFa FL Gluc IC50 (nM) | H929 EC50 (nM) | Prl IC50 (nM) | VCAM ss IC50 (nM) | HER3 ss IC50 (nM) | BT 474 EC50 (nM) | JJN-3 EC50 (nM) | U266 EC50 (nM) |
|---|---|---|---|---|---|---|---|---|---|
| C-82 | 42 | 104 | 649 | 506 | | 98 | | | I.A. |
| C-83 | 42 | 103 | 603 | 1086 | | 81 | | | I.A. |
| C-84 | 37 | 77 | 608 | 802 | | 72 | | | I.A. |
| C-85 | 1136 | I.A. | I.A. | I.A. | | 7 | | | I.A. |
| C-86 | 567 | I.A. | I.A. | I.A. | | 10 | | | I.A. |
| C-87 | I.A. | I.A. | I.A. | I.A. | | 11 | | | I.A. |
| C-88 | 149 | 1381 | 5642 | I.A. | | 65 | | | I.A. |
| C-89 | 172 | 879 | 3732 | I.A. | | 33 | | | I.A. |
| C-90 | 520 | 2880 | I.A. | I.A. | | 38 | | | I.A. |
| C-91 | 274 | 986 | 4875 | 9799 | | 124 | | | I.A. |
| C-92 | 813 | 3864 | 9884 | I.A. | | 98 | | | I.A. |
| C-93 | 278 | 672 | 3388 | 5705 | | 38 | | | 16171 |
| C-94 | 425 | 1239 | 6050 | 19277 | | 74 | | | I.A. |
| C-95 | 19 | 93 | 588 | 391 | | 35 | | | I.A. |
| C-96 | 472 | 3844 | 8398 | I.A. | | 6 | | | I.A. |
| C-97 | 709 | I.A. | >20 μM | I.A. | | 6 | | | I.A. |
| C-98 | 259 | 889 | 4004 | 17913 | | 35 | | | I.A. |
| C-99 | 149 | 605 | 5257 | 19781 | | 30 | | | I.A. |

I.A. indicates IC50 > 25 μM.

What is claimed:

1. A compound, or pharmaceutically acceptable salt thereof, having a structure of Formula (I):

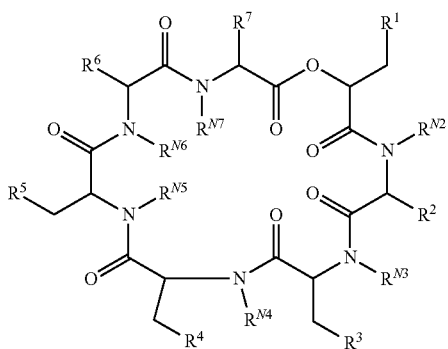

wherein
$R^1$ is H, $C_{0-3}$alkylene-CN, or $C_{2-6}$alkynyl;
$R^2$ is isobutyl, $C_{2-8}$alkenyl, $C_{1-8}$haloalkyl, $C_{1-8}$hydroxyalkyl, $C_{0-3}$alkylene-$C_{3-8}$cycloalkyl, $C_{0-3}$alkylene-$C_{3-8}$cycloalkenyl, $C_{0-3}$alkylene-$C_{3-6}$heterocycloalkyl, or $C_{0-3}$alkylene-$C_{3-6}$heterocycloalkenyl;
$R^3$ is $C_{1-6}$alkyl, $C_{2-8}$alkenyl, $C_{1-6}$haloalkyl, $C_{1-8}$hydroxyalkyl, $C_{0-3}$alkylene-$C_{3-8}$cycloalkyl, or $C_{0-3}$alkylene-$C_{3-8}$cycloalkenyl;
$R^4$ is $C_{1-8}$alkyl, $C_{2-8}$alkenyl, $C_{1-8}$hydroxyalkyl, $C_{0-3}$alkylene-$C_{3-8}$cycloalkyl, $C_{0-3}$alkylene-$C_{3-8}$cycloalkenyl, or $C_{0-3}$alkylene-$C_{3-6}$heterocycloalkyl;
$R^5$ is $C_{3-8}$cycloalkyl, $C_{3-8}$cycloalkenyl, halo-substituted aryl, benzothiophenyl, tetrahydrobenzothiophenyl, triazolyl, quinolinyl, quinolinonyl, quinolonyl, tetrahydroquinolinyl, tetrahydroquinolinonyl, tetrahydroquinolonyl or indolyl,
wherein the indolyl is N-substituted, and the quinolonyl or tetraquinolonyl is optionally N-substituted, and the N-substituent comprises $C_{3-8}$alkynyl, $C_{0-2}$alkylene-$C_{3-8}$cycloalkyl, $C_{0-2}$alkylene- $C_{3-8}$cycloalkenyl, $C_{0-2}$alkylene-substituted aryl, or $C_{0-2}$alkylene-heteroaryl, and the substituted aryl is substituted with one or more groups selected from halo, alkyl, haloalkyl, OH, and alkoxy; and
the benzothiophenyl is substituted with one or more groups selected from halo, haloalkyl, alkyl, OH, and alkoxy;
$R^6$ is $CH_3$, $CH_2CH(CH_3)_2$, $CH_2CH(CH_3)(CH_2)_3CH_3$, $C_{1-8}$haloalkyl, or $C_{0-3}$alkylene-$C_{3-8}$cycloalkyl;
$R^7$ is $C_{1-8}$alkyl; and
each of $R^{N2}$, $R^{N3}$, $R^{N4}$, $R^{N5}$, $R^{N6}$, and $R^{N7}$ is independently H or $C_{1-3}$alkyl.

2. The compound or salt of claim 1, wherein $R^1$ is:
(i) $CH_2CN$; or
(ii) $(CH_2)_{0-2}C\equiv CH$; or
(iii) H.

3. The compound or salt of claim 1, wherein $R^2$ is isobutyl, $C_{1-8}$haloalkyl, $C_{0-3}$alkylene-$C_{3-8}$cycloalkenyl or $C_{0-3}$alkylene-$C_{3-8}$cycloalkyl.

4. The compound or salt of claim 1, wherein $R^2$ is $CH_2CF_3$, $CH_2CH_2CF_3$, $CH_2$-1-cyclohexenyl, $CH_2$-1-cyclopentenyl, $CH_2$-cyclopropyl, $CH_2$-cyclopentyl, $CH_2$-cyclohexyl, or $CH_2$-4-tetrahydropyranyl.

5. The compound or salt of claim 1, wherein $R^3$ is:
(i) $CH(CH_3)_2$; or
(ii) $C_{1-8}$haloalkyl, $C_{0-3}$alkylene-$C_{3-8}$cycloalkyl, or $C_{0-3}$alkylene-$C_{3-8}$cycloalkenyl.

6. The compound or salt of claim 1, wherein $R^4$ is $CH(CH_3)_2$, $C(CH_3)_3$, $CH_3$, $CH_2CH_3$, $CF_3$, $CH_2CF_3$, tetrahydropyranyl, or cyclopentyl.

7. The compound or salt of claim 1, wherein $R^4$ is $C_{1-8}$haloalkyl, $C_{0-3}$alkylene-$C_{3-8}$cycloalkyl or $C_{0-3}$alkylene-$C_{3-8}$cycloalkenyl.

8. The compound or salt of claim 1, wherein $R^5$ comprises:
(i) cyclohexyl, cyclopentyl, or cyclopentenyl; or
(ii) quinolinyl, quinolinonyl, quinolonyl, tetrahydroquinolinyl, tetrahydroquinolinonyl, or tetrahydroquinolonyl, and $R^5$ is substituted with one or more of $C_{3-8}$alkynyl, $C_{0-2}$alkylene-$C_{3-8}$cycloalkyl, $C_{0-2}$alkylene-$C_{3-8}$cycloalkenyl, $C_{0-2}$alkylene- aryl, or $C_{0-2}$alkylene-heteroaryl.

9. The compound or salt of claim 1, wherein $R^5$ is

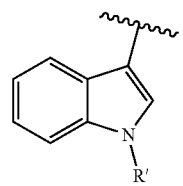

and R' is $C_4$alkynyl, $CH_2$-fluoropyridyl, $CH_2$-methylpyridyl, $CH_2$-methoxyphenyl, $CH_2$-methylphenyl, $CH_2$-fluorophenyl, $CH_2$-chlorophenyl, $CH_2$-bromophenyl, CH2-difluorophenyl, $CH_2$-fluoromethoxyphenyl, or $CH_2$-methylisooxazolyl, optionally wherein R' is para-fluorobenzyl, para-chlorobenzyl, para-methylbenzyl, or para-bromobenzyl.

10. The compound or salt of claim 1, wherein $R^5$ comprises benzothiophenyl, and the benzothiophenyl is substituted with one or more of chloro, fluoro, bromo, methyl, and methoxy.

11. The compound or salt of claim 1, wherein $R^6$ is $CH_3$, $CH_2CH(CH_3)_2$, $CH_2CH(CH_3)(CH_2)_3CH_3$, $CH_2CF_3$, or $CH_2CH_2CF_3$.

12. The compound or salt of claim 1, wherein $R^6$ is $C_{1-8}$haloalkyl or $C_{0-3}$alkylene-$C_{3-8}$cycloalkyl.

13. The compound or salt of claim 1, wherein:
(i) $R^3$ is 1-cyclopentenyl or 1-cyclohexenyl; or
(ii) $R^4$ is 1-cyclopentenyl or 1-cyclohexenyl; or
(iii) $R^6$ is $CH_2$-1-cyclopentenyl or $CH_2$-1-cyclohexenyl; or
(iv) a combination of the foregoing.

14. The compound or salt of claim 1, wherein $R^7$ is $CH_3$.

15. The compound or salt of claim 1, wherein:
(i) at least one of $R^{N2}$, $R^{N3}$, $R^{N4}$, $R^{N5}$, $RN^6$, and $R^{N7}$ is H; or
(ii) at least one of $R^{N2}$, $R^{N3}$, $R^{N4}$, $R^{N5}$, $R^{N6}$, and $R^{N7}$ is $CH_3$; or
(iii) both (i) and (ii).

16. The compound or salt of claim 1, wherein $R^{N2}$ is H, $R^{N3}$ is $CH_3$, $R^{N4}$ is H, $R^{N5}$ is $CH_3$, $R^{N6}$ is H, and $R_7$ is $CH_3$.

17. The compound of claim 1, as listed in Table A, or a pharmaceutically acceptable salt thereof;

TABLE A
C-03
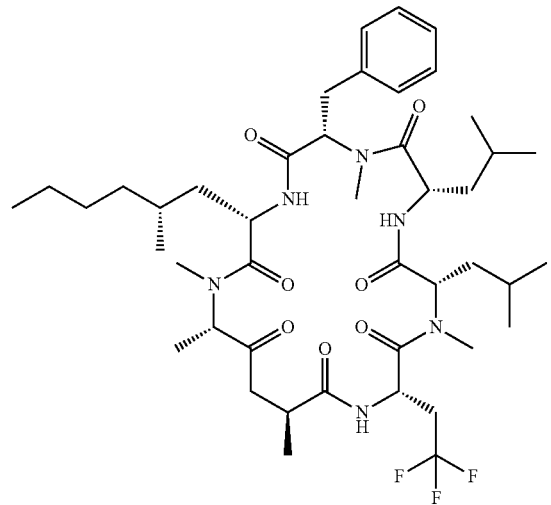 [SMILES: CCCC[C@@H](C)C[C@@H]1NC(=O)[C@H](Cc2ccccc2)N(C)C(=O)[C@H](CC(C)C)NC(=O)[C@H](CC(C)C)N(C)C(=O)[C@H](CC(F)(F)F)NC(=O)[C@@H](C)CC(=O)[C@H](C)N(C)C1=O]
C-04
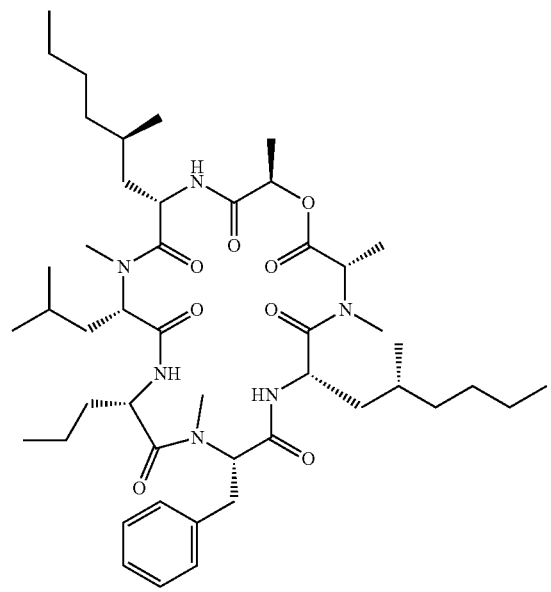 [SMILES: CCCC[C@@H](C)C[C@@H]1NC(=O)[C@H](Cc2ccccc2)N(C)C(=O)[C@H](CCC)NC(=O)[C@H](CC(C)C)N(C)C(=O)[C@H](C[C@H](C)CCCC)NC(=O)[C@@H](C)OC(=O)[C@H](C)N(C)C1=O]
C-05
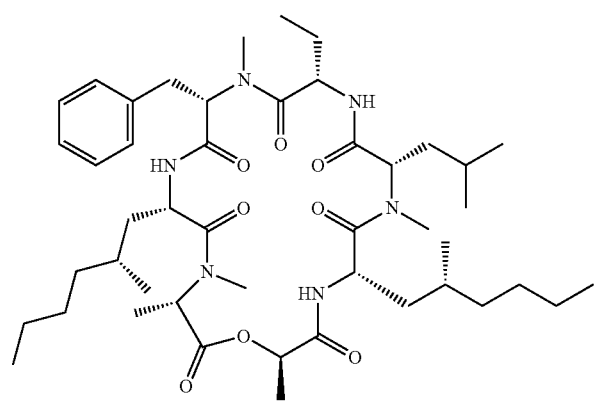 [SMILES: CCCC[C@@H](C)C[C@@H]1NC(=O)[C@H](Cc2ccccc2)N(C)C(=O)[C@H](CC)NC(=O)[C@H](CC(C)C)N(C)C(=O)[C@H](C[C@H](C)CCCC)NC(=O)[C@@H](C)OC(=O)[C@H](C)N(C)C1=O]

TABLE A-continued
C-06
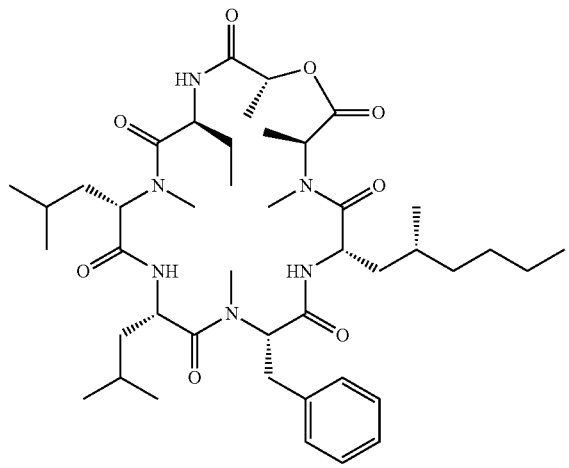 [SMILES: CCCC[C@@H](C)C[C@@H]1NC(=O)[C@H](Cc2ccccc2)N(C)C(=O)[C@H](CC(C)C)NC(=O)[C@H](CC(C)C)N(C)C(=O)[C@H](CC)NC(=O)[C@@H](C)OC(=O)[C@H](C)N(C)C1=O]
C-07
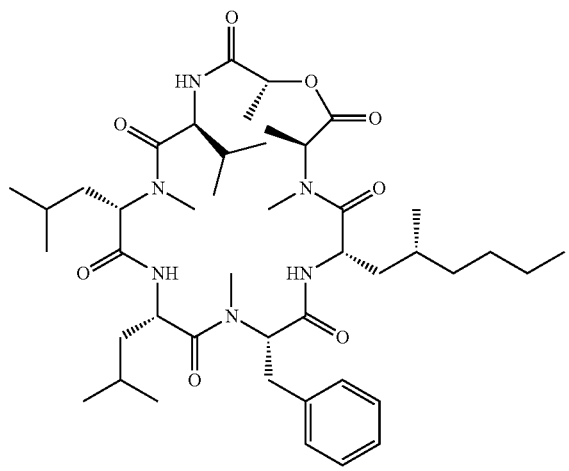 [SMILES: CCCC[C@@H](C)C[C@@H]1NC(=O)[C@H](Cc2ccccc2)N(C)C(=O)[C@H](CC(C)C)NC(=O)[C@H](CC(C)C)N(C)C(=O)[C@H](C(C)C)NC(=O)[C@@H](C)OC(=O)[C@H](C)N(C)C1=O]
C-08
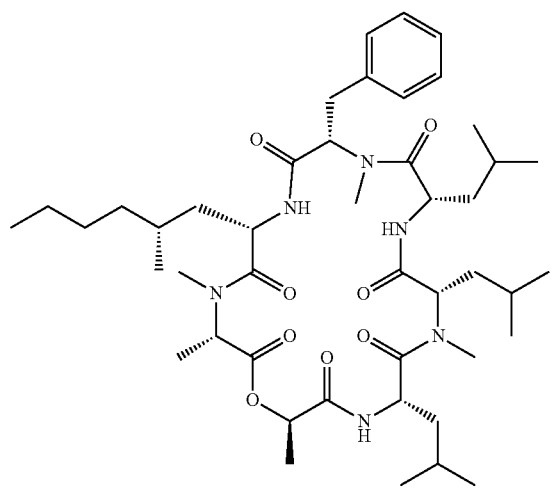 [SMILES: CCCC[C@@H](C)C[C@@H]1NC(=O)[C@H](Cc2ccccc2)N(C)C(=O)[C@H](CC(C)C)NC(=O)[C@H](CC(C)C)N(C)C(=O)[C@H](CC(C)C)NC(=O)[C@@H](C)OC(=O)[C@H](C)N(C)C1=O]

TABLE A-continued
C-09
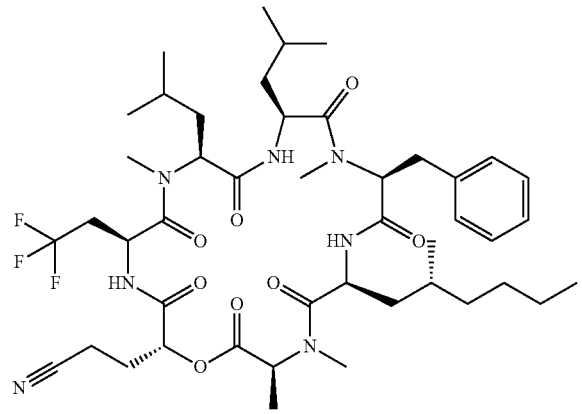 [SMILES: CCCC[C@@H](C)C[C@@H]1NC(=O)[C@H](Cc2ccccc2)N(C)C(=O)[C@H](CC(C)C)NC(=O)[C@H](CC(C)C)N(C)C(=O)[C@H](CC(F)(F)F)NC(=O)[C@@H](CCC#N)OC(=O)[C@H](C)N(C)C1=O]
C-10
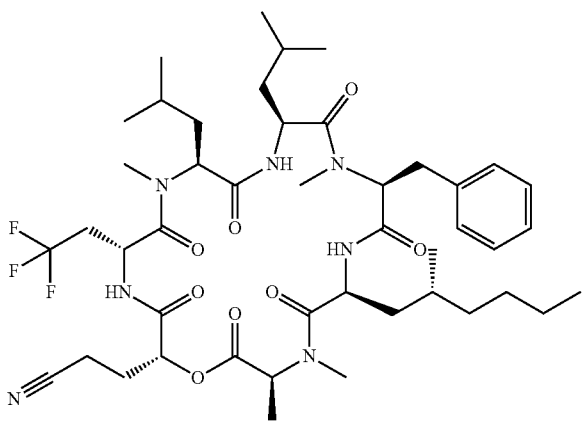 [SMILES: CCCC[C@@H](C)C[C@@H]1NC(=O)[C@H](Cc2ccccc2)N(C)C(=O)[C@H](CC(C)C)NC(=O)[C@H](CC(C)C)N(C)C(=O)[C@@H](CC(F)(F)F)NC(=O)[C@@H](CCC#N)OC(=O)[C@H](C)N(C)C1=O]
C-11
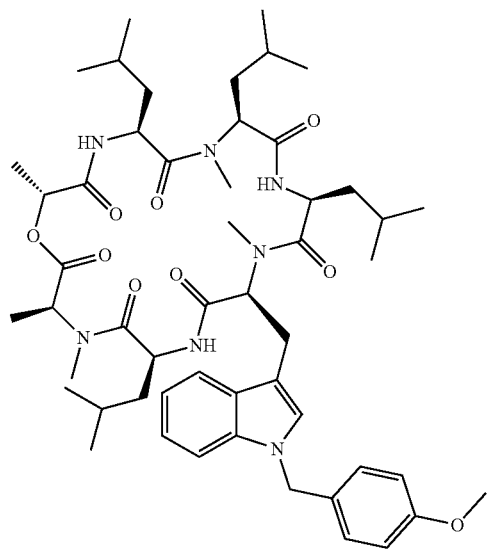

TABLE A-continued
C-12
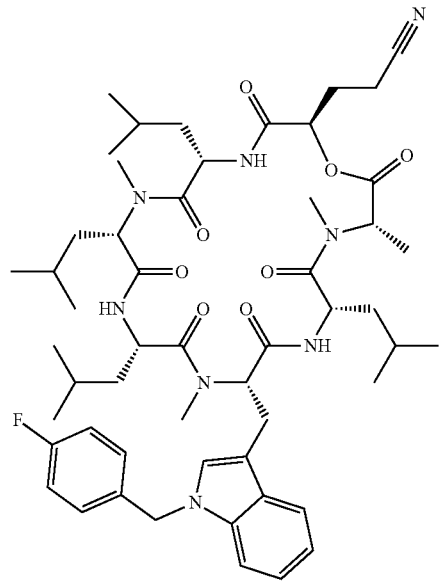 [SMILES: CC(C)C[C@@H]1NC(=O)[C@H](Cc2cn(Cc3ccc(F)cc3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]
C-13
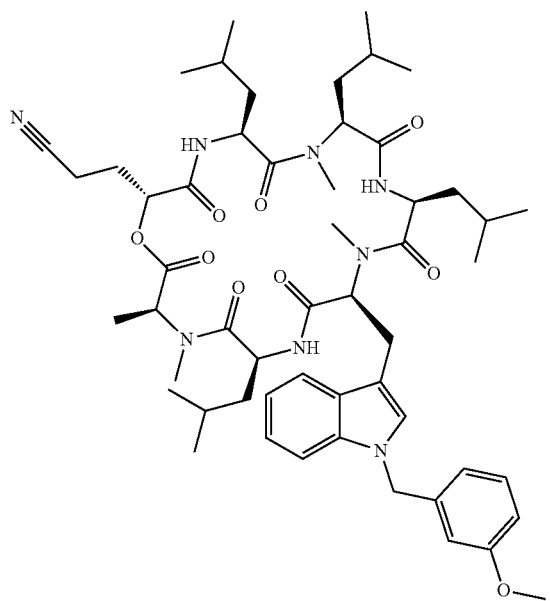 [SMILES: COc1cccc(Cn2cc(C[C@H]3C(=O)N[C@@H](CC(C)C)C(=O)N(C)[C@@H](C)C(=O)O[C@H](CCC#N)C(=O)N[C@@H](CC(C)C)C(=O)N(C)[C@@H](CC(C)C)C(=O)N[C@@H](CC(C)C)C(=O)N3C)c3ccccc32)c1]

TABLE A-continued
C-14
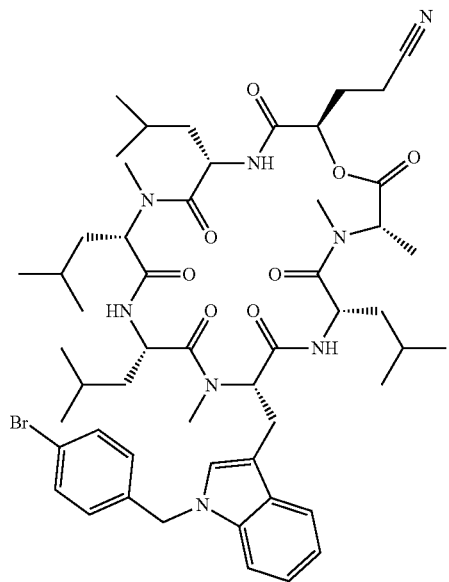 [SMILES: CC(C)C[C@@H]1NC(=O)[C@H](Cc2cn(Cc3ccc(Br)cc3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]
C-15
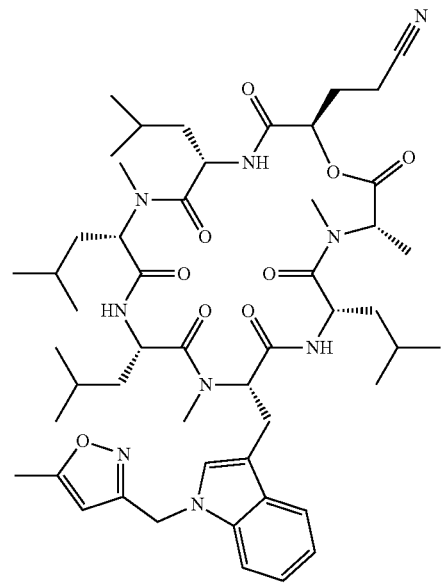 [SMILES: Cc1cc(Cn2cc(C[C@H]3C(=O)N[C@@H](CC(C)C)C(=O)N(C)[C@@H](C)C(=O)O[C@H](CCC#N)C(=O)N[C@@H](CC(C)C)C(=O)N(C)[C@@H](CC(C)C)C(=O)N[C@@H](CC(C)C)C(=O)N3C)c3ccccc32)no1]

TABLE A-continued
C-16
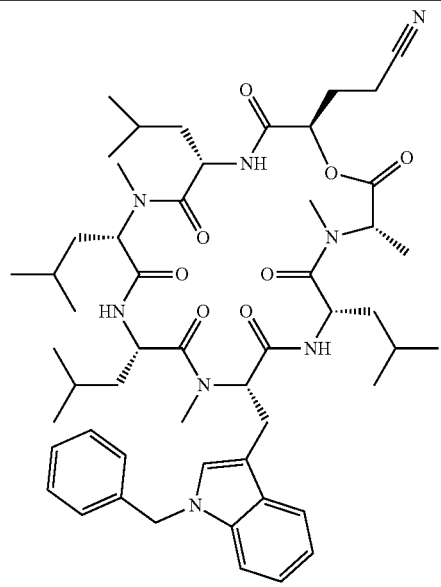
C-17
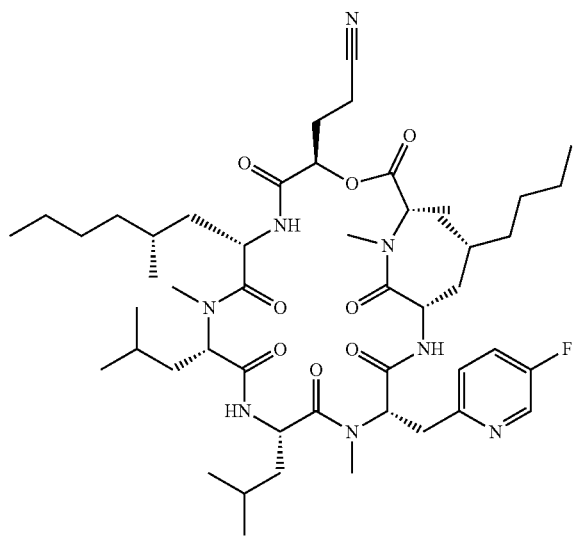 [SMILES: CCCC[C@@H](C)C[C@@H]1NC(=O)[C@H](Cc2ccc(F)cn2)N(C)C(=O)[C@H](CC(C)C)NC(=O)[C@H](CC(C)C)N(C)C(=O)[C@H](C[C@H](C)CCCC)NC(=O)[C@@H](CCC#N)OC(=O)[C@H](C)N(C)C1=O]
C-18
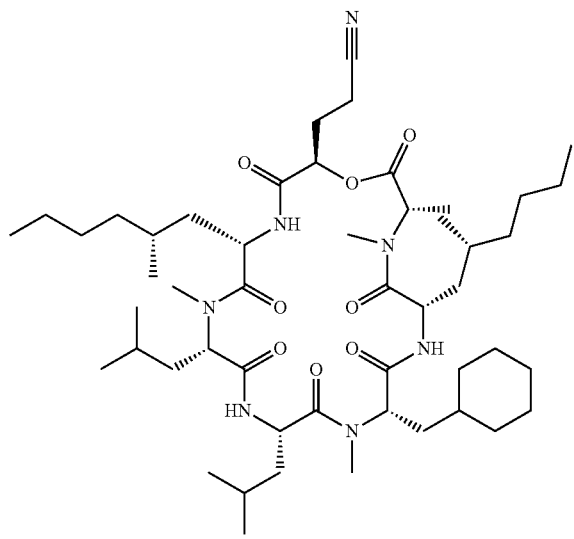 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](C[C@H](C)CCCC)NC(=O)[C@@H](CCC#N)OC(=O)[C@H](C)N(C)C1=O]

TABLE A-continued
C-19
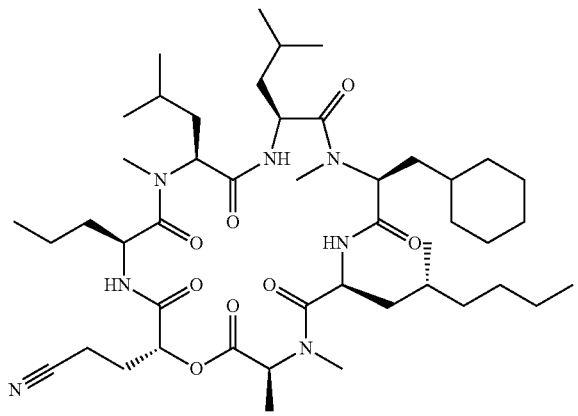 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CCC)NC(=O)[C@@H](CCC#N)OC(=O)[C@H](C)N(C)C1=O]
C-20
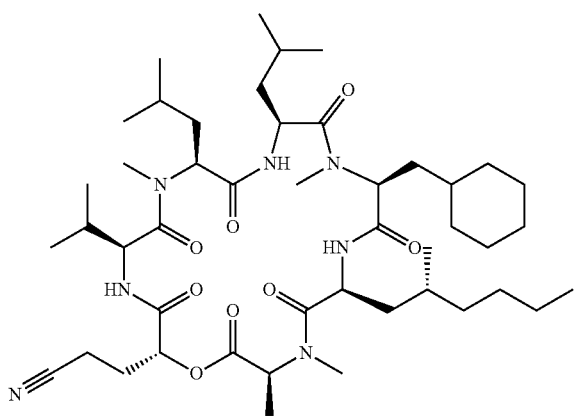 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](C(C)C)NC(=O)[C@@H](CCC#N)OC(=O)[C@H](C)N(C)C1=O]
C-21
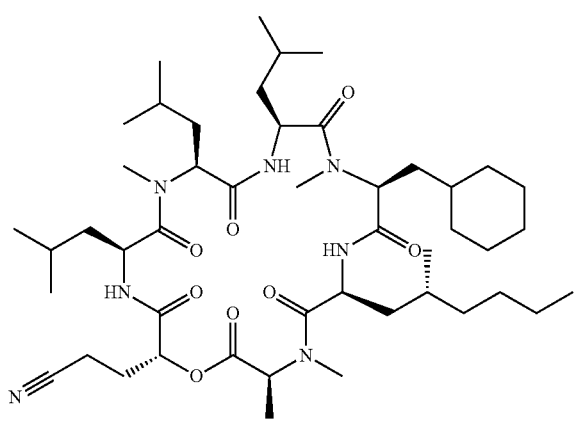 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]

TABLE A-continued
C-22
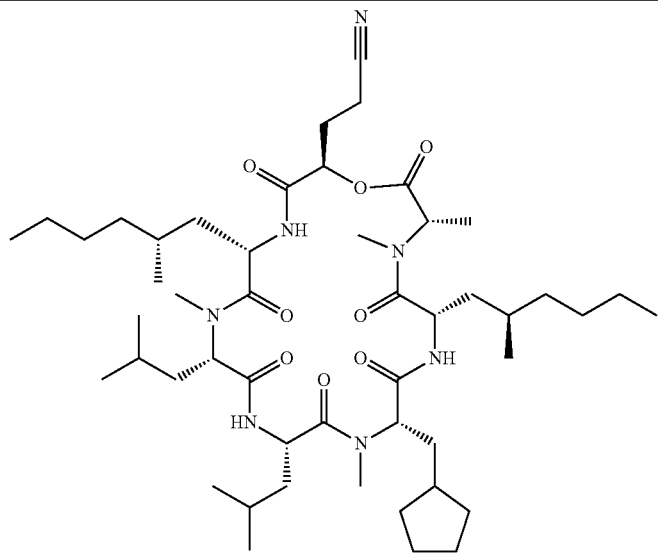
C-23
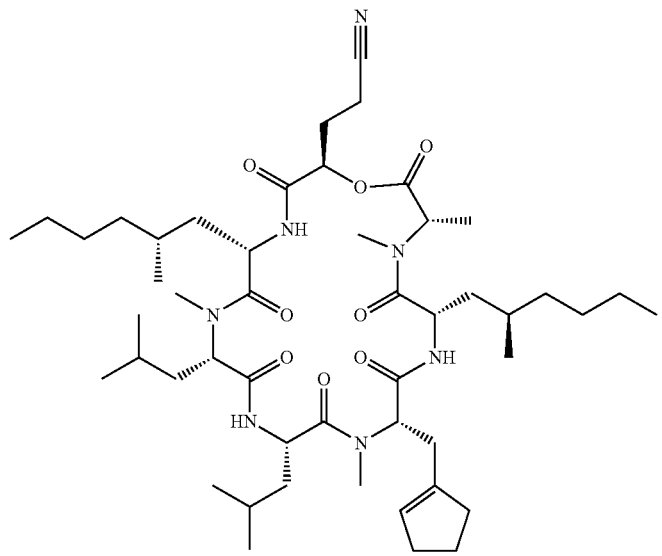 [SMILES: CCCC[C@@H](C)C[C@@H]1NC(=O)[C@H](CC2=CCCC2)N(C)C(=O)[C@H](CC(C)C)NC(=O)[C@H](CC(C)C)N(C)C(=O)[C@H](C[C@H](C)CCCC)NC(=O)[C@@H](CCC#N)OC(=O)[C@H](C)N(C)C1=O]
C-24
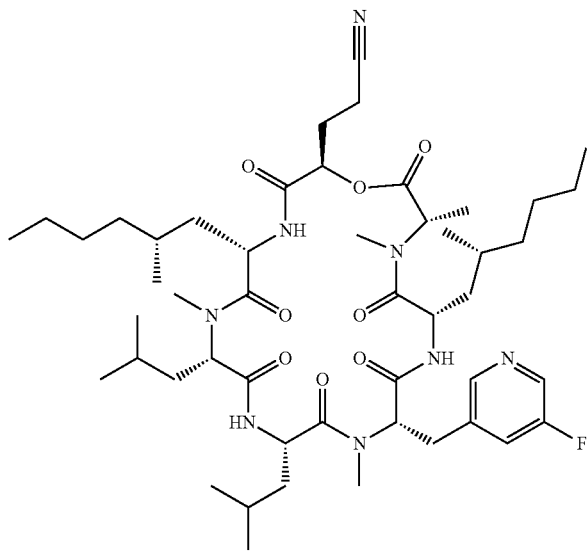 [SMILES: CCCC[C@@H](C)C[C@@H]1NC(=O)[C@H](Cc2cncc(F)c2)N(C)C(=O)[C@H](CC(C)C)NC(=O)[C@H](CC(C)C)N(C)C(=O)[C@H](C[C@H](C)CCCC)NC(=O)[C@@H](CCC#N)OC(=O)[C@H](C)N(C)C1=O]

TABLE A-continued
C-26
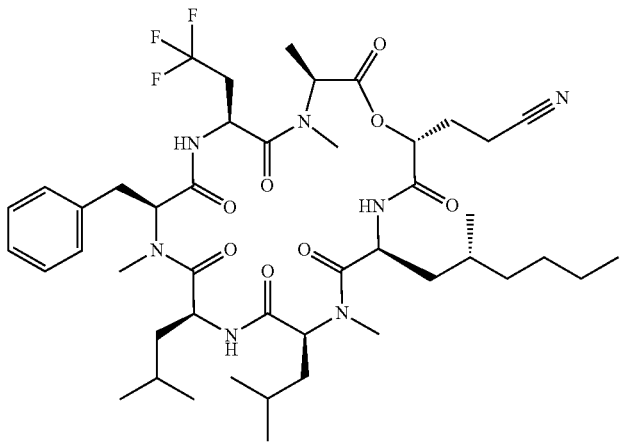 [SMILES: CCCC[C@@H](C)C[C@@H]1NC(=O)[C@@H](CCC#N)OC(=O)[C@H](C)N(C)C(=O)[C@H](CC(F)(F)F)NC(=O)[C@H](Cc2ccccc2)N(C)C(=O)[C@H](CC(C)C)NC(=O)[C@H](CC(C)C)N(C)C1=O]
C-27
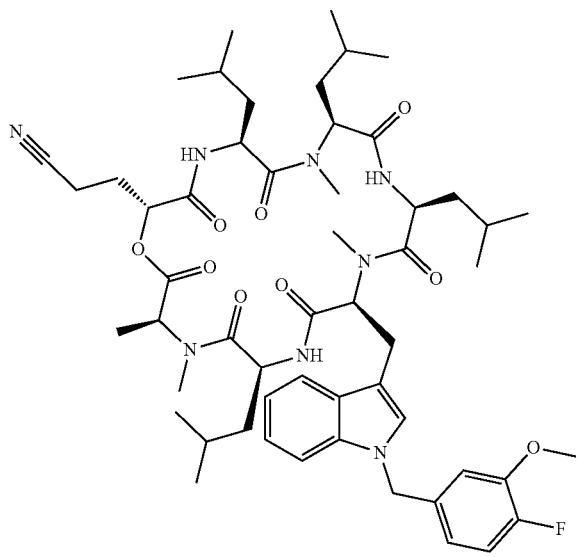 [SMILES: COc1cc(Cn2cc(C[C@H]3C(=O)N[C@@H](CC(C)C)C(=O)N(C)[C@@H](C)C(=O)O[C@H](CCC#N)C(=O)N[C@@H](CC(C)C)C(=O)N(C)[C@@H](CC(C)C)C(=O)N[C@@H](CC(C)C)C(=O)N3C)c3ccccc32)ccc1F]
C-28
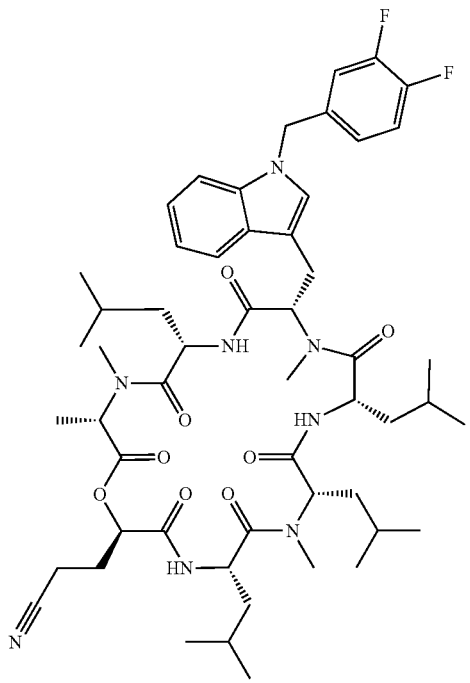 [SMILES: CC(C)C[C@@H]1NC(=O)[C@H](Cc2cn(Cc3ccc(F)c(F)c3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]

TABLE A-continued
C-29
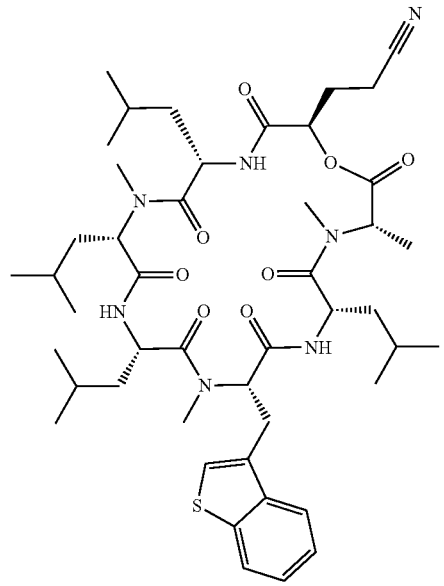 [SMILES: CC(C)C[C@@H]1NC(=O)[C@H](Cc2csc3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]
C-30
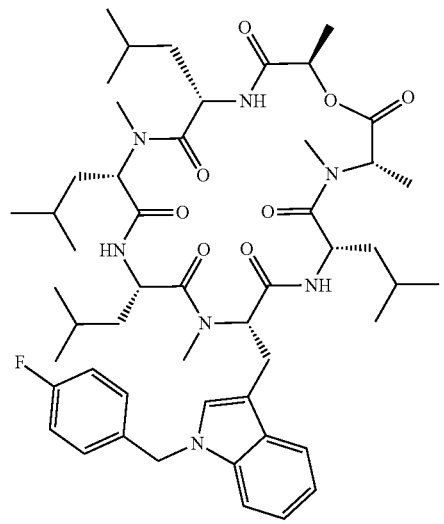 [SMILES: CC(C)C[C@@H]1NC(=O)[C@H](Cc2cn(Cc3ccc(F)cc3)c3ccccc23)N(C)C(=O)[C@H](CC(C)C)NC(=O)[C@H](CC(C)C)N(C)C(=O)[C@H](CC(C)C)NC(=O)[C@@H](C)OC(=O)[C@H](C)N(C)C1=O]

TABLE A-continued
C-31
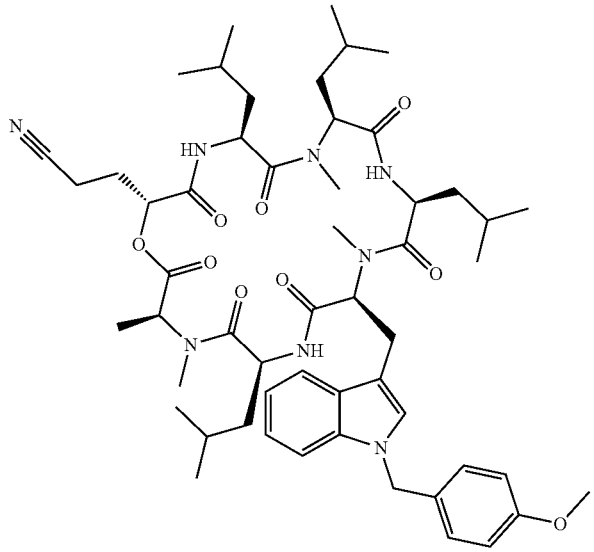 [SMILES: COc1ccc(Cn2cc(C[C@H]3C(=O)N[C@@H](CC(C)C)C(=O)N(C)[C@@H](C)C(=O)O[C@H](CCC#N)C(=O)N[C@@H](CC(C)C)C(=O)N(C)[C@@H](CC(C)C)C(=O)N[C@@H](CC(C)C)C(=O)N3C)c3ccccc32)cc1]
C-32
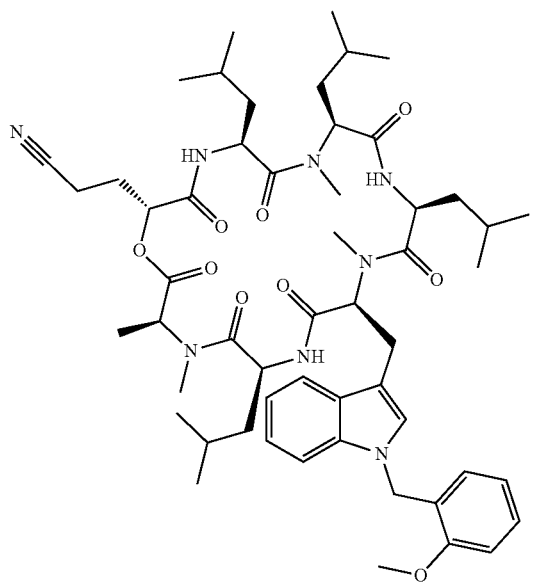 [SMILES: COc1ccccc1Cn1cc(C[C@H]2C(=O)N[C@@H](CC(C)C)C(=O)N(C)[C@@H](C)C(=O)O[C@H](CCC#N)C(=O)N[C@@H](CC(C)C)C(=O)N(C)[C@@H](CC(C)C)C(=O)N[C@@H](CC(C)C)C(=O)N2C)c2ccccc21]

TABLE A-continued
C-33
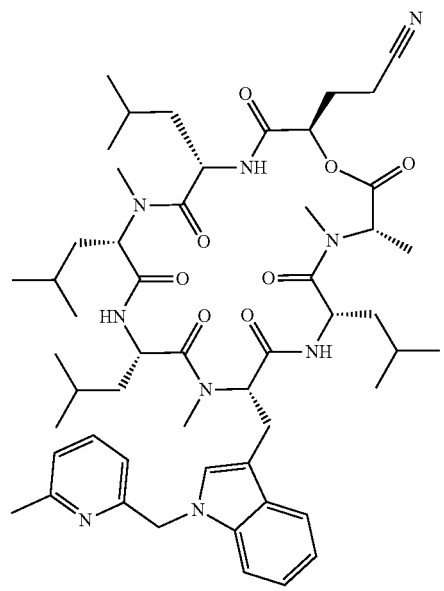 [SMILES: Cc1cccc(Cn2cc(C[C@H]3C(=O)N[C@@H](CC(C)C)C(=O)N(C)[C@@H](C)C(=O)O[C@H](CCC#N)C(=O)N[C@@H](CC(C)C)C(=O)N(C)[C@@H](CC(C)C)C(=O)N[C@@H](CC(C)C)C(=O)N3C)c3ccccc32)n1]
C-34
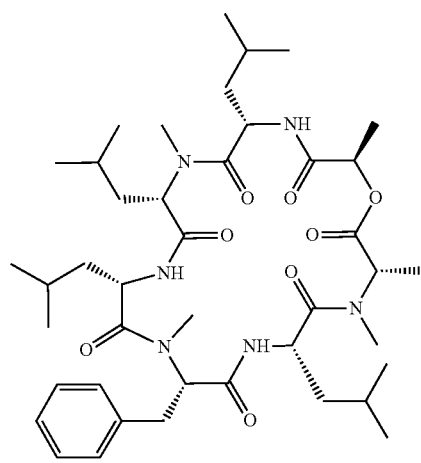 [SMILES: CC(C)C[C@@H]1NC(=O)[C@H](Cc2ccccc2)N(C)C(=O)[C@H](CC(C)C)NC(=O)[C@H](CC(C)C)N(C)C(=O)[C@H](CC(C)C)NC(=O)[C@@H](C)OC(=O)[C@H](C)N(C)C1=O]
C-35
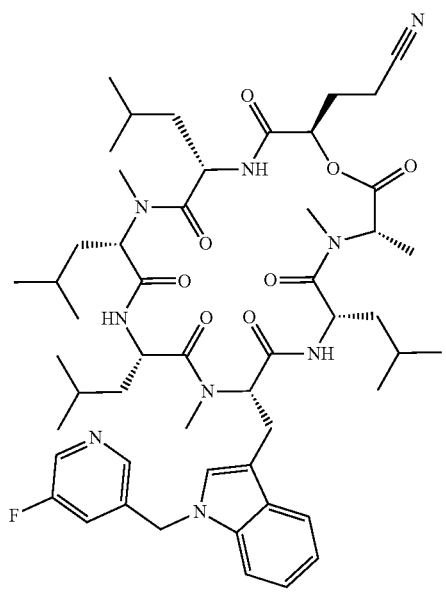 [SMILES: CC(C)C[C@@H]1NC(=O)[C@H](Cc2cn(Cc3cncc(F)c3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]

TABLE A-continued
C-36
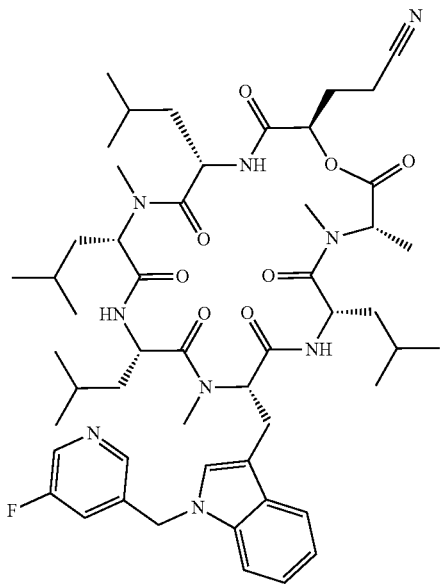 [SMILES: CC(C)C[C@@H]1NC(=O)[C@H](Cc2cn(Cc3cncc(F)c3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]
C-37
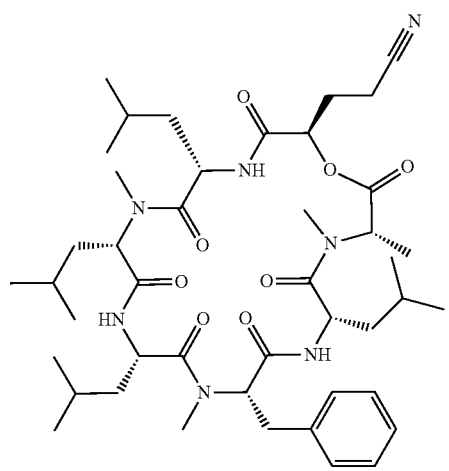 [SMILES: CC(C)C[C@@H]1NC(=O)[C@H](Cc2ccccc2)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]
C-38
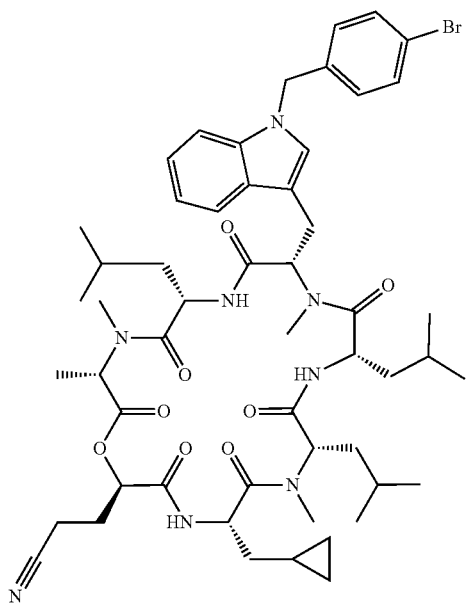 [SMILES: CC(C)C[C@@H]1NC(=O)[C@H](Cc2cn(Cc3ccc(Br)cc3)c3ccccc23)N(C)C(=O)[C@H](CC(C)C)NC(=O)[C@H](CC(C)C)N(C)C(=O)[C@H](CC2CC2)NC(=O)[C@@H](CCC#N)OC(=O)[C@H](C)N(C)C1=O]

TABLE A-continued
C-39
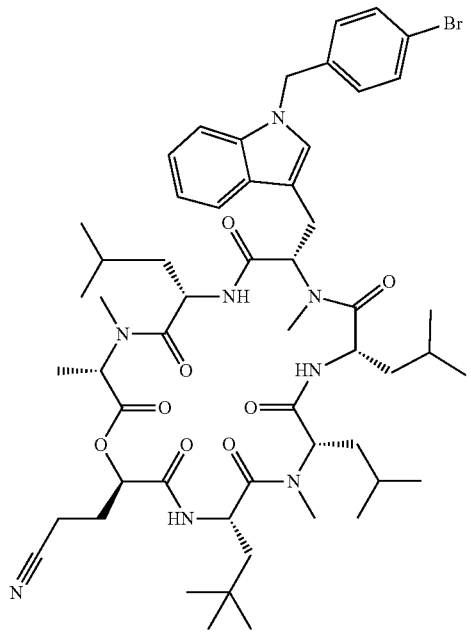 [SMILES: CC(C)C[C@@H]1NC(=O)[C@H](Cc2cn(Cc3ccc(Br)cc3)c3ccccc23)N(C)C(=O)[C@H](CC(C)C)NC(=O)[C@H](CC(C)C)N(C)C(=O)[C@H](CC(C)(C)C)NC(=O)[C@@H](CCC#N)OC(=O)[C@H](C)N(C)C1=O]
C-40
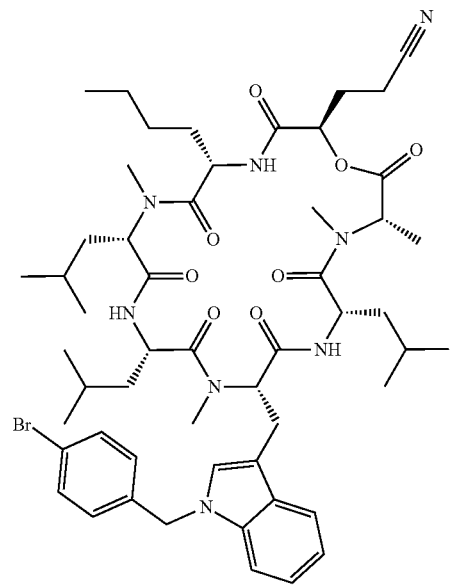 [SMILES: CCCC[C@@H]1NC(=O)[C@@H](CCC#N)OC(=O)[C@H](C)N(C)C(=O)[C@H](CC(C)C)NC(=O)[C@H](Cc2cn(Cc3ccc(Br)cc3)c3ccccc23)N(C)C(=O)[C@H](CC(C)C)NC(=O)[C@H](CC(C)C)N(C)C1=O]

TABLE A-continued
C-41
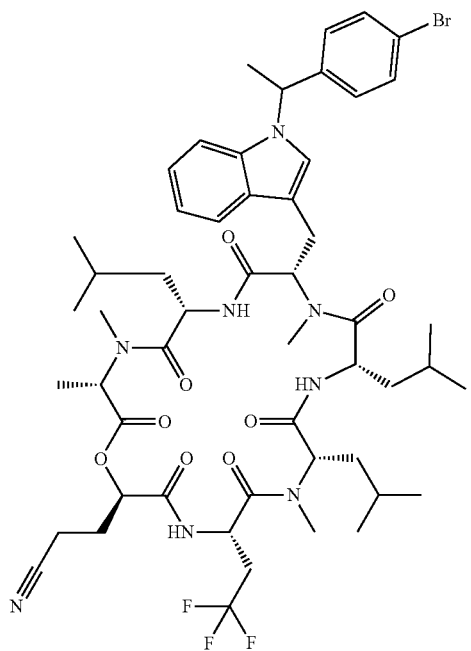 [SMILES: CC(C)C[C@@H]1NC(=O)[C@H](Cc2cn(C(C)c3ccc(Br)cc3)c3ccccc23)N(C)C(=O)[C@H](CC(C)C)NC(=O)[C@H](CC(C)C)N(C)C(=O)[C@H](CC(F)(F)F)NC(=O)[C@@H](CCC#N)OC(=O)[C@H](C)N(C)C1=O]
C-42
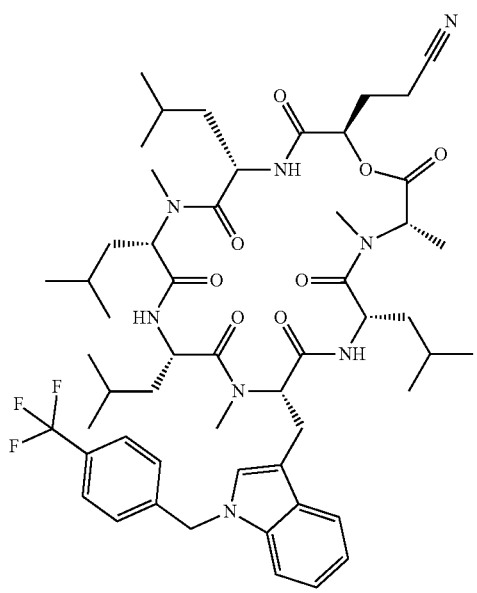 [SMILES: CC(C)C[C@@H]1NC(=O)[C@H](Cc2cn(Cc3ccc(C(F)(F)F)cc3)c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]
C-43
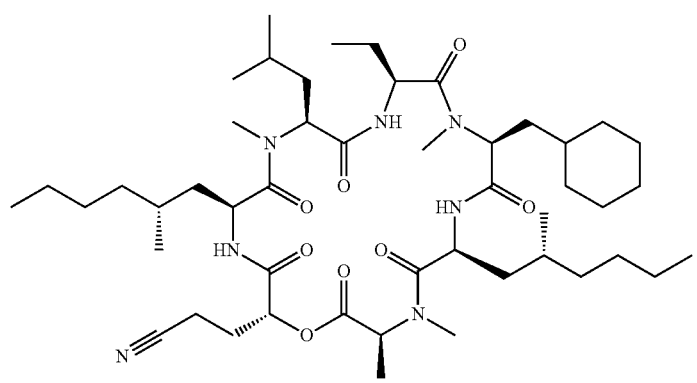 [SMILES: CCCC[C@@H](C)C[C@@H]1NC(=O)[C@H](CC2CCCCC2)N(C)C(=O)[C@H](CC)NC(=O)[C@H](CC(C)C)N(C)C(=O)[C@H](C[C@H](C)CCCC)NC(=O)[C@@H](CCC#N)OC(=O)[C@H](C)N(C)C1=O]

TABLE A-continued
C-44
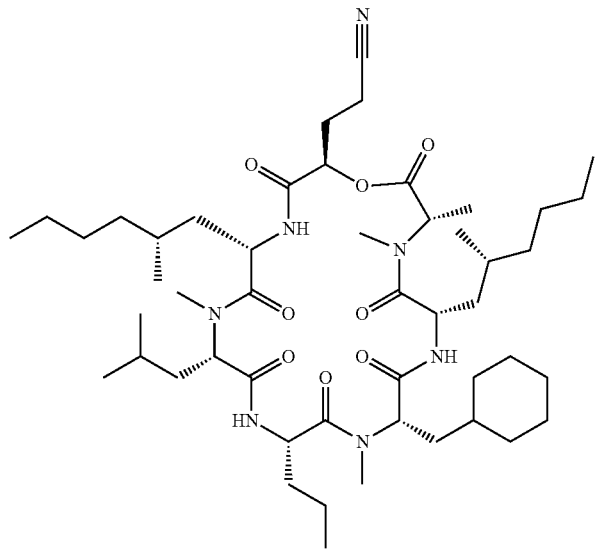 [SMILES: CCCC[C@@H](C)C[C@@H]1NC(=O)[C@H](CC2CCCCC2)N(C)C(=O)[C@H](CCC)NC(=O)[C@H](CC(C)C)N(C)C(=O)[C@H](C[C@H](C)CCCC)NC(=O)[C@@H](CCC#N)OC(=O)[C@H](C)N(C)C1=O]
C-45
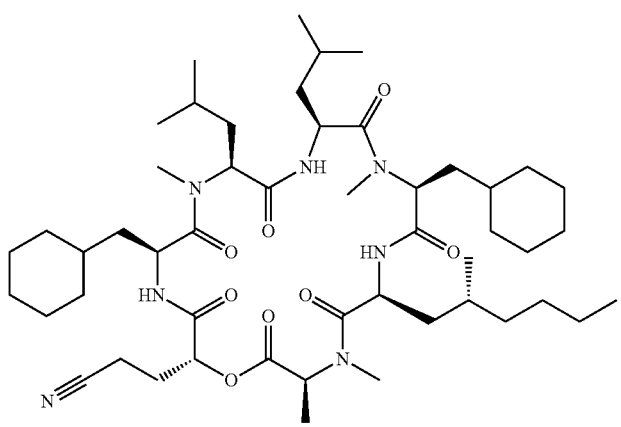 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CC2CCCCC2)NC(=O)[C@@H](CCC#N)OC(=O)[C@H](C)N(C)C1=O]
C-46
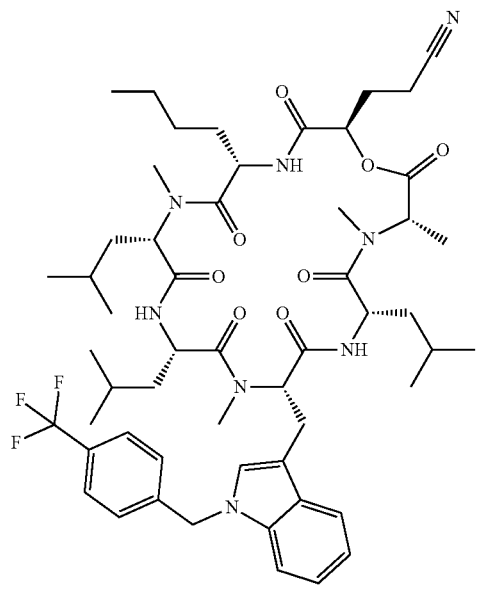 [SMILES: CCCC[C@@H]1NC(=O)[C@@H](CCC#N)OC(=O)[C@H](C)N(C)C(=O)[C@H](CC(C)C)NC(=O)[C@H](Cc2cn(Cc3ccc(C(F)(F)F)cc3)c3ccccc23)N(C)C(=O)[C@H](CC(C)C)NC(=O)[C@H](CC(C)C)N(C)C1=O]

TABLE A-continued
C-47
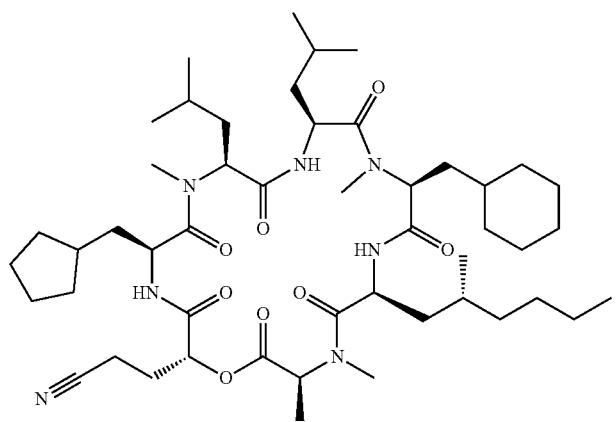 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CC2CCCC2)NC(=O)[C@@H](CCC#N)OC(=O)[C@H](C)N(C)C1=O]
C-48
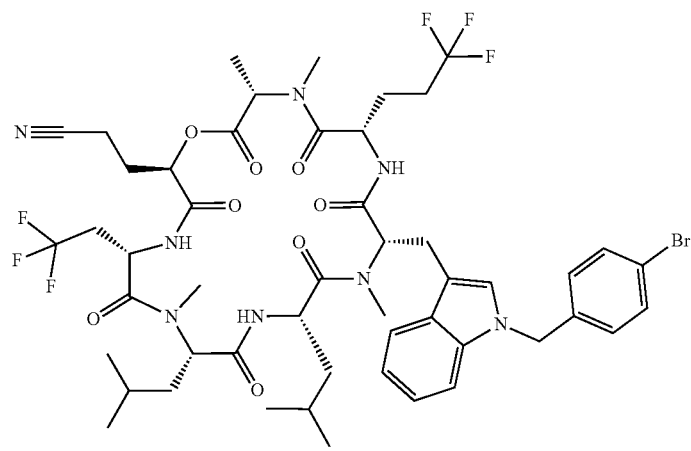 [SMILES: CC(C)C[C@@H]1NC(=O)[C@H](CC(C)C)N(C)C(=O)[C@H](CC(F)(F)F)NC(=O)[C@@H](CCC#N)OC(=O)[C@H](C)N(C)C(=O)[C@H](CCC(F)(F)F)NC(=O)[C@H](Cc2cn(Cc3ccc(Br)cc3)c3ccccc23)N(C)C1=O]
C-49
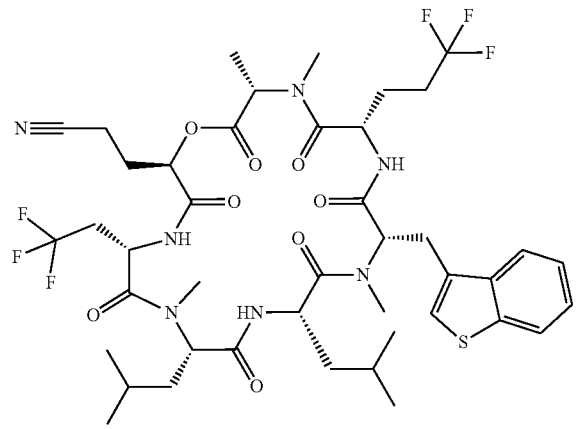 [SMILES: CC(C)C[C@@H]1NC(=O)[C@H](CC(C)C)N(C)C(=O)[C@H](CC(F)(F)F)NC(=O)[C@@H](CCC#N)OC(=O)[C@H](C)N(C)C(=O)[C@H](CCC(F)(F)F)NC(=O)[C@H](Cc2csc3ccccc23)N(C)C1=O]

TABLE A-continued
C-50
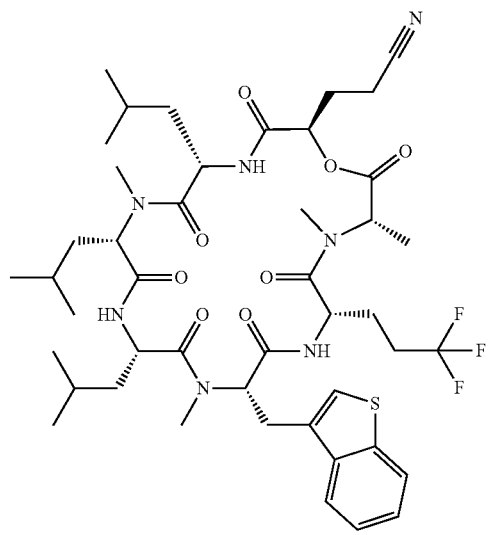 [SMILES: CC(C)C[C@@H]1NC(=O)[C@@H](CCC#N)OC(=O)[C@H](C)N(C)C(=O)[C@H](CCC(F)(F)F)NC(=O)[C@H](Cc2csc3ccccc23)N(C)C(=O)[C@H](CC(C)C)NC(=O)[C@H](CC(C)C)N(C)C1=O]
C-51
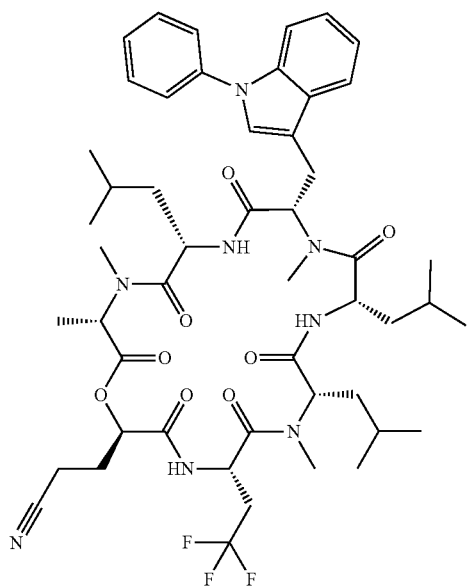 [SMILES: CC(C)C[C@@H]1NC(=O)[C@H](Cc2cn(-c3ccccc3)c3ccccc23)N(C)C(=O)[C@H](CC(C)C)NC(=O)[C@H](CC(C)C)N(C)C(=O)[C@H](CC(F)(F)F)NC(=O)[C@@H](CCC#N)OC(=O)[C@H](C)N(C)C1=O]
C-52
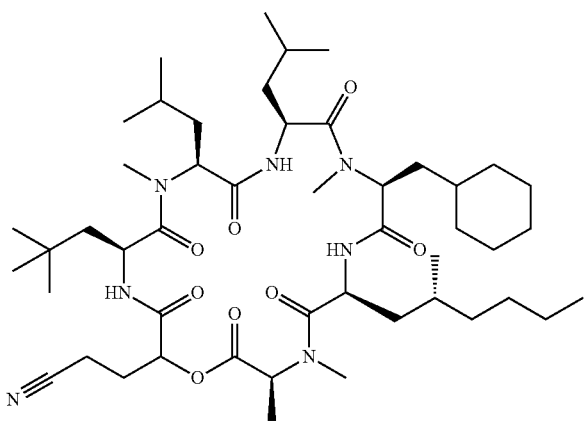 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CC(C)(C)C)NC(=O)C(CCC#N)OC(=O)[C@H](C)N(C)C1=O]

TABLE A-continued
C-53
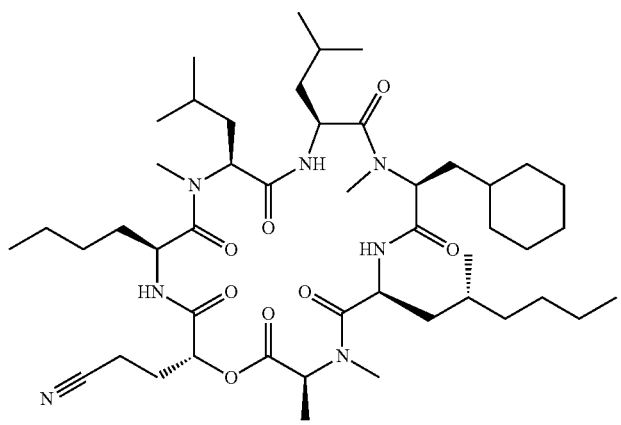 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CCCC)NC(=O)[C@@H](CCC#N)OC(=O)[C@H](C)N(C)C1=O]
C-54
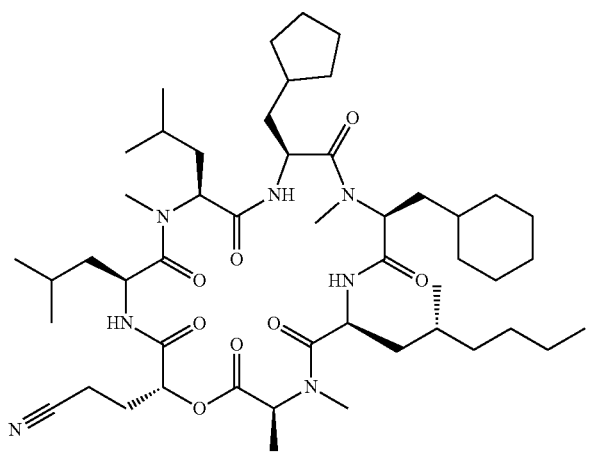 [SMILES: CCCC[C@@H](C)C[C@@H]1NC(=O)[C@H](CC2CCCCC2)N(C)C(=O)[C@H](CC2CCCC2)NC(=O)[C@H](CC(C)C)N(C)C(=O)[C@H](CC(C)C)NC(=O)[C@@H](CCC#N)OC(=O)[C@H](C)N(C)C1=O]
C-55
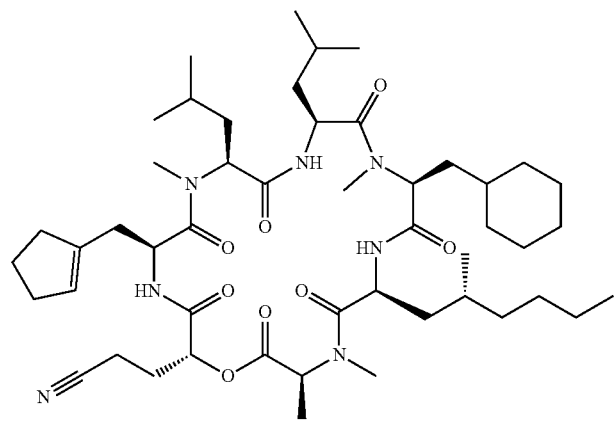 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CC2=CCCC2)NC(=O)[C@@H](CCC#N)OC(=O)[C@H](C)N(C)C1=O]

TABLE A-continued
C-56
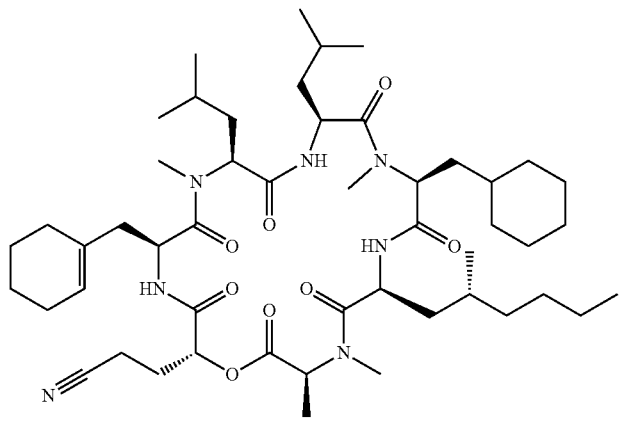 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CC2=CCCCC2)NC(=O)[C@@H](CCC#N)OC(=O)[C@H](C)N(C)C1=O]
C-57
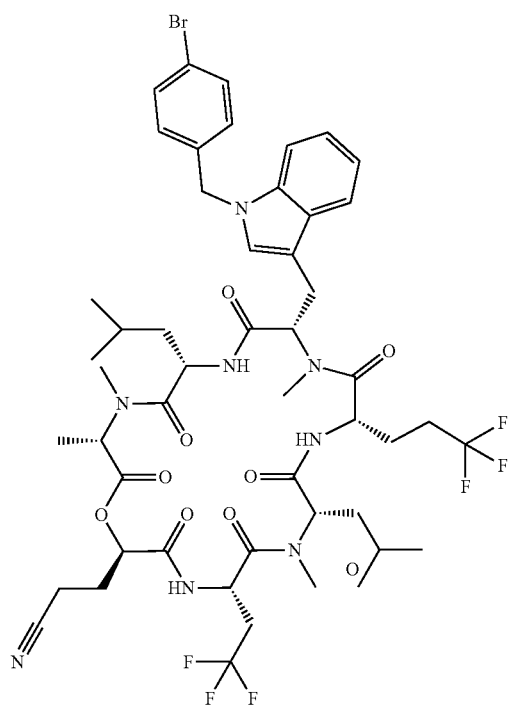

TABLE A-continued
C-58
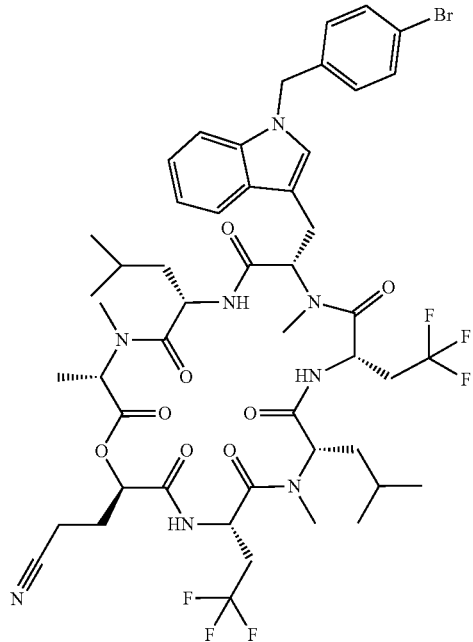 [SMILES: CC(C)C[C@@H]1NC(=O)[C@H](Cc2cn(Cc3ccc(Br)cc3)c3ccccc23)N(C)C(=O)[C@H](CC(F)(F)F)NC(=O)[C@H](CC(C)C)N(C)C(=O)[C@H](CC(F)(F)F)NC(=O)[C@@H](CCC#N)OC(=O)[C@H](C)N(C)C1=O]
C-60
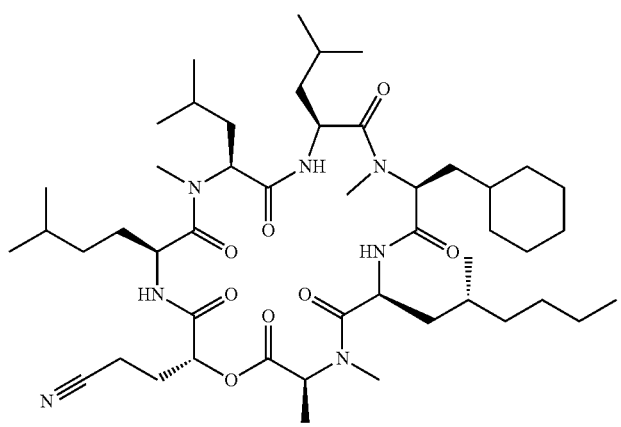 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CCC(C)C)NC(=O)[C@@H](CCC#N)OC(=O)[C@H](C)N(C)C1=O]
C-61
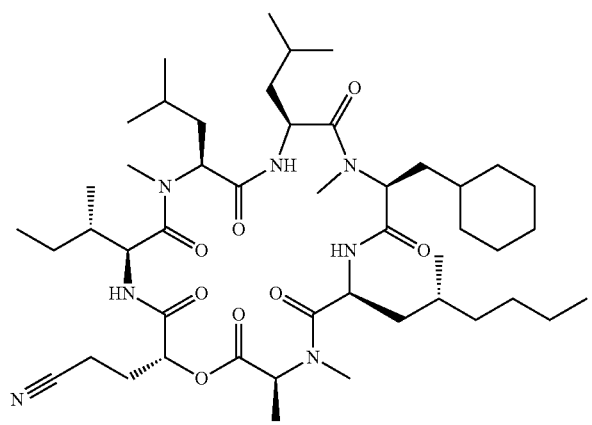 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H]([C@@H](C)CC)NC(=O)[C@@H](CCC#N)OC(=O)[C@H](C)N(C)C1=O]

TABLE A-continued
C-62
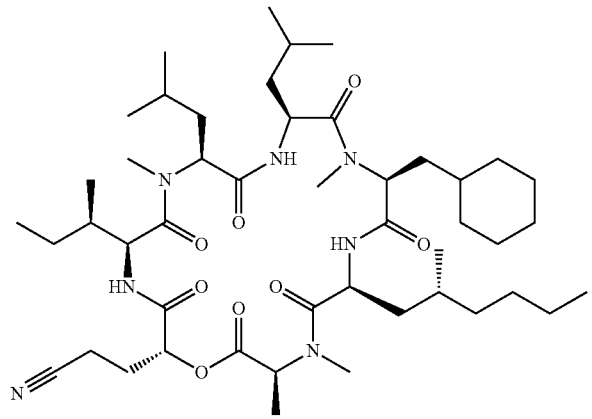 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H]([C@H](C)CC)NC(=O)[C@@H](CCC#N)OC(=O)[C@H](C)N(C)C1=O]
C-63
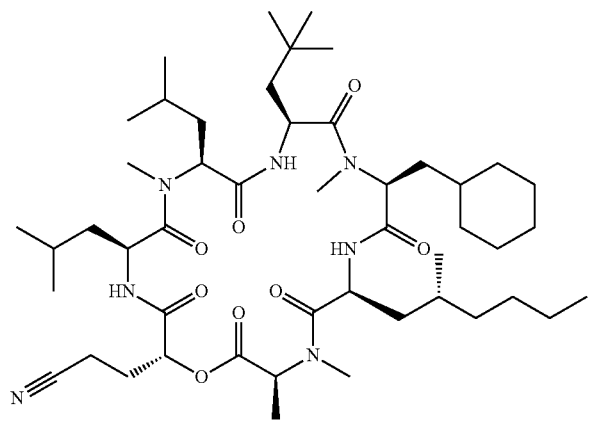 [SMILES: CCCC[C@@H](C)C[C@@H]1NC(=O)[C@H](CC2CCCCC2)N(C)C(=O)[C@H](CC(C)(C)C)NC(=O)[C@H](CC(C)C)N(C)C(=O)[C@H](CC(C)C)NC(=O)[C@@H](CCC#N)OC(=O)[C@H](C)N(C)C1=O]
C-64
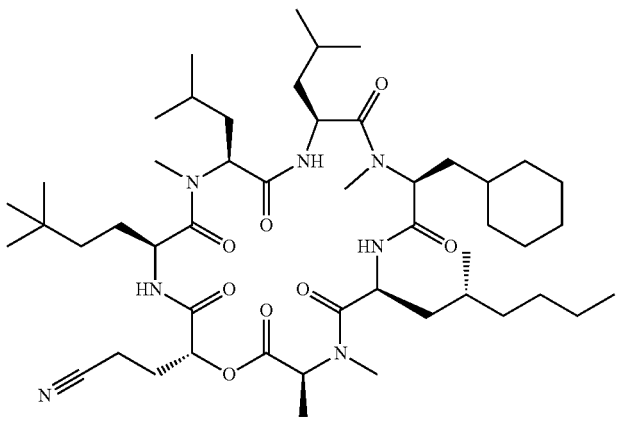 [SMILES: CCCC[C@@H](C)C[C@@H]1NC(=O)[C@H](CC2CCCCC2)N(C)C(=O)[C@H](CC(C)C)NC(=O)[C@H](CC(C)C)N(C)C(=O)[C@H](CCC(C)(C)C)NC(=O)[C@@H](CCC#N)OC(=O)[C@H](C)N(C)C1=O]

TABLE A-continued
C-65
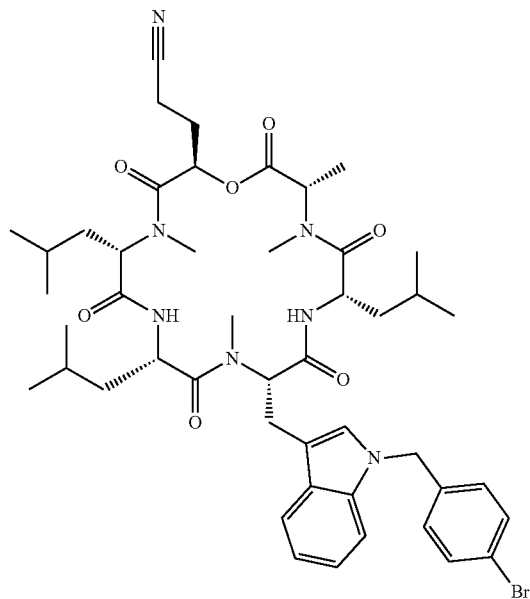 [SMILES: CC(C)C[C@@H]1NC(=O)[C@H](Cc2cn(Cc3ccc(Br)cc3)c3ccccc23)N(C)C(=O)[C@H](CC(C)C)NC(=O)[C@H](CC(C)C)N(C)C(=O)[C@@H](CCC#N)OC(=O)[C@H](C)N(C)C1=O]
C-66
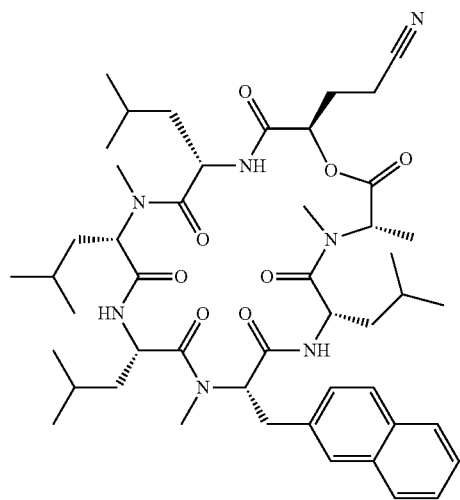 [SMILES: CC(C)C[C@@H]1NC(=O)[C@H](Cc2ccc3ccccc3c2)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]

TABLE A-continued
C-67
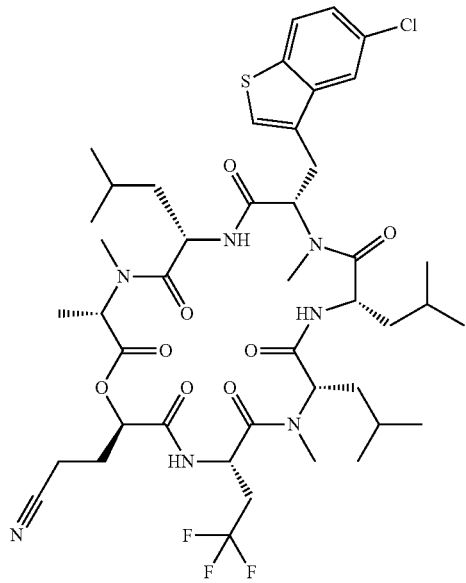 [SMILES: CC(C)C[C@@H]1NC(=O)[C@H](Cc2csc3ccc(Cl)cc23)N(C)C(=O)[C@H](CC(C)C)NC(=O)[C@H](CC(C)C)N(C)C(=O)[C@H](CC(F)(F)F)NC(=O)[C@@H](CCC#N)OC(=O)[C@H](C)N(C)C1=O]
C-68
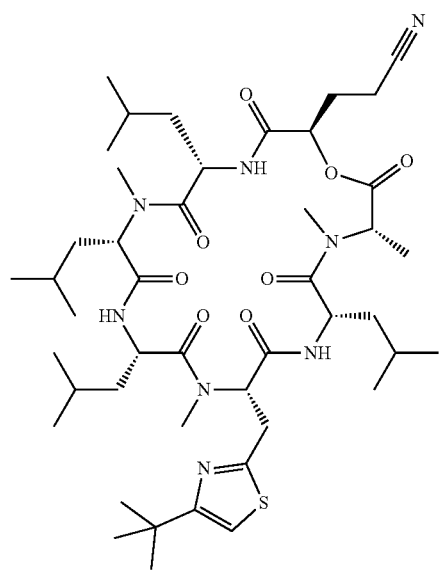 [SMILES: CC(C)C[C@@H]1NC(=O)[C@H](Cc2nc(C(C)(C)C)cs2)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]
C-69
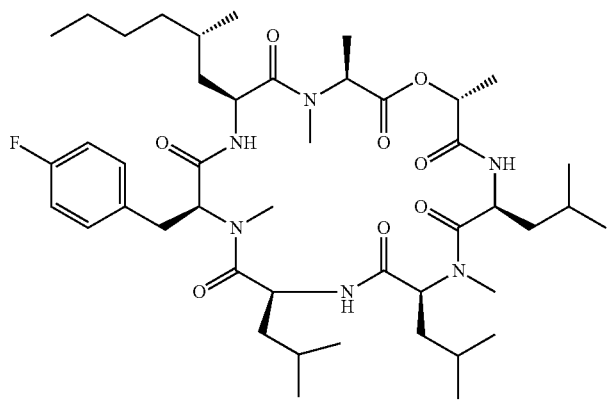 [SMILES: CCCC[C@H](C)C[C@@H]1NC(=O)[C@H](Cc2ccc(F)cc2)N(C)C(=O)[C@H](CC(C)C)NC(=O)[C@H](CC(C)C)N(C)C(=O)[C@H](CC(C)C)NC(=O)[C@@H](C)OC(=O)[C@H](C)N(C)C1=O]

TABLE A-continued
C-71
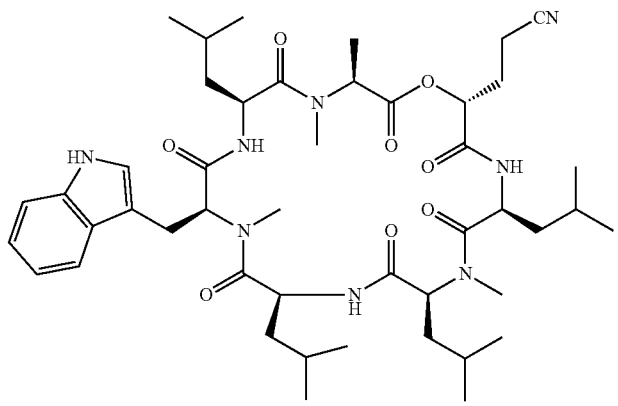 [SMILES: CC(C)C[C@@H]1NC(=O)[C@H](Cc2c[nH]c3ccccc23)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]
C-72
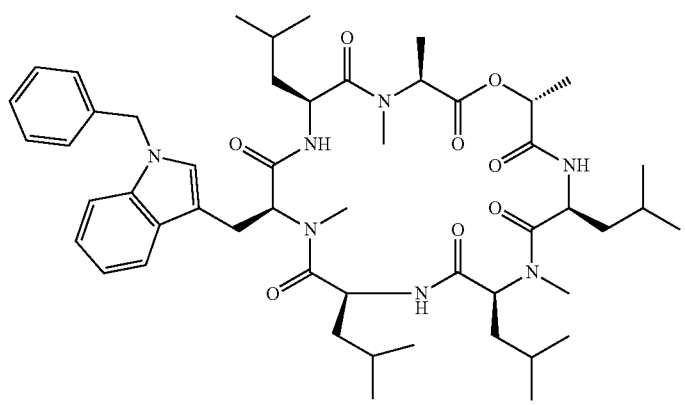 [SMILES: CC(C)C[C@@H]1NC(=O)[C@H](Cc2cn(Cc3ccccc3)c3ccccc23)N(C)C(=O)[C@H](CC(C)C)NC(=O)[C@H](CC(C)C)N(C)C(=O)[C@H](CC(C)C)NC(=O)[C@@H](C)OC(=O)[C@H](C)N(C)C1=O]
C-73
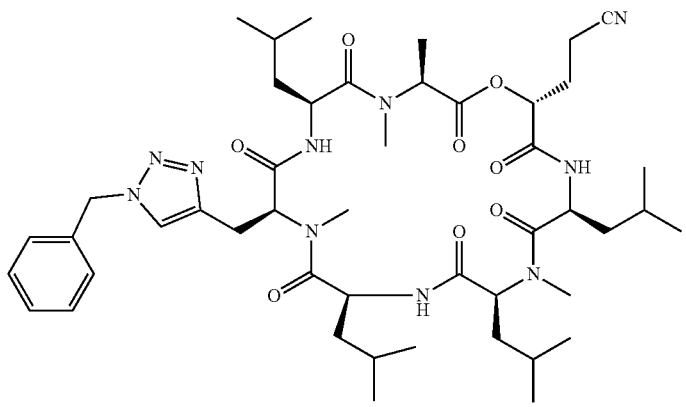 [SMILES: CC(C)C[C@@H]1NC(=O)[C@H](Cc2cn(Cc3ccccc3)nn2)N(C)C(=O)[C@H](CC(C)C)NC(=O)[C@H](CC(C)C)N(C)C(=O)[C@H](CC(C)C)NC(=O)[C@@H](CCC#N)OC(=O)[C@H](C)N(C)C1=O]
C-74
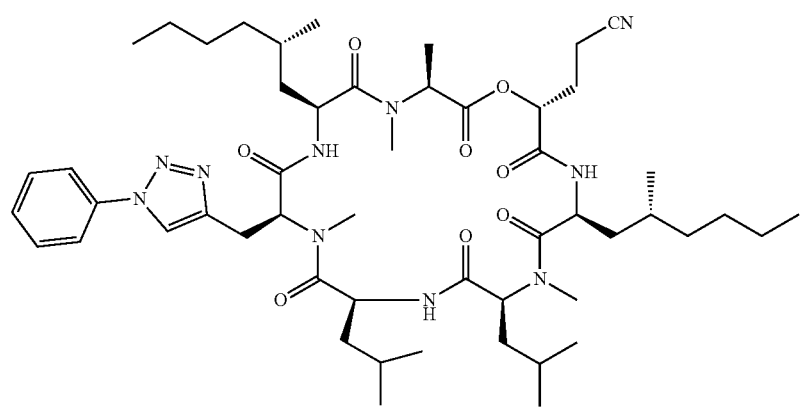 [SMILES: CCCC[C@@H](C)C[C@@H]1NC(=O)[C@@H](CCC#N)OC(=O)[C@H](C)N(C)C(=O)[C@H](C[C@@H](C)CCCC)NC(=O)[C@H](Cc2cn(-c3ccccc3)nn2)N(C)C(=O)[C@H](CC(C)C)NC(=O)[C@H](CC(C)C)N(C)C1=O]

TABLE A-continued
C-75
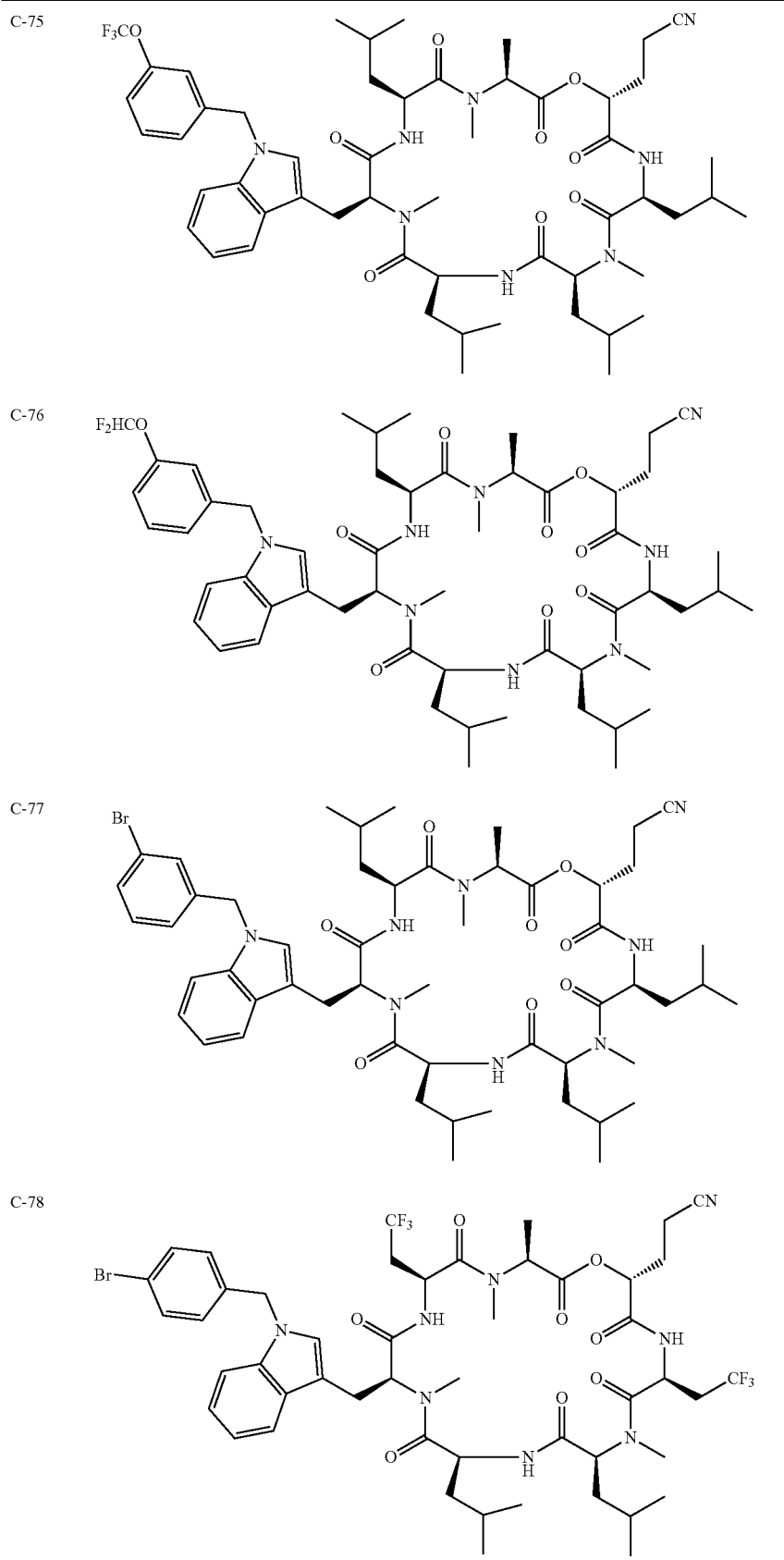
C-76
C-77
C-78

TABLE A-continued
C-79
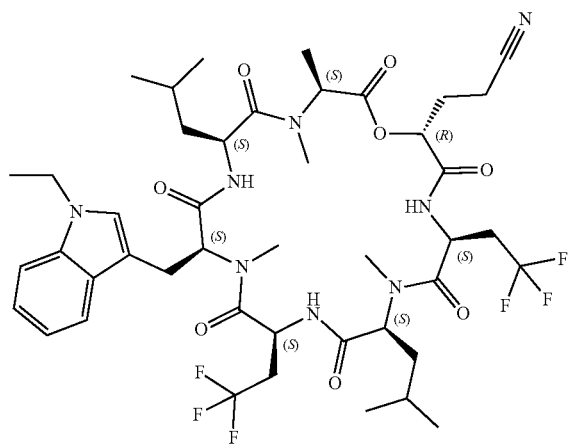
C-80
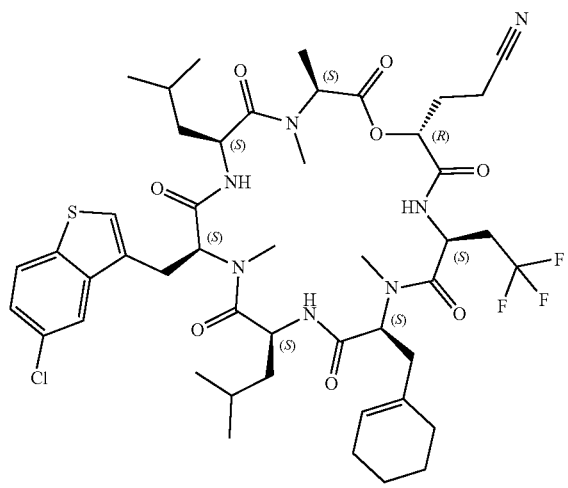
C-81
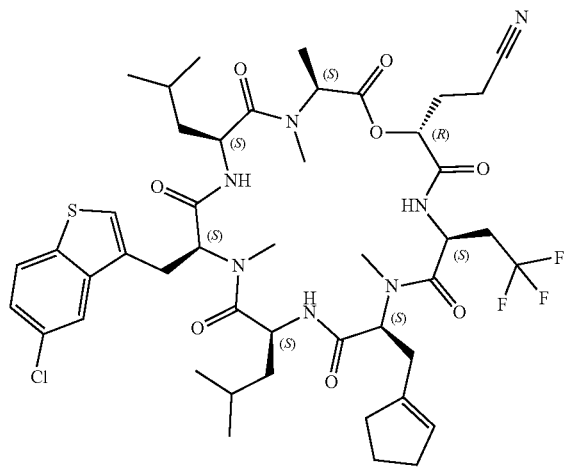

TABLE A-continued
C-82
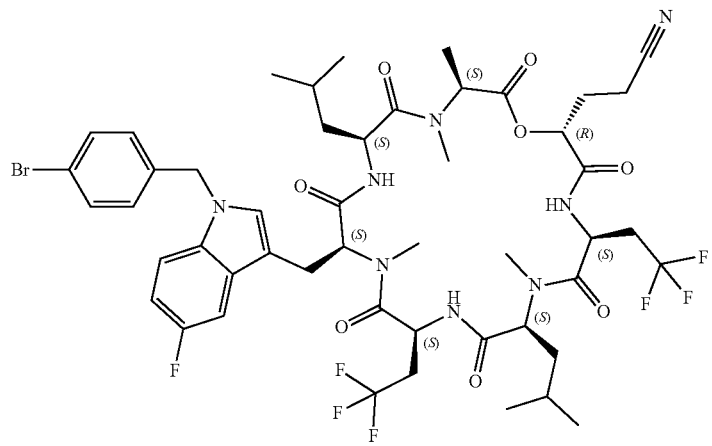
C-83
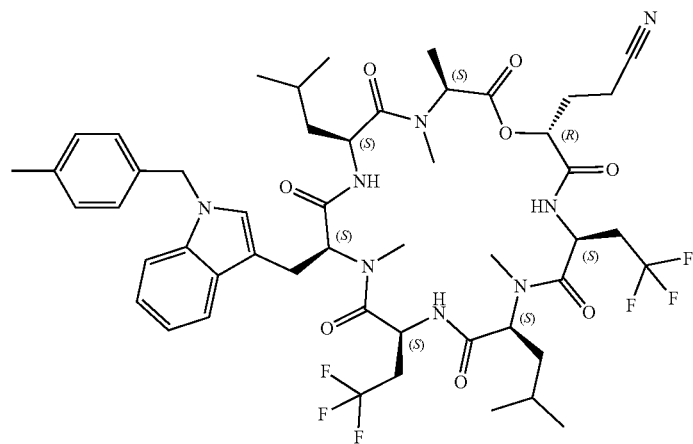
C-84
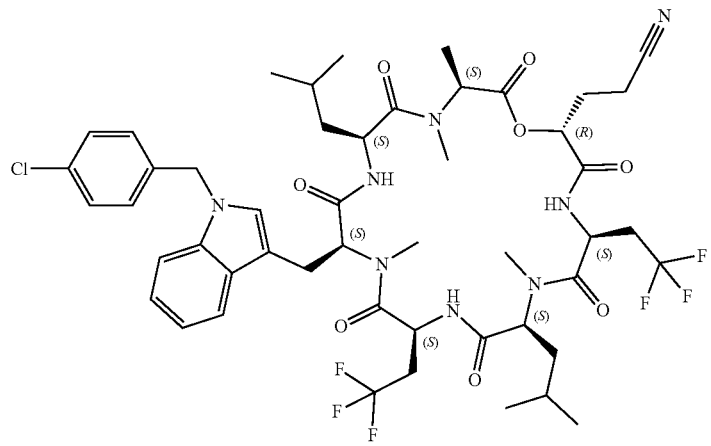

TABLE A-continued
C-85
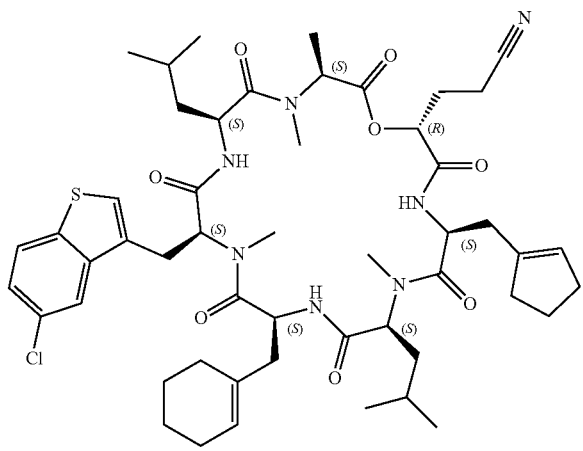
C-86
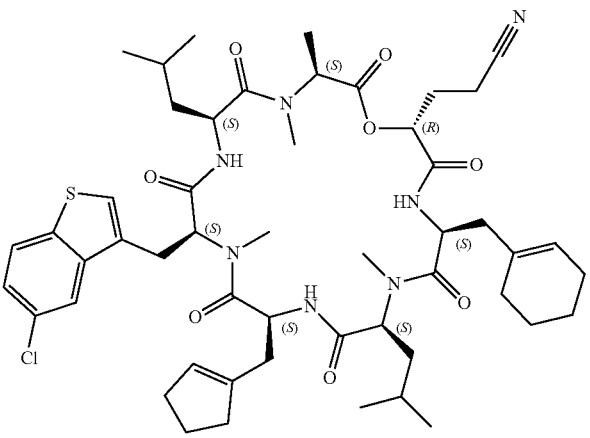
C-87
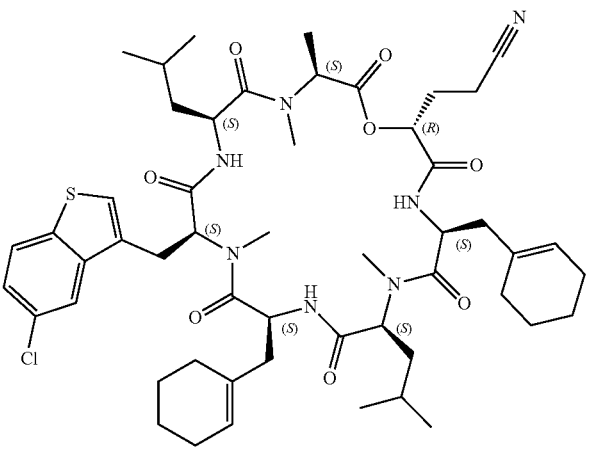

TABLE A-continued
C-88
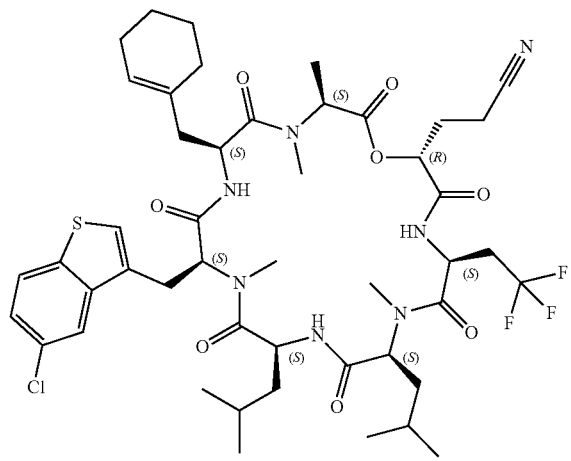
C-89
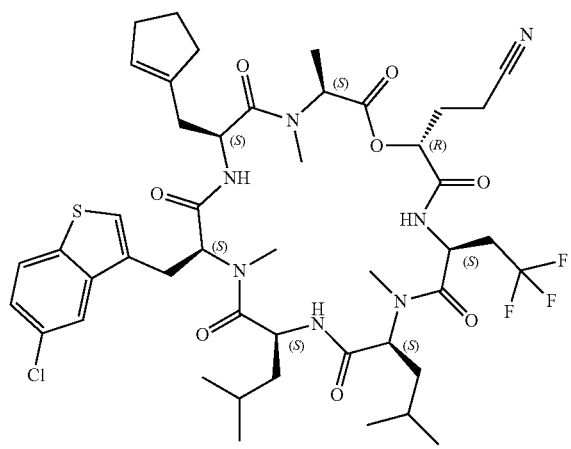
C-90
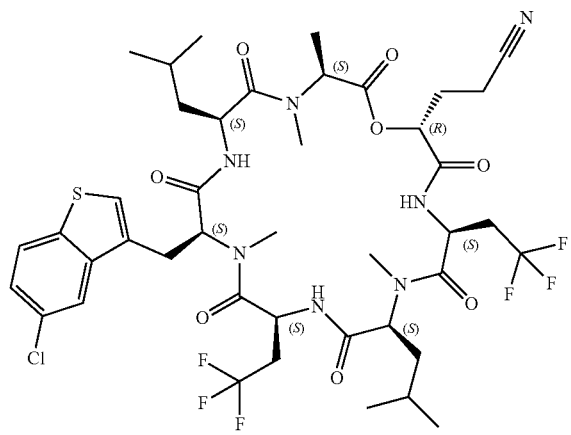

TABLE A-continued
C-91
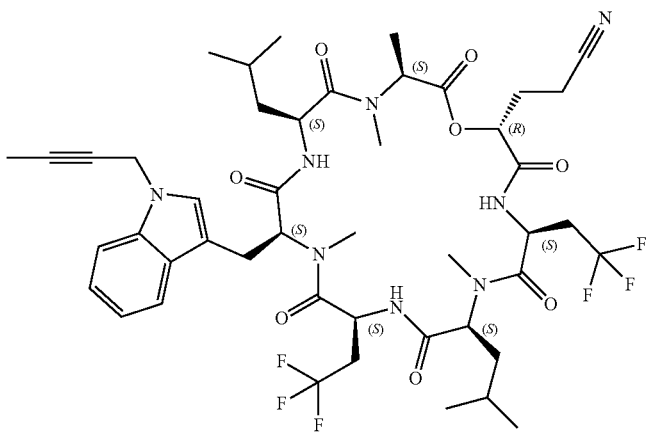
C-92
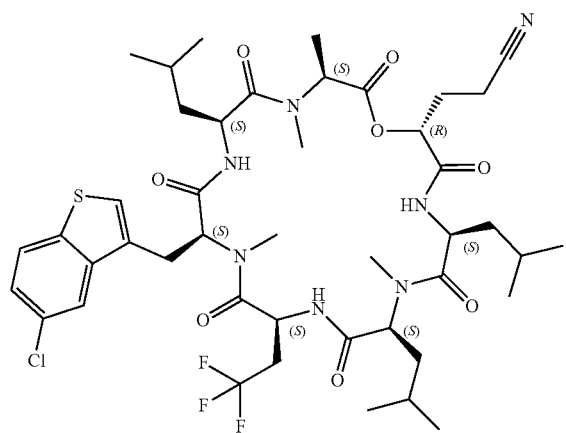
C-93
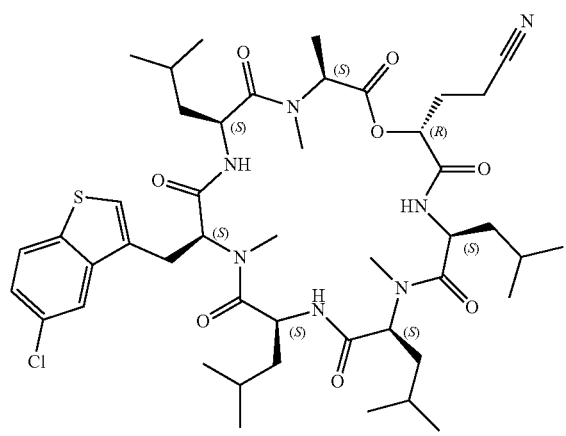

TABLE A-continued
C-94
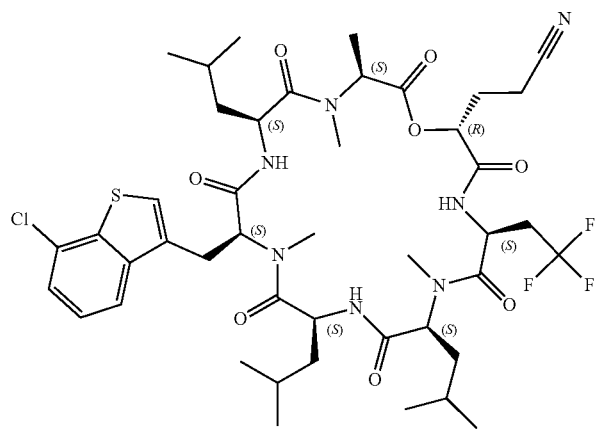
C-95
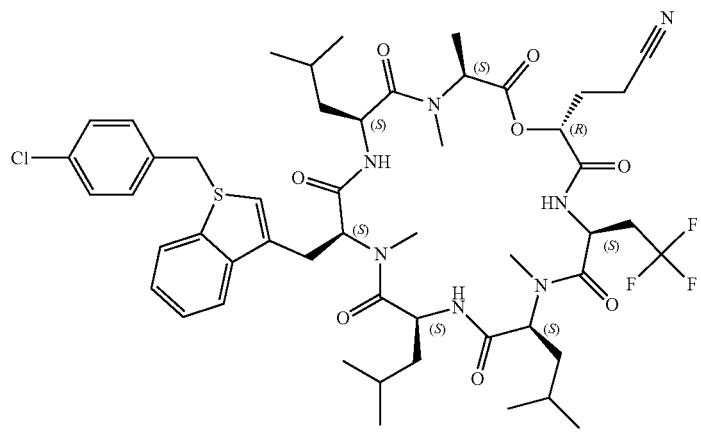
C-96
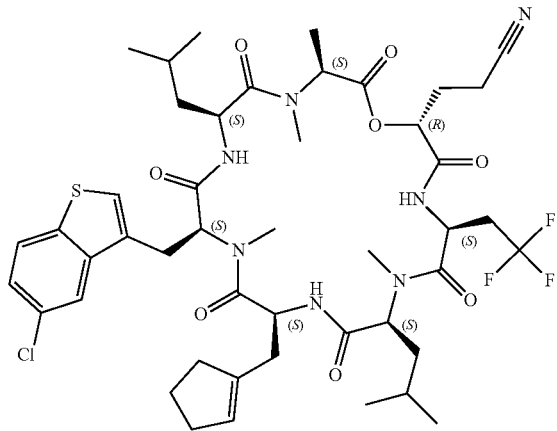

TABLE A-continued

C-97

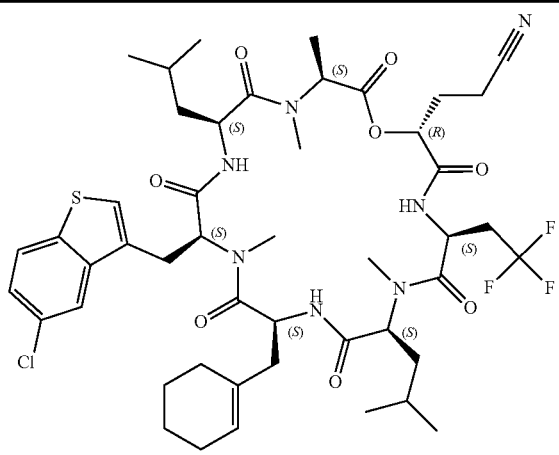

C-98

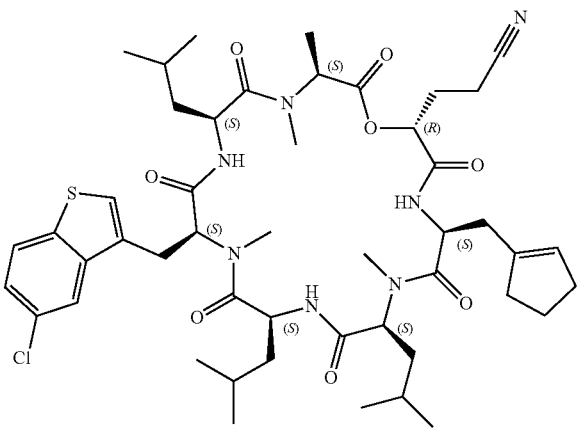

C-99

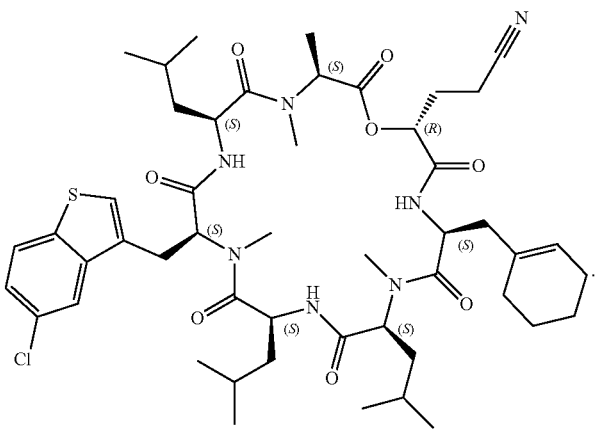

18. A pharmaceutical composition comprising the compound or salt of claim 1 and a pharmaceutically acceptable excipient.

19. A method of treating a cancer, arthritis, or inflammation in a subject comprising administering the compound or salt of claim 1 to the subject in an amount effective to treat the cancer, arthritis, or inflammation.

20. The method of claim 19, wherein the cancer is breast or melanoma, and $R^5$ optionally comprises a benzothiophenyl.

* * * * *

SEQUENCE LISTING

<160> NUMBER OF SEQ ID NOS: 8

<210> SEQ ID NO 1
<211> LENGTH: 34
<212> TYPE: PRT
<213> ORGANISM: Gaussia princeps

<400> SEQUENCE: 1

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
            20                  25                  30

Ser Arg

<210> SEQ ID NO 2
<211> LENGTH: 34
<212> TYPE: PRT
<213> ORGANISM: Gaussia princeps

<400> SEQUENCE: 2

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
            20                  25                  30

Ser Arg

<210> SEQ ID NO 3
<211> LENGTH: 30
<212> TYPE: PRT
<213> ORGANISM: Gaussia princeps

<400> SEQUENCE: 3

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg
            20                  25                  30

```
<210> SEQ ID NO 4
<211> LENGTH: 38
<212> TYPE: PRT
<213> ORGANISM: Gaussia princeps

<400> SEQUENCE: 4

Met Asn Ile Lys Gly Ser Pro Trp Lys Gly Ser Leu Leu Leu Leu Leu
1               5                   10                  15

Val Ser Asn Leu Leu Leu Cys Gln Ser Val Ala Pro Leu Pro Ile Cys
            20                  25                  30

Pro Gly Gly Ala Ala Arg
        35

<210> SEQ ID NO 5
<211> LENGTH: 38
<212> TYPE: PRT
<213> ORGANISM: Gaussia princeps

<400> SEQUENCE: 5

Met Asn Ile Lys Gly Ser Pro Trp Lys Gly Ser Leu Leu Leu Leu Leu
1               5                   10                  15

Val Ser Asn Leu Leu Leu Cys Gln Ser Val Ala Pro Leu Pro Ile Cys
            20                  25                  30

Pro Gly Gly Ala Ala Arg
        35

<210> SEQ ID NO 6
<211> LENGTH: 24
<212> TYPE: PRT
<213> ORGANISM: Gaussia princeps

<400> SEQUENCE: 6

Met Thr Ile Leu Gly Thr Thr Phe Gly Met Val Phe Ser Leu Leu Gln
1               5                   10                  15

Val Val Ser Gly Glu Ser Gly Tyr
            20

<210> SEQ ID NO 7
<211> LENGTH: 30
<212> TYPE: PRT
<213> ORGANISM: Gaussia princeps

<400> SEQUENCE: 7

Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu
            20                  25                  30

<210> SEQ ID NO 8
<211> LENGTH: 23
<212> TYPE: PRT
<213> ORGANISM: Gaussia princeps

<400> SEQUENCE: 8

Met Arg Ala Asn Asp Ala Leu Gln Val Leu Gly Leu Leu Phe Ser Leu
1               5                   10                  15

Ala Arg Gly Ser Glu Val Gly
            20
```